US012691133B2

(12) United States Patent
Krieg et al.

(10) Patent No.: US 12,691,133 B2
(45) **Date of Patent: *Jul. 28, 2026**

(54) SYNTHETIC RIG-I-LIKE RECEPTOR AGONISTS

(71) Applicant: Checkmate Pharmaceuticals, Inc., Cambridge, MA (US)

(72) Inventors: Arthur M. Krieg, Cambridge, MA (US); Aaron Jay Morris, Brighton, MA (US); Evan David Walters, Cambridge, MA (US)

(73) Assignee: CHECKMATE PHARMACEUTICALS, INC., Cambridge, MA (US)

( * ) Notice: Subject to any disclaimer, the term of this patent is extended or adjusted under 35 U.S.C. 154(b) by 1130 days.

This patent is subject to a terminal disclaimer.

(21) Appl. No.: 17/770,881

(22) PCT Filed: Oct. 23, 2020

(86) PCT No.: PCT/US2020/057099

§ 371 (c)(1),
(2) Date: Apr. 21, 2022

(87) PCT Pub. No.: WO2021/081353

PCT Pub. Date: Apr. 29, 2021

(65) Prior Publication Data

US 2022/0378817 A1 Dec. 1, 2022

Related U.S. Application Data

(60) Provisional application No. 62/925,120, filed on Oct. 23, 2019.

(51) Int. Cl.

| | |
|---|---|
| ***A61K 31/7105*** | (2006.01) |
| ***A61K 31/4745*** | (2006.01) |
| ***A61K 31/519*** | (2006.01) |
| ***A61K 31/711*** | (2006.01) |
| ***A61K 31/713*** | (2006.01) |
| ***A61K 35/76*** | (2015.01) |
| ***A61K 39/395*** | (2006.01) |
| ***A61K 45/06*** | (2006.01) |
| ***A61P 35/00*** | (2006.01) |
| ***A61P 37/04*** | (2006.01) |

(52) U.S. Cl.

CPC ...... *A61K 31/7105* (2013.01); *A61K 31/4745* (2013.01); *A61K 31/519* (2013.01); *A61K 31/711* (2013.01); *A61K 31/713* (2013.01); *A61K 35/76* (2013.01); *A61K 39/3955* (2013.01); *A61K 45/06* (2013.01); *A61P 35/00* (2018.01); *A61P 37/04* (2018.01)

(58) Field of Classification Search

None

See application file for complete search history.

(56) References Cited

U.S. PATENT DOCUMENTS

| | | | |
|---|---|---|---|
| 3,710,795 A | 1/1973 | Higuchi et al. | |
| 3,773,919 A | 11/1973 | Boswell et al. | |
| 4,863,457 A | 9/1989 | Lee | |
| 5,071,651 A | 12/1991 | Sabara et al. | |
| 5,138,045 A | 8/1992 | Cook et al. | |
| 5,218,105 A | 6/1993 | Cook et al. | |
| 5,374,426 A | 12/1994 | Sabara et al. | |
| 5,459,255 A | 10/1995 | Cook et al. | |
| 5,501,856 A | 3/1996 | Ohtori et al. | |
| 6,964,769 B2 | 11/2005 | Sebbel et al. | |
| 7,138,252 B2 | 11/2006 | Bachmann et al. | |
| 7,229,624 B2 | 6/2007 | Renner et al. | |
| 7,264,810 B2 | 9/2007 | Renner et al. | |
| 7,595,048 B2 | 9/2009 | Honjo et al. | |
| 7,943,743 B2 | 5/2011 | Korman et al. | |
| 8,008,449 B2 | 8/2011 | Korman et al. | |
| 8,354,509 B2 | 1/2013 | Carven et al. | |
| 8,728,474 B2 | 5/2014 | Honjo et al. | |
| 8,779,105 B2 | 7/2014 | Korman et al. | |
| 8,900,587 B2 | 12/2014 | Carven et al. | |
| 8,952,136 B2 | 2/2015 | Carven et al. | |
| 9,067,999 B1 | 6/2015 | Honjo et al. | |
| 9,073,994 B2 | 7/2015 | Honjo et al. | |
| 9,381,208 B2 | 7/2016 | Hartmann et al. | |
| 9,518,095 B2 | 12/2016 | Emmerling et al. | |
| 9,657,065 B2 | 5/2017 | Richter et al. | |
| 9,950,055 B2 | 4/2018 | Bachmann et al. | |
| 10,907,161 B2 * | 2/2021 | Krieg | C12N 15/117 |

(Continued)

FOREIGN PATENT DOCUMENTS

| | | |
|---|---|---|
| EP | 0360676 A1 | 3/1990 |
| EP | 0580481 A1 | 1/1994 |

(Continued)

OTHER PUBLICATIONS

Guo et al. PLOS One, 2012, p. 1-9.*

U.S. Appl. No. 16/389,432 2020/0063141 U.S. Pat. No. 10,907,161, filed Apr. 19, 2019 Feb. 27, 2020 Feb. 2, 2021, Arthur M. Krieg, Synthetic RIG-I-Like Receptor Agonists.

U.S. Appl. No. 17/132,448 2021/0207148, filed Dec. 23, 2020 Jul. 8, 2021, Arthur M. Krieg, Synthetic RIG-I-Like Receptor Agonists.

U.S. Appl. No. 17/770,881 2022/0378817, filed Oct. 23, 2020 Dec. 1, 2022, Arthur M. Krieg, Synthetic RIG-I-Like Receptor Agonists.

Adhin, et al., Nucleotide Sequence From the Ssrna Bacteriophage JP34 Resolves the Discrepancy Between Serological and Biophysical Classification, Virology, vol. 170, No. 1, pp. 238-242, 1989.

(Continued)

*Primary Examiner* — Agnieszka Boesen

(74) *Attorney, Agent, or Firm* — LATHROP GPM LLP; James H. Velema; James V. DeGiulio

(57) ABSTRACT

The present disclosure relates to, inter alia, RNA molecules (e.g., RNA hairpin agonists) that bind to and agonize RIG-I-like receptors (RLRs), and to use of the molecules, including RLR agonists packaged in vims like particles (VLPs), in methods for treating, or ameliorating one or more symptoms of, a disorder (e.g., cancer).

22 Claims, 3 Drawing Sheets

Specification includes a Sequence Listing.

(56) References Cited

U.S. PATENT DOCUMENTS

| | | | |
|---|---|---|---|
| 12,123,003 | B2 | 10/2024 | Krieg et al. |
| 2003/0175290 | A1 | 9/2003 | Renner et al. |
| 2008/0241223 | A1 | 10/2008 | Nivaggioli et al. |
| 2011/0184045 | A1 | 7/2011 | Hartmann et al. |
| 2012/0107272 | A1 | 5/2012 | Manoharan et al. |
| 2015/0017207 | A1 | 1/2015 | Gale et al. |
| 2019/0184006 | A1 | 6/2019 | Chan et al. |
| 2020/0063141 | A1 | 2/2020 | Krieg et al. |
| 2021/0207148 | A1 | 7/2021 | Krieg et al. |
| 2022/0378817 | A1 | 12/2022 | Krieg et al. |
| 2024/0368607 | A1 | 11/2024 | Krieg et al. |

FOREIGN PATENT DOCUMENTS

| | | | |
|---|---|---|---|
| EP | 0880046 | A1 | 11/1998 |
| EP | 1330988 | A2 | 7/2003 |
| EP | 1430949 | A1 | 6/2004 |
| EP | 2161336 | A1 | 3/2010 |
| EP | 2170959 | A1 | 4/2010 |
| EP | 1537878 | B1 | 9/2010 |
| EP | 3781689 | A1 | 2/2021 |
| EP | 4048795 | A1 | 8/2022 |
| EP | 4300539 | A1 | 1/2024 |
| WO | WO 1992/011291 | A1 | 7/1992 |
| WO | WO 1993/015722 | A1 | 8/1993 |
| WO | WO 1994/020069 | A1 | 9/1994 |
| WO | WO 1994/026764 | A1 | 11/1994 |
| WO | WO 1996/030523 | A2 | 10/1996 |
| WO | WO 1998/015631 | A1 | 4/1998 |
| WO | WO 2000/023955 | A1 | 4/2000 |
| WO | WO 2000/032227 | A2 | 6/2000 |
| WO | WO 2001/077158 | A1 | 10/2001 |
| WO | WO 2001/085208 | A2 | 11/2001 |
| WO | WO 2001/098333 | A2 | 12/2001 |
| WO | WO 2002/014478 | A2 | 2/2002 |
| WO | WO 2002/056905 | A2 | 7/2002 |
| WO | WO 2003/024481 | A2 | 3/2003 |
| WO | WO 2004/016282 | A1 | 2/2004 |
| WO | WO 2004/084940 | A1 | 10/2004 |
| WO | WO 2006/063252 | A2 | 6/2006 |
| WO | WO 2008/017473 | A2 | 2/2008 |
| WO | WO 2009/095226 | A2 | 8/2009 |
| WO | WO 2009/141146 | A1 | 11/2009 |
| WO | WO 2010/027827 | A2 | 3/2010 |
| WO | WO 2010/077634 | A1 | 7/2010 |
| WO | WO 2011/066342 | A2 | 6/2011 |
| WO | WO 2012/045075 | A1 | 4/2012 |
| WO | WO 2012/130886 | A1 | 10/2012 |
| WO | WO 2013/052523 | A1 | 4/2013 |
| WO | WO 2013/064584 | A1 | 5/2013 |
| WO | WO 2013/079174 | A1 | 6/2013 |
| WO | WO 2013/097965 | A1 | 7/2013 |
| WO | WO 2013/151666 | A2 | 10/2013 |
| WO | WO 2013/173223 | A1 | 11/2013 |
| WO | WO 2014/049079 | A1 | 4/2014 |
| WO | WO 2014/081507 | A1 | 5/2014 |
| WO | WO 2014/093924 | A1 | 6/2014 |
| WO | WO 2014/124433 | A1 | 8/2014 |
| WO | WO 2014/159813 | A1 | 10/2014 |
| WO | WO 2014/159990 | A1 | 10/2014 |
| WO | WO 2014/164253 | A1 | 10/2014 |
| WO | WO 2014/169049 | A1 | 10/2014 |
| WO | WO 2015/038746 | A1 | 3/2015 |
| WO | WO 2015/091578 | A1 | 6/2015 |
| WO | WO 2015/144736 | A1 | 10/2015 |
| WO | WO 2016/011324 | A2 | 1/2016 |
| WO | WO 2016/106159 | A1 | 6/2016 |
| WO | WO 2017/121494 | A1 | 7/2017 |
| WO | WO 2017/173427 | A1 | 10/2017 |
| WO | WO 2017/185180 | A1 | 11/2017 |
| WO | WO 2017/221076 | A1 | 12/2017 |
| WO | WO 2018/172546 | A1 | 9/2018 |
| WO | WO 2019/126240 | A1 | 6/2019 |
| WO | WO 2019/197965 | A1 | 10/2019 |
| WO | WO 2019/204743 | A1 | 10/2019 |
| WO | WO 2019/246450 | A1 | 12/2019 |
| WO | WO 2021/081353 | A1 | 4/2021 |

OTHER PUBLICATIONS

Akke et al., Base Dynamics in a UUCG Tetraloop RNA Hairpin Characterized by 15N Spin Relaxation: Correlations With Structure and Stability, RNA, vol. 3, pp. 702-709, 1997.

Baek et al., Dependence of RIG-I Nucleic Acid-Binding and ATP Hydrolysis on Activation of Type I Interferon Response, Immune Network, vol. 16, No. 4, pp. 249-255, Aug. 2016.

Beljanski, et al., Enhanced Influenza Virus-Like Particle Vaccination with a Structurally Optimized RIG-I Agonist as Adjuvant, Journal of Virology, vol. 89, No. 20, pp. 10612-10624, Oct. 15, 2015.

Berge et al., Pharmaceutical Salts, Journal of Pharmaceutical Sciences, vol. 66, No. 1, pp. 1-19, Jan. 1977.

Besch et al., Proapoptotic Signaling Induced by RIG-I and MDA-5 Results in Type I Interferon-independent Apoptosis in Human Melanoma Cells, Journal of Clinical Investigation, vol. 119, No. 8, pp. 2399-2411, Aug. 2009.

Borisova, et al., Hybrid Hepatitis B Virus Nucleocapsid Bearing an Immunodominant Region From Hepatitis B Virus Surface Antigen, Journal of Virology, Jun. 1993, vol. 67, No. 6, pp. 3696-3701.

Chiang et al., Sequence-Specific Modifications Enhance the Broad-Spectrum Antiviral Response Activated by RIG-I Agonists, Journal of Virology, vol. 89, No. 15, pp. 8011-8025, Aug. 2015.

Civril et al., The RIG-I ATPase Domain Structure Reveals Insights Into ATP-dependent Antiviral Signalling, European Molecular Biology Organization, vol. 12, pp. 1127-1134, Oct. 7, 2011.

Clarke, et al., Presentation and Immunogenicity of Viral Epitopes on the Surface of Hybrid Hepatitis B Virus Core Particles Produced in Bacteria, Journal of General Virology, 1990, vol. 71, No. 5, pp. 1109-1117.

Cui et al., The C-Terminal Regulatory Domain Is the RNA 50 -Triphosphate Sensor of RIG-I, Molecular Cell, vol. 29, pp. 169-179, Feb. 1, 2008.

De Mesmaeker et al., Antisense Oligonucleotides, Accounts of Chemical Research, vol. 28, No. 9, pp. 366-374, 1995.

Ellermeier et al., Therapeutic Efficacy of Bifunctional siRNA Combining TGF-β1 Silencing with RIG-I Activation in Pancreatic Cancer, Cancer Research, vol. 73, No. 6, pp. 1709-1720, Mar. 15, 2013.

Elliott et al., The Use of Phosphate Bioisosteres in Medicinal Chemistry and Chemical Biology, MedChemComm, vol. 3, No. 7, pp. 735-751, 2012.

EMR, [21] Heterologous Gene Expression in Yeast, Methods in Enzymology, 1990, vol. 185, pp. 231-233.

Eppstein et al., Biological Activity of Liposome-Encapsulated Murine Interferon Gamma Is Mediated by a Cell Membrane Receptor, Proceedings of the National Academy of Sciences, vol. 82, No. 11, pp. 3688-3692, 1985.

Fang, et al., Functional RNAs: Combined Assembly and Packaging in VLPs, Nucleic Acids Research, Nov. 28, 2016, vol. 45, No. 6, pp. 3519-3527.

Fitzgerald et al., Selective RNA Targeting and Regulated Signaling by RIG-I is Controlled by Coordination of RNA and ATP Binding, Nucleic Acids Research, vol. 45, No. 3, pp. 1442-1454, Sep. 12, 2016.

Gebeyehu et al., Novel Biotinylated Nucleotide—Analogs for Labeling and Colorimetric Detection of DNA, Nucleic Acids Research, vol. 15, No. 11, pp. 4513-4534, 1987.

Genbank Database, A1-protein [Enterobacteria phage NL95], "GenBank Accession No. AAC14704.1, Retrieved from: <<https://www.ncbi.nlm.nih.gov/protein/AAC14704>>", 1 Page.

Genbank Database, antiviral innate immune response receptor RIG-I isoform 1 [*Homo sapiens*], NCBI Reference Sequence: NP_055129.2, Retrieved from: <<https://www.ncbi.nlm.nih.gov/protein/NP_055129.2>>, 4 Pages.

(56) References Cited

OTHER PUBLICATIONS

Genbank Database, ATP-dependent RNA helicase DHX58 [*Homo sapiens*], NCBI Reference Sequence: NP_077024.2, Retrieved from: <<https://www.ncbi.nlm.nih.gov/protein/NP_077024.2>>, 3 Pages.

Genbank Database, Cloning vector pUC4K linker and kanamycin region, "GenBank Accession No. X06404.1, Retrieved from: <<https://www.ncbi.nlm.nih.gov/nuccore/X06404>>", 2 Pages.

Genbank Database, Coat Protein [Enterobacteria phage M11], "GenBank Accession No. AAC06250.1, Retrieved from: <<https://www.ncbi.nlm.nih.gov/protein/AAC06250>>", 1 Page.

Genbank Database, Coat Protein [*Escherichia* virus BZ13], "NCBI Reference Sequence: NP_040754.1, Retrieved from: <<https://www.ncbi.nlm.nih.gov/protein/NP_040754.1?report=genpept>>", 2 Pages.

Genbank Database, Interferon-induced helicase C domain-containing protein 1 [*Homo sapiens*], "NCBI Reference Sequence:NP_071451.2, Retrieved from: <<https://www.ncbi.nlm.nih.gov/protein/NP_071451.2>>", 4 Pages.

Genbank Database, Major Coat Protein [*Escherichia* phage Qbeta], "GenBank Accession No. AAC14699.1, Retrieved from: <<https://www.ncbi.nlm.nih.gov/protein/AAC14699>>", 1 Page.

Genbank Database, Phage Q-beta coat protein and A1 protein genes, complete cds, "GenBank Accession No. M99039.1, Retrieved from: <<https://www.ncbi.nlm.nih.gov/nuccore/M99039>>", 2 Pages.

Genbank Database, pKK223-3 cloning vector from PL-Pharmacia, "GenBank Accession No. M77749.1, Retrieved from: <<https://www.ncbi.nlm.nih.gov/nuccore/M77749>>", 3 Pages.

Genbank Database, RecName: Full=Capsid protein; Short=CP; AltName: Full=Coat protein, "GenBank Accession No. P03611.1, Retrieved from: <<https://www.ncbi.nlm.nih.gov/protein/P03611>>", 2 Pages.

Genbank Database, Unnamed Protein Product [Enterobacteria phage SP], GenBank. GenBank Accession No. CAA30374.1, 1 Page.

Golmohammadi, et al., The Crystal Structure of Bacteriophage Qb at 3.5 A Resolution, Structure, May 15, 1996, vol. 4, No. 5, pp. 543-554.

Gomes, et al., Type of RNA Packed in VLPs Impacts IgG Class Switching-Implications for an Influenza Vaccine Design, Vaccines, 2019, vol. 7, No. 47, pp. 1-13.

Goodchild, Conjugates of Oligonucleotides and Modified Oligonucleotides: A Review of Their Synthesis and Properties, Bioconjugate Chemistry, 1990, vol. 1, No. 3 pp. 165-187.

Gooding et al., Oligonucleotide Conjugates—Candidates for Gene Silencing Therapeutics, European Journal of Pharmaceutics and Biopharmaceutics, vol. 107, pp. 321-340, 2016.

Goubau et al., Antiviral Immunity via RIG-I-mediated Recognition of RNA Bearing 5'-diphosphates, Nature, vol. 514, pp. 372-375, 2014.

Goulet et al., Systems Analysis of a RIG-I Agonist Inducing Broad Spectrum Inhibition of Virus Infectivity, PLOS Pathogens, vol. 9, No. 4, Article No. e1003298, pp. 1-19, Apr. 2013.

Gurp et al., Phase 1 dose-escalation study of CP-690 550 in stable renal allograft recipients: preliminary findings of safety, tolerability, effects on lymphocyte subsets and pharmacokinetics, American Journal of Transplantation, vol. 8, No. 8, pp. 1711-1718, 2008.

Hanauske et al., Phase 1b Dose Escalation Study of Erlotinib in Combination with Infusional 5-Fluorouracil, Leucovorin, and Oxaliplatin in Patients with Advanced Solid Tumors, Clinical Cancer Research, vol. 13, No. 2, pp. 523-531, Jan. 15, 2007.

Hetherington et al., Phase I Dose Escalation Study to Evaluate the Safety and Pharmacokinetic Profile of Tefibazumab in Subjects with End-Stage Renal Disease Requiring Hemodialysis, Antimicrobial Agents and Chemotherapy, vol. 50, No. 10, pp. 3499-3500, 2006.

Hoffmann et al., Phylogenetic Perspectives in Innate Immunity, Science, vol. 284, No. 5418, pp. 1313-1318, 1999.

Hornung et al., 5'-triphosphate RNA is the Ligand for RIG-I, Science, vol. 314, No. 5801, pp. 994-997, 2006.

Huston, et al., Protein Engineering of Single-chain Fv Analogs and Fusion Proteins, In Methods in Enzymology, 1991, vol. 203, Academic Press, pp. 46-88.

Hwang et al., 5'-Triphosphate-RNA-independent Activation of RIG-I via RNA Aptamer With Enhanced Antiviral Activity, Nucleic Acids Research, vol. 40, No. 6, pp. 2724-2733, Nov. 29, 2011.

Intemational Search Report and Written Opinion for PCT International Patent Application No. PCT/US2019/028343, dated Aug. 19, 2019.

International Search Report and Written Opinion for PCT International Patent Application No. PCT/US2020/057099, dated Feb. 23, 2021.

Jagath et al., Important Role of the Tetraloop Region of 4.5S RNA in SRP Binding to Its Receptor FtsY, RNA, vol. 7, No. 2, pp. 293-301, 2001.

Jiang et al., Structural Basis of RNA Recognition and Activation by Innate Immune Receptor RIG-I, Nature, vol. 479, No. 7373, pp. 423-427, 2011.

Jiang, et al., Norwalk Virus Genome Cloning and Characterization, Science, 1990, vol. 250, No. 4987, pp. 1580-1583.

Kabanov et al., A New Class of Antivirals: Antisense Oligonucleotides Combined With a Hydrophobic Substituent Effectively Inhibit Influenza Virus Reproduction and Synthesis of Virus-Specific Proteins in MDCK Cells, FEBS Letters, vol. 259, Issue 2, pp. 327-330, Jan. 1, 1990.

Kastelein, et al., Effect of the Sequences Upstream From the Ribosome-binding Site on the Yield of Protein From the Cloned Gene for Phage MS2 Coat Protein, Gene, 1983, vol. 23, No. 3, pp. 245-254.

Kato et al., Differential Roles of MDA5 and RIG-I Helicases in the Recognition of RNA Viruses, Nature, vol. 441, pp. 101-105, 2006.

Kell et al., RIG-I in RNA Virus Recognition, Virology, vols. 479-480, pp. 110-121, 2015.

Kiliszek et al., Stabilization of RNA Hairpins Using Non-Nucleotide Linkers and Circularization, Nucleic Acids Research, vol. 45, No. 10, e92 Page., Feb. 21, 2017.

Kim et al., Specific Recognition of HIV TAR RNA by the Dsrna Binding Domains (dsRBD1-dsRBD2) of PKR, Journal of Molecular Biology, vol. 358, No. 2, pp. 430-442, 2006.

Klovins, et al., Nucleotide Sequence of a ssRNA Phage From Acinetobacter: Kinship to Coliphages, Journal of General Virology, 2002, vol. 83, pp. 1523-1533.

Kohlway et al., Defining the Functional Determinants for RNA Surveillance by Rig-I, EMBO Reports, vol. 14, pp. 772-779, 2013.

Kowalinski et al., Structural Basis for the Activation of Innate Immune Pattern-Recognition Receptor RIG-I by Viral RNA, Cell, vol. 147, No. 2, pp. 423-435, Oct. 14, 2011.

Kozlovska, et al., Recombinant RNA Phage qβ Capsid Particles Synthesized and Self-assembled in *Escherichia coli,* Gene, 1993, vol. 137, No. 1, pp. 133-137.

Kozlovska, et al., RNA Phage Qβ Coat Protein as a Carrier for Foreign Epitopes, Intervirology, 1996, vol. 39, No. 1-2, pp. 9-15.

Kratz, et al., Native Display of Complete Foreign Protein Domains on the Surface of Hepatitis B Virus Capsids, PNAS USA, Mar. 1999, vol. 96, No. 5, pp. 1915-1920.

Langer et al., Biocompatibility of Polymeric Delivery Systems for Macromolecules, Journal of Biomedical Materials Research, vol. 15, pp. 267-277, 1981.

Lee et al., Structural Features of Influenza a Virus Panhandle RNA Enabling the Activation of RIG-I Independently of 5'-triphosphatev, Nucleic Acids Research, vol. 44, No. 17, pp. 8407-8416, Jun. 10, 2016.

Letsinger et al., Cholesteryl-Conjugated Oligonucleotides: Synthesis, Properties, And Activity as Inhibitors of Replication of Human Immunodeficiency Virus in Cell Culture, Proceedings of the National Academy of Sciences of the United States of America, vol. 86, No. 17, pp. 6553-6556, Sep. 1, 1989.

Liao et al., Inosine-Containing RNA Is a Novel Innate Immune Recognition Element and Reduces RSV Infection, PLoS One, vol. 6, No. 10, Article No. e26463, pp. 1-14, 2011.

Lim, et al., The RNA-Binding Site of Bacteriophage Qβ Coat Protein, Journal of Biological Chemistry, 1996, vol. 271, No. 50, pp. 31839-31845.

Linehan et al., A Minimal RNA Ligand for Potent RIG-I Activation in Living Mice, Science Advances, vol. 4, No. 2, pp. 1-10, 2018.

(56) References Cited

OTHER PUBLICATIONS

Linehan et al., Supplementary Materials for a Minimal RNA Ligand for Potent RIG-I Activation in Living Mice, Science Advances, vol. 4, No. 2, pp. 1-7, 2018.
Liu et al., Influenza A Virus Panhandle Structure Is Directly Involved in RIG-I Activation and Interferon Induction, Journal of Virology, vol. 89, No. 11, pp. 6067-6079, Jun. 2015.
Loo et al., Distinct RIG-I and MDA5 Signaling by RNA Viruses in Innate Immunity, Journal of Virology, vol. 82, pp. 335-345, Jan. 1, 2008.
Loo et al., Immune Signaling by RIG-I-like Receptors, Immunity, vol. 34, pp. 680-692, May 27, 2011.
Lu et al., Chemical Strategies for the Synthesis of Peptide-Oligonucleotide Conjugates, Bioconjugate Chemistry, vol. 21, No. 2, pp. 187-202, 2010.
Lu et al., The Structural Basis of 5' Triphosphate Double-Stranded RNA Recognition by RIG-I C-Terminal Domain, Structure, vol. 18, pp. 1032-1043, Aug. 11, 2010.
Luo et al., Structural Insights into RNA Recognition by RIG-I, Cell, vol. 147, No. 2, pp. 409-422, Oct. 14, 2011.
Luo et al., Visualizing the Determinants of Viral RNA Recognition by Innate Immune Sensor RIG-I, Structure, vol. 20, pp. 1983-1988, Nov. 7, 2012.
Manoharan et al., Chemical Modifications to Improve Uptake and Bioavailability of Antisense Oligonucleotides, Annals of the New York Academy of Sciences, vol. 660, Issue 1, pp. 306-309, Oct. 1992.
Manoharan et al., Cholic Acid-Oligonucleotide Conjugates for Antisense Applications, Bioorganic & Medicinal Chemistry Letters, vol. 4, Issue 8, pp. 1053-1060, Apr. 21, 1994.
Manoharan et al., Introduction of a Lipophilic Thioether Tether in the Minor Groove of Nucleic Acids for Antisense Applications, Bioorganic & Medicinal Chemistry Letters, vol. 3, Issue 12, pp. 2765-2770, Dec. 1, 1993.
Manoharan et al., Lipidic Nucleic Acids, Tetrahedron Letters, vol. 36, Issue 21, pp. 3651-3654, May 22, 1995.
Manoharan et al., Oligonucleotide Conjugates: Alteration of the Pharmacokinetic Properties of Antisense Agents, Nucleosides, Nucleotides & Nucleic Acids, vol. 14, Issue 3-5, pp. 969-973, 1995.
Marques et al., A Structural Basis for Discriminating Between Self and Nonself Double-stranded RNAs in Mammalian Cells, Nature Biotechnology, vol. 24, pp. 559-565, 2006.
Martin et al., A New Access to 2'-O-Alkylated Ribonucleosides and Properties of 2'-O-Alkylated Oligoribonucleotides, Helvetica Chimica Acta, vol. 78, No. 2 (Abstract Only), pp. 486-504, Mar. 1995.
Matsui, et al., The Isolation and Characterization of a Norwalk Virus-Specific cDNA, Journal of Clinical Investigation, 1991, vol. 87, No. 4, pp. 1456-1461.
Menzi et al., Polyamine-oligonucleotide Conjugates: a Promising Direction for Nucleic Acid Tools and Therapeutics, Future Medicinal Chemistry, vol. 7, No. 13, pp. 1733-1749, 2015.
Moerke, Nathan J., Fluorescence Polarization (FP) Assays for Monitoring Peptide-Protein or Nucleic Acid-Protein Binding, Current Protocols in Chemical Biology, vol. 1, No. 1, pp. 1-15, Dec. 2009.
Myers et al., Optimal Alignments In Linear Space, Computer Applications in the Biosciences, vol. 4, No. 1, pp. 11-17, Mar. 1, 1988.
Nakajima, A Novel Therapy for Melanoma and Prostate Cancer Using a Non-Replicating Sendai Virus Particle (HVJ-E), Novel Gene Therapy Approaches, Chapter 8, Feb. 13, 2013, pp. 157-181.
Needleman et al., A General Method Applicable to the Search for Similarities in the Amino Acid Sequence of Two Proteins, Journal of Molecular Biology, vol. 48, No. 3, pp. 443-453, Mar. 1970.
Ni, et al., Crystal Structure of the Coat Protein From the Ga Bacteriophage: Model of the Unassembled Dimer, Protein Science, 1996, vol. 5, pp. 2485-2493.
Oberhauser et al., Effective Incorporation of 2'-O-Methyl-Oligoribonuclectides Into Liposomes and Enhanced Cell Association Through Modification With Thiocholesterol, Nucleic Acids Research, vol. 20, Issue 3, pp. 533-538, Feb. 11, 1992.
Oda et al., NMR Studies for Identification of dI:dG Mismatch Base-pairing Structure in DNA, Nucleic Acids Research, vol. 19, No. 19, pp. 5263-5267, 1991.
Paredes et al., RNA Labeling, Conjugation and Ligation, Methods, vol. 54, No. 2, pp. 251-259, 2011.
Pearson et al., Improved Tools for Biological Sequence Comparison, Proceedings of the National Academy of the Science of the United States of America, vol. 85, No. 8, pp. 2444-2448, Apr. 1, 1988.
Peisley et al., Multi-level Regulation of Cellular Recognition of Viral dsRNA, Cellular and Molecular Life Sciences, vol. 70, No. 11, pp. 1949-1963, 2013.
Pichlmair et al., RIG-I-Mediated Antiviral Responses to Single-Stranded RNA Bearing 5'-Phosphates, Science, vol. 314, No. 5801, pp. 997-1001, 2006.
Poeck et al., Recognition of RNA Virus by RIG-I Results in Activation of CARD9 and Inflammasome Signaling for Interleukin 1β Production, Nature Immunology, vol. 11, pp. 63-69, 2010.
Priano, et al., A Complete Plasmid-based Complementation System for RNA Coliphage Qβ: Three Proteins of Bacteriophages Qβ (Group III) and SP (Group IV) Can Be Interchanged, Journal of Molecular Biology, 1995, vol. 249, No. 2, pp. 283-297.
Ramos et al., RNA Recognition by a Staufen Double-stranded RNA-binding Domain, European Molecular Biology Organization, vol. 19, No. 5, pp. 997-1009, 2000.
Ranoa et al., Cancer Therapies Activate RIG-I-like Receptor Pathway Through Endogenous Non-coding RNAs, Oncotarget, vol. 7, No. 18, pp. 26496-26515, Mar. 28, 2016.
Rawling et al., Establishing the Role of ATP for the Function of the RIG-I Innate Immune Sensor, eLife, vol. 4, pp. 1-21, Sep. 15, 2015.
Rock et al., A Family of Human Receptors Structurally Related to Drosophila Toll, Proceedings of the National Academy of Sciences of the United States of America, vol. 95, pp. 588-593, Jan. 1998.
Roers et al., Recognition of Endogenous Nucleic Acids by the Innate Immune System, Immunity, vol. 44, pp. 739-754, Apr. 19, 2016.
Rumney et al., Structural Optimization of Non-Nucleotide Loop Replacements for Duplex and Triplex DNAs, Journal of the American Chemical Society, vol. 117, No. 21, pp. 5635-5646, 1995.
Rye et al., Phosphate Isosteres in Medicinal Chemistry, Current Medicinal Chemistry, vol. 12, No. 26, pp. 3127-3141, 2005.
Saison-Behmoaras et al., Short Modified Antisense Oligonucleotides Directed Against Ha-ras Point Mutation Induce Selective Cleavage of the mRNA and Inhibit T24 Cells Proliferation, European Molecular Biology Organization, vol. 10, No. 5, pp. 1111-1118, 1991.
Sarvestani et al., Inosine-Mediated Modulation of RNA Sensing by Toll-Like Receptor 7 (TLR7) and TLR8, Journal of Virology, vol. 88, No. 2, pp. 799-810, 2013.
Sasnauskas, et al., Yeast Cells Allow High-Level Expression and Formation of Polyomavirus-Like Particles, Biological Chemistry, 1999, vol. 380, No. 3, pp. 381-386.
Schlee et al., Approaching the RNA Ligand for RIG-I?, Immunological Reviews, vol. 227, pp. 66-74, 2009.
Schlee et al., Discriminating Self From Non-self in Nucleic Acid Sensing, Nature Reviews Immunology, vol. 16, pp. 566-580, Sep. 2016.
Schlee et al., Recognition of 5' Triphosphate by RIG-I Helicase Requires Short Blunt Double-Stranded RNA as Contained in Panhandle of Negative-Strand Virus, Immunity, vol. 31, pp. 25-34, Jul. 17, 2009.
Schlee et al., The Chase for the RIG-I Ligand-Recent Advances, The American Society of Gene & Cell Therapy, vol. 18, No. 7, pp. 1254-1262, 2010.
Schlee, Martin, Master Sensors of Pathogenic RNA-RIG-I Like Receptors, Immunobiology, vol. 218, No. 11, pp. 1322-1335, 2013.
Schmidt et al., 5'-Triphosphate RNA Requires Base-paired Structures to Activate Antiviral Signaling via RIG-I, Proceedings of the National Academy of Sciences of the United States of America, vol. 106, No. 29, pp. 12067-12072, Jul. 21, 2009.

(56) References Cited

OTHER PUBLICATIONS

Shah et al., Combined Roles of ATP and Small Hairpin RNA in the Activation of RIG-I Revealed by Solution-based Analysis, Nucleic Acids Research, vol. 46, No. 6, pp. 3169-3186, Jan. 13, 2018.
Sidman et al., Controlled Release of Macromolecules and Pharmaceuticals From Synthetic Polypeptides Based on Glutamic Acid, Biopolymers, vol. 22, pp. 547-556, 1983.
Simon et al., RNA Conformational Changes in the Life Cycles of RNA Viruses, Viroids, and Virus-associated RNAs, Biochimica et Biophysica Acta (BBA)—Gene Regulatory Mechanisms, vol. 1789, No. 9-10, pp. 571-583, 2009.
Singh et al., Recent Developments in Oligonucleotide Conjugation, Chemical Society Reviews, vol. 39, No. 6, pp. 2054-2070, 2010.
Smiley, et al., Enhanced Readthrough of Opal (UGA) Stop Codons and Production of Mycoplasma Pneumoniae P1 Epitopes in *Escherichia coli,* Gene, 1993, vol. 134, No. 1, pp. 33-40.
Smith et al., Comparison of Biosequences, Advances in Applied Mathematics, vol. 2, No. 4, pp. 482-489, Dec. 1981.
Stoll, et al., Revised Amino Acid Sequence of Qbeta Coat Protein Between Positions 1 and 60, Journal of Biological Chemistry, Feb. 10, 1977, vol. 252, No. 3, pp. 990-993.
Studier, et al., Use of T7 Rna Polymerase to Direct Expression of Cloned Genes, Methods in Enzymology, 1990, vol. 185, pp. 60-89.
Svinarchuk et al., Inhibition of HIV Proliferation in MT-4 Cells by Antisense Oligonucleotide Conjugated to Lipophilic Groups, Biochimie, vol. 75, Issues 1-2, pp. 49-54, Jan. 1, 1993.
Svoboda et al., Hairpin RNA: A Secondary Structure of Primary Importance, Cellular and Molecular Life Sciences, vol. 63, No. 7-8, pp. 901-908, Apr. 2006.
Taskova et al., Synthetic Nucleic Acid Analogues in Gene Therapy: An Update for Peptide-Oligonucleotide Conjugates, ChemBioChem, vol. 18, No. 17, pp. 1671-1682, 2017.
Twomey, et al., Structure and Immunogenicity of Experimental Foot-and-mouth Disease and Poliomyelitis Vaccines, Vaccine, 1995, vol. 13, No. 16, pp. 1603-1610.
Ulrich, et al., Core Particles of Hepatitis B Virus as Carrier for Foreign Epitopes, Advances in Virus Research, 1998, vol. 50, pp. 141-182.
Verma et al., Modified Oligonucleotides: Synthesis and Strategy for Users, Annual Review of Biochemistry, vol. 67, pp. 99-134, 1998.
Wang et al., Structural and Functional Insights Into 5'-ppp RNA Pattern Recognition by the Innate Immune Receptor RIG-I, Nature Structural & Molecular Biology, vol. 17, pp. 781-787, 2010.
Warnes, et al., Expression of the Measles Virus Nucleoprotein Gene in *Escherichia coli* and Assembly of Nucleocapsid-like Structures, Gene, 1995, vol. 160, No. 2, pp. 173-178.
Winkler et al., Oligonucleotide Conjugates for Therapeutic Applications, Therapeutic Delivery, vol. 4, No. 7, pp. 791-809, Jul. 24, 2013.
Witherell, et al., Specific RNA Binding by Q. beta. Coat Protein, Biochemistry, 1989, vol. 28, pp. 71-76.
Yoneyama et al., Viral Rna Detection by RIG-I-like Receptors, Current Opinion in Immunology, vol. 32, pp. 48-53, 2015.
Yuan, et al., Subtype-Independent Immature Secretion and Subtype-Dependent Replication Deficiency of a Highly Frequent, Naturally Occurring Mutation of Human Hepatitis B Virus Core Antigen, Journal of Virology, Dec. 1, 1999, vol. 73, No. 12, pp. 10122-10128.
Zhan et al., “From Monoclonal Antibodies to Small Molecules: the Development of Inhibitors Targeting the PD-1/PD-L1 Pathway”, Drug Discovery Today, 2016, vol. 21, No. 6, pp. 1027-1036.
Zhou, et al., Cys Residues of the Hepatitis B Virus Capsid Protein Are Not Essential for the Assembly of Viral Core Particles but Can Influence Their Stability, Journal of Virology, Sep. 1992, vol. 66, No. 9, pp. 5393-5398.
Dickey et al., RNA binding activates RIG-I by releasing an autopressed signaling domain, Science Advances, 2019, 5(10): eaax3641.

* cited by examiner

SYNTHETIC RIG-I-LIKE RECEPTOR AGONISTS

CROSS REFERENCE TO RELATED APPLICATIONS

This application is a U.S. National Phase Application, filed under 35 U.S.C. § 371, of International Application No. PCT/US2020/057099, filed Oct. 23, 2020, which claims the benefit of U.S. Provisional Patent Application Ser. No. 62/925,120, filed Oct. 23, 2019. The entire contents of the above-referenced applications are incorporated herein by reference.

REFERENCE TO SEQUENCE LISTING

The instant application contains a Sequence Listing, which has been submitted electronically in ASCII format via EFS-Web and is hereby incorporated by reference in its entirety. Said ASCII copy, created on Apr. 12, 2022, is named CHCK_002_N01US ST25.txt and is 213,807 bytes in size.

BACKGROUND

Exogenous nucleic acids, particularly viral nucleic acids, introduced into cells induce an innate immune response, resulting in, among other events, interferon (IFN) production and cell death. Upon sensing viral RNA, RIG-I-like receptors induce type I interferon (IFN) secretion leading to upregulation of antiviral IFN-induced proteins in the infected and neighboring cells, which inhibits virus replication. Further downstream events attract immune cells and trigger the adaptive immune response. In addition, RIG-I ligands have been reported to induce the apoptosis of many different types of tumor cells, but not of normal cells.

Virus-like particles (VLPs) are supermolecular structures built in a symmetric manner from many protein molecules of one or more types. They lack the viral genome and, therefore, are noninfectious. VLPs can often be produced in large quantities by heterologous expression and can be easily be purified.

VLPs are used in the fields of vaccinology, immunology and medicine because of both their structural properties and their non-infectious nature. VLPs have been shown to be efficiently presented on MHC class I molecules as they, presumably after uptake by micropinocytosis or other cell uptake pathways, are efficiently processed and cross-primed onto MHC class I.

There remains a need for additional and improved compositions and methods to modulate the activity of immunomodulatory proteins. Such agents can be used for cancer immunotherapy and treatment of other conditions, such as chronic infection. There is a need to develop improved RIG-I-like receptor ligands, including improved delivery methods, for diverse therapeutic immunomodulatory applications.

SUMMARY OF THE DISCLOSURE

The present disclosure is based, at least in part, on the discovery of synthetic RNA molecules that function as RIG-I-like receptor (RLR) agonists. The disclosure also provides compositions and methods for improving biological activity by packaging immunostimulatory nucleic acids, in particular RLR agonists, into VLPs (RIG-VLPs). The compositions described herein can be used to induce strong and sustained immune responses particularly useful for the treatment of tumors.

Accordingly, in some aspects, the disclosure provides a composition comprising:

(a) a virus-like particle; and (b) at least one synthetic RIG-I like receptor (RLR) agonist that specifically binds to a RIG-I-like receptor (RLR), wherein the RLR agonist comprises a ribonucleic acid (RNA) of 10-100 nucleotides in length, wherein the 5' most nucleotide of the RNA comprises a 5'diphosphate or triphosphate moiety, or derivative or analog thereof, wherein the at least one RLR agonist is packaged in the virus-like particle.

In some aspects, the disclosure provides a composition comprising:

(a) a virus-like particle of an RNA-phage Qβ; and (b) at least one synthetic RIG-I like receptor (RLR) agonist that specifically binds to a RIG-I-like receptor (RLR), wherein the RLR agonist comprises a ribonucleic acid (RNA) of 10-100 nucleotides in length, wherein the 5' most nucleotide of the RNA comprises a 5'diphosphate or triphosphate moiety, or derivative or analog thereof, wherein the at least one RLR agonist is packaged in the virus-like particle.

In any of the foregoing or related aspects, the RNA is singled stranded. In other aspects, some or all of the RNA is double stranded.

In any of the foregoing or related aspects, the RNA of the RLR agonist is 10-15, 15-20, 20-25, 25-30 or 30-35 nucleotides in length.

In any of the foregoing or related aspects, the RLR agonist comprises a first polynucleotide and a second polynucleotide, wherein the first polynucleotide is sufficiently complementary to the second polynucleotide to form a duplex. In some aspects, the duplex comprises a hairpin. In some aspects, the duplex comprises 10-15, 15-20, 20-25, 25-30 or 30-35 base pairs. In some aspects, the duplex comprises less than 19 base pairs. In some aspects, the first polynucleotide is connected to the second polynucleotide by a linker.

In any of the foregoing or related aspects, the RLR agonist comprises a sequence motif that provides at least one biological activity mediated by the RLR relative to an agonist that does not comprise the sequence motif.

In some aspects, the disclosure provides a composition comprising:

(a) a virus-like particle; and (b) at least one synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, and wherein the agonist comprises a sequence motif that provides at least one improved biological activity mediated by the RLR relative to an agonist that does not comprise the sequence motif. In some aspects, the first polynucleotide comprises the sequence motif, wherein the at least one RLR agonist is packaged in the virus-like particle.

In some aspects, the disclosure provides a composition comprising:

(a) a virus-like particle of an RNA-phage Qβ; and (b) at least one synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, and wherein the agonist comprises a sequence motif that provides at least one improved biological activity mediated by the RLR relative to an agonist that does not comprise the sequence motif. In some aspects, the first polynucleotide comprises the sequence motif, wherein the at least one RLR agonist is packaged in the virus-like particle.

In any of the foregoing or related aspects, the RLR agonist comprises a sequence motif selected from the group consisting of:

(i) a GT-repeat motif;
(ii) a GA-repeat motif;
(iii) a AUCG-repeat motif;
(iv) an AU-repeat motif;
(v) a dipyrimidine motif;
(vi) a dipurine motif;
(vii) a pyrimidine triplet motif;
(viii) a purine triplet motif;
(ix) a palindromic sequence motif; and
(x) a combination of any of (i)-(ix).

In some aspects, the disclosure provides a composition comprising:

(a) a virus-like particle of an RNA-phage Qβ; and (b) at least one synthetic RIG-I like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, and wherein the agonist comprises a sequence motif selected from:

(i) a GT-repeat motif;
(ii) a GA-repeat motif;
(iii) a AUCG-repeat motif;
(iv) an AU-repeat motif;
(v) a dipyrimidine motif;
(vi) a dipurine motif;
(vii) a pyrimidine triplet motif;
(viii) a purine triplet motif;
(ix) a palindromic sequence motif; and
(x) a combination of any of (i)-(ix), wherein the at least one RLR agonist is packaged in the virus-like particle.

In some aspects, the RLR agonists of the disclosure comprise a combination of sequence motifs. In some aspects the combination of sequence motifs is a GT-repeat motif and a purine triplet motif. In some aspects, the combination of sequence motifs is an AUCG-repeat motif and a dipyrimidine motif. In some aspects, the combination of sequence motifs is an AUCG-repeat motif and a dipurine motif.

In any of the foregoing or related aspects, the RLR agonists of the disclosure comprise a sequence motif that provides at least one improved biological activity mediated by the RLR relative to an agonist that does not comprise the sequence motif, wherein the at least one improved biological activity is selected from:

(i) an increase in RLR-mediated cytokine production;
(ii) an increase in RLR-mediated expression of interferon-stimulated genes;
(iii) an increase in RLR-mediated intracellular signaling;
(iv) an increase in binding affinity to RLRs; and
(v) a combination of any of (i)-(iv).

In any of the foregoing or related aspects, the RLR agonists of the disclosure comprise a sequence motif that increases RLR-mediated type I interferon (e.g., IFN-α, IFN-β) production relative to an agonist that does not comprise the sequence motif. In some aspects, the RLR agonists of the disclosure comprise a sequence motif that increases RLR-mediated IL-1β production relative to an agonist that does not comprise the sequence motif. In some aspects, the RLR agonists of the disclosure comprise a sequence motif that increases RLR-mediated IP-10 production relative to an agonist that does not comprise the sequence motif. In some aspects, the RLR agonists of the disclosure comprise a sequence motif that increases RLR-mediated IL-6, IL-12p70, MCP-1 and/or MIP-1β production relative to an agonist that does not comprise the sequence motif.

In any of the foregoing or related aspects, the RLR agonists of the disclosure comprise a sequence motif, wherein the sequence motif is a GT-repeat motif (e.g., GTGTGT) comprising a sequence of <19, about 15-18, about 15, about 10-15, about 10, about 5-10, about 5, about 4, 18, 17, 16, 15, 14, 13, 12, 11, 10, 9, 8, 7, 6, 5, or 4 guanine and thymine nucleotides, or derivatives or analogs thereof. In some aspects, the sequence motif is a GT-repeat motif comprising a sequence of <19 guanine and thymine nucleotides, or derivatives or analogs thereof. In some aspects, the sequence motif is a GT-repeat motif comprising a sequence of about 15-18 guanine and thymine nucleotides, or derivatives or analogs thereof. In some aspects, the sequence motif is a GT-repeat motif comprising a sequence of about 15 guanine and thymine nucleotides, or derivatives or analogs thereof. In some aspects, the sequence motif is a GT-repeat motif comprising a sequence of about 10-15 guanine and thymine nucleotides, or derivatives or analogs thereof. In some aspects, the sequence motif is a GT-repeat motif comprising a sequence of about 10 guanine and thymine nucleotides, or derivatives or analogs thereof. In some aspects, the sequence motif is a GT-repeat motif comprising a sequence of about 5-10 guanine and thymine nucleotides, or derivatives or analogs thereof. In some aspects, the sequence motif is a GT-repeat motif comprising a sequence of about 5 guanine and thymine nucleotides, or derivatives or analogs thereof. In some aspects, the sequence motif is a GT-repeat motif comprising a sequence of about 4 guanine and thymine nucleotides, or derivatives or analogs thereof. In some aspects, the GT-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise a sequence motif, wherein the sequence motif is a GT-repeat motif comprising a sequence of 18, 17, 16, 15, 14, 13, 12, 11, 10, 9, 8, 7, 6, 5, or 4 guanine and thymine nucleotides, or derivatives or analogs thereof. In some aspects, the sequence motif is a GT-repeat motif comprising a sequence of 18 guanine and thymine nucleotides, or derivatives or analogs thereof. In some aspects, the sequence motif is a GT-repeat motif comprising a sequence of 16 guanine and thymine nucleotides, or derivatives or analogs thereof. In some aspects, the sequence motif is a GT-repeat motif comprising a sequence of 14 guanine and thymine nucleotides, or derivatives or analogs thereof. In some aspects, the sequence motif is a GT-repeat motif comprising a sequence of 12 guanine and thymine nucleotides, or derivatives or analogs thereof. In some aspects, the sequence motif is a GT-repeat motif comprising a sequence of 10 guanine and thymine nucleotides, or derivatives or analogs thereof. In some aspects, the sequence motif is a GT-repeat motif comprising a sequence of 8 guanine and thymine nucleotides, or derivatives or analogs thereof. In some aspects, the sequence motif is a GT-repeat motif comprising a sequence of 6 guanine and thymine nucleotides, or derivatives or analogs thereof. In some aspects, the sequence motif is a GT-repeat motif comprising a sequence of 4 guanine and thymine nucleotides, or derivatives or analogs thereof. In some aspects, the RLR agonists of the disclosure comprise a sequence motif, wherein the sequence motif is a GT-repeat motif, wherein the GT-repeat motif is $[GT]_n$, wherein n=2 to 9, 3-7, or 4-8. In some aspects, the GT-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides a composition comprising:

(a) a virus-like particle; and (b) at least one RLR agonist that specifically binds to an RLR, wherein the agonist comprises a blunt-ended, hairpin RNA comprising a first polynucleotide connected to (operably linked to) a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GT-repeat motif comprising a sequence of about 14 guanine and thymine nucleotides, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to an RLR, wherein the agonist comprises a blunt-ended, hairpin RNA comprising a first polynucleotide connected to (operably linked to) a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GT-repeat motif comprising a sequence of about 14 guanine and thymine nucleotides, wherein the at least one RLR agonist is packaged in the virus-like particle.

In some aspects, the sequence motif is a GT-repeat motif, wherein the GT-repeat motif is $[GT]_7$. In some aspects, the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides a composition comprising:

(a) a virus-like particle; and (b) at least one RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GT-repeat motif comprising a sequence of 6 guanine and thymine nucleotides, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GT-repeat motif comprising a sequence of 6 guanine and thymine nucleotides, wherein the at least one RLR agonist is packaged in the virus-like particle.

In some aspects, the sequence motif is a GT-repeat motif, wherein the GT-repeat motif is $[GT]_3$. In some aspects, the sequence motif is a GT-repeat motif, wherein the GT-repeat motif is $[GT]_3$, and wherein the GT-repeat is followed by a purine triplet and UCG, respectively. In some aspects, the purine triplet is GGA. In some aspects, the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise a sequence motif, wherein the sequence motif is a GA-repeat motif (e.g., GAGAGA) comprising a sequence of <19, about 15-18, about 15, about 10-15, about 10, about 5-10, about 5, about 4, 18, 17, 16, 15, 14, 13, 12, 11, 10, 9, 8, 7, 6, 5, or 4 guanine and adenine nucleotides, or derivatives or analogs thereof. In some aspects, the sequence motif is a GA-repeat motif comprising a sequence of <19 guanine and adenine nucleotides, or derivatives or analogs thereof. In some aspects, the sequence motif is a GA-repeat motif comprising a sequence of about 15-18 guanine and adenine nucleotides, or derivatives or analogs thereof. In some aspects, the sequence motif is a GA-repeat motif comprising a sequence of about 15 guanine and adenine nucleotides, or derivatives or analogs thereof. In some aspects, the sequence motif is a GA-repeat motif comprising a sequence of about 10-15 guanine and adenine nucleotides, or derivatives or analogs thereof. In some aspects, the sequence motif is a GA-repeat motif comprising a sequence of about 10 guanine and adenine nucleotides, or derivatives or analogs thereof. In some aspects, the sequence motif is a GA-repeat motif comprising a sequence of about 5-10 guanine and adenine nucleotides, or derivatives or analogs thereof. In some aspects, the sequence motif is a GA-repeat motif comprising a sequence of about 5 guanine and adenine nucleotides, or derivatives or analogs thereof. In some aspects, the sequence motif is a GA-repeat motif comprising a sequence of about 4 guanine and adenine nucleotides, or derivatives or analogs thereof. In some aspects, the GA-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise a sequence motif is a GA-repeat motif comprising a sequence of 18, 17, 16, 15, 14, 13, 12, 11, 10, 9, 8, 7, 6, 5, or 4 guanine and adenine nucleotides, or derivatives or analogs thereof. In some aspects, the sequence motif is a GA-repeat motif comprising a sequence of 18 guanine and adenine nucleotides, or derivatives or analogs thereof. In some aspects, the sequence motif is a GA-repeat motif comprising a sequence of 16 guanine and adenine nucleotides, or derivatives or analogs thereof. In some aspects, the sequence motif is a GA-repeat motif comprising a sequence of 14 guanine and adenine nucleotides, or derivatives or analogs thereof. In some aspects, the sequence motif is a GA-repeat motif comprising a sequence of 12 guanine and adenine nucleotides, or derivatives or analogs thereof. In some aspects, the sequence motif is a GA-repeat motif comprising a sequence of 8 guanine and adenine nucleotides, or derivatives or analogs thereof. In some aspects, the sequence motif is a GA-repeat motif comprising a sequence of 6 guanine and adenine nucleotides, or derivatives or analogs thereof. In some aspects, the sequence motif is a GA-repeat motif comprising a sequence of 4 guanine and adenine nucleotides, or derivatives or analogs thereof.

In any of the foregoing or related aspects, the RLR agonists of the disclosure comprise a sequence motif, wherein the sequence motif is a GA-repeat motif, wherein the GA-repeat motif is $[GA]_n$, where n=2 to 9, 3 to 7 or 4 to 8. In some aspects, the GA-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides composition comprising:

(a) a virus-like particle; and (b) at least one RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GA-repeat motif comprising a sequence of about 14 guanine and adenine nucleotides, wherein the at least one RLR agonist is packaged in the virus-like particle.

In some aspects, the disclosure provides composition comprising:

(a) a virus-like particle of an RNA-phage Qβ; and (b) at least one RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GA-repeat motif comprising a sequence of about 14 guanine and adenine nucleotides, wherein the at least one RLR agonist is packaged in the virus-like particle.

In some aspects, the sequence motif is a GA-repeat motif, wherein the GA-repeat motif is $[GA]_7$. In some aspects, the GA-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise a sequence motif, wherein the sequence motif is a AUCG-repeat motif (e.g., AUCGAUCG) comprising a sequence of <19, about 16, about 12-16, about 12, about 8-12, about 6, 16, 12, 8 adenine, uracil, cytosine, and guanine nucleotides, or derivatives or analogs thereof. In some aspects, the sequence motif is a AUCG-repeat motif comprising a sequence of <19 adenine, uracil, cytosine, and guanine nucleotides, or derivatives or analogs thereof. In some aspects, the sequence motif is a AUCG-repeat motif comprising a sequence of about 16 adenine, uracil, cytosine, and guanine nucleotides, or derivatives or analogs thereof. In some aspects, the sequence motif is a AUCG-repeat motif comprising a sequence of about 12-16 adenine, uracil, cytosine, and guanine nucleotides, or derivatives or analogs thereof. In some aspects, the sequence motif is a AUCG-repeat motif comprising a sequence of about 12 adenine, uracil, cytosine, and guanine nucleotides, or derivatives or analogs thereof. In some aspects, the sequence motif is a AUCG-repeat motif comprising a sequence of about 8-12 adenine, uracil, cytosine, and guanine nucleotides, or derivatives or analogs thereof. In some aspects, the sequence motif is a AUCG-repeat motif comprising a sequence of about 6 adenine, uracil, cytosine, and guanine nucleotides, or derivatives or analogs thereof. In some aspects, the sequence motif is a AUCG-repeat motif comprising a sequence of 16 adenine, uracil, cytosine, and guanine nucleotides, or derivatives or analogs thereof. In some aspects, the sequence motif is a AUCG-repeat motif comprising a sequence of 12 adenine, uracil, cytosine, and guanine nucleotides, or derivatives or analogs thereof. In some aspects, the sequence motif is a AUCG-repeat motif comprising a sequence of 8 adenine, uracil, cytosine, and guanine nucleotides, or derivatives or analogs thereof. In some aspects, the AUCG-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise a sequence motif, wherein the sequence motif is an AUCG-repeat motif, wherein the AUCG-repeat motif is $[AUCG]_n$, where n=2 to 4 or 2, 3 or 4. In some aspects, the AUCG-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides a composition comprising:

(a) a virus-like particle; and (b) at least one RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a AUCG-repeat motif comprising a sequence of about 12 guanine and adenine nucleotides. In some aspects, the AUCG-repeat motif is $[AUCG]_3$, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a AUCG-repeat motif comprising a sequence of about 12 guanine and adenine nucleotides. In some aspects, the AUCG-repeat motif is $[AUCG]_3$, wherein the at least one RLR agonist is packaged in the virus-like particle.

In some aspects, the AUCG-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise a AUCG-repeat motif, wherein the motif is preceded by a CG or a dipyrimidine motif. In some aspects, the AUCG-repeat motif is preceded by a CG. In some aspects, the AUCG-repeat motif is $[AUCG]_3$ and is preceded by a CG. In some aspects, the AUCG-repeat motif is $[AUCG]_3$ and is preceded by the dipyrimidine motif CC.

In any of the foregoing or related aspects, the RLR agonists of the disclosure comprise an AUCG-repeat motif, wherein the motif is preceded by a dipurine motif. In some aspects, the dipurine motif is GA. In some aspects, the AUCG-repeat motif is $[AUCG]_3$ and is preceded by the dipurine motif GA. In some aspects, the AUCG-repeat motif is preceded by the dipurine motif II.

In any of the foregoing or related aspects, the RLR agonists of the disclosure comprise an AUCG-repeat motif, wherein one or more uridine nucleosides (U) are substituted with a modified nucleoside. In some aspects, wherein the modified nucleoside is ribothymidine (T). In some aspects, the AUGC-repeat motif is $[AUCG]_3$, wherein the one or more uridine nucleosides (U) comprising the AUCG-repeat motif are substituted with a modified nucleoside, wherein the modified nucleoside is ribothymidine (T). In some aspects, the AUGC-repeat motif is $[AUCG]_3$, wherein the one or more uridine nucleosides (U) comprising the AUCG-repeat motif are substituted with a modified nucleoside, wherein the modified nucleoside is ribothymidine (T), and wherein the AUGC-repeat motif is preceded by GG.

In any of the foregoing or related aspects, the RLR agonists of the disclosure comprise an AUCG-repeat motif, wherein one or more guanosine nucleosides (G) are substituted with a modified nucleoside. In some aspects, the modified nucleoside is inosine (I). In some aspects, the AUGC-repeat motif is $[AUCG]_3$, wherein the one or more guanosine nucleosides (G) comprising the AUCG-repeat motif are substituted with a modified nucleoside, wherein the modified nucleoside is ribothymidine (T), and wherein the AUGC-repeat motif is preceded by GG.

In any of the foregoing or related aspects, the RLR agonists of the disclosure comprise a AUCG-repeat motif, wherein the motif is preceded by a IG. In some aspects, the AUCG-repeat motif is $[AUCG]_3$ and is preceded by a IG.

In any of the foregoing or related aspects, the RLR agonists of the disclosure comprise an AUCG-repeat, wherein one or more guanosine nucleosides (G) are substituted with an inosine (I), wherein the AUCG-repeat is preceded by an inosine (I). In some aspects, the guanosine nucleosides (G) comprising the AUCG-repeat are substituted with an inosine (I), wherein the AUCG-repeat is preceded by an inosine (I), wherein the 5' most nucleotide of the first polynucleotide comprises inosine (I).

In any of the foregoing or related aspects, the RLR agonists of the disclosure comprise an AUCG-repeat motif, wherein the AUCG-repeat motif is $[AUCG]_2$. In some aspects, the sequence motif is an AUCG-repeat motif, wherein the AUCG-repeat motif is $[AUCG]_2$, and wherein the AUCG-repeat motif is preceded by a dipurine motif. In some aspects, the sequence motif is an AUCG-repeat motif, wherein the AUCG-repeat motif is $[AUCG]_2$, wherein the AUCG-repeat motif is preceded by a dipurine motif, and wherein the dipurine motif is GG.

In any of the foregoing or related aspects, the RLR agonists of the disclosure comprise an AUCG-repeat motif, wherein the AUCG-repeat motif is $[AUCG]_2$, and wherein the AUCG-repeat motif is preceded by a purine triplet motif. In some aspects, the purine triplet motif is GGG. In some aspects, the sequence motif is an AUCG-repeat motif, wherein the AUCG-repeat motif is $[AUCG]_2$, wherein the AUCG-repeat motif is preceded by a purine triplet motif, and wherein the purine triplet motif is GGG. In some aspects, the sequence motif is an AUCG-repeat motif, wherein the AUCG-repeat motif is $[AUCG]_2$, and wherein the AUCG-repeat motif is preceded by CCCCCG. In some aspects, the sequence motif is an AUCG-repeat motif, wherein the AUCG-repeat motif is $[AUCG]_2$, and wherein the AUCG-repeat motif is preceded by TCGUCG.

In some aspects, the disclosure provides a composition comprising:

(a) a virus-like particle; and (b) at least one synthetic RLR agonist that specifically binds to RLRs, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof; wherein the agonist comprises a [AUCG]n repeat motif, where n=2-4; wherein the 5' most AUCG repeat motif is preceded by GG, CG, or IG, and wherein the at least one RLR agonist is packaged in the virus-like particle. In some aspects, n=3. In some aspects, each G in the AUCG motif is substituted by inosine.

In some aspects, the disclosure provides a composition comprising:

(a) a virus-like particle of an RNA-phage Qβ; and (b) at least one synthetic RLR agonist that specifically binds to RLRs, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof; wherein the agonist comprises a [AUCG]n repeat motif, where n=2-4; wherein the 5' most AUCG repeat motif is preceded by GG, CG, or IG, and wherein the at least one RLR agonist is packaged in the virus-like particle. In some aspects, n=3. In some aspects, each G in the AUCG motif is substituted by inosine.

In any of the foregoing or related aspects, the RLR agonists of the disclosure comprise a sequence motif, wherein the sequence motif is a palindromic sequence comprising a sequence of <19, about 15-18, about 15, about 10-15, about 10, about 18, 17, 16, 15, 14, 13, 12, 11, 10, 9, 8, 7, 6, 5, or 4 nucleotides, or derivatives or analogs thereof, linked in any order that results in a palindrome. In some aspects, the sequence motif is a palindromic sequence comprising a sequence of <19 nucleotides, or derivatives or analogs thereof, linked in any order that results in a palindrome. In some aspects, the sequence motif is a palindromic sequence comprising a sequence of about 15-18 nucleotides, or derivatives or analogs thereof, linked in any order that results in a palindrome. In some aspects, the sequence motif is a palindromic sequence comprising a sequence of about 15 nucleotides, or derivatives or analogs thereof, linked in any order that results in a palindrome. In some aspects, the sequence motif is a palindromic sequence comprising a sequence of about 10-15 nucleotides, or derivatives or analogs thereof, linked in any order that results in a palindrome. In some aspects, the sequence motif is a palindromic sequence comprising a sequence of about 10 nucleotides, or derivatives or analogs thereof, linked in any order that results in a palindrome. In some aspects, the sequence motif is a palindromic sequence comprising a sequence of 18 nucleotides, or derivatives or analogs thereof, linked in any order that results in a palindrome. In some aspects, the sequence motif is a palindromic sequence comprising a sequence 17 nucleotides, or derivatives or analogs thereof, linked in any order that results in a palindrome. In some aspects, the sequence motif is a palindromic sequence comprising a sequence of 16 nucleotides, or derivatives or analogs thereof, linked in any order that results in a palindrome. In some aspects, the sequence motif is a palindromic sequence comprising a sequence of 15 nucleotides, or derivatives or analogs thereof, linked in any order that results in a palindrome. In some aspects, the sequence motif is a palindromic sequence comprising a sequence of 14 nucleotides, or derivatives or analogs thereof, linked in any order that results in a palindrome. In some aspects, the sequence motif is a palindromic sequence comprising a sequence of 13 nucleotides, or derivatives or analogs thereof, linked in any order that results in a palindrome. In some aspects, the sequence motif is a palindromic sequence comprising a sequence of 12 nucleotides, or derivatives or analogs thereof, linked in any order that results in a palindrome. In some aspects, the sequence motif is a palindromic sequence comprising a sequence of 11 nucleotides, or derivatives or analogs thereof, linked in any order that results in a palindrome. In some aspects, the sequence motif is a palindromic sequence comprising a sequence of 10 nucleotides, or derivatives or analogs thereof, linked in any order that results in a palindrome. In some aspects, the sequence motif is a palindromic sequence comprising a sequence of 9 nucleotides, or derivatives or analogs thereof, linked in any order that results in a palindrome. In some aspects, the sequence motif is a palindromic sequence comprising a sequence of 8 nucleotides, or derivatives or analogs thereof, linked in any order that results in a palindrome. In some aspects, the sequence motif is a palindromic sequence comprising a sequence of 7 nucleotides, or derivatives or analogs thereof, linked in any order that results in a palindrome. In some aspects, the sequence motif is a palindromic sequence comprising a sequence of 6 nucleotides, or derivatives or analogs thereof, linked in any order that results in a palindrome. In some aspects, the sequence motif is a palindromic sequence comprising a sequence of 5 nucleotides, or derivatives or analogs thereof, linked in any order that results in a palindrome. In some aspects, the sequence motif is a palindromic sequence comprising a sequence of 4 nucleotides, or derivatives or analogs thereof, linked in any order that results in a palindrome.

In any of the foregoing or related aspects, the RLR agonists of the disclosure comprise a linker, wherein the linker is flanked by AU. In some aspects, the linker is flanked by an AU-repeat motif, wherein the AU-repeat motif is $[AU]_n$, where n=2 to 3. In some aspects, the AU-repeat motif is $[AU]_2$.

In some aspects, the disclosure provides a composition comprising:

(a) a virus-like particle; and (b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$, (ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is a linker that operably links the first polynucleotide and the second polynucleotide, wherein at least one of N1, N2, N3, and N4 is inosine and/or at least one of X1 and/or X2 comprises at least one inosine nucleoside, and wherein the inosine nucleoside base pairs with cytidine in the hairpin RNA, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (iv) ($N_1$—$N_2$—$X_1$) comprises a first polynucleotide comprising linked nucleotides $N_1$, $N_2$ and $X_1$, (v) ($X_2$—$N_3$—$N_4$) comprises a second polynucleotide comprising linked nucleotides $X_2$, $N_3$ and $N_4$;

(vi) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to X2;

(ix) $X_1$ and $X_2$ are each 12 nucleotides to 16 nucleotides in length and are the same length, and;

(x) L is a linker that operably links the first polynucleotide and the second polynucleotide, wherein at least one of N1, N2, N3, and N4 is inosine and/or at least one of X1 and/or X2 comprises at least one inosine nucleoside, and wherein the inosine nucleoside base pairs with cytidine in the hairpin RNA, wherein the at least one RLR agonist is packaged in the virus-like particle.

In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides a composition comprising:

(a) a virus-like particle; and (b) at least one RLR agonist that specifically binds to RLRs, wherein the agonist comprises a blunt-ended, hairpin RNA comprising a non-nucleotide linker, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein inosine, if present, base pairs with cytidine, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to RLRs, wherein the agonist comprises a blunt-ended, hairpin RNA comprising a non-nucleotide linker, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with N4;

(v) $N_2$ base pairs with N3;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein inosine, if present, base pairs with cytidine, wherein the at least one RLR agonist is packaged in the virus-like particle.

In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, N1 comprises inosine and N4 comprises cytidine. In some aspects, N1 comprises inosine and N4 comprises cytidine and X1 and X2 are each 12 nucleotides in length. In some aspects, N1 comprises cytidine and N4 comprises inosine. In some aspects, N2 comprise inosine and N3 comprises cytidine. In some aspects, N2 comprises cytidine and N3 comprises inosine. In some aspects, N1 comprises guanosine. In some aspects, N2 comprises guanosine. In some aspects, N1 comprises cytidine. In some aspects, N2 comprises cytidine. In some aspects, N1 and N2 comprise guanosine and N3 and N4 comprise cytidine. In some aspects, N1 and N2 comprise cytidine and N3 and N4 comprise guanosine. In some aspects, N1 and N2 comprise inosine and N3 and N4 comprise cytidine. In some aspects, N1 and N2 comprise cytidine and N3 and N4 comprise inosine.

In any of the foregoing or related aspects, the RLR agonists of the disclosure comprise the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein inosine, if present, base pairs with cytidine, and wherein N1 comprises inosine and N4 comprises cytidine, and X1 and/or X2 each comprise at least one inosine. In some aspects, N2 comprises inosine and N3 comprises cytidine, and X1 and/or X2 each comprise at least one inosine. In some aspects, N1 and N2 comprise guanosine N3 and N4 comprise cytidine, and X1 and/or X2 each comprise at least one inosine. In some aspects, N1 and N2 comprise guanosine and N3 and N4 comprise cytidine, and X1 and X2 each comprise at least one inosine. In some aspects, N1 and N2 comprise guanosine and N3 and N4 comprise cytidine, X1 and X2 each comprise at least one inosine, and X1 and X2 are each 12 nucleotides in length. In some aspects, N1 and N2 comprise cytidine and N3 and N4 comprise guanosine, and X1 and X2 each comprise at least one inosine. In some aspects, N1 and N2 comprise guanosine and N3 and N4 comprise cytidine, and X1 and X2 each comprise inosine and no guanosine nucleosides. In some aspects, N1 and N2 comprise guanosine and N3 and N4 comprise cytidine, X1 and X2 each comprise at least one inosine, and X1 and X2 are each 12 nucleotides in length. In some aspects, N1 and N2 comprise cytidine and N3 and N4 comprise guanosine, and X1 and X2 each comprise inosine and no guanosine nucleosides. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to X2;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein inosine, if present, base pairs with cytidine, and wherein N1 and N2 comprise inosine and N3 and N4 comprise cytidine, and X1 and/or X2 each comprise at least one inosine. In some aspects, N1 and N2 comprise inosine and N3 and N4 comprise cytidine, X1 and X2 each comprise at least one inosine, and X1 and X2 are each 12 nucleotides in length. In some aspects, N1 and N2 comprise inosine and N3 and N4 comprise cytidine, and X1 and X2 each comprise at least one inosine. In some aspects, N1 and N2 comprise inosine and N3 and N4 comprise cytidine, X1 and X2 each comprise at least one inosine, and X1 and X2 are each 12 nucleotides in length. In some aspects, N1 and N2 comprise cytidine and N3 and N4 comprise inosine, and X1 and/or X2 each comprise at least one inosine. In some aspects, N1 and N2 comprise inosine and N3 and N4 comprise cytidine, and X1 and X2 comprise inosine and no guanosine nucleosides. In some aspects, N1 and N2 comprise cytidine and N3 and N4 comprise inosine, and X1 and X2 comprise inosine and no guanosine nucleosides. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonists of the disclosure comprise the formula:

5'-($N_1$—$N_2$—$X_1$)-L-($X_2$—$N_3$—$N_4$)-3', wherein X1 and X2 are each 12 nucleotides and comprise 1, 2, 3 or 4 inosine nucleosides. In some aspects, X1 and X2 are each 13 nucleotides and comprise 1, 2, 3, 4 or 5 inosine nucleosides. In some aspects, X1 and X2 are each 14 nucleotides and comprise 1, 2, 3, 4, 5 or 6 inosine nucleosides. In some aspects, X1 and X2 are each 15 nucleotides and comprise 1, 2, 3, 4, 5, 6, or 7 inosine nucleosides. In some aspects, X1 and X2 are each 16 nucleotides and each comprise 1, 2, 3, 4, 5, 6, 7, or 8 inosine nucleosides. In some aspects, X1 and X2 are each 12 nucleotides and comprise at least 10%, 20%, 30% or 40% inosine nucleosides. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides a composition comprising:

(a) a virus-like particle; and (b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$, (ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ comprises a sequence motif $[AUCN_5]_x$, wherein $N_5$ is comprises guanosine or inosine, wherein x is an integer whose value indicates the number of sequence motifs, and wherein x=2-4;

(viii) $X_2$ comprises a sequence motif $[CN_6AU]_y$, wherein N6 comprises guanosine or inosine, wherein y is an integer whose value indicates the number of sequence motifs, and wherein y=2-4;

(ix) L is a linker that operably links the first polynucleotide and the second polynucleotide, optionally, wherein at least one of N1, N2, N3, and N4 is inosine, and wherein the inosine nucleoside base pairs with cytidine in the hairpin RNA, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (iv) ($N_1$—$N_2$—$X_1$) comprises a first polynucleotide comprising linked nucleotides $N_1$, $N_2$ and $X_1$, (v) ($X_2$—$N_3$—$N_4$) comprises a second polynucleotide comprising linked nucleotides $X_2$, $N_3$ and $N_4$;

(vi) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ comprises a sequence motif $[AUCN_5]_x$, wherein $N_5$ is comprises guanosine or inosine, wherein x is an integer whose value indicates the number of sequence motifs, and wherein x=2-4;

(viii) $X_2$ comprises a sequence motif $[CN_6AU]_y$, wherein N6 comprises guanosine or inosine, wherein y is an integer whose value indicates the number of sequence motifs, and wherein y=2-4;

(ix) L is a linker that operably links the first polynucleotide and the second polynucleotide, optionally, wherein at least one of N1, N2, N3, and N4 is inosine, and wherein the inosine nucleoside base pairs with cytidine in the hairpin RNA, wherein the at least one RLR agonist is packaged in the virus-like particle.

In some aspects, N5 comprises inosine and N6 comprises inosine. In some aspects, N5 comprises guanosine and N6 comprises inosine. In some aspects, N5 comprises inosine and N6 comprises guanosine. In some aspects, N5 comprises guanosine (G) and N6 comprises guanosine (G). In some aspects, x=2 and y=2. In some aspects, x=3 and y=3. In some aspects, x=4 and y=4. In some aspects, N1 comprises inosine (I) and N4 comprises cytidine (C). In some aspects, N2 comprises inosine (I) and N3 comprises cytidine (C). In some aspects, N3 comprises inosine (I) and N2 comprises cytidine (C). In some aspects, N4 comprises inosine (I) and N1 comprises cytidine (C). In some aspects, N1 comprises guanosine (G). In some aspects, N2 comprises guanosine (G). In some aspects, N1 comprises cytidine (C). In some aspects, N2 comprises cytidine (C). In some aspects, N1 and N2 comprise guanosine (G) and N3 and N4 comprise cytidine (C). In some aspects, N1 and N2 comprise cytidine (C) and N3 and N4 comprise guanosine (G). In some aspects, N1 and N2 comprise inosine (I) and N3 and N4 comprise cytidine (C). In some aspects, N1 and N2 comprise cytidine (C) and N3 and N4 comprise inosine (I). In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In any of the foregoing or related aspects, the RLR agonist of the disclosure comprises a linker, wherein the linker is a nucleotide linker or a non-nucleotide linker. In some aspects, the linker is a non-nucleotide linker. In some aspects, the linker is a nucleotide linker. In some aspects, the nucleotide linker comprises a tetraloop, wherein the nucleotide sequence of the tetraloop is selected from the group consisting of:

(a) UNCG, wherein N=A, C, G, or U;
(b) GNRA, wherein N=A, C, G, or U, and wherein R=A or G;
(c) ANYA, wherein N=A, C, G, or U, and wherein Y=C or T;
(d) CUYG, wherein Y=C or T;
(e) UMAC, wherein M=A or C; and
(f) CUUG.

In some aspects, the sequence of the tetraloop is UUCG. In some aspects, the sequence of the tetraloop is GAUC.

In any of the foregoing or related aspects, the RLR agonist of the disclosure comprises a nucleotide linker, wherein the nucleotide linker comprises the nucleotide sequence UUUGAU or UGUUU. In some aspects, the nucleotide linker comprises the nucleotide sequence UUUGAU. In some aspects, the nucleotide linker comprises the nucleotide sequence UGUUU.

In any of the foregoing or related aspects, the RLR agonist of the disclosure comprises a non-nucleotide linker, wherein the non-nucleotide linker is selected from the group consisting of:

(a) an ethylene glycol linker; and
(b) an alkyl linker.

In some aspects, the non-nucleotide linker is a hexaethylene glycol linker. In some aspects, the non-nucleotide linker is a C9 alkyl linker.

In any of the foregoing or related aspects, the RLR agonist of the disclosure comprises a 5' diphosphate moiety, or a derivative or analog thereof. In some aspects, the agonist comprises a 5' triphosphate moiety, or a derivative or analog thereof. In some aspects, the derivative or analog thereof comprises a phosphate bioisostere is selected from: a phosphonate, a thiophosphonate, a phosphorothioate, a sulfate, a sulfonate, a sulfamate, a thiazolidinone, a carboxylate, a malonate, a boronic acid, a benzoxaborole, a boranophosphate, a squaramide.

In any of the foregoing or related aspects, the RLR agonist of the disclosure comprises a modified nucleotide, a modified nucleoside, or a modified nucleobase, or a combination thereof. In some aspects, the agonist comprises a modification to the internucleotide linkages or to the polynucleotide backbone.

In any of the foregoing or related aspects, the RLR agonist of the disclosure exhibits one or more of the following properties:

(a) specifically binds to one or more RLRs (e.g. RIG-1, MDA5 and/or LGP2);
(b) increases RLR-mediated cytokine production;
(c) increases RLR-mediated expression of interferon-stimulated genes (ISGs);
(d) increases RLR-dependent intracellular signaling;
(e) increases stability of the duplex;
(f) increases binding affinity to RLRs;
(g) decreases off-target binding;
(h) increases biological half-life;
(i) increases biodistribution and bioavailability;
(j) increases and/or enhances uptake into cells and/or tissues;
(k) decreases immunogenicity; and
(l) a combination of any of (a)-(k).

In some aspects, the disclosure provides a composition comprising:

(a) a virus-like particle; and
(b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;
(ii) ($X_2$—$N_3$—$N_4$) comprises a second polynucleotide comprising linked nucleotides $X_2$, $N_3$ and $N_4$;
(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to $X_2$;
(ix) $X_1$ and $X_2$ are each 12 nucleotides to 16 nucleotides in length and are the same length, and;
(x) L is a linker that operably links the first polynucleotide and the second polynucleotide, wherein N1 and N2 each comprise guanosine, wherein N3 and N4 each comprise cytidine, wherein $X_1$ and $X_2$ are each 12 nucleotides in length, wherein $X_1$ and $X_2$ each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG, wherein the at least one RLR agonist is packaged in the virus-like particle.

In some aspects, the disclosure provides a composition comprising:

(a) a virus-like particle of an RNA-phage Qβ; and
(b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;
(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to $X_2$;
(ix) $X_1$ and $X_2$ are each 12 nucleotides to 16 nucleotides in length and are the same length, and;
(x) L is a linker that operably links the first polynucleotide and the second polynucleotide, wherein N1 and N2 each comprise guanosine, wherein N3 and N4 each comprise cytidine, wherein $X_1$ and $X_2$ are each 12 nucleotides in length, wherein $X_1$ and $X_2$ each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG, wherein the at least one RLR agonist is packaged in the virus-like particle.

In some aspects, the disclosure provides a composition comprising:

(a) a virus-like particle; and
(b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;
(ii) ($X_2$—$N_3$—$N_4$) comprises a second polynucleotide comprising linked nucleotides $X_2$, $N_3$ and $N_4$;
(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to $X_2$;
(ix) $X_1$ and $X_2$ are each 12 nucleotides to 16 nucleotides in length and are the same length, and;
(x) L is a linker that operably links the first polynucleotide and the second polynucleotide, wherein N1 comprises inosine and N2 comprise guanosine, wherein N3 and N4 each comprise cytidine, wherein $X_1$ and $X_2$ are each 12 nucleotides in length, wherein $X_1$ and $X_2$ each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG, wherein the at least one RLR agonist is packaged in the virus-like particle.

In some aspects, the disclosure provides a composition comprising:

(a) a virus-like particle of an RNA-phage Qβ; and
(b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;
(ii) ($X_2$—$N_3$—$N_4$) comprises a second polynucleotide comprising linked nucleotides $X_2$, $N_3$ and $N_4$;
(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to $X_2$;
(ix) $X_1$ and $X_2$ are each 12 nucleotides to 16 nucleotides in length and are the same length, and;
(x) L is a linker that operably links the first polynucleotide and the second polynucleotide, wherein N1 comprises inosine and N2 comprise guanosine, wherein N3 and N4 each comprise cytidine, wherein $X_1$ and $X_2$ are each 12 nucleotides in length, wherein $X_1$ and $X_2$ each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG, wherein the at least one RLR agonist is packaged in the virus-like particle.

In some aspects, the disclosure provides a composition comprising:

(a) a virus-like particle; and
(b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;
(ii) ($X_2$—$N_3$—$N_4$) comprises a second polynucleotide comprising linked nucleotides $X_2$, $N_3$ and $N_4$;
(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to $X_2$;
(ix) $X_1$ and $X_2$ are each 12 nucleotides to 16 nucleotides in length and are the same length, and;
(x) L is a linker that operably links the first polynucleotide and the second polynucleotide, wherein N1 and N2 comprise inosine and N3 and N4 comprise cytidine, wherein $X_1$ and $X_2$ are each 12 nucleotides in length, wherein $X_1$ and $X_2$ each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to RLRs, wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is a linker that operably links the first polynucleotide and the second polynucleotide, wherein N1 and N2 comprise inosine and N3 and N4 comprise cytidine, wherein $X_1$ and $X_2$ are each 12 nucleotides in length, wherein $X_1$ and $X_2$ each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG, wherein the at least one RLR agonist is packaged in the virus-like particle.

In some aspects, the disclosure provides a composition comprising:

(a) a virus-like particle; and (b) at least one RLR agonist that specifically binds to RLRs, wherein the agonist comprises a blunt-ended, hairpin RNA comprising a non-nucleotide linker, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein N1 and N2 comprise guanosine, wherein N3 and N4 comprise cytidine, wherein $X_1$ and $X_2$ are each 12 nucleotides in length, and wherein the non-nucleotide linker is a C9 alkyl linker, wherein the at least one RLR agonist is packaged in the virus-like particle.

In some aspects, the disclosure provides a composition comprising:

(a) a virus-like particle; and (b) at least one RLR agonist that specifically binds to RLRs, wherein the agonist comprises a blunt-ended, hairpin RNA comprising a non-nucleotide linker, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein N1 and N2 comprise guanosine, wherein N3 and N4 comprise cytidine, wherein $X_1$ and $X_2$ are each 12 nucleotides in length, and wherein the non-nucleotide linker is a hexaethylene glycol linker, wherein the at least one RLR agonist is packaged in the virus-like particle.

In some aspects, the disclosure provides a composition comprising:

(a) a virus-like particle; and (b) at least one RLR agonist that specifically binds to RLR, wherein the 5' most nucleotide of the agonist comprises a 5' diphosphate or triphosphate moiety, or derivative or analog thereof, and wherein the agonist comprises the nucleotide sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and 36, wherein the at least one RLR agonist is packaged in the virus-like particle.

In some aspects, the disclosure provides a composition comprising:

(a) a virus-like particle; and (b) at least one RLR agonist that specifically binds to RLRs, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, and wherein the first polynucleotide and the second polynucleotide comprise the nucleotide sequences selected from the group consisting of:

(i) SEQ ID NO: 37 and 68, respectively;
(ii) SEQ ID NO: 38 and 69, respectively;
(iii) SEQ ID NO: 39 and 70, respectively;
(iv) SEQ ID NO: 40 and 71, respectively;
(v) SEQ ID NO: 41 and 72, respectively;
(vi) SEQ ID NO: 42 and 73, respectively;
(vii) SEQ ID NO: 43 and 74, respectively;
(viii) SEQ ID NO: 44 and 75, respectively;
(ix) SEQ ID NO: 45 and 76, respectively;
(x) SEQ ID NO: 46 and 77, respectively;
(xi) SEQ ID NO: 47 and 78, respectively;
(xii) SEQ ID NO: 48 and 79, respectively;
(xiii) SEQ ID NO: 49 and 80, respectively;
(xiv) SEQ ID NO: 50 and 81, respectively;
(xv) SEQ ID NO: 51 and 82, respectively;
(xvi) SEQ ID NO: 52 and 83, respectively;
(xvii) SEQ ID NO: 53 and 84, respectively;
(xviii) SEQ ID NO: 54 and 85, respectively;
(xix) SEQ ID NO: 55 and 86, respectively;
(xx) SEQ ID NO: 56 and 87, respectively;
(xxi) SEQ ID NO: 57 and 88, respectively;
(xxii) SEQ ID NO: 58 and 89, respectively;
(xxiii) SEQ ID NO: 59 and 89, respectively;
(xxiv) SEQ ID NO: 60 and 90, respectively;
(xxv) SEQ ID NO: 61 and 91, respectively;
(xxvi) SEQ ID NO: 62 and 92, respectively;
(xxvii) SEQ ID NO: 63 and 91, respectively;
(xxviii) SEQ ID NO: 64 and 93, respectively;
(xxix) SEQ ID NO: 65 and 94, respectively;
(xxx) SEQ ID NO: 66 and 95, respectively;
(xxxi) SEQ ID NO: 67 and 96, respectively; and
(xxxii) SEQ ID NO: 63 and 97, respectively, wherein the at least one RLR agonist is packaged in the virus-like particle.

In some aspects, the disclosure provides a composition comprising:

(a) a virus-like particle; and (b) at least one RLR agonist that specifically binds to RLRs, wherein the agonist comprises a blunt-ended, hairpin RNA comprising at least one or more nucleotides comprising inosine which base pairs with cytidine, and wherein the agonist comprises the nucleotide sequence selected from the group consisting of SEQ ID NOs: 22, 23 and 25, wherein the at least one RLR agonist is packaged in the virus-like particle.

In some aspects, the disclosure provides a composition comprising:

(a) a virus-like particle; and (b) at least one RLR agonist that specifically binds to RLRs, wherein the agonist comprises a blunt-ended, hairpin RNA comprising at least one or more nucleotides comprising inosine which base pairs with cytidine, wherein the agonist comprises the formula 5'-($N_1$—$N_2$—$X_1$)-L-($X_2$—$N_3$—$N_4$)-3', wherein ($N_1$—$N_2$—$X_1$) comprises a first polynucleotide and ($X_2$—$N_3$—$N_4$) comprises a second polynucleotide, and wherein the first polynucleotide and the second polynucleotide comprise the nucleotide sequences selected from the group consisting of:

(i) SEQ ID NO: 58 and 89, respectively;
(ii) SEQ ID NO: 59 and 89, respectively; and
(iii) SEQ ID NO: 61 and 91, respectively.

wherein the at least one RLR agonist is packaged in the virus-like particle.

In some aspects, the disclosure provides a composition comprising:

(a) a virus-like particle; and (b) at least one RLR agonist that specifically binds to RLRs, wherein the agonist comprises a blunt-ended, hairpin RNA comprising a non-nucleotide linker, wherein the agonist comprises the formula 5'-($N_1$—$N_2$—$X_1$)-L-($X_2$—$N_3$—$N_4$)-3', wherein ($N_1$—$N_2$—$X_1$) comprises a first polynucleotide and ($X_2$—$N_3$—$N_4$) comprises a second polynucleotide, and wherein the first polynucleotide and the second polynucleotide comprise the nucleotide sequences selected from the group consisting of:

(i) SEQ ID NO: 37 and 68, respectively;
(ii) SEQ ID NO: 38 and 69, respectively;
(iii) SEQ ID NO: 39 and 70, respectively;
(iv) SEQ ID NO: 40 and 71, respectively;
(v) SEQ ID NO: 41 and 72, respectively;
(vi) SEQ ID NO: 42 and 73, respectively;
(vii) SEQ ID NO: 43 and 74, respectively;
(viii) SEQ ID NO: 44 and 75, respectively;
(ix) SEQ ID NO: 45 and 76, respectively;
(x) SEQ ID NO: 46 and 77, respectively;
(xi) SEQ ID NO: 47 and 78, respectively;
(xii) SEQ ID NO: 48 and 79, respectively;
(xiii) SEQ ID NO: 49 and 80, respectively;
(xiv) SEQ ID NO: 50 and 81, respectively;
(xv) SEQ ID NO: 51 and 82, respectively;
(xvi) SEQ ID NO: 52 and 83, respectively;
(xvii) SEQ ID NO: 53 and 84, respectively;
(xviii) SEQ ID NO: 54 and 85, respectively;
(xix) SEQ ID NO: 55 and 86, respectively;
(xx) SEQ ID NO: 56 and 87, respectively;
(xxi) SEQ ID NO: 57 and 88, respectively;
(xxii) SEQ ID NO: 58 and 89, respectively;
(xxiii) SEQ ID NO: 59 and 89, respectively;
(xxiv) SEQ ID NO: 60 and 90, respectively;
(xxv) SEQ ID NO: 61 and 91, respectively;
(xxvi) SEQ ID NO: 62 and 92, respectively;
(xxvii) SEQ ID NO: 63 and 91, respectively;
(xxviii) SEQ ID NO: 64 and 93, respectively;
(xxix) SEQ ID NO: 65 and 94, respectively;
(xxx) SEQ ID NO: 66 and 95, respectively;
(xxxi) SEQ ID NO: 67 and 96, respectively; and
(xxxii) SEQ ID NO: 63 and 97, respectively, wherein the at least one RLR agonist is packaged in the virus like particle.

In some aspects, the disclosure provides a composition comprising:

(a) a virus-like particle of an RNA-phage Qβ; and (b) at least one RLR agonist that specifically binds to RLRs, wherein the agonist comprises a blunt-ended, hairpin RNA comprising a non-nucleotide linker, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein N1 and N2 comprise guanosine, wherein N3 and N4 comprise cytidine, wherein $X_1$ and $X_2$ are each 12 nucleotides in length, and wherein the non-nucleotide linker is a C9 alkyl linker, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to RLRs, wherein the agonist comprises a blunt-ended, hairpin RNA comprising a non-nucleotide linker, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein N1 and N2 comprise guanosine, wherein N3 and N4 comprise cytidine, wherein $X_1$ and $X_2$ are each 12 nucleotides in length, and wherein the non-nucleotide linker is a hexaethylene glycol linker, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to RLR, wherein the 5' most nucleotide of the agonist comprises a 5' diphosphate or triphosphate moiety, or derivative or analog thereof, and wherein the agonist comprises the nucleotide sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and 36, wherein the at least one RLR agonist is packaged in the virus-like particle.

In some aspects, the disclosure provides a composition comprising:

(a) a virus-like particle of an RNA-phage Qβ; and (b) at least one RLR agonist that specifically binds to RLRs, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, and wherein the first polynucleotide and the second polynucleotide comprise the nucleotide sequences selected from the group consisting of:

(i) SEQ ID NO: 37 and 68, respectively;

(ii) SEQ ID NO: 38 and 69, respectively;

(iii) SEQ ID NO: 39 and 70, respectively;

(iv) SEQ ID NO: 40 and 71, respectively;

(v) SEQ ID NO: 41 and 72, respectively;

(vi) SEQ ID NO: 42 and 73, respectively;

(vii) SEQ ID NO: 43 and 74, respectively;

(viii) SEQ ID NO: 44 and 75, respectively;

(ix) SEQ ID NO: 45 and 76, respectively;

(x) SEQ ID NO: 46 and 77, respectively;

(xi) SEQ ID NO: 47 and 78, respectively;

(xii) SEQ ID NO: 48 and 79, respectively;

(xiii) SEQ ID NO: 49 and 80, respectively;

(xiv) SEQ ID NO: 50 and 81, respectively;

(xv) SEQ ID NO: 51 and 82, respectively;

(xvi) SEQ ID NO: 52 and 83, respectively;

(xvii) SEQ ID NO: 53 and 84, respectively;

(xviii) SEQ ID NO: 54 and 85, respectively;

(xix) SEQ ID NO: 55 and 86, respectively;

(xx) SEQ ID NO: 56 and 87, respectively;

(xxi) SEQ ID NO: 57 and 88, respectively;

(xxii) SEQ ID NO: 58 and 89, respectively;

(xxiii) SEQ ID NO: 59 and 89, respectively;

(xxiv) SEQ ID NO: 60 and 90, respectively;

(xxv) SEQ ID NO: 61 and 91, respectively;

(xxvi) SEQ ID NO: 62 and 92, respectively;

(xxvii) SEQ ID NO: 63 and 91, respectively;

(xxviii) SEQ ID NO: 64 and 93, respectively;

(xxix) SEQ ID NO: 65 and 94, respectively;

(xxx) SEQ ID NO: 66 and 95, respectively;
(xxxi) SEQ ID NO: 67 and 96, respectively; and
(xxxii) SEQ ID NO: 63 and 97, respectively,
wherein the at least one RLR agonist is packaged in the virus-like particle.

In some aspects, the disclosure provides a composition comprising:
(a) a virus-like particle of an RNA-phage Qβ; and
(b) at least one RLR agonist that specifically binds to RLRs, wherein the agonist comprises a blunt-ended, hairpin RNA comprising at least one or more nucleotides comprising inosine which base pairs with cytidine, and wherein the agonist comprises the nucleotide sequence selected from the group consisting of SEQ ID NOs: 22, 23 and 25,
wherein the at least one RLR agonist is packaged in the virus-like particle.

In some aspects, the disclosure provides a composition comprising:
(a) a virus-like particle of an RNA-phage Qβ; and
(b) at least one RLR agonist that specifically binds to RLRs, wherein the agonist comprises a blunt-ended, hairpin RNA comprising at least one or more nucleotides comprising inosine which base pairs with cytidine, wherein the agonist comprises the formula 5'-($N_1$—$N_2$—$X_1$)-L-($X_2$—$N_3$—$N_4$)-3', wherein ($N_1$—$N_2$—$X_1$) comprises a first polynucleotide and ($X_2$—$N_3$—$N_4$) comprises a second polynucleotide, and wherein the first polynucleotide and the second polynucleotide comprise the nucleotide sequences selected from the group consisting of:
(i) SEQ ID NO: 58 and 89, respectively;
(ii) SEQ ID NO: 59 and 89, respectively; and
(iii) SEQ ID NO: 61 and 91, respectively.
wherein the at least one RLR agonist is packaged in the virus-like particle.

In some aspects, the disclosure provides a composition comprising:
(a) a virus-like particle of an RNA-phage Qβ; and
(b) at least one RLR agonist that specifically binds to RLRs, wherein the agonist comprises a blunt-ended, hairpin RNA comprising a non-nucleotide linker, wherein the agonist comprises the formula 5'-($N_1$—$N_2$—$X_1$)-L-($X_2$—$N_3$—$N_4$)-3', wherein ($N_1$—$N_2$—$X_1$) comprises a first polynucleotide and ($X_2$—$N_3$—$N_4$) comprises a second polynucleotide, and wherein the first polynucleotide and the second polynucleotide comprise the nucleotide sequences selected from the group consisting of:
(i) SEQ ID NO: 37 and 68, respectively;
(ii) SEQ ID NO: 38 and 69, respectively;
(iii) SEQ ID NO: 39 and 70, respectively;
(iv) SEQ ID NO: 40 and 71, respectively;
(v) SEQ ID NO: 41 and 72, respectively;
(vi) SEQ ID NO: 42 and 73, respectively;
(vii) SEQ ID NO: 43 and 74, respectively;
(viii) SEQ ID NO: 44 and 75, respectively;
(ix) SEQ ID NO: 45 and 76, respectively;
(x) SEQ ID NO: 46 and 77, respectively;
(xi) SEQ ID NO: 47 and 78, respectively;
(xii) SEQ ID NO: 48 and 79, respectively;
(xiii) SEQ ID NO: 49 and 80, respectively;
(xiv) SEQ ID NO: 50 and 81, respectively;
(xv) SEQ ID NO: 51 and 82, respectively;
(xvi) SEQ ID NO: 52 and 83, respectively;
(xvii) SEQ ID NO: 53 and 84, respectively;
(xviii) SEQ ID NO: 54 and 85, respectively;
(xix) SEQ ID NO: 55 and 86, respectively;
(xx) SEQ ID NO: 56 and 87, respectively;
(xxi) SEQ ID NO: 57 and 88, respectively;
(xxii) SEQ ID NO: 58 and 89, respectively;
(xxiii) SEQ ID NO: 59 and 89, respectively;
(xxiv) SEQ ID NO: 60 and 90, respectively;
(xxv) SEQ ID NO: 61 and 91, respectively;
(xxvi) SEQ ID NO: 62 and 92, respectively;
(xxvii) SEQ ID NO: 63 and 91, respectively;
(xxviii) SEQ ID NO: 64 and 93, respectively;
(xxix) SEQ ID NO: 65 and 94, respectively;
(xxx) SEQ ID NO: 66 and 95, respectively;
(xxxi) SEQ ID NO: 67 and 96, respectively; and
(xxxii) SEQ ID NO: 63 and 97, respectively,
wherein the at least one RLR agonist is packaged in the virus like particle.

In any of the foregoing or related aspects, the nucleotide sequence comprising the RLR agonist is not complementary to a genomic DNA sequence or mRNA sequence, wherein the RLR agonist does not participate in RNA interference, and wherein the RLR agonist does not silence gene expression.

In any of the foregoing or related aspects, a virus-like particle described herein lacks a lipoprotein-containing envelope.

In any of the foregoing or related aspects, a virus-like particle described herein is a recombinant virus-like particle. In some aspects, the recombinant virus-like particle is selected from the group consisting of:
(a) recombinant proteins of Hepatitis B virus;
(b) recombinant proteins of measles virus;
(c) recombinant proteins of Sinbis virus;
(d) recombinant proteins of Rotavirus;
(e) recombinant proteins of Foot-and-Mouth-Disease virus;
(f) recombinant proteins of Retrovirus;
(g) recombinant proteins of Norwalk virus;
(h) recombinant proteins of human Papilloma virus;
(i) recombinant proteins of BK virus;
(j) recombinant proteins of bacteriophages;
(k) recombinant proteins of RNA-phages;
(l) recombinant proteins of Qβ-phage;
(m) recombinant proteins of GA-phage
(n) recombinant proteins of fr-phage;
(o) recombinant proteins of AP 205-phage;
(p) recombinant proteins of Ty; and
(q) fragments of any of the recombinant proteins from (a) to (p).

In any of the foregoing or related aspects, a virus-like particle described herein comprises recombinant proteins of an RNA-phage, wherein said RNA-phage is selected from the group consisting of: (a) bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; (j) bacteriophage f2; (k) bacteriophage PP7; and (l) bacteriophage AP205.

In any of the foregoing or related aspects, a virus-like particle described herein comprises recombinant proteins of bacteriophage Qβ. In some aspects, the recombinant proteins of bacteriophage Qβ comprise coat proteins having the amino acid sequence of SEQ ID NO: 112. In some aspects, the recombinant proteins of bacteriophage Qβ comprise coat proteins having an amino acid sequence at least 80%, 85%, 90%, 95%, 96%, 97%, 98% or 99% identical to SEQ ID NO: 112.

In some aspects, the disclosure provides a composition comprising:

(a) a virus-like particle of an RNA-phage Qβ comprising coat proteins having the amino acid sequence of SEQ ID NO: 112; and (b) at least one synthetic RIG-I like receptor (RLR) agonist that specifically binds to a RIG-I-like receptor (RLR), wherein the RLR agonist comprises a ribonucleic acid (RNA) of 10-100 nucleotides in length, wherein the 5' most nucleotide of the RNA comprises a 5'diphosphate or triphosphate moiety, or derivative or analog thereof, wherein the at least one RLR agonist is packaged in the virus-like particle.

In some aspects, the disclosure provides a composition comprising:

(a) a virus-like particle of an RNA-phage Qβ; and (b) at least one synthetic RIG-I like receptor (RLR) agonist that specifically binds to a RIG-I-like receptor (RLR), wherein the agonist the nucleotide sequence of SEQ ID NO: 23, and wherein the 5' most nucleotide of the agonist comprises a 5' diphosphate or triphosphate moiety, or derivative or analog thereof, wherein the at least one RLR agonist is packaged in the virus-like particle.

In any of the foregoing or related aspects, the RLR agonist is non-covalently bounds to the virus-particle.

In any of the foregoing or related aspects, the RLR agonist is bound to a virus-like particle site selected from the group consisting of an oligonucleotide binding site, a DNA binding site and an RNA binding site. In some aspects, the virus-like particle comprises an arginine-rich repeat.

In any of the foregoing or related aspects, the compositions described herein comprise at least one antigen or antigenic determinant bound to a virus-like particle. In some aspects, the at least one antigen or antigenic determinant is bound to the virus-like particle by at least one covalent bond. In some aspects, the at least one antigen or antigenic determinant is bound to the virus-like particle by a non-peptide bond. In other aspects, the antigen or antigenic determinant is fused to the virus-like particle. In some aspects, the virus-like particle comprises at least one first attachment site and wherein the antigen or antigenic determinant comprises at least one second attachment site selected from the group consisting of (a) an attachment site not naturally occurring within the antigen or antigenic determinant; and (b) an attachment site naturally occurring within the antigen or antigenic determinant, and wherein the binding of the antigen or antigenic determinant to the virus-like particle is effected through association between the first attachment site and the second attachment site, optionally wherein the association is through at least one non-peptide bond. In some aspects, the first attachment site comprises an amino group or a lysine residue, and wherein the second attachment site comprises a sulfhydryl group or a cysteine residue.

In some aspects, the disclosure provides a pharmaceutical composition for stimulating an immune response, treating or delaying progression of a cancer, or reducing or inhibiting tumor growth in a subject in need thereof, comprising a composition provided by the disclosure, and a pharmaceutically acceptable carrier. In some aspects, the composition is formulated in a polyethylenimine (PEI) carrier. In some aspects, the PEI carrier is JetPEI®.

In some aspects, the disclosure provides a method to increase RLR-mediated production of one or more cytokines in a cell, the method comprising contacting the cell with a composition provided by the disclosure, wherein the composition increases RLR-mediated cytokine production in a cell. In some aspects, the composition increases RLR-mediated type I interferon (e.g., IFN-α, IFN-β) production in a cell. In some aspects, the composition increases RLR-mediated IL-1β production in a cell. In some aspects, the composition increases RLR-mediated IP-10 production in a cell. In some aspects, the composition increases RLR-mediated IL-6, IL-12p70, MCP-1 and/or MIP-1β production in a cell.

In some aspects, the disclosure provides a method to increase RLR-mediated expression of one or more interferon-stimulated genes in a cell, the method comprising contacting the cell with a composition provided by the disclosure, wherein the composition increases RLR-mediated expression of one or more interferon-stimulated genes in a cell.

In some aspects, the disclosure provides a method to increase RLR-dependent intracellular signaling in a cell, the method comprising contacting the cell with a composition provided by the disclosure, wherein the composition increases RLR-dependent intracellular signaling.

In some aspects, the disclosure provides a method of stimulating an immune response in a subject, the method comprising administering to the subject an effective amount of a composition provided by the disclosure.

In some aspects, the disclosure provides a method of treating or delaying progression of a cancer in a subject, the method comprising administering to the subject an effective amount of a composition provided by the disclosure.

In some aspects, the disclosure provides a method of reducing or inhibiting tumor growth in a subject in need thereof, the method comprising administering to the subject an effective amount of a composition provided by the disclosure.

In some aspects, the disclosure provides a method for stimulating an immune response, treating or delaying progression of a cancer, or inhibiting tumor growth in a subject in need thereof, the method comprising administering to the subject an effective amount of a composition provided by the disclosure, wherein the composition, increases RLR-mediated production of one or more cytokines in a cell, increases RLR-mediated expression of one or more interferon-stimulated genes in a cell, and or increases RLR-dependent intracellular signaling in a cell, thereby stimulating the immune response, treating or delaying progression of the cancer, or inhibiting growth of the tumor.

In some aspects of, a composition provided by the disclosure is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator or agonist of a costimulatory molecule, an inhibitor of an inhibitory molecule, a vaccine, a cellular immunotherapy, or a combination thereof.

In some aspects, a composition provided by the disclosure is administered preceding or subsequent to administration of the one or more additional therapeutic agents or wherein the one or more additional therapeutic agents is administered concurrently with, preceding or subsequent to the administration of the agonist or pharmaceutical composition.

In some aspects, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a Toll-like receptor 3 (TLR3) agonist, a Toll-like receptor 7 (TLR7) agonist, a Toll-like receptor 9 (TLR9) agonist.

In some aspects, the one or more additional therapeutic agents is an agonist comprising an polypeptide (e.g., antibody, or antigen binding portion thereof) that specifically binds to CD137 (4-1BB).

In some aspects, the one or more additional therapeutic agents is an agonist comprising an polypeptide (e.g., antibody, or antigen binding portion thereof) that specifically binds to CD134 (OX40).

In some aspects, the one or more additional therapeutic agents is a PD-1/PD-L1 antagonist. In some aspects, the PD-1/PD-L1 antagonist is selected from the group consisting of: PDR001, KEYTRUDA® (pembrolizumab), OPDIVO® (nivolumab), pidilizumab, MEDI0680, REGN2810, TSR-042, PF-06801591, and AMP-224. In some aspects, the PD-1/PD-L1 antagonist is selected from the group consisting of: FAZ053, TENCENTRIQ® (atezolizumab), BAVENCIO® (avelumab), IMFINZI® (durvalumab), and BMS-936559.

In some aspects, the one or more additional therapeutic agents is a TIM-3 antagonist.

In some aspects, the one or more additional therapeutic agents is a VISTA antagonist.

In some aspects, the one or more additional therapeutic agents is an adenosine A2AR antagonist.

In some aspects, the one or more additional therapeutic agents is a B7-H3 antagonist.

In some aspects, the one or more additional therapeutic agents is a B7-H4 antagonist.

In some aspects, the one or more additional therapeutic agents is a BTLA antagonist.

In some aspects, the one or more additional therapeutic agents is a CTLA-4 antagonist.

In some aspects, the one or more additional therapeutic agents is a IDO antagonist.

In some aspects, the one or more additional therapeutic agents is a KIR antagonist.

In some aspects, the one or more additional therapeutic agents is a LAG-3 antagonist.

In some aspects, the one or more additional therapeutic agents is a Toll-like receptor 3 (TLR3) agonist. In some aspects, the TLR3 agonist is polyinosinic:polycytidylic acid (poly I:C). In some aspects, the TLR3 agonist is HILTONOL® (poly ICLC). In some aspects, the TLR3 agonist is polyadenylic-polyuridylic acid (poly A:U). In some aspects, the TLR3 agonist is RIBOXXIM® (RGIC®100). In some aspects, the TLR3 agonist is RIBOXXON® (RGIC®50 bioconjugate). In some aspects, the TLR3 agonist is RIBOXXOL® (RGIC®50).

In some aspects, the one or more additional therapeutic agents is a Toll-like receptor 7 (TLR7) agonist. In some aspects, the TLR7 agonist is GS-9620 (Vesatolimod). In some aspects, the TLR7 agonist is imiquimod (ALDARA™). In some aspects, the TLR7 agonist is resiquimod (R-848).

In some aspects, the one or more additional therapeutic agents is a Toll-like receptor 9 (TLR9) agonist. In some aspects, the TLR9 agonist is a CpG oligodeoxynucleotide (CpG ODN). In some aspects, the CpG ODN is a Class A CpG ODN (CpG-A ODN). In some aspects, the CpG ODN is a Class B CpG ODN (CpG-B ODN). In some aspects, the CpG ODN is a Class C CpG ODN (CpG-C ODN).

In some aspects, the disclosure provides a use a composition provided by the disclosure, for stimulating an immune response, treating or delaying progression of a cancer, or inhibiting tumor growth in a subject in need thereof, optionally for use in combination with one or more additional therapeutic agents.

In some aspects, the disclosure provides a use of a composition provided by the disclosure, in the manufacture of a medicament for stimulating an immune response, treating or delaying progression of a cancer, or inhibiting tumor growth in a subject in need thereof, optionally for use in combination with one or more additional therapeutic agents. In some aspects, the composition is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator of a costimulatory molecule, an inhibitor of an inhibitory molecule, a vaccine, a cellular immunotherapy, or a combination thereof. In some aspects, the composition is administered preceding or subsequent to administration of the one or more additional therapeutic agents or wherein the one or more additional therapeutic agents is administered concurrently with, preceding or subsequent to the administration of the composition.

In some aspects, the disclosure provides a kit comprising a composition provided by the disclosure and instructions for use in stimulating an immune response in a subject, or treating or delaying progression of a cancer, or inhibiting tumor growth in a subject, optionally with instructions for use in combination with one or more additional therapeutic agents. In some aspects, the kit comprises instructions for administering the composition in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator of a costimulatory molecule, an inhibitor of an inhibitory molecule, a vaccine, a cellular immunotherapy, or a combination thereof. In some aspects, the composition is administered preceding or subsequent to administration of the one or more additional therapeutic agents or wherein the one or more additional therapeutic agents is administered concurrently with, preceding or subsequent to the administration of the composition.

In any of the foregoing or related aspects, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a Toll-like receptor 3 (TLR3) agonist, a Toll-like receptor 7 (TLR7) agonist, a Toll-like receptor 9 (TLR9) agonist.

In any of the foregoing or related aspects, the one or more additional therapeutic agents is an agonist comprising an polypeptide (e.g., antibody, or antigen binding portion thereof) that specifically binds to CD137 (4-1BB).

In any of the foregoing or related aspects, the one or more additional therapeutic agents is an agonist comprising an polypeptide (e.g., antibody, or antigen binding portion thereof) that specifically binds to CD134 (OX40).

In some aspects, the disclosure provides a method of producing a composition as described herein, the method comprising:

(a) disassembling the virus-like particle;

(b) adding the RLR agonist; and (c) reassembling the virus-like particle.

In some aspects, the method comprises removing nucleic acids of the disassembled virus-like particle. In some aspects, the method comprises purifying the composition after reassembly. In some aspects, the method comprises (d) binding an antigen or antigenic determinant to the virus-like particle. In some aspects, the antigen or antigenic determinant is bound to the virus-like particle before disassembling the virus-like particle. In other aspects, the antigen or antigenic determinant is bound to the virus-like particle after reassembling the virus-like particle.

DETAILED DESCRIPTION

Overview

Figure 1:
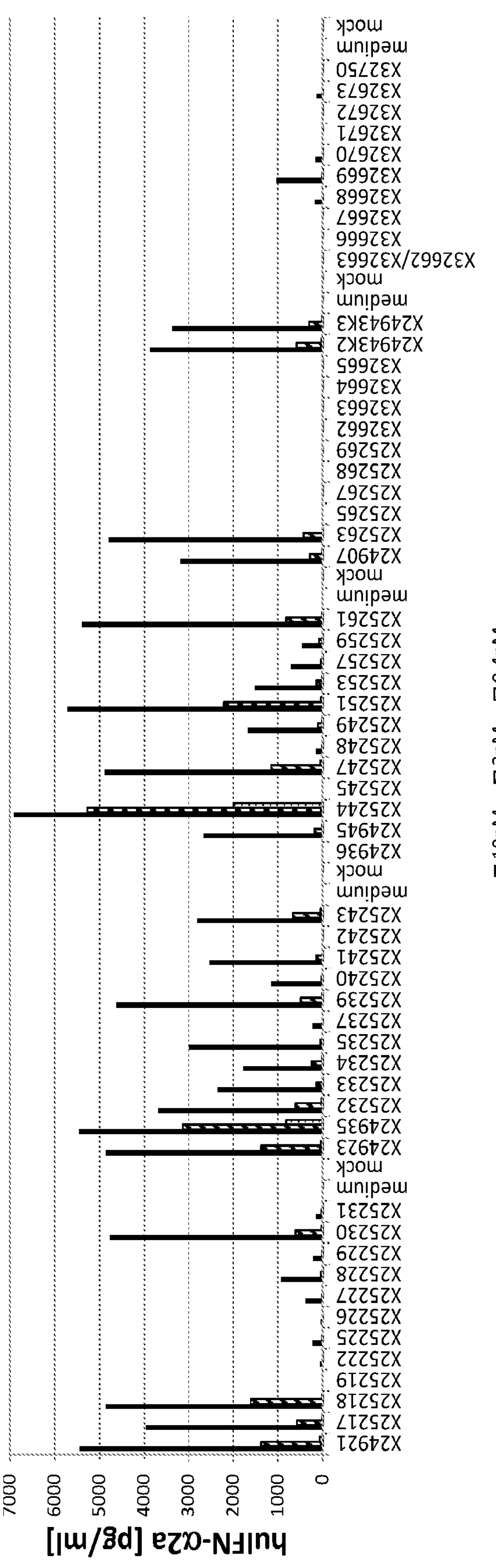
FIG. 1 provides a bar graph depicting the quantification of cytokine secretion: IFN-α2a from human PBMCs treated with 0.4 nM, 2 nM, and 10 nM of RLR agonists comprising various modifications.

The RIG-I-like receptors (RLRs) are a family of cytosolic pattern recognition receptors that are essential for detecting viral RNA and initiating the innate immune response. The RLR family includes three members: Retinoic acid-inducible gene I (RIG-I), Melanoma differentiation-associated gene 5 (MDA5), and Laboratory of genetics and physiology 2 (LGP2). These receptors are expressed in both immune and non-immune cell types and regulate signaling pathways that promote the IRF3-, IRF7-dependent expression of type I and type III interferons (IFNs), and the NF-kappa B-dependent expression of pro-inflammatory cytokines.

All three RLR family receptors have a DExD/H box RNA helicase domain with ATPase activity. This domain along with the adjacent C-terminal domain is required for RNA binding. In addition, the C-terminal domains of RIG-I and LGP2 have been shown to act as repressor domains, ensuring that the receptors remain in an inactive conformation until they are bound by an activating RNA.

The present disclosure provides RLR agonists comprising synthetic RNA molecules that fold to form a duplexed, dsRNA and that comprise one or more sequence motifs that provides one or more improved biological activities. The present disclosure also provides a composition comprising at least one RLR agonist packaged into VLPs, and demonstrates improved immunostimulatory potency, e.g. induction of cytokine expression, compared to VLPs alone. The RIG-VLPs provides an improved immunostimulatory compositions for use in prophylactic or therapeutic regimens against, e.g., tumors.

RIG-I-Like Receptors and their Ligands

The present disclosure provides synthetic RNA ligands that specifically bind to RIG-I-like receptors (RLRs) and agonize RLRs (RLR agonists). In some aspects, the disclosure provides RLR agonists that are useful for the treatment of cancer. In some aspects, the disclosure provides RLR agonists that are useful for the treatment of infectious disease. In some embodiments, the RLR agonists induce cytokine production. In some embodiments, the RLR agonists increase the number of CD8+ T cells in the tumor microenvironment. In some embodiments, the RLR agonists induce protective anti-tumor immunity RIG-I-like receptors (RLRs) comprise a family of DExD/H box RNA helicases that function as cytosolic pattern recognition receptors (PRRs) that sense the presence of pathogenic agents via the recognition of pathogen-associated molecular patterns (PAMPs). In particular, the intracellular presence of non-self (e.g., viral) RNA is sensed by an infected cell via binding of the RNA to RLRs and results in the initiation and modulation of antiviral immunity. Like most viral RNAs, endogenous mRNA and RNA polymerase III transcripts are also 5'-triphosphorylated, but eukaryotic mRNAs possess a 5' cap structure linked to a guanosine methylated at N7 that prevents RIG-I activation. These structural differences between viral and self RNAs, together with differences in intracellular localization, are thought to enable the effective function of RIG-I as a defense against viral infection by the preferential detection of viral RNA. The molecular recognition and binding of non-self RNA ligands to RLRs propagates specific intracellular signal events culminating in the activation of transcription factors that drive type 1 interferon (IFN) production and antiviral gene expression. The RLR-mediated induction of IFN and inflammatory cytokines production as well as antiviral gene expression elicits an immune response to control virus infection (Yoneyama et al., (2015) Curr Opin Immunol 32:48-53).

Three RLR family members have been identified: RIG-I (retinoic acid-inducible gene I)—the founding member and best characterized of RLR family, MDA5 (melanoma differentiation associated factor 5), and LGP2 (laboratory of genetics and physiology 2 and a homolog of mouse D111gp2). RIG-I is an important component of the innate immune system and plays a critical role in the defense against infection by RNA viruses. In contrast to the Toll-like receptors TLR3, TLR7, TLR8, and TLR9, that detect nucleic acids in the endosomes of a subset of immune cells, RIG-I is a cytosolic innate immune receptor that is expressed in all cell types (Kato et al., (2006) Nature 441(7089):101-105; Loo et al., (2008) J Virol 82(1):335-345). Two early studies independently established that RIG-I specifically detects and is activated by viral RNAs (Hornung et al., (2006) Science 314(5801):994-997; Pichlmair et al., (2006) Science 314 (5801):997-1001).

High-resolution structures of RIG-I/ligand complexes have provided the molecular detail of RIG-I binding to RNA ligands, specifically to the activating ligand, double-stranded 5'-triphosphorylated RNA (ppp-dsRNA) (Civril et al., (2011) EMBO Reports 12(11): 1127-1134; Jiang et al., (2011) Nature 479(7373):423-427; Kowalinski et al., (2011) Cell 147(2):423-435; Lu et al., (2010) Structure 18(8): 1032-1043; Luo et al., (2011) Cell 147(2) 409-422; Wang et al., (2010) Nature Structural & Molecular Biology 17(7): 781-787; Hornung et al., (2006) Science 314(5801):994-997; Pichlmair et al., (2006) Science 314(5801):997-1001; Schlee et al., (2009) Immunity 31(1):25-34)). The crystal structures of RIG-I/RNA complexes show protein binding to the backbone, not the bases, suggesting that the RNA sequence may not affect RIG-I binding or that RNA sequence may exhibit as of yet uncharacterized effects or activity. To date, evidence for sequence—dependent differential interaction or affinity with, and activation of, RIG-I-like receptors is not described in the art (Schlee and Hartmann (2010) Molecular Therapy 18(7):1254-1262).

Accordingly, the disclosure provides synthetic RIG-I-like receptor (RLR) agonists comprising non-naturally occurring, synthetic, and or engineered RLR RNA ligands. In some embodiments, the RLR agonist comprises a ribonucleic acid (RNA) of 10-100 nucleotides in length. In some aspects the RNA is 10-15, 15-20, 20-25, 25-30, 30-35, 35-40, 40-45, 45-50, 50-55, 55-60, 60-65, 65-70, 70-75, 75-80, 80-85, 85-90, 90-95, or 95-100 nucleotides in length.

In some embodiments, the RLR agonist may be single-stranded, single-stranded containing a self-complementary sequence which can form a duplex, a stem-loop or a hairpin structure, double-stranded, or partially double-stranded oligonucleotide.

In some embodiments, the double-strand oligonucleotide is fully double-stranded. In this case, the oligonucleotide is composed of two single-stranded oligonucleotides which have the same length and which have sequences that are 100% complementary to each other.

In some embodiments, the double-strand oligonucleotide is partially double-stranded. In this case, the two strands forming the oligonucleotide have different lengths, sequences which are not 100% complementary to each other, or both. In other words, the at least one fully double-stranded section of the oligonucleotide is connected with a single-stranded structure at one or both ends.

In some embodiments the duplex, hairpin, or stem-loop structure comprises 10-15, 15-20, 20-25, 25-30, 30-35, 30-35, 35-40, 40-45, 45-50, 50-55 base pairs.

In some embodiments, the oligonucleotide forms a duplex comprising less than 19 base pairs. In some embodiments, the complementary bases of the duplex are connected by a nucleotide or non-nucleotide linker In some embodiments, the oligonucleotide is single-stranded, single-stranded containing a self-complementary sequence or double-stranded, the length of the oligonucleotide is the length of a single-strand.

In some aspects, the oligonucleotide is partially double-stranded, the length of the oligonucleotide is the length of the longer strand. Therefore, the oligonucleotide of the present invention includes partially double-stranded oligonucleotides wherein at least one of the strands is at 10-15, 15-20, 20-25, 25-30, 30-35, 35-40, 40-45, 45-50, 50-55, 55-60, 60-65, 65-70, 70-75, 75-80, 80-85, or 85-90 nucleotides in length.

In some aspects, the oligonucleotide is double-stranded or partially double-stranded oligonucleotide, at least one of the strands comprises at least one 5' di- or tri-phosphate group. When both strands comprise 5' di- or tri-phosphate groups, the number of phosphate groups may be the same or may be different on the two strands. In some aspects, the oligonucleotide is a partially double-stranded oligonucleotide, the at least 1 ribonucleotide at the 5' end which comprises the at least one 5' diphosphate or triphosphate can be on either the long or the short strand, wherein at least the long strand is 10-15, 15-20, 20-25, 25-30, 30-35, 35-40, 40-45, 45-50, 50-55, 55-60, 60-65, 65-70, 70-75, 75-80, 80-85, or 85-90 nucleotides in length.

In some aspects, the degree of complementarity is preferably at least 50%, 60%, 70%, more preferably at least 75%, 80%, 85%, 90%, even more preferably at least 95%, 96%, 97%, 98%, 99%, and most preferably 100%. As used in the art, the term "degree of complementarity" between two oligonucleotides/polynucleotides refers to the percentage of complementary bases in the overlapping region of the two oligonucleotides. Two bases are complementary to each other if they can form a base pair via hydrogen bonding. Base pairs include both Watson-Crick base pairs and wobble base pairs. Watson-Crick base pairs include A-T, C-G, A-U; wobble base pairs include G-U, I-U, I-A, I-C. The degree of complementarily can be determined by a skilled person using any known methods in the art, either manually or automatically by various engines such as BLAST. For example, ATCG has 100% complementarity to CGAT and CGATGG, and 75% complementarity to CGTT and CGTTGG.

In some aspects, the disclosure provides an RLR agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first polynucleotide comprises a 5' diphosphate or triphosphate moiety, or derivative or analog thereof, and wherein the agonist comprises a sequence motif that provides at least one improved biological activity mediated by the RLR relative to an agonist that does not comprise the sequence motif.

In some embodiments, the RLR agonists of the disclosure comprise a sequence motif, wherein the sequence motif is selected from the group consisting of:

(i) a GT-repeat motif;
(ii) a GA-repeat motif;
(iii) a AUCG-repeat motif;
(iv) an AU-repeat motif;
(v) a dipyrimidine motif;
(vi) a dipurine motif;
(vii) a pyrimidine triplet motif;
(viii) a purine triplet motif;
(ix) a palindromic sequence motif; and
(x) a combination of any of (i)-(ix).

In some embodiments, the RLR agonists of the disclosure comprise at least one improved biological activity, wherein the improved biological activity is selected from:

(i) an increase in RLR-mediated cytokine production;
(ii) an increase in RLR-mediated expression of interferon-stimulated genes;
(iii) an increase in RLR-mediated intracellular signaling;
(iv) an increase in binding affinity to RLRs; and
(v) a combination of any of (i)-(iv).

In some embodiments, the RLR agonists of the disclosure comprise a sequence motif, wherein the sequence motif is a GT-repeat motif comprises a sequence of <19, about 15-18, about 15, about 10-15, about 10, about 5-10, about 5, about 4 about 18, 17, 16, 15, 14, 13, 12, 11, 10, 9, 8, 7, 6, 5, or 4 guanine and thymine nucleotides, or derivatives or analogs thereof. In some embodiments, the GT-repeat motif is $[GT]_n$, wherein n=2 to 9. In some embodiments, the GT-repeat motif is $[GT]_7$. In some embodiments, the GT-repeat motif is $[GT]_3$, and wherein the GT-repeat motif is followed by a purine triplet and UCG, respectively. In some embodiments, the purine triplet is GGA.

In some embodiments, the sequence motif is a GA-repeat motif comprises a sequence of <19, about 15-18, about 15, about 10-15, about 10, about 5-10, about 5, about 4 about 18, 17, 16, 15, 14, 13, 12, 11, 10, 9, 8, 7, 6, 5, or 4 guanine and adenine nucleotides, or derivatives or analogs thereof. In some embodiments, the GA-repeat motif is $[GA]_n$, where n=2 to 9. In some embodiments, the GA-repeat motif is $[GA]_7$.

In some embodiments, the RLR agonists of the disclosure comprise a sequence motif, wherein the sequence motif is a AUCG-repeat motif comprising a sequence of <19, about 16, about 12-16, about 12, about 8-12, about 6, about 16, 12, 8 adenine, uracil, cytosine, and guanine nucleotides, or derivatives or analogs thereof.

In some embodiments, the AUCG-repeat motif is $[AUCG]_n$, where n=2 to 4. In some embodiments, the AUCG-repeat motif is $[AUCG]_3$.

In some embodiments, the AUCG-repeat motif is preceded by a CG or a dipyrimidine motif. In some embodiments, the AUCG-repeat motif is preceded by a CG. In some embodiments, the dipyrimidine motif is CC. In some embodiments, the AUCG-repeat motif is preceded by a dipurine motif. In some embodiments, the dipurine motif is GA. In some embodiments, the dipurine motif is GG.

In some embodiments, the RLR agonists of the disclosure comprise an AUCG-repeat motif, wherein one or more uridine nucleosides (U) are substituted with a modified nucleoside. In some embodiments, wherein the modified nucleoside is ribothymidine (T). In some embodiments, the AUGC-repeat motif is $[AUCG]_3$, wherein the one or more uridine nucleosides (U) comprising the AUCG-repeat motif are substituted with a modified nucleoside, wherein the modified nucleoside is ribothymidine (T). In some embodiments, the AUGC-repeat motif is $[AUCG]_3$, wherein the one or more uridine nucleosides (U) comprising the AUCG-repeat motif are substituted with a modified nucleoside, wherein the modified nucleoside is ribothymidine (T), and wherein the AUGC-repeat motif is preceded by GG.

In some embodiments, the RLR agonists of the disclosure comprise an AUCG-repeat motif, wherein one or more guanosine nucleosides (G) are substituted with a modified nucleoside. In some embodiments, the modified nucleoside is inosine (I). In some embodiments, the AUGC-repeat motif is $[AUCG]_3$, wherein the one or more guanosine nucleosides (G) comprising the AUCG-repeat motif are substituted with a modified nucleoside, wherein the modified nucleoside is ribothymidine (T), and wherein the AUGC-repeat motif is preceded by GG.

In some embodiments, the RLR agonists of the disclosure comprise a AUCG-repeat motif, wherein the motif is preceded by a IG. In some embodiments, the AUCG-repeat motif is $[AUCG]_3$ and is preceded by a IG.

In some embodiments, the RLR agonists of the disclosure comprise an AUCG-repeat, wherein one or more guanosine nucleosides (G) are substituted with an inosine (I), wherein the AUCG-repeat is preceded by an inosine (I). In some embodiments, the guanosine nucleosides (G) comprising the AUCG-repeat are substituted with an inosine (I), wherein the AUCG-repeat is preceded by an inosine (I), wherein the 5' most nucleotide of the first polynucleotide comprises inosine (I).

In some embodiments, the 5' most nucleotide of the first polynucleotide comprises inosine (I).

In some embodiments, the RLR agonists of the disclosure comprise a AUCG-repeat sequence motif, wherein the AUCG-repeat motif is $[AUCG]_2$. In some embodiments, the AUCG-repeat motif is preceded by a dipurine motif. In some embodiments, the dipurine motif is GG. In some embodiments, the AUCG-repeat motif is preceded by a purine triplet. In some embodiments, the purine triplet is GGG. In some embodiments, the AUCG-repeat motif is preceded by CCCCCG. In some embodiments, the AUCG-repeat motif is preceded by TCGUCG.

In some embodiments, the RLR agonists of the disclosure comprise a palindromic sequence, wherein the palindromic sequence comprises a sequence of <19, about 15-18, about 15, about 10-15, about 10, about 18, 17, 16, 15, 14, 13, 12, 11, 10, 9, 8, 7, 6, 5, or 4 nucleotides, or derivatives or analogs thereof, linked in any order that results in a palindrome.

In some embodiments, the linker is flanked by AU. In some embodiments, the linker is flanked by an AU-repeat motif, wherein the AU-repeat motif is $[AU]_n$, where n=2 to 3. In some embodiments, the AU-repeat motif is $[AU]_2$.

In some aspects, the disclosure provides an RLR agonist that specifically binds to a RLRs, wherein the agonist comprises a blunt-ended, hairpin RNA comprising at least one or more nucleotides comprising inosine which base pairs with cytidine, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is a linker that covalently links the first polynucleotide and the second polynucleotide.

In other aspects, the disclosure provides a synthetic RIG-I-like receptor (RLR) agonist that specifically binds to RIG-I-like receptors (RLRs), wherein the agonist comprises a blunt-ended, hairpin RNA comprising a non-nucleotide linker, and wherein the agonist comprises the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$;

(ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide.

In some embodiments, inosine, if present in the RLR agonist, base pairs with cytidine.

In some embodiments, the linker (L) is a nucleotide linker or a non-nucleotide linker.

In some aspects, the disclosure provides an RLR agonist that specifically binds to RLRs, wherein the agonist comprises a blunt-ended, hairpin RNA comprising a nucleotide or non-nucleotide linker. RNA hairpins are among the most common RNA secondary structural elements, wherein the hybridized portion or "stem" of the hairpin are frequently capped by RNA tetraloops. RNA tetraloops are composed of characteristic four-loop nucleotides that form a compact and stable structure. While they can be formed by many different nucleotide sequences, UNCG (N=A, C, G, or U), GNRA (R=A or G), and CUUG tetraloops are found most often. Tetraloops usually help initiate RNA-folding processes and provide sites for tertiary contacts within or between RNAs and for protein binding, thereby facilitating the assembly of ribonucleoprotein particles. Further description of tetraloops can be found in Cheong, H., Kim, N. and Cheong, C. (2015). RNA Structure: Tetraloops. In eLS, John Wiley & Sons, Ltd (Ed.), which is incorporated herein by reference in its entirety.

Accordingly, in some embodiments, the RLR agonists of the disclosure comprise a nucleotide linker comprising a tetraloop. In some embodiments, the nucleotide sequence of the tetraloop is selected from the group consisting of:

(a) UNCG, wherein N=A, C, G, or U;

(b) GNRA, wherein N=A, C, G, or U, and wherein R=A or G;

(c) ANYA, wherein N=A, C, G, or U, and wherein Y=C or T;

(d) CUYG, wherein Y=C or T;

(e) UMAC, wherein M=A or C; and (f) CUUG.

In some embodiments, the nucleotide linker comprises the nucleotide sequence UUUGAU or UGUUU. In some embodiments, the sequence of the tetraloop is UUCG. In some embodiments, the sequence of the tetraloop is GAUC. In some embodiments, the nucleotide linker comprises the nucleotide sequence UUUGAU. In some embodiments, the nucleotide linker comprises the nucleotide sequence UGUUU.

In other aspects, the RLR agonists of the disclosure comprise a non-nucleotide linker. As described herein nucleic acid loops (e.g., tetraloops) are a common element found in nucleic acid secondary structure. Nucleotide loops arise in folded domains occurring in intrastrand duplexes. Synthetic nucleic acids designed to contain hairpin loops comprising non-nucleotide linking groups (e.g., non-nucleotide linkers) can replace several nucleotides bridging a folded duplex structure. Non-nucleotide groups have been used as linkers in non-folded structures as well. Such linking groups may be useful replacements of natural nucleotide linkers (e.g., tetraloops). For example, they can shorten the synthesis of nucleic acid with a desired secondary structure by several steps, since one relatively long non-nucleotide linking group replaces several individual nucleotides which may normally constitute a loop. Such non-natural loops or linkers (e.g., non-nucleotide linkers) can confer resistance to degradation by nucleases which would ordinarily act on a natural loop structure in biological contexts (e.g., in a cell or in the circulation of a subject upon administration). A non-nucleotide linking group also has the potential to provide a more stable folded structure than occurs with the nucleotide loops and or linkers. Further description of non-nucleotide linkers can be found in Rumney and Kool (1995) J Am Chem Soc 117:5635-5646, which is incorporated herein by reference in its entirety.

Accordingly, in some embodiments, the RLR agonists of the disclosure comprise a non-nucleotide linker selected from the group consisting of:

(a) an ethylene glycol linker; and (b) an alkyl linker.

In some embodiments, the non-nucleotide linker is a hexaethylene glycol linker. In some embodiments, the non-nucleotide linker is a C9 alkyl linker.

In some embodiments, the RLR agonist comprises a 5' diphosphate moiety, or a derivative or analog thereof. In some embodiments, the agonist comprises a 5' triphosphate moiety, or a derivative or analog thereof. In some embodiments, the derivative or analog thereof comprises a phosphate bioisostere is selected from: a phosphonate, a thiophosphonate, a phosphorothioate, a sulfate, a sulfonate, a sulfamate, a thiazolidinone, a carboxylate, a malonate, a boronic acid, a benzoxaborole, a boranophosphate, a squaramide.

In some embodiments, the agonist comprises a modified nucleotide, a modified nucleoside, or a modified nucleobase, or a combination thereof. In some embodiments, the agonist comprises a modification to the internucleotide linkages or to the polynucleotide backbone.

In some aspects, the RLR agonist of the disclosure exhibits at least one or more of the following properties:

(a) specifically binds to one or more RLRs (e.g. RIG-1, MDA5 and/or LGP2);

(b) increases RLR-mediated cytokine production;

(c) increases RLR-mediated expression of interferon-stimulated genes (ISGs);

(d) increases RLR-dependent intracellular signaling;

(e) increases stability of the duplex;

(f) increases binding affinity to RLRs;

(g) decreases off-target binding;

(h) increases biological half-life;

(i) increases biodistribution and bioavailability;

(j) increases and/or enhances uptake into cells and/or tissues;

(k) decreases immunogenicity; and (l) a combination of any of (a)-(k).

In some aspects, the disclosure provides a synthetic RIG-I-like receptor (RLR) agonist that specifically binds to a RIG-I-like receptor (RLR), wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$, (ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is a linker that operably links the first polynucleotide and the second polynucleotide, wherein at least one of N1, N2, N3, and N4 is inosine and/or at least one of $X_1$ and/or $X_2$ comprises at least one inosine nucleoside, and wherein the inosine nucleoside base pairs with cytidine in the hairpin RNA.

In some embodiments, N1 comprises inosine and N4 comprises cytidine. In some embodiments, N1 comprises cytidine and N4 comprises inosine. In some embodiments, N2 comprise inosine and N3 comprises cytidine. In some embodiments, N2 comprises cytidine and N3 comprises inosine. In some embodiments, N1 comprises guanosine. In some embodiments, N2 comprises guanosine. In some embodiments, N1 comprises cytidine. In some embodiments, N2 comprises cytidine. In some embodiments, N1 and N2 comprise guanosine and N3 and N4 comprise cytidine. In some embodiments, N1 and N2 comprise cytidine and N3 and N4 comprise guanosine. In some embodiments, N1 and N2 comprise inosine and N3 and N4 comprise cytidine. In some embodiments, N1 and N2 comprise cytidine and N3 and N4 comprise inosine. In some embodiments, N1 comprises inosine and N4 comprises cytidine, and X1 and/or X2 each comprise at least one inosine. In some embodiments, N2 comprises inosine and N3 comprises cytidine, and X1 and/or X2 each comprise at least one inosine. In some embodiments, N1 and N2 comprise guanosine N3 and N4 comprise cytidine, and X1 and/or X2 each comprise at least one inosine. In some embodiments, N1 and N2 comprise guanosine and N3 and N4 comprise cytidine, and X1 and X2 each comprise at least one inosine. In some embodiments, N1 and N2 comprise cytidine and N3 and N4 comprise guanosine, and X1 and X2 each comprise at least one inosine. In some embodiments, N1 and N2 comprise guanosine and N3 and N4 comprise cytidine, and X1 and X2 each comprise inosine and no guanosine nucleosides. In some embodiments, N1 and N2 comprise cytidine and N3 and N4 comprise guanosine, and X1 and X2 each comprise inosine and no guanosine nucleosides. In some embodiments, N1 and N2 comprise inosine and N3 and N4 comprise cytidine, and X1 and/or X2 each comprise at least one inosine. In some embodiments, N1 and N2 comprise inosine and N3 and N4 comprise cytidine, and X1 and X2 each comprise at least one inosine. In some embodiments, N1 and N2 comprise cytidine and N3 and N4 comprise inosine, and X1 and/or X2 each comprise at least one inosine. In some embodiments, N1 and N2 comprise inosine and N3 and N4 comprise cytidine, and X1 and X2 comprise inosine and no guanosine nucleosides. In some embodiments, N1 and N2 comprise cytidine and N3 and N4 comprise inosine, and X1 and X2 comprise inosine and no guanosine nucleosides. In some embodiments, X1 and X2 are each 12 nucleotides and comprise 1, 2, 3 or 4 inosine nucleosides. In some embodiments, X1 and X2 are each 13 nucleotides and comprise 1, 2, 3, 4 or 5 inosine nucleosides. In some embodiments, X1 and X2 are each 14 nucleotides and comprise 1, 2, 3, 4, 5 or 6 inosine nucleosides. In some embodiments, X1 and X2 are each 15 nucleotides and comprise 1, 2, 3, 4, 5, 6, or 7 inosine nucleosides. In some embodiments, X1 and X2 are each 16 nucleotides and each comprise 1, 2, 3, 4, 5, 6, 7, or 8 inosine nucleosides. In some embodiments, X1 and X2 are each 12 nucleotides and comprise at least 10%, 20%, 30% or 40% inosine nucleosides.

In some aspects, the disclosure provides a synthetic RIG-I-like receptor (RLR) agonist that specifically binds to a RIG-I-like receptor (RLR), wherein the agonist comprises a blunt-ended, hairpin RNA comprising the formula:

5'-($N_1$—$N_2$—$X_1$)-L-($X_2$—$N_3$—$N_4$)-3', wherein (i) ($N_1$—$N_2$—$X_1$) comprises a first polynucleotide comprising linked nucleotides $N_1$, $N_2$ and $X_1$, (ii) ($X_2$—$N_3$—$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ comprises a sequence motif $[AUCN_5]_x$, wherein $N_5$ is comprises guanosine or inosine, wherein x is an integer whose value indicates the number of sequence motifs, and wherein x=3 or 4;

(viii) $X_2$ comprises a sequence motif $[CN_6AU]_y$, wherein N6 comprises guanosine or inosine, wherein y is an integer whose value indicates the number of sequence motifs, and wherein y=3 or 4;

(ix) L is a linker that operably links the first polynucleotide and the second polynucleotide, optionally, wherein at least one of N1, N2, N3, and N4 is inosine, and wherein the inosine nucleoside base pairs with cytidine in the hairpin RNA. In some embodiments, N5 comprises inosine and N6 comprises inosine. In some embodiments, N5 comprises guanosine and N6 comprises inosine. In some embodiments, N5 comprises inosine and N6 comprises guanosine. In some embodiments, N5 comprises guanosine (G) and N6 comprises guanosine (G). In some embodiments, x=3 and y=3. In some embodiments, x=4 and y=4. In some embodiments, N1 comprises inosine (I) and N4 comprises cytidine (C). In some embodiments, N2 comprises inosine (I) and N3 comprises cytidine (C). In some embodiments, N3 comprises inosine (I) and N2 comprises cytidine (C). In some embodiments, N4 comprises inosine (I) and N1 comprises cytidine (C). In some embodiments, N1 comprises guanosine (G). In some embodiments, N2 comprises guanosine (G). In some embodiments, N1 comprises cytidine (C). In some embodiments, N2 comprises cytidine (C). In some embodiments, N1 and N2 comprise guanosine (G) and N3 and N4 comprise cytidine (C). In some embodiments, N1 and N2 comprise cytidine (C) and N3 and N4 comprise guanosine (G). In some embodiments, N1 and N2 comprise inosine (I) and N3 and N4 comprise cytidine (C). In some embodiments, N1 and N2 comprise cytidine (C) and N3 and N4 comprise inosine (I).

In some embodiments, the linker (L) is a nucleotide linker or a non-nucleotide linker. In some embodiments, the linker (L) is a nucleotide linker comprising a tetraloop, wherein the nucleotide sequence of the tetraloop is selected from the group consisting of:

(a) UNCG, wherein N=A, C, G, or U;

(b) GNRA, wherein N=A, C, G, or U, and wherein R=A or G;

(c) ANYA, wherein N=A, C, G, or U, and wherein Y=C or T;

(d) CUYG, wherein Y=C or T;

(e) UMAC, wherein M=A or C; and (f) CUUG.

In some embodiments, the linker (L) is a nucleotide linker comprising the nucleotide sequence UUUGAU or UGUUU. In some embodiments, the nucleotide linker comprises the nucleotide sequence UUUGAU. In some embodiments, the nucleotide linker comprises the nucleotide sequence UGUUU.

In some embodiments, the linker (L) is a nucleotide linker comprising a tetraloop, wherein the sequence of the tetraloop is UUCG. In some embodiments, the sequence of the tetraloop is GAUC.

In some embodiments, the linker (L) is a non-nucleotide linker selected from the group consisting of:

(a) an ethylene glycol linker; and (b) an alkyl linker.

In some embodiments, the non-nucleotide linker is a hexaethylene glycol linker. In some embodiments, the non-nucleotide linker is a C9 alkyl linker.

In some embodiments, the RLR agonist comprises a 5' diphosphate moiety, or a derivative or analog thereof. In some embodiments, the agonist comprises a 5' triphosphate moiety, or a derivative or analog thereof. In some embodiments, the derivative or analog thereof comprises a phosphate bioisostere is selected from: a phosphonate, a thiophosphonate, a phosphorothioate, a sulfate, a sulfonate, a sulfamate, a thiazolidinone, a carboxylate, a malonate, a boronic acid, a benzoxaborole, a boranophosphate, a squaramide.

In some embodiments, the RLR agonist comprises a modified nucleotide, a modified nucleoside, or a modified nucleobase, or a combination thereof. In some embodiments, the agonist comprises a modification to the internucleotide linkages or to the polynucleotide backbone.

In some embodiments, the RLR agonist exhibits at least one or more of the following properties:

(a) specifically binds to one or more RLRs (e.g. RIG-1, MDA5 and/or LGP2);

(b) increases RLR-mediated cytokine production;

(c) increases RLR-mediated expression of interferon-stimulated genes (ISGs);

(d) increases RLR-dependent intracellular signaling;

(e) increases stability of the duplex;

(f) increases binding affinity to RLRs;

(g) decreases off-target binding;

(h) increases biological half-life;

(i) increases biodistribution and bioavailability;

(j) increases and/or enhances uptake into cells and/or tissues;

(k) decreases immunogenicity; and (l) a combination of any of (a)-(k).

In some aspects, the disclosure provides a synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first polynucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, and wherein the agonist comprises the nucleotide sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and 36.

In some aspects, the disclosure provides a synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first polynucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, and wherein the first polynucleotide and the second polynucleotide comprise the nucleotide sequences selected from the group consisting of:

(i) SEQ ID NO: 37 and 68, respectively;

(ii) SEQ ID NO: 38 and 69, respectively;

(iii) SEQ ID NO: 39 and 70, respectively;

(iv) SEQ ID NO: 40 and 71, respectively;

(v) SEQ ID NO: 41 and 72, respectively;

(vi) SEQ ID NO: 42 and 73, respectively;

(vii) SEQ ID NO: 43 and 74, respectively;

(viii) SEQ ID NO: 44 and 75, respectively;

(ix) SEQ ID NO: 45 and 76, respectively;

(x) SEQ ID NO: 46 and 77, respectively;

(xi) SEQ ID NO: 47 and 78, respectively;

(xii) SEQ ID NO: 48 and 79, respectively;

(xiii) SEQ ID NO: 49 and 80, respectively;

(xiv) SEQ ID NO: 50 and 81, respectively;

(xv) SEQ ID NO: 51 and 82, respectively;

(xvi) SEQ ID NO: 52 and 83, respectively;

(xvii) SEQ ID NO: 53 and 84, respectively;

(xviii) SEQ ID NO: 54 and 85, respectively;

(xix) SEQ ID NO: 55 and 86, respectively;

(xx) SEQ ID NO: 56 and 87, respectively;

(xxi) SEQ ID NO: 57 and 88, respectively;

(xxii) SEQ ID NO: 58 and 89, respectively;

(xxiii) SEQ ID NO: 59 and 89, respectively;

(xxiv) SEQ ID NO: 60 and 90, respectively;

(xxv) SEQ ID NO: 61 and 91, respectively;

(xxvi) SEQ ID NO: 62 and 92, respectively;

(xxvii) SEQ ID NO: 63 and 91, respectively;

(xxviii) SEQ ID NO: 64 and 93, respectively;

(xxix) SEQ ID NO: 65 and 94, respectively;

(xxx) SEQ ID NO: 66 and 95, respectively;

(xxxi) SEQ ID NO: 67 and 96, respectively; and (xxxii) SEQ ID NO: 63 and 97, respectively.

In some aspects, the disclosure provides a synthetic RIG-I-like receptor (RLR) agonist that specifically binds to a RIG-I-like receptor (RLR), wherein the agonist comprises a blunt-ended, hairpin RNA comprising at least one or more nucleotides comprising inosine which base pairs with cytidine, and wherein the agonist comprises the nucleotide sequence selected from the group consisting of SEQ ID NOs: 22, 23 and 25.

In some aspects, the disclosure provides a synthetic RIG-I-like receptor (RLR) agonist that specifically binds to a RIG-I-like receptor (RLR), wherein the agonist comprises a blunt-ended, hairpin RNA comprising at least one or more nucleotides comprising inosine which base pairs with cytidine, wherein the agonist comprises the formula 5'-($N_1$—$N_2$—$X_1$)-L-($X_2$—$N_3$—$N_4$)-3', wherein ($N_1$—$N_2$—$X_1$) comprises a first polynucleotide and ($X_2$—$N_3$—$N_4$) comprises a second polynucleotide, and wherein the first polynucleotide and the second polynucleotide comprise the nucleotide sequences selected from the group consisting of:

(i) SEQ ID NO: 58 and 89, respectively;
(ii) SEQ ID NO: 59 and 89, respectively; and
(iii) SEQ ID NO: 61 and 91, respectively.

In some aspects, the disclosure provides a synthetic RIG-I-like receptor (RLR) agonist that specifically binds to RIG-I-like receptors (RLRs), wherein the agonist comprises a blunt-ended, hairpin RNA comprising a non-nucleotide linker, wherein the agonist comprises the formula 5'-($N_1$—$N_2$—$X_1$)-L-($X_2$—$N_3$—$N_4$)-3', wherein ($N_1$—$N_2$—$X_1$) comprises a first polynucleotide and ($X_2$—$N_3$—$N_4$) comprises a second polynucleotide, and wherein the first polynucleotide and the second polynucleotide comprise the nucleotide sequences selected from the group consisting of:

(i) SEQ ID NO: 37 and 68, respectively;
(ii) SEQ ID NO: 38 and 69, respectively;
(iii) SEQ ID NO: 39 and 70, respectively;
(iv) SEQ ID NO: 40 and 71, respectively;
(v) SEQ ID NO: 41 and 72, respectively;
(vi) SEQ ID NO: 42 and 73, respectively;
(vii) SEQ ID NO: 43 and 74, respectively;
(viii) SEQ ID NO: 44 and 75, respectively;
(ix) SEQ ID NO: 45 and 76, respectively;
(x) SEQ ID NO: 46 and 77, respectively;
(xi) SEQ ID NO: 47 and 78, respectively;
(xii) SEQ ID NO: 48 and 79, respectively;
(xiii) SEQ ID NO: 49 and 80, respectively;
(xiv) SEQ ID NO: 50 and 81, respectively;
(xv) SEQ ID NO: 51 and 82, respectively;
(xvi) SEQ ID NO: 52 and 83, respectively;
(xvii) SEQ ID NO: 53 and 84, respectively;
(xviii) SEQ ID NO: 54 and 85, respectively;
(xix) SEQ ID NO: 55 and 86, respectively;
(xx) SEQ ID NO: 56 and 87, respectively;
(xxi) SEQ ID NO: 57 and 88, respectively;
(xxii) SEQ ID NO: 58 and 89, respectively;
(xxiii) SEQ ID NO: 59 and 89, respectively;
(xxiv) SEQ ID NO: 60 and 90, respectively;
(xxv) SEQ ID NO: 61 and 91, respectively;
(xxvi) SEQ ID NO: 62 and 92, respectively;
(xxvii) SEQ ID NO: 63 and 91, respectively;
(xxviii) SEQ ID NO: 64 and 93, respectively;
(xxix) SEQ ID NO: 65 and 94, respectively;
(xxx) SEQ ID NO: 66 and 95, respectively;
(xxxi) SEQ ID NO: 67 and 96, respectively; and
(xxxii) SEQ ID NO: 63 and 97, respectively.

In some aspects, the disclosure provides RLR agonists wherein the nucleotide sequence comprising the agonist is not complementary to a genomic DNA sequence or mRNA sequence, wherein the RLR agonist does not participate in RNA interference, and wherein the RLR agonist does not silence gene expression.

RLR Agonists Comprising Modified Nucleobases, Nucleosides, or Nucleotides

In some embodiments, an RLR agonist of the disclosure comprises one or more modified nucleobases, nucleosides, or nucleotides. In some embodiments, modified RLR agonists may have useful properties, including enhanced stability, intracellular retention, enhanced target binding, and/or an increase in induction of the innate immune response of a cell into which the RLR agonist is introduced, as compared to a reference unmodified RLR agonist. Therefore, use of modified RLR agonists may enhance the efficiency of target binding, intracellular retention of nucleic acids, as well as possess reduced immunogenicity. In one embodiment, the agonist provided by the disclosure is comprised of one or more oligonucleotides that comprise at least one region modified to increase target binding affinity. Affinity of an oligonucleotide for its target polypeptide (e.g. an RLR receptor) can be determined by, for example, measuring the degree of fluorescence polarization (FP) upon binding of a fluorescently-labeled oligonucleotide to its target (Moerke (2009) Curr Protoc Chem Biol 1(1):1-15).

In another embodiment, the RLR agonist provided by the disclosure is comprised of at least one oligonucleotide comprising at least one region comprising at least one modified nucleobase, nucleoside, or nucleotide that increases the stability of the duplex. The stability of the duplex can be routinely determined by measuring the Tm of the duplex, which is the temperature at which the two oligonucleotide strands comprising the duplex dissociate; dissociation is detected spectrophotometrically. The higher the Tm, the greater the stability of the duplex.

In one embodiment, the region of the oligonucleotide which is modified to increase duplex stability comprises at least one nucleotide modified at the 2' position of the sugar, most preferably a 2'-O-alkyl, 2'-O-alkyl-O-alkyl or 2'-fluoro-modified nucleotide. In another embodiment, an oligonucleotide comprising an RLR agonist is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than an unmodified oligonucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. In one embodiment, oligonucleotides which contain at least one phosphorothioate modification are used. In some cases, oligonucleotide modifications which enhance target binding affinity are also, independently, able to enhance nuclease resistance (De Mesmaeker et al., 1995, Acc. Chem. Res. 28:366-374).

Specific examples of some oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. In some embodiments, oligonucleotides with phosphorothioate backbones (including those synthesized in a stereo-specific manner) and those with heteroatom backbones, particularly CH2-NH—O—CH2, CH2-N (CH3)-O—CH2 [known as a methylene(methylimino) or MMI backbone], CH2-O—N(CH3)-CH2, CH2-N(CH3)-N (CH3)-CH2 and O—N(CH3)-CH2-CH2 backbones, wherein the native phosphodiester backbone is represented as O—P—O—CH2) are used. The amide backbones disclosed by De Mesmaeker et al. (1995, Acc. Chem. Res. 28:366-374) are also used in some embodiments. Oligonucleotides may also contain one or more substituted sugar moieties. In some embodiments, oligonucleotides comprise one of the following at the 2' position: OH, SH, SCH3, F, OCN, OCH3OCH3, OCH3O(CH2)nCH3, O(CH2)nNH2 or O(CH2)nCH3 where n is from 1 to about 10; C1 to C10 lower alkyl, alkoxyalkoxy (also known in the art as O-alkyl-O-alkyl), substituted lower alkyl, alkaryl or aralkyl; Cl; Br; CN; CF3; OCF3; O—, S—, or N-alkyl; O—, S—, or N-alkenyl; SOCH3; SO2CH3; ONO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In one embodiment, a modification includes 2'-methoxyethoxy [2'-O—CH2CH2OCH3, also known as 2'-O-(2-methoxyethyl) or 2'-MOE] (Martin et al., Helv. Chim. Acta, 1995, 78, 486). In some embodiments, modifications include 2'-methoxy (2'-O—CH3), 2'-propoxy (2'-OCH2CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, N6(6-aminohexyl)adenine and 2,6-diaminopurine. Kornberg, A., DNA Replication, W.H. Freeman & Co., San Francisco, 1980, pp 75-77; Gebeyehu, G., et al., 1987, Nucl. Acids Res. 15:4513). A "universal" base known in the art, e.g., inosine, may be included. 5-me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently used in some embodiments as base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA, 1989, 86, 6553), cholic acid (Manoharan et al., Bioorg. Med. Chem. Let., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764.

It is not necessary for all positions in a given oligonucleotide to be uniformly modified, and in fact more than one of the aforementioned modifications may be incorporated in a single oligonucleotide or even at within a single nucleoside within an oligonucleotide.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the knowledge and ability of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In some embodiments, an RLR agonist includes one or more (e.g., 1, 2, 3 or 4) different modified nucleobases, nucleosides, or nucleotides. In some embodiments, an RLR agonist includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified RLR agonist may have reduced degradation in a cell into which the RLR agonist is introduced, relative to a corresponding unmodified RLR agonist.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s$^2$U), 4-thio-uridine (s$^4$U), 4-thio-pseudouridine, 2-thio-pseudouridine, 5-hydroxy-uridine (ho$^5$U), 5-aminoallyl-uridine, 5-halo-uridine (e.g., 5-iodo-uridineor 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine (™$^5$U), 1-taurinomethyl-pseudouridine, 5-taurinomethyl-2-thio-uridine (τm$^5$s$^2$U), 1-taurinomethyl-4-thio-pseudouridine, 5-methyl-uridine (m$^5$U, i.e., having the nucleobase deoxythymine), 1-methyl-pseudouridine (m$^1$ψ), 5-methyl-2-thio-uridine (m$^5$s$^2$U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^42$ Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2, 6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2$ $m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl)adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine (m6t6A), 2-methylthio-N6-threonylcarbamoyl-adenosine ($ms^2g^6A$), N6,N6-dimethyl-adenosine ($m^62$ A), N6-hydroxynorvalylcarbamoyl-adenosine ($hn^6A$), 2-methylthio-N6-hydroxynoryalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^62$ Am), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^22$ G), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, a-thio-guanosine, 2'-O-methyl-guanosine (Gm), N2-methyl-2'-O-methyl-guanosine ($m^2Gm$), N2,N2-dimethyl-2'-O-methyl-guanosine ($m^22$ Gm), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, O6-methyl-guanosine, 2'-F-ara-guanosine, and 2'-F-guanosine.

In some embodiments, an RLR agonist of the disclosure includes a combination of one or more of the aforementioned modified nucleobases (e.g., a combination of 2, 3 or 4 of the aforementioned modified nucleobases.)

In certain embodiments, an RLR agonist of the disclosure is uniformly modified (i.e., fully modified, modified through-out the entire sequence) for a particular modification. For example, an RLR agonist can be uniformly modified with 5-methyl-cytidine ($m^5C$), meaning that all cytosine residues in the mRNA sequence are replaced with 5-methyl-cytidine ($m^5C$). Similarly, an RLR agonist of the disclosure can be uniformly modified for any type of nucleoside residue present in the sequence by replacement with a modified residue such as those set forth above.

Examples of nucleoside modifications and combinations thereof that may be present in an RLR agonist of the present disclosure include, but are not limited to, those described in PCT Patent Application Publications: WO2012045075, WO2014081507, WO2014093924, WO2014164253, and WO2014159813.

The RLR agonists of the disclosure can include a combination of modifications to the sugar, the nucleobase, and/or the internucleoside linkage. These combinations can include any one or more modifications described herein.

Examples of modified nucleosides and modified nucleoside combinations are provided below in Table 1 and Table 2. These combinations of modified nucleotides can be used to form the RLR agonists of the disclosure. In certain embodiments, the modified nucleosides may be partially or completely substituted for the natural nucleotides of the RLR agonists of the disclosure. As a non-limiting example, the natural nucleotide uridine may be substituted with a modified nucleoside described herein. In another non-limiting example, the natural nucleoside uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9% of the natural uridines) with at least one of the modified nucleoside disclosed herein.

TABLE 1

Combinations of Nucleoside Modifications

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

TABLE 2

| Modified Nucleosides and Combinations Thereof |
|---|
| 1-(2,2,2-Trifluoroethyl)pseudo-UTP |
| 1-Ethyl-pseudo-UTP |
| 1-Methyl-pseudo-U-alpha-thio-TP |
| 1-methyl-pseudouridine TP, ATP, GTP, CTP |
| 1-methyl-pseudo-UTP/5-methyl-CTP/ATP/GTP |
| 1-methyl-pseudo-UTP/CTP/ATP/GTP |
| 1-Propyl-pseudo-UTP |
| 25% 5-Aminoallyl-CTP + 75% CTP/25% 5-Methoxy-UTP + 75% UTP |
| 25% 5-Aminoallyl-CTP + 75% CTP/75% 5-Methoxy-UTP + 25% UTP |
| 25% 5-Bromo-CTP + 75% CTP/25% 5-Methoxy-UTP + 75% UTP |

TABLE 2-continued

| Modified Nucleosides and Combinations Thereof |
|---|
| 25% 5-Bromo-CTP + 75% CTP/75% 5-Methoxy-UTP + 25% UTP |
| 25% 5-Bromo-CTP + 75% CTP/1-Methyl-pseudo-UTP |
| 25% 5-Carboxy-CTP + 75% CTP/25% 5-Methoxy-UTP + 75% UTP |
| 25% 5-Carboxy-CTP + 75% CTP/75% 5-Methoxy-UTP + 25% UTP |
| 25% 5-Ethyl-CTP + 75% CTP/25% 5-Methoxy-UTP + 75% UTP |
| 25% 5-Ethyl-CTP + 75% CTP/75% 5-Methoxy-UTP + 25% UTP |
| 25% 5-Ethynyl-CTP + 75% CTP/25% 5-Methoxy-UTP + 75% UTP |
| 25% 5-Ethynyl-CTP + 75% CTP/75% 5-Methoxy-UTP + 25% UTP |
| 25% 5-Fluoro-CTP + 75% CTP/25% 5-Methoxy-UTP + 75% UTP |
| 25% 5-Fluoro-CTP + 75% CTP/75% 5-Methoxy-UTP + 25% UTP |
| 25% 5-Formyl-CTP + 75% CTP/25% 5-Methoxy-UTP + 75% UTP |
| 25% 5-Formyl-CTP + 75% CTP/75% 5-Methoxy-UTP + 25% UTP |
| 25% 5-Hydroxymethyl-CTP + 75% CTP/25% 5-Methoxy-UTP + 75% UTP |
| 25% 5-Hydroxymethyl-CTP + 75% CTP/75% 5-Methoxy-UTP + 25% UTP |
| 25% 5-Iodo-CTP + 75% CTP/25% 5-Methoxy-UTP + 75% UTP |
| 25% 5-Iodo-CTP + 75% CTP/75% 5-Methoxy-UTP + 25% UTP |
| 25% 5-Methoxy-CTP + 75% CTP/25% 5-Methoxy-UTP + 75% UTP |
| 25% 5-Methoxy-CTP + 75% CTP/75% 5-Methoxy-UTP + 25% UTP |
| 25% 5-Methyl-CTP + 75% CTP/25% 5-Methoxy-UTP + 75% 1-Methyl-pseudo-UTP |
| 25% 5-Methyl-CTP + 75% CTP/25% 5-Methoxy-UTP + 75% UTP |
| 25% 5-Methyl-CTP + 75% CTP/50% 5-Methoxy-UTP + 50% 1-Methyl-pseudo-UTP |
| 25% 5-Methyl-CTP + 75% CTP/50% 5-Methoxy-UTP + 50% UTP |
| 25% 5-Methyl-CTP + 75% CTP/5-Methoxy-UTP |
| 25% 5-Methyl-CTP + 75% CTP/75% 5-Methoxy-UTP + 25% 1-Methyl-pseudo-UTP |
| 25% 5-Methyl-CTP + 75% CTP/75% 5-Methoxy-UTP + 25% UTP |
| 25% 5-Phenyl-CTP + 75% CTP/25% 5-Methoxy-UTP + 75% UTP |
| 25% 5-Phenyl-CTP + 75% CTP/75% 5-Methoxy-UTP + 25% UTP |
| 25% 5-Trifluoromethyl-CTP + 75% CTP/25% 5-Methoxy-UTP + 75% UTP |
| 25% 5-Trifluoromethyl-CTP + 75% CTP/75% 5-Methoxy-UTP + 25% UTP |
| 25% 5-Trifluoromethyl-CTP + 75% CTP/1-Methyl-pseudo-UTP |
| 25% N4-Ac-CTP + 75% CTP/25% 5-Methoxy-UTP + 75% UTP |
| 25% N4-Ac-CTP + 75% CTP/75% 5-Methoxy-UTP + 25% UTP |
| 25% N4-Bz-CTP + 75% CTP/25% 5-Methoxy-UTP + 75% UTP |
| 25% N4-Bz-CTP + 75% CTP/75% 5-Methoxy-UTP + 25% UTP |
| 25% N4-Methyl-CTP + 75% CTP/25% 5-Methoxy-UTP + 75% UTP |
| 25% N4-Methyl-CTP + 75% CTP/75% 5-Methoxy-UTP + 25% UTP |
| 25% Pseudo-iso-CTP + 75% CTP/25% 5-Methoxy-UTP + 75% UTP |
| 25% Pseudo-iso-CTP + 75% CTP/75% 5-Methoxy-UTP + 25% UTP |
| 25% 5-Bromo-CTP/75% CTP/Pseudo-UTP |
| 25% 5-methoxy-UTP/25% 5-methyl-CTP/ATP/GTP |
| 25% 5-methoxy-UTP/5-methyl-CTP/ATP/GTP |
| 25% 5-methoxy-UTP/75% 5-methyl-CTP/ATP/GTP |
| 25% 5-methoxy-UTP/CTP/ATP/GTP |
| 25% 5-metoxy-UTP/50% 5-methyl-CTP/ATP/GTP |
| 2-Amino-ATP |
| 2-Thio-CTP |
| 2-thio-pseudouridine TP, ATP, GTP, CTP |
| 2-Thio-pseudo-UTP |
| 2-Thio-UTP |
| 3-Methyl-CTP |
| 3-Methyl-pseudo-UTP |
| 4-Thio-UTP |
| 50% 5-Bromo-CTP + 50% CTP/1-Methyl-pseudo-UTP |
| 50% 5-Hydroxymethyl-CTP + 50% CTP/1-Methyl-pseudo-UTP |
| 50% 5-methoxy-UTP/5-methyl-CTP/ATP/GTP |
| 50% 5-Methyl-CTP + 50% CTP/25% 5-Methoxy-UTP + 75% 1-Methyl-pseudo-UTP |
| 50% 5-Methyl-CTP + 50% CTP/25% 5-Methoxy-UTP + 75% UTP |
| 50% 5-Methyl-CTP + 50% CTP/50% 5-Methoxy-UTP + 50% 1-Methyl-pseudo-UTP |
| 50% 5-Methyl-CTP + 50% CTP/50% 5-Methoxy-UTP + 50% UTP |
| 50% 5-Methyl-CTP + 50% CTP/5-Methoxy-UTP |
| 50% 5-Methyl-CTP + 50% CTP/75% 5-Methoxy-UTP + 25% 1-Methyl-pseudo-UTP |
| 50% 5-Methyl-CTP + 50% CTP/75% 5-Methoxy-UTP + 25% UTP |
| 50% 5-Trifluoromethyl-CTP + 50% CTP/1-Methyl-pseudo-UTP |
| 50% 5-Bromo-CTP/50% CTP/Pseudo-UTP |
| 50% 5-methoxy-UTP/25% 5-methyl-CTP/ATP/GTP |
| 50% 5-methoxy-UTP/50% 5-methyl-CTP/ATP/GTP |
| 50% 5-methoxy-UTP/75% 5-methyl-CTP/ATP/GTP |
| 50% 5-methoxy-UTP/CTP/ATP/GTP |

TABLE 2-continued

| Modified Nucleosides and Combinations Thereof |
|---|
| 5-Aminoallyl-CTP |
| 5-Aminoallyl-CTP/5-Methoxy-UTP |
| 5-Aminoallyl-UTP |
| 5-Bromo-CTP |
| 5-Bromo-CTP/5-Methoxy-UTP |
| 5-Bromo-CTP/1-Methyl-pseudo-UTP |
| 5-Bromo-CTP/Pseudo-UTP |
| 5-bromocytidine TP, ATP, GTP, UTP |
| 5-Bromo-UTP |
| 5-Carboxy-CTP/5-Methoxy-UTP |
| 5-Ethyl-CTP/5-Methoxy-UTP |
| 5-Ethynyl-CTP/5-Methoxy-UTP |
| 5-Fluoro-CTP/5-Methoxy-UTP |
| 5-Formyl-CTP/5-Methoxy-UTP |
| 5-Hydroxy-methyl-CTP/5-Methoxy-UTP |
| 5-Hydroxymethyl-CTP |
| 5-Hydroxymethyl-CTP/1-Methyl-pseudo-UTP |
| 5-Hydroxymethyl-CTP/5-Methoxy-UTP |
| 5-hydroxymethyl-cytidine TP, ATP, GTP, UTP |
| 5-Iodo-CTP/5-Methoxy-UTP |
| 5-Me-CTP/5-Methoxy-UTP |
| 5-Methoxy carbonyl methyl-UTP |
| 5-Methoxy-CTP/5-Methoxy-UTP |
| 5-methoxy-uridine TP, ATP, GTP, UTP |
| 5-methoxy-UTP |
| 5-Methoxy-UTP |
| 5-Methoxy-UTP/N6-Isopentenyl-ATP |
| 5-methoxy-UTP/25% 5-methyl-CTP/ATP/GTP |
| 5-methoxy-UTP/5-methyl-CTP/ATP/GTP |
| 5-methoxy-UTP/75% 5-methyl-CTP/ATP/GTP |
| 5-methoxy-UTP/CTP/ATP/GTP |
| 5-Methyl-2-thio-UTP |
| 5-Methylaminomethyl-UTP |
| 5-Methyl-CTP/5-Methoxy-UTP |
| 5-Methyl-CTP/5-Methoxy-UTP(cap 0) |
| 5-Methyl-CTP/5-Methoxy-UTP(No cap) |
| 5-Methyl-CTP/25% 5-Methoxy-UTP + 75% 1-Methyl-pseudo-UTP |
| 5-Methyl-CTP/25% 5-Methoxy-UTP + 75% UTP |
| 5-Methyl-CTP/50% 5-Methoxy-UTP + 50% 1-Methyl-pseudo-UTP |
| 5-Methyl-CTP/50% 5-Methoxy-UTP + 50% UTP |
| 5-Methyl-CTP/5-Methoxy-UTP/N6-Me-ATP |
| 5-Methyl-CTP/75% 5-Methoxy-UTP + 25% 1-Methyl-pseudo-UTP |
| 5-Methyl-CTP/75% 5-Methoxy-UTP + 25% UTP |
| 5-Phenyl-CTP/5-Methoxy-UTP |
| 5-Trifluoro-methyl-CTP/5-Methoxy-UTP |
| 5-Trifluoromethyl-CTP |
| 5-Trifluoromethyl-CTP/5-Methoxy-UTP |
| 5-Trifluoromethyl-CTP/1-Methyl-pseudo-UTP |
| 5-Trifluoromethyl-CTP/Pseudo-UTP |
| 5-Trifluoromethyl-UTP |
| 5-trifluromethylcytidine TP, ATP, GTP, UTP |
| 75% 5-Aminoallyl-CTP + 25% CTP/25% 5-Methoxy-UTP + 75% UTP |
| 75% 5-Aminoallyl-CTP + 25% CTP/75% 5-Methoxy-UTP + 25% UTP |
| 75% 5-Bromo-CTP + 25% CTP/25% 5-Methoxy-UTP + 75% UTP |
| 75% 5-Bromo-CTP + 25% CTP/75% 5-Methoxy-UTP + 25% UTP |
| 75% 5-Carboxy-CTP + 25% CTP/25% 5-Methoxy-UTP + 75% UTP |
| 75% 5-Carboxy-CTP + 25% CTP/75% 5-Methoxy-UTP + 25% UTP |
| 75% 5-Ethyl-CTP + 25% CTP/25% 5-Methoxy-UTP + 75% UTP |
| 75% 5-Ethyl-CTP + 25% CTP/75% 5-Methoxy-UTP + 25% UTP |
| 75% 5-Ethynyl-CTP + 25% CTP 25% 5-Methoxy-UTP + 75% UTP |
| 75% 5-Ethynyl-CTP + 25% CTP/75% 5-Methoxy-UTP + 25% UTP |
| 75% 5-Fluoro-CTP + 25% CTP/25% 5-Methoxy-UTP + 75% UTP |
| 75% 5-Fluoro-CTP + 25% CTP/75% 5-Methoxy-UTP + 25% UTP |
| 75% 5-Formyl-CTP + 25% CTP/25% 5-Methoxy-UTP + 75% UTP |
| 75% 5-Formyl-CTP + 25% CTP/75% 5-Methoxy-UTP + 25% UTP |
| 75% 5-Hydroxymethyl-CTP + 25% CTP/25% 5-Methoxy-UTP + 75% UTP |
| 75% 5-Hydroxymethyl-CTP + 25% CTP/75% 5-Methoxy-UTP + 25% UTP |
| 75% 5-Iodo-CTP + 25% CTP/25% 5-Methoxy-UTP + 75% UTP |
| 75% 5-Iodo-CTP + 25% CTP/75% 5-Methoxy-UTP + 25% UTP |
| 75% 5-Methoxy-CTP + 25% CTP/25% 5-Methoxy-UTP + 75% UTP |
| 75% 5-Methoxy-CTP + 25% CTP/75% 5-Methoxy-UTP + 25% UTP |
| 75% 5-methoxy-UTP/5-methyl-CTP/ATP/GTP |
| 75% 5-Methyl-CTP + 25% CTP/25% 5-Methoxy-UTP + 75% 1-Methyl-pseudo-UTP |
| 75% 5-Methyl-CTP + 25% CTP/25% 5-Methoxy-UTP + 75% UTP |
| 75% 5-Methyl-CTP + 25% CTP/50% 5-Methoxy-UTP + 50% 1-Methyl-pseudo-UTP |
| 75% 5-Methyl-CTP + 25% CTP/50% 5-Methoxy-UTP + 50% UTP |
| 75% 5-Methyl-CTP + 25% CTP/5-Methoxy-UTP |
| 75% 5-Methyl-CTP + 25% CTP/75% 5-Methoxy-UTP + 25% 1-Methyl-pseudo-UTP |
| 75% 5-Methyl-CTP + 25% CTP/75% 5-Methoxy-UTP + 25% UTP |
| 75% 5-Phenyl-CTP + 25% CTP/25% 5-Methoxy-UTP + 75% UTP |
| 75% 5-Phenyl-CTP + 25% CTP/75% 5-Methoxy-UTP + 25% UTP |
| 75% 5-Trifluoromethyl-CTP + 25% CTP/5% 5-Methoxy-UTP + 75% UTP |
| 75% 5-Trifluoromethyl-CTP + 25% CTP/75% 5-Methoxy-UTP + 25% UTP |
| 75% 5-Trifluoromethyl-CTP + 25% CTP/1-Methyl-pseudo-UTP |
| 75% N4-Ac-CTP + 25% CTP/25% 5-Methoxy-UTP + 75% UTP |
| 75% N4-Ac-CTP + 25% CTP/75% 5-Methoxy-UTP + 25% UTP |
| 75% N4-Bz-CTP + 25% CTP/25% 5-Methoxy-UTP + 75% UTP |
| 75% N4-Bz-CTP + 25% CTP/75% 5-Methoxy-UTP + 25% UTP |
| 75% N4-Methyl-CTP + 25% CTP/25% 5-Methoxy-UTP + 75% UTP |
| 75% N4-Methyl-CTP + 25% CTP/75% 5-Methoxy-UTP + 25% UTP |
| 75% Pseudo-iso-CTP + 25% CTP/25% 5-Methoxy-UTP + 75% UTP |
| 75% Pseudo-iso-CTP + 25% CTP/75% 5-Methoxy-UTP + 25% UTP |
| 75% 5-Bromo-CTP/25% CTP/1-Methyl-pseudo-UTP |
| 75% 5-Bromo-CTP/25% CTP/Pseudo-UTP |
| 75% 5-methoxy-UTP/25% 5-methyl-CTP/ATP/GTP |
| 75% 5-methoxy-UTP/50% 5-methyl-CTP/ATP/GTP |
| 75% 5-methoxy-UTP/75% 5-methyl-CTP/ATP/GTP |
| 75% 5-methoxy-UTP/CTP/ATP/GTP |
| 8-Aza-ATP |
| Alpha-thio-CTP |
| CTP/25% 5-Methoxy-UTP + 75% 1-Methyl-pseudo-UTP |
| CTP/25% 5-Methoxy-UTP + 75% UTP |
| CTP/50% 5-Methoxy-UTP + 50% 1-Methyl-pseudo-UTP |
| CTP/50% 5-Methoxy-UTP + 50% UTP |
| CTP/5-Methoxy-UTP |
| CTP/5-Methoxy-UTP (cap 0) |
| CTP/5-Methoxy-UTP(No cap) |
| CTP/75% 5-Methoxy-UTP + 25% 1-Methyl-pseudo-UTP |
| CTP/75% 5-Methoxy-UTP + 25% UTP |
| CTP/UTP(No cap) |
| N1-Me-GTP |
| N4-Ac-CTP |
| N4Ac-CTP/1-Methyl-pseudo-UTP |
| N4Ac-CTP/5-Methoxy-UTP |
| N4-acetyl-cytidine TP, ATP, GTP, UTP |
| N4-Bz-CTP/5-Methoxy-UTP |
| N4-methyl CTP |
| N4-Methyl-CTP/5-Methoxy-UTP |
| Pseudo-iso-CTP/5-Methoxy-UTP |
| PseudoU-alpha-thio-TP |
| pseudouridine TP, ATP, GTP, CTP |
| pseudo-UTP/5-methyl-CTP/ATP/GTP |
| UTP-5-oxyacetic acid Me ester |
| Xanthosine |

According to the disclosure, polynucleotides of the disclosure may be synthesized to comprise the combinations or single modifications of Table 1 or Table 2.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

Methods of Making RLR Agonists

RLR agonists of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In one embodiment, RLR agonists are made using IVT enzymatic synthesis methods. Methods of making polynucleotides by IVT are known in the art and are described in International Application PCT/US2013/30062, the contents of which are incorporated herein by reference in their entirety. Accordingly, the present disclosure also includes polynucleotides, e.g., DNA, constructs and vectors that may be used to in vitro transcribe an RLR agonist described herein.

Non-natural modified nucleobases may be introduced into polynucleotides, e.g., RNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

Either enzymatic or chemical ligation methods may be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

The synthesis of oligonucleotides, polynucleotides, and conjugations and ligations thereof, is further described in Taskova et al., (2017) Chembiochem 18(17):1671-1682; Gooding et al., (2016) Eur J Pharm Biopharm 107:321-40; Menzi et al., (2015) Future Med Chem 7(13):1733-49; Winkler J., (2013) Ther Deliv. (7):791-809; Singh et al., (2010) Chem Soc Rev 39(6):2054-70; and Lu et al., (2010) Bioconjug Chem 21(2):187-202.

Virus-Like Particles (VLPs)

In some embodiments, the disclosure provides compositions comprising at least one RLR agonist described and a virus-like particle (VLP). In some embodiments, an RLR agonist is bound to the VLP. In some embodiments, an RLR agonist is packaged in the VLP.

Virus-like particles in the context of the present application refer to structures resembling a virus particle, but which are not pathogenic. In general, virus-like particles lack the viral genome and, therefore, are noninfectious. Also, virus-like particles can be produced in large quantities by heterologous expression and can be easily purified.

Exemplary virus-like particles suitable for use in the compositions described herein are provided in PCT Publication Nos. WO 2003/024481 and WO 2004/084940, each of which is herein incorporated in its entirety by this reference.

In some embodiments, the virus-like particle is a recombinant virus-like particle. The skilled artisan can produce VLPs using recombinant DNA technology and virus coding sequences which are readily available to the public and described herein. For example, the coding sequence of a virus envelope or core protein can be engineered for expression in a baculovirus expression vector using a commercially available baculovirus vector, under the regulatory control of a virus promoter, with appropriate modifications of the sequence to allow functional linkage of the coding sequence to the regulatory sequence. The coding sequence of a virus envelope or core protein can also be engineered for expression in a bacterial expression vector, for example.

Examples of VLPs include, but are not limited to, the capsid proteins of Hepatitis B virus (Ulrich, et al., Virus Res. 50:141-182 (1998)), measles virus (Wanes, et al., Gene 160:173-178 (1995)), Sindbis virus, rotavirus (U.S. Pat. Nos. 5,071,651 and 5,374,426), foot-and-mouth-disease virus (Twomey, et al., Vaccine 13:1603-1610, (1995)), Norwalk virus (Jiang, X., et al., Science 250:1580-1583 (1990); Matsui, S. M., et al., J. Clin. Invest. 87:1456-1461 (1991)), the retroviral GAG protein (PCT Patent Appl. No. WO 96/30523), the retrotransposon Ty protein p1, the surface protein of Hepatitis B virus (WO 92/11291), human papilloma virus (WO 98/15631), human polyoma virus (Sasnauskas K., et al., Biol. Chem. 380(3):381-386 (1999); Sasnauskas K., et al., Generation of recombinant virus-like particles of different polyomaviruses in yeast 3rd International Workshop "Virus-like particles as vaccines." Berlin, Sep. 26-29, 2001), RNA phages, Ty, fr-phage, GA-phage, AP 205-phage and, in particular, Qβ-phage.

As will be readily apparent to those skilled in the art, the VLP of the disclosure is not limited to any specific form. The particle can be synthesized chemically or through a biological process, which can be natural or non-natural. By way of example, this type of embodiment includes a virus-like particle or a recombinant form thereof. In some embodiments, the VLP comprises recombinant polypeptides of Rotavirus; recombinant polypeptides of Norwalk virus; recombinant polypeptides of Alphavirus; recombinant proteins which form bacterial pili or pilus-like structures; recombinant polypeptides of Foot and Mouth Disease virus; recombinant polypeptides of measles virus, recombinant polypeptides of Sindbis virus, recombinant polypeptides of Retrovirus; recombinant polypeptides of Hepatitis B virus (e.g., a HBcAg); recombinant polypeptides of Tobacco mosaic virus; recombinant polypeptides of Flock House Virus; recombinant polypeptides of human Papillomavirus; recombinant polypeptides of Polyoma virus and, in particular, recombinant polypeptides of human Polyoma virus, and in particular recombinant polypeptides of BK virus; recombinant polypeptides of bacteriophages, recombinant polypeptides of RNA phages; recombinant polypeptides of Ty; recombinant polypeptides of fr-phage, recombinant polypeptides of GA-phage, recombinant polypeptides of AP 205-phage and, in particular, recombinant polypeptides of Qβ-phage. The virus-like particle can further comprise, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts.

In some embodiments, the virus-like particle comprises recombinant proteins, or fragments thereof, of a RNA-phage. In some embodiments, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; and 1) bacteriophage PP7.

In some embodiments, the virus-like particle comprises recombinant proteins, or fragments thereof, of the RNA-bacteriophage Qβ or of the RNA-bacteriophage fr. In some embodiments, the virus-like particle comprises recombinant proteins, or fragments thereof, of the RNA-bacteriophage Qβ.

In some embodiments, the recombinant proteins comprise coat proteins of RNA phages.

RNA-phage coat proteins forming capsids or VLPs, or fragments of the bacteriophage coat proteins compatible with self-assembly into a capsid or a VLP, are, therefore, further embodiments of the present disclosure. Bacteriophage Qβ coat proteins, for example, can be expressed recombinantly in *E. coli*. Further, upon such expression these proteins spontaneously form capsids. Additionally, these capsids form a structure with an inherent repetitive organization.

Examples of bacteriophage coat proteins which can be used to prepare compositions of the disclosure include the coat proteins of RNA bacteriophages such as bacteriophage Qβ (SEQ ID NO: 112; PIR Database, Accession No. VCBPQb referring to Qβ CP and SEQ ID NO: 113; Accession No. AAA16663 referring to Qβ A1 protein), bacteriophage R17 (SEQ ID NO: 114; PIR Accession No. VCBPR7), bacteriophage fr (SEQ ID NO: 115; PIR Accession No. VCBPFR), bacteriophage GA (SEQ ID NO: 116; GenBank Accession No. NP-040754), bacteriophage SP (SEQ ID NO: 117; GenBank Accession No. CAA30374 referring to SP CP and SEQ ID NO: 118; Accession No. referring to SP A1 protein), bacteriophage MS2 (SEQ ID NO: 119; PIR Accession No. VCBPM2), bacteriophage M11 (SEQ ID NO: 120; GenBank Accession No. AAC06250), bacteriophage MX1 (SEQ ID NO: 121; GenBank Accession No. AAC14699), bacteriophage NL95 (SEQ ID NO: 122; GenBank Accession No. AAC14704), bacteriophage f2 (SEQ ID NO: 123; GenBank Accession No. P03611), bacteriophage PP7 (SEQ ID NO: 124). Furthermore, the A1 protein of bacteriophage Qβ or C-terminal truncated forms missing as much as 100, 150 or 180 amino acids from its C-terminus may be incorporated in a capsid assembly of Qβ coat proteins. Generally, the percentage of Qβ A1 protein relative to Qβ CP in the capsid assembly will be limited, in order to ensure capsid formation.

Qβ coat protein has also been found to self-assemble into capsids when expressed in *E. coli* (Kozlovska T M. et al., GENE 137: 133-137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., Structure 4: 543-5554 (1996)) leading to a remarkable stability of the capsid of Qβ coat protein. Capsids or VLPs made from recombinant Qβ coat protein may contain, however, subunits not linked via disulfide links to other subunits within the capsid, or incompletely linked. Thus, upon loading recombinant Qβ capsid on non-reducing SDS-PAGE, bands corresponding to monomeric Qβ coat protein as well as bands corresponding to the hexamer or pentamer of Qβ coat protein are visible. Incompletely disulfide-linked subunits could appear as dimer, trimer or even tetramer bands in non-reducing SDS-PAGE. Qβ capsid protein also shows unusual resistance to organic solvents and denaturing agents. It has been observed that DMSO and acetonitrile concentrations as high as 30%, and Guanidinium concentrations as high as 1 M do not affect the stability of the capsid. The high stability of the capsid of Qβ coat protein is an advantageous feature, in particular, for its use in immunization and vaccination of mammals and humans in accordance of the present invention.

Upon expression in *E. coli*, the N-terminal methionine of Qβ coat protein is usually removed, as observed by N-terminal Edman sequencing described in Stoll, E. et al. J. Biol. Chem. 252:990-993 (1977). VLP composed from Qβ coat proteins where the N-terminal methionine has not been removed, or VLPs comprising a mixture of Qβ coat proteins where the N-terminal methionine is either cleaved or present are also within the scope of the present disclosure.

Further RNA phage coat proteins have also been shown to self-assemble upon expression in a bacterial host (Kastelein, R A. et al., Gene 23: 245-254 (1983), Kozlovskaya, T M. et al., Dokl. Akad. Nauk SSSR 287: 452-455 (1986), Adhin, M R. et al., Virology 170: 238-242 (1989), Ni, C Z., et al., Protein Sci. 5: 2485-2493 (1996), Priano, C. et al., J. Mol. Biol. 249: 283-297 (1995)). The Qβ phage capsid contains, in addition to the coat protein, the so called read-through protein A1 and the maturation protein A2. A1 is generated by suppression at the UGA stop codon and has a length of 329 aa. In some embodiments, the capsid of phage Qβ recombinant coat protein used in the disclosure is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. Biochemistry 28: 71-76 (1989); Lim F. et al., J. Biol. Chem. 271: 31839-31845 (1996)). The stem loop and RNA in general are known to be involved in the virus assembly (Golmohammadi, R. et al., Structure 4: 543-5554 (1996)).

In some embodiments, the virus-like particle comprises recombinant proteins, or fragments thereof, of a RNA-phage, wherein the recombinant proteins comprise mutant coat proteins of a RNA phage, preferably of mutant coat proteins of the RNA phages mentioned above. In some embodiments, the mutant coat proteins of the RNA phage have been modified by removal of at least one lysine residue by way of substitution, or by addition of at least one lysine residue by way of substitution; alternatively, the mutant coat proteins of the RNA phage have been modified by deletion of at least one lysine residue, or by addition of at least one lysine residue by way of insertion.

In some embodiments, the virus-like particle comprises recombinant proteins, or fragments thereof, of the RNA-bacteriophage Qβ, wherein the recombinant proteins comprise coat proteins having an amino acid sequence of SEQ ID NO: 112, or a mixture of coat proteins having amino acid sequences of SEQ ID NO: 112 and of SEQ ID NO: 113 or mutants of SEQ ID NO: 113 and wherein the N-terminal methionine is preferably cleaved.

In some embodiments, the virus-like particle comprises recombinant proteins of Qβ or fragments thereof, wherein the recombinant proteins comprise mutant Qβ coat proteins. In some embodiments, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLPs can, thus, be used in the practice of the invention: "Qβ240" (Lys13-Arg; SEQ ID NO: 125), "Qβ-243" (Asn 10-Lys; SEQ ID NO: 126), "Qβ-250" (Lys 2-Arg, Lys13-Arg; SEQ ID NO: 127), "Qβ-251" (SEQ ID NO: 128) and "Qβ-259" (Lys 2-Arg, Lys16-Arg; SEQ ID NO: 129). Thus, in some embodiments, the virus-like particle comprises recombinant proteins of mutant Qβ coat proteins, which comprise proteins having an amino acid sequence selected from the group of a) the amino acid sequence of SEQ ID NO: 125; b) the amino acid sequence of SEQ ID NO: 126; c) the amino acid sequence of SEQ ID NO: 127; d) the amino acid sequence of SEQ ID NO: 128; and e) the amino acid sequence of SEQ ID NO: 129. The construction, expression and purification of the above indicated Qβ coat proteins, mutant Qβ coat protein VLPs and capsids, respectively, are disclosed in US Publication US 2003-0175290, herein incorporated by this reference in its entirety. In particular is hereby referred to Example 18 of above mentioned application.

In some embodiments, the virus-like particle comprises recombinant proteins of Qβ, or fragments thereof, wherein the recombinant proteins comprise a mixture of either one of the foregoing Qβ mutants and the corresponding A1 protein.

In some embodiments, the virus-like particle comprises recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., J. Gen. Virol. 83: 1523-33 (2002)). AP205 coat protein can be expressed from plasmid pAP283-58 (SEQ ID NO: 79), which is a derivative of pQb10 (Kozlovska, T. M. et al., Gene 137:133-37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in U.S. Pat. No. 7,138,252, which is incorporated by reference in its entirety. Vectors pQb10 and pQb185 are vectors derived from pGEM vector, and expression of the cloned genes in these vectors is controlled by the trp promoter (Kozlovska, T. M. et al., Gene 137:133-37 (1993)). Plasmid pAP283-58 (SEQ ID NO: 130) comprises a putative AP205 ribosomal binding site in the following sequence, which is downstream of the XbaI site, and immediately upstream of the ATG start codon of the AP205 coat protein: tctagaATTTTCTGCGCACCCATCCCGGGTGGCGCCCAAAGTGAGGAAAATCAC atg (SEQ ID NO: 131). The vector pQb185 comprises a Shine Delagarno sequence downstream from the XbaI site and upstream of the start codon (tctagaTTAACCCAACGCGTAGGAGTCAGGCCatg, Shine Delagarno sequence underlined, SEQ ID NO: 132).

In some embodiments, the virus-like particle comprises recombinant coat proteins, or fragments thereof, of the RNA-phage AP205.

In some embodiments, AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 133) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In some embodiments, the virus-like particle comprises recombinant mutant coat proteins, or fragments thereof, of the RNA-phage AP205.

In some embodiments, assembly-competent mutant forms of AP205 VLPs, including AP205 coat protein with the substitution of proline at amino acid 5 to threonine (SEQ ID NO: 134), are used in the practice of the disclosure. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 135), which is derived directly from pQb185, and which contains the mutant AP205 coat protein gene instead of the Qβ coat protein gene. Vectors for expression of the AP205 coat protein are transfected into *E. coli* for expression of the AP205 coat protein.

In some embodiments, the disclosure provides compositions comprising proteins having amino acid sequences which are at least 80%, 85%, 90%, 95%, 97%, or 99% identical to wild-type proteins which form ordered arrays and have an inherent repetitive structure.

In some embodiments, the disclosure provides nucleic acid molecules which encode proteins used to prepare compositions of the present invention.

In some embodiments, the compositions described herein comprise proteins comprising amino acid sequences which are at least 80%, 85%, 90%, 95%, 97%, or 99% identical to any of the amino acid sequences shown in SEQ ID NOs: 112-129.

Proteins suitable for use in the present disclosure also include C-terminal truncation mutants of proteins which form capsids or capsid-like structures, or VLPs. Specific examples of such truncation mutants include proteins having an amino acid sequence shown in any of SEQ ID NOs: 112-129 where 1, 2, 5, 7, 9, 10, 12, 14, 15, or 17 amino acids have been removed from the C-terminus. Typically, these C-terminal truncation mutants will retain the ability to form capsids or capsid-like structures.

Further proteins suitable for use in the present disclosure also include N-terminal truncation mutants of proteins which form capsids or capsid-like structures. Specific examples of such truncation mutants include proteins having an amino acid sequence shown in any of SEQ ID NOs:112-129 where 1, 2, 5, 7, 9, 10, 12, 14, 15, or 17 amino acids have been removed from the N-terminus. Typically, these N-terminal truncation mutants will retain the ability to form capsids or capsid-like structures.

Additional proteins suitable for use in the present disclosure include N- and C-terminal truncation mutants which form capsids or capsid-like structures. Suitable truncation mutants include proteins having an amino acid sequence shown in any of SEQ ID NOs:112-129 where 1, 2, 5, 7, 9, 10, 12, 14, 15, or 17 amino acids have been removed from the N-terminus and 1, 2, 5, 7, 9, 10, 12, 14, 15, or 17 amino acids have been removed from the C-terminus. Typically, these N-terminal and C-terminal truncation mutants will retain the ability to form capsids or capsid-like structures.

Fragments of VLPs which retain the ability to induce an immune response can comprise, or alternatively consist of, polypeptides which are about 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450 or 500 amino acids in length, but will obviously depend on the length of the sequence of the subunit composing the VLP. Examples of such fragments include fragments of proteins discussed herein which are suitable for the preparation of the immune response enhancing composition.

In some embodiments, the VLP's are free of a lipoprotein envelope or a lipoprotein-containing envelope. In some embodiments, the VLP's are free of an envelope altogether.

The lack of a lipoprotein envelope or lipoprotein-containing envelope and, in particular, the complete lack of an envelope leads to a more defined virus-like particle in its structure and composition. Such more defined virus-like particles, therefore, may minimize side-effects. Moreover, the lack of a lipoprotein-containing envelope or, in particular, the complete lack of an envelope avoids or minimizes incorporation of potentially toxic molecules and pyrogens within the virus-like particle.

In some embodiments, the particles used in compositions of the disclosure are composed of a Hepatitis B capsid (core) protein (HBcAg) or a fragment of a HBcAg which has been modified to either eliminate or reduce the number of free cysteine residues. Zhou et al. (J. Virol. 66:5393-5398 (1992)) demonstrated that HBcAgs which have been modified to remove the naturally resident cysteine residues retain the ability to associate and form multimeric structures. Thus, core particles suitable for use in compositions of the disclosure include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified and their amino acids sequences are readily available to those skilled in the art. For example, the HBcAg protein having the amino acid sequence shown SEQ ID NO: 136 is 185 amino acids in length and is generated by the processing of a 212 amino acid Hepatitis B core antigen precursor protein. This processing results in the removal of 29 amino acids from the N-terminus of the Hepatitis B core antigen precursor protein. Similarly, the HBcAg protein that is 185 amino acids in length is generated by the processing of a 214 amino acid Hepatitis B core antigen precursor protein.

In some embodiments, compositions of the disclosure will be prepared using the processed form of a HBcAg (i.e., a HBcAg from which the N-terminal leader sequence of the Hepatitis B core antigen precursor protein have been removed).

Further, when HBcAgs are produced under conditions where processing will not occur, the HBcAgs will generally be expressed in "processed" form. For example, bacterial systems, such as *E. coli*, generally do not remove the leader sequences, also referred to as "signal peptides," of proteins which are normally expressed in eukaryotic cells. Thus, when an *E. coli* expression system directing expression of the protein to the cytoplasm is used to produce HBcAgs of the disclosure, these proteins will generally be expressed such that the N-terminal leader sequence of the Hepatitis B core antigen precursor protein is not present.

The preparation of Hepatitis B virus-like particles, which can be used for the present disclosure, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in pending U.S. Publication No. US 2003-0175290. For the latter application, it is in particular referred to Example 23, 24, 31 and 51. All three documents are explicitly incorporated herein by reference.

The present disclosure also includes HBcAg variants which have been modified to delete or substitute one or more additional cysteine residues. Thus, the vaccine compositions of the invention include compositions comprising HBcAgs in which cysteine residues not present in the amino acid sequence shown SEQ ID NO: 136 have been deleted.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together.

In view of the above, one advantage to the use of HBcAgs in compositions which have been modified to remove naturally resident cysteine residues is that sites to which toxic species can bind when antigens or antigenic determinants are attached would be reduced in number or eliminated altogether.

A number of naturally occurring HBcAg variants suitable for use in the practice of the present disclosure have been identified. Yuan et al., (J. Virol. 73:10122-10128 (1999)), for example, describe variants in which the isoleucine residue at position corresponding to position 97 in SEQ ID NO: 137 is replaced with either a leucine residue or a phenylalanine residue. The amino acid sequences of a number of HBcAg variants, as well as several Hepatitis B core antigen precursor variants, are disclosed in GenBank reports AAF121240 (SEQ ID NO: 138), AF121239 (SEQ ID NO: 139), X85297 (SEQ ID NO: 140), X02496 (SEQ ID NO: 141), X85305 (SEQ ID NO: 142), X85303 (SEQ ID NO: 143), AF151735 (SEQ ID NO: 144), X85259 (SEQ ID NO: 145), X85286 (SEQ ID NO: 146), X85260 (SEQ ID NO: 147), X85317 (SEQ ID NO: 148), X85298 (SEQ ID NO: 149), AF043593 (SEQ ID NO: 150), M20706 (SEQ ID NO: 151), X85295 (SEQ ID NO: 152), X80925 (SEQ ID NO: 153), X85284 (SEQ ID NO: 154), X85275 (SEQ ID NO: 155), X72702 (SEQ ID NO: 156), X85291 (SEQ ID NO: 157), X65258 (SEQ ID NO: 158), X85302 (SEQ ID NO: 159), M32138 (SEQ ID NO: 160), X85293 (SEQ ID NO: 161), X85315 (SEQ ID NO: 162), U95551 (SEQ ID NO: 163), X85256 (SEQ ID NO: 164), X85316 (SEQ ID NO: 165), X85296 (SEQ ID NO: 166), AB033559 (SEQ ID NO: 167), X59795 (SEQ ID NO: 168), X85299 (SEQ ID NO: 169), X85307 (SEQ ID NO: 170), X65257 (SEQ ID NO: 171), X85311 (SEQ ID NO: 172), X85301 (SEQ ID NO: 173), X85314 (SEQ ID NO: 174), X85287 (SEQ ID NO: 175), X85272 (SEQ ID NO: 176), X85319 (SEQ ID NO: 177), AB010289 (SEQ ID NO: 178), X85285 (SEQ ID NO: 179), AB010289 (SEQ ID NO:180), AF121242 (SEQ ID NO: 181), M90520 (SEQ ID NO: 182), P03153 (SEQ ID NO: 183), AF110999 (SEQ ID NO: 184), and M95589 (SEQ ID NO: 185), the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:77. Further HBcAg variants suitable for use in the compositions of the invention, and which may be further modified according to the disclosure of this specification are described in WO 00/198333, WO 00/177158 and WO 00/214478.

HBcAgs suitable for use in the present disclosure can be derived from any organism so long as they are able to enclose or to be coupled or otherwise attached to, in particular as long as they are capable of packaging, a RLR agonist and induce an immune response.

In some embodiments, the compositions comprise an HBcAg variant capable of associating to form dimeric or multimeric structures. In some embodiments, the compositions comprise HBcAg polypeptides comprising amino acid sequences which are at least 80%, 85%, 90%, 95%, 97% or 99% identical to any of the wild-type amino acid sequences, and forms of these proteins which have been processed, where appropriate, to remove the N-terminal leader sequence.

Whether the amino acid sequence of a polypeptide has an amino acid sequence that is at least 80%, 85%, 90%, 95%, 97% or 99% identical to one of the wild-type amino acid sequences, or a subportion thereof, can be determined conventionally using known computer programs such the Bestfit program. When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed.

The HBcAg variants and precursors having the amino acid sequences set out in SEQ ID NOs: 138-181 and 182-185 are relatively similar to each other. Thus, reference to an amino acid residue of a HBcAg variant located at a position which corresponds to a particular position in SEQ ID NO: 186, refers to the amino acid residue which is present at that position in the amino acid sequence shown in SEQ ID NO: 186. The homology between these HBcAg variants is for the most part high enough among Hepatitis B viruses that infect mammals so that one skilled in the art would have little difficulty reviewing the amino acid sequence shown in SEQ ID NO: 186 and in SEQ ID NO: 136, and that of a particular HBcAg variant and identifying "corresponding" amino acid residues. Furthermore, the HBcAg amino acid sequence shown in SEQ ID NO: 182, which shows the amino acid sequence of a HBcAg derived from a virus which infect woodchucks, has enough homology to the HBcAg having the amino acid sequence shown in SEQ ID NO: 186 that it is readily apparent that a three amino acid residue insert is present in SEQ ID NO: 182 between amino acid residues 155 and 156 of SEQ ID NO: 186.

As discussed above, the elimination of free cysteine residues reduces the number of sites where toxic components can bind to the HBcAg, and also eliminates sites where cross-linking of lysine and cysteine residues of the same or of neighboring HBcAg molecules can occur. Therefore, in some embodiments, one or more cysteine residues of the Hepatitis B virus capsid protein have been either deleted or substituted with another amino acid residue.

In some embodiments, compositions described herein comprise HBcAgs from which the C-terminal region (e.g., amino acid residues 145-185 or 150-185 of SEQ ID NO: 186) has been removed. Thus, additional modified HBcAgs suitable for use in the practice of the present disclosure include C-terminal truncation mutants. Suitable truncation mutants include HBcAgs where 1, 5, 10, 15, 20, 25, 30, 34, 35, amino acids have been removed from the C-terminus.

HBcAgs suitable for use in the practice of the present disclosure also include N-terminal truncation mutants. Suitable truncation mutants include modified HBcAgs where 1, 2, 5, 7, 9, 10, 12, 14, 15, or 17 amino acids have been removed from the N-terminus.

Further HBcAgs suitable for use in the practice of the present disclosure include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, amino acids have been removed from the C-terminus.

In some embodiments, compositions comprising HBcAg polypeptides comprise amino acid sequences which are at least 80%, 85%, 90%, 95%, 97%, or 99% identical to the above described truncation mutants.

In some embodiments, a lysine residue is introduced into a HBcAg polypeptide, to mediate the binding of the antigen or antigenic determinant to the VLP of HBcAg. In some embodiments, compositions described herein are prepared using a HBcAg comprising amino acids 1-144, or 1-149, 1-185 of SEQ ID NO:186, which is modified so that the amino acids corresponding to positions 79 and 80 are replaced with a peptide having the amino acid sequence of Gly-Gly-Lys-Gly-Gly (SEQ ID NO:187). These compositions are particularly useful in those embodiments where an antigenic determinant is coupled to a VLP of HBcAg. In some embodiments, the cysteine residues at positions 48 and 107 of SEQ ID NO:186 are mutated to serine. In some embodiments, the compositions described herein comprise the corresponding polypeptides having amino acid sequences shown in any of SEQ ID NOs:138-183 which also have above noted amino acid alterations. Further included within the scope of the disclosure are additional HBcAg variants which are capable of associating to form a capsid or VLP and have the above noted amino acid alterations. Thus, the disclosure further includes compositions comprising HBcAg polypeptides which comprise amino acid sequences at least 80%, 85%, 90%, 95%, 97% or 99% identical to any of the wild-type amino acid sequences, and forms of these proteins which have been processed, where appropriate, to remove the N-terminal leader sequence and modified with above noted alterations.

In some embodiments, compositions described herein comprise mixtures of different HBcAgs. Thus, these compositions may be composed of HBcAgs which differ in amino acid sequence. For example, compositions could be prepared comprising a "wild-type" HBcAg and a modified HBcAg in which one or more amino acid residues have been altered (e.g., deleted, inserted or substituted).

The crystal structure of several RNA bacteriophages has been determined (Golmohammadi, R. et al., Structure 4:543-554 (1996)). Using such information, surface exposed residues can be identified and, thus, RNA-phage coat proteins can be modified such that one or more reactive amino acid residues can be inserted by way of insertion or substitution. As a consequence, those modified forms of bacteriophage coat proteins can also be used for the present disclosure. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2, bacteriophage AP 205) can also be used to prepare compositions described herein.

Although the sequence of the variants proteins discussed above will differ from their wild-type counterparts, these variant proteins will generally retain the ability to form capsids or capsid-like structures. Thus, the invention further includes compositions which further includes variants of proteins which form capsids or capsid-like structures, as well as methods for preparing such compositions, individual protein subunits used to prepare such compositions, and nucleic acid molecules which encode these protein subunits. Thus, included within the scope of the disclosure are variant forms of wild-type proteins which form capsids or capsid-like structures and retain the ability to associate and form capsids or capsid-like structures.

Antigen and Antigenic Determinants

In some embodiments, the compositions described herein comprise an antigen or antigenic determinant bound to the virus-like particle. The disclosure provides for compositions that vary according to the antigen or antigenic determinant selected in consideration of the desired therapeutic effect. Exemplary antigens or antigenic determinants suitable for use in the present invention are disclosed in U.S. Pat. No. 7,229,624, in U.S. Pat. No. 6,964,769 and in U.S. Pat. No. 7,264,810, the disclosures of which are herewith incorporated by reference in their entireties.

The antigen can be any antigen of known or yet unknown provenance. It can be isolated from bacteria, viruses or other pathogens or can be a recombinant antigen obtained from expression of suitable nucleic acid coding therefor. It can also be isolated from prions, tumors, self-molecules, non-peptidic hapten molecules, allergens and hormones. In some embodiments, the antigen is a recombinant antigen. The selection of the antigen is, of course, dependent upon the immunological response desired and the host.

In some embodiments, an immune response is induced against the VLP itself. In some embodiments, a virus-like particle is coupled, fused or otherwise attached to an antigen/immunogen against which an enhanced immune response is desired.

In some embodiments, the at least one antigen or antigenic determinant is fused to the virus-like particle. As outlined above, a VLP is typically composed of at least one subunit assembling into a VLP. Thus, in some embodiments, the antigen or antigenic determinant is fused to at least one subunit of the virus-like particle or of a protein capable of being incorporated into a VLP generating a chimeric VLP-subunit-antigen fusion.

Fusion of the antigen or antigenic determinant can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting antigen or antigenic determinant sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. In some embodiments, antigens or antigenic determinants are fused to either the N- or C-terminus of the truncation mutants VLP-subunits. Likewise, fusion of an epitope into the sequence of the VLP subunit may also be effected by substitution, where for example for the specific VLP HBcAg, amino acids 79-81 are replaced with a foreign epitope. Thus, fusion, as referred to hereinafter, may be effected by insertion of the antigen or antigenic determinant sequence in the sequence of a VLP subunit, by substitution of part of the sequence of the VLP subunit with the antigen or antigenic determinant, or by a combination of deletion, substitution or insertions.

The chimeric antigen or antigenic determinant-VLP subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In some embodiments, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of, and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In some embodiments, the at least one antigen or antigenic determinant is fused to a Qβ coat protein. Fusion protein constructs wherein epitopes have been fused to the C-terminus of a truncated form of the A1 protein of Qβ or inserted within the A1 protein have been described (Kozlovska, T. M., et al., Intervirology, 39:9-15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in *E. coli*, and such is the case for N-termini of the Qβ coat proteins. The part of the A1 gene, 3' of the UGA amber codon encodes the CP extension, which has a length of 195 amino acids. Insertion of the at least one antigen or antigenic determinant between position 72 and 73 of the CP extension leads to further embodiments of the invention (Kozlovska, T. M., et al., Intervirology 39:9-15 (1996)). Fusion of an antigen or antigenic determinant at the C-terminus of a C-terminally truncated Qβ A1 protein leads to further embodiments of the invention. For example, Kozlovska et al., (Intervirology, 39: 9-15 (1996)) describe Qβ A1 protein fusions where the epitope is fused at the C-terminus of the Qβ CP extension truncated at position 19.

As described by Kozlovska et al. (Intervirology, 39: 9-15 (1996)), assembly of the particles displaying the fused epitopes typically requires the presence of both the A1 protein-antigen fusion and the wild-type CP to form a mosaic particle. However, embodiments comprising virus-like particles, and hereby in particular the VLPs of the RNA phage Qβ coat protein, which are exclusively composed of VLP subunits having at least one antigen or antigenic determinant fused thereto, are also within the scope of the present disclosure.

The production of mosaic particles may be effected in a number of ways. Kozlovska et al., Intervirology, 39:9-15 (1996), describe three methods, which all can be used in the practice of the disclosure. In the first approach, efficient display of the fused epitope on the VLPs is mediated by the expression of the plasmid encoding the Qβ A1 protein fusion having a UGA stop codon between CP and CP extension in a *E. coli* strain harboring a plasmid encoding a cloned UGA suppressor tRNA which leads to translation of the UGA codon into Trp (pISM3001 plasmid (Smiley B. K., et al., Gene 134:33-40 (1993))). In another approach, the CP gene stop codon is modified into UAA, and a second plasmid expressing the A1 protein-antigen fusion is cotransformed. The second plasmid encodes a different antibiotic resistance and the origin of replication is compatible with the first plasmid (Kozlovska, T. M., et al., Intervirology 39:9-15 (1996)). In a third approach, CP and the A1 protein-antigen fusion are encoded in a bicistronic manner, operatively linked to a promoter such as the Trp promoter, as described in FIG. 1 of Kozlovska et al., Intervirology, 39:9-15 (1996).

In some embodiments, recombinant DNA technology can be utilized to fuse a heterologous protein to a VLP protein (Kratz, P. A., et al., Proc. Natl. Acad. Sci. USA 96:1915 (1999)). For example, the present disclosure encompasses VLPs recombinantly fused or chemically conjugated (including both covalently and non covalently conjugations) to an antigen (or portion thereof, preferably at least 10, 20 or 50 amino acids) to generate fusion proteins or conjugates. The fusion does not necessarily need to be direct, but can occur through linker sequences. More generally, in the case that epitopes, either fused, conjugated or otherwise attached to the virus-like particle, are used as antigens in accordance with the invention, spacer or linker sequences are typically added at one or both ends of the epitopes. Such linker sequences preferably comprise sequences recognized by the proteasome, proteases of the endosomes or other vesicular compartment of the cell.

One way of coupling is by a peptide bond, in which the conjugate can be a contiguous polypeptide, i.e. a fusion protein. In some embodiments, different peptides or polypeptides are linked in frame to each other to form a contiguous polypeptide. Thus a first portion of the fusion protein comprises an antigen or immunogen and a second portion of the fusion protein, either N-terminal or C-terminal to the first portion, comprises a VLP. Alternatively, internal insertion into the VLP, with optional linking sequences on both ends of the antigen, can also be used in accordance with the present invention.

A flexible linker sequence (e.g. a polyglycine/polyserine-containing sequence such as [Gly4 Ser]2 (Huston et al., Meth. Enzymol 203:46-88 (1991)) can be inserted into the fusion protein between the antigen and ligand. Also, the fusion protein can be constructed to contain an "epitope tag", which allows the fusion protein to bind an antibody (e.g. monoclonal antibody) for example for labeling or purification purposes. An example of an epitope tag is a Glu-Glu-Phe tripeptide which is recognized by the monoclonal antibody YL1/2.

The disclosure also relates to the chimeric DNA which contains a sequence coding for the VLP and a sequence coding for the antigen/immunogen. The DNA can be expressed, for example, in insect cells transformed with Baculoviruses, in yeast or in bacteria. There are no restrictions regarding the expression system, of which a large selection is available for routine use. Preferably, a system is used which allows expression of the proteins in large amounts. In general, bacterial expression systems are used on account of their efficiency. One example of a bacterial expression system suitable for use within the scope of the present invention is the one described by Clarke et al., J. Gen. Virol. 71: 1109-1117 (1990); Borisova et al., J. Virol. 67: 3696-3701 (1993); and Studier et al., Methods Enzymol. 185:60-89 (1990). An example of a suitable yeast expression system is the one described by Emr, Methods Enzymol. 185:231-3 (1990); Baculovirus systems, which have previously been used for preparing capsid proteins, are also suitable. Constitutive or inducible expression systems can be used. By the choice and possible modification of available expression systems it is possible to control the form in which the proteins are obtained.

In some embodiments, the at least one antigen or antigenic determinant is bound to the virus-like particle by at least one covalent bond. In some embodiments, the least one antigen or antigenic determinant is bound to the virus-like particle by at least one covalent bond, said covalent bond being a non-peptide bond leading to an antigen or antigenic determinant array and antigen or antigenic determinant-VLP conjugate, respectively. This antigen or antigenic determinant array and conjugate, respectively, has typically and preferably a repetitive and ordered structure since the at least one antigen or antigenic determinant is bound to the VLP in an oriented manner. In some embodiments, equal and more than 120, equal and more than 180, more than 270, and equal and more than 360 antigens are bound to the VLP. The formation of a repetitive and ordered antigen or antigenic determinant-VLP array and conjugate, respectively, is ensured by an oriented and directed as well as defined binding and attachment, respectively, of the at least one antigen or antigenic determinant to the VLP as will become apparent in the following. Furthermore, the typical inherent highly repetitive and organized structure of the VLPs advantageously contributes to the display of the antigen or antigenic determinant in a highly ordered and repetitive fashion leading to a highly organized and repetitive antigen or antigenic determinant-VLP array and conjugate, respectively.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In some embodiments, the first attachment site is a lysine residue and/or the second attachment comprises sulfhydryl group or a cysteine residue. In some embodiments, the first attachment site is a lysine residue and the second attachment is a cysteine residue.

In some embodiments, the antigen or antigenic determinant is bound via a cysteine residue, to lysine residues of the VLP of RNA phage coat protein, and in particular to the VLP of Q □ □ coat protein.

The use of the VLPs as carriers allow the formation of robust antigen arrays and conjugates, respectively, with variable antigen density. In particular, the use of VLPs of RNA phages, and hereby in particular the use of the VLP of RNA phage Qβ coat protein allows to achieve very high epitope density. In particular, a density of more than 1.5 epitopes per subunit has been reached by coupling for example the human AP 1-6 peptide to the VLP of Qβ coat protein (WO 2004/016282). The preparation of compositions of VLPs of RNA phage coat proteins with a high epitope density can be effected using the teaching of this application. In some embodiments, when an antigen or antigenic determinant is coupled to the VLP Qβ coat protein, an average number of antigen or antigenic determinant per subunit of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 2.5, 2.6, 2.7, 2.8, 2.9, or higher is used.

The second attachment site, as defined herein, may be either naturally or non-naturally present with the antigen or the antigenic determinant. In the case of the absence of a suitable natural occurring second attachment site on the antigen or antigenic determinant, such a, then non-natural second attachment has to be engineered to the antigen.

As described above, four lysine residues are exposed on the surface of the VLP of Qβ coat protein. Typically these residues are derivatized upon reaction with a cross-linker molecule. In the instance where not all of the exposed lysine residues can be coupled to an antigen, the lysine residues which have reacted with the cross-linker are left with a cross-linker molecule attached to the .quadrature.-amino group after the derivatization step. This leads to disappearance of one or several positive charges, which may be detrimental to the solubility and stability of the VLP. By replacing some of the lysine residues with arginines, as in the disclosed Qβ coat protein mutants described below, we prevent the excessive disappearance of positive charges since the arginine residues do not react with the cross-linker. Moreover, replacement of lysine residues by arginines may lead to more defined antigen arrays, as fewer sites are available for reaction to the antigen.

In some embodiments, exposed lysine residues are replaced by arginines in the following Qβ coat protein mutants and mutant Qβ VLPs disclosed herein: Q0-240 (Lys13-Arg; SEQ ID NO: 125), Q0-250 (Lys 2-Arg, Lys13-Arg; SEQ ID NO: 127) and Q0-259 (Lys 2-Arg, Lys16-Arg; SEQ ID NO: 129).

In some embodiments, a Qβ mutant coat protein comprises one additional lysine residue, suitable for obtaining even higher density arrays of antigens. This mutant Qβ coat protein, Q0-243 (Asn 10-Lys; SEQ ID NO: 126), was cloned, the protein expressed, and the capsid or VLP isolated and purified, showing that introduction of the additional lysine residue is compatible with self-assembly of the subunits to a capsid or VLP. Thus, antigen or antigenic determinant arrays and conjugates, respectively, may be prepared using VLP of Qβ coat protein mutants. A particularly favored method of attachment of antigens to VLPs, and in particular to VLPs of RNA phage coat proteins is the linking of a lysine residue present on the surface of the VLP of RNA phage coat proteins with a cysteine residue added to the antigen. In order for a cysteine residue to be effective as second attachment site, a sulfhydryl group must be available for coupling. Thus, a cysteine residue has to be in its reduced state, that is, a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or .β-mercaptoethanol is required. The concentration of reductand, and the molar excess of reductand over antigen has to be adjusted for each antigen. A titration range, starting from concentrations as low as 10 μM or lower, up to 10 to 20 mM or higher reductand if required is tested, and coupling of the antigen to the carrier assessed. Although low concentrations of reductand are compatible with the coupling reaction as described in WO 02/056905, higher concentrations inhibit the coupling reaction, as a skilled artisan would know, in which case the reductand has to be removed or its concentration decreased, e.g. by dialysis, gel filtration or reverse phase HPLC. Advantageously, the pH of the dialysis or equilibration buffer is lower than 7, preferably 6. The compatibility of the low pH buffer with antigen activity or stability has to be tested.

Epitope density on the VLP of RNA phage coat proteins can be modulated by the choice of cross-linker and other reaction conditions. For example, the cross-linkers Sulfo-GMBS and SMPH typically allow reaching high epitope density. Derivatization is positively influenced by high concentration of reactands, and manipulation of the reaction conditions can be used to control the number of antigens coupled to VLPs of RNA phage coat proteins, and in particular to VLPs of Qβ coat protein.

Prior to the design of a non-natural second attachment site the position at which it should be fused, inserted or generally engineered has to be chosen. The selection of the position of the second attachment site may, by way of example, be based on a crystal structure of the antigen. Such a crystal structure of the antigen may provide information on the availability of the C- or N-termini of the molecule (determined for example from their accessibility to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction, with e.g. 2-mercaptoethylamine, TCEP, β-mercaptoethanol or DTT. Mild reduction conditions not affecting the immunogenicity of the antigen will be chosen. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will be selected such that steric hindrance from the second attachment site or any amino acid linker containing the same is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In some embodiments, the antigen or antigenic determinant comprises a single second attachment site or a single reactive attachment site capable of association with the first attachment sites on the core particle and the VLPs or VLP subunits, respectively. This further ensures a defined and uniform binding and association, respectively, of the at least one, but typically more than one, preferably more than 10, 20, 40, 80, 120, 150, 180, 210, 240, 270, 300, 360, 400, 450 antigens to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine- (as the first attachment site) and cysteine- (as a second attachment site) interaction, it is ensured, in accordance with one embodiment of the invention, that only one cysteine residue per antigen, independent whether this cysteine residue is naturally or non-naturally present on the antigen, is capable of binding and associating, respectively, with the VLP and the first attachment site of the core particle, respectively.

In some embodiments, engineering of a second attachment site onto the antigen require the fusion of an amino acid linker containing an amino acid suitable as second attachment site according to the disclosures of this invention. Therefore, in some embodiments, an amino acid linker is bound to the antigen or the antigenic determinant by way of at least one covalent bond.

In some embodiments, the amino acid linker comprises the second attachment site. In some embodiments, the amino acid linker comprises a sulfhydryl group or a cysteine residue. In some embodiments, the amino acid linker is cysteine.

In some embodiments, the virus-like particle comprises at least one first attachment site and the antigen or antigenic determinant comprises at least one second attachment site. In some embodiments, the first attachment site comprises an amino group or a lysine residue. In some embodiments, the second attachment site is selected from the group consisting of (a) an attachment site not naturally occurring with said antigen or antigenic determinant; and (b) an attachment site naturally occurring with said antigen or antigenic determinant. In some embodiments, the second attachment site comprises a sulfhydryl group or a cysteine residue. In some embodiments, the binding of the antigen or antigenic determinant to the virus-like particle is effected through association between the first attachment site and the second attachment site, wherein the association is through at least one non-peptide bond, and wherein the antigen or antigenic determinant and the virus-like particle interact through said association to form an ordered and repetitive antigen array. In some embodiments, the first attachment site is a lysine residue and the second attachment site is a cysteine residue. In some embodiments, the first attachment site is an amino group and the second attachment site is a sulfhydryl group.

The present disclosure is applicable to a wide variety of antigens. In some embodiments, the antigen is a protein, polypeptide or peptide. In some embodiments, the antigen is DNA. The antigen can also be a lipid, a carbohydrate, or an organic molecule, in particular a small organic molecule such as nicotine.

Methods for Making VLPs and Packaging RLR Agonists in VLPs

Methods for expression of the coat protein and the mutant coat protein, respectively, leading to self-assembly into VLPs are described in U.S. Pat. No. 7,138,252, which is incorporated by reference in its entirety. Suitable *E. coli* strains include, but are not limited to, *E. coli* K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., Gene 137:133-37 (1993)).

An advantage of using VLPs derived from RNA phages is their high expression yield in bacteria that allows production of large quantities of material at affordable cost. Methods for making the virus-like particles described herein, including methods scalable to a commercial scale, are described in U.S. Pat. Nos. 9,518,095 and 9,657,065, herein incorporated by reference in their entirety.

The disclosure also provides a method of producing a composition comprising a VLP and a RLR agonist package into the VLP which comprises incubating the VLP with the RLR agonist, adding RNase and purifying said composition. In some embodiments, the method further comprises the step of binding an antigen or antigenic determinant to said virus-like particle. In some embodiments, the antigen or antigenic determinant is bound to the virus-like particle before incubating the virus-like particle with the RLR agonist. In some embodiments, the antigen or antigenic determinant is bound to the virus-like particle after purifying the composition. In some embodiments, the method comprises incubating the VLP with RNase, adding the RLR agonist and purifying the composition. In some embodiments, the method further comprises the step of binding an antigen or antigenic determinant to said virus-like particle. In some embodiments, the antigen or antigenic determinant is bound to the virus-like particle before incubating the virus-like particle with the RNase. In some embodiments, the antigen or antigenic determinant is bound to the virus-like particle after purifying the composition. In some embodiments, the VLP is produced in a bacterial expression system. In another embodiment, the RNase is RNase A.

The disclosure further provides a method of producing a composition comprising a RLR agonist packaged into a VLP, which comprises disassembling the VLP, adding the RLR agonist, and reassembling the VLP. In some embodiments, the disassembled VLP is produced when manufacturing the VLP. In some embodiments, disassembled VLP comprises isolated dimers of a coat protein (e.g., Qβ dimers). In some embodiments, the isolated dimers assemble into the VLP around the RLR agonist to package the agonist into the VLP. The method can further comprise removing nucleic acids of the disassembled VLP and/or purifying the composition after reassembly. In some embodiments, the method further comprises the step of binding an antigen or antigenic determinant to the virus-like particle. In some embodiments, the antigen or antigenic determinant is bound to the virus-like particle before disassembling the virus-like particle. In some embodiments, the antigen or antigenic determinant is bound to the virus-like particle after reassembling the virus-like particle and preferably after purifying the composition.

The present disclosure provides methods of binding of antigen or antigenic determinant to VLPs. As indicated, in some embodiments, the at least one antigen or antigenic determinant is bound to the VLP by way of chemical cross-linking, typically and preferably by using a heterobifunctional cross-linker. Several hetero-bifunctional cross-linkers are known to the art. In some embodiments, the hetero-bifunctional cross-linker contains a functional group which can react with first attachment sites, i.e. with the side-chain amino group of lysine residues of the VLP or at least one VLP subunit, and a further functional group which can react with a second attachment site, i.e. a cysteine residue fused to the antigen or antigenic determinant and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigen or antigenic determinant is reacted with the activated VLP, and this step is typically called the coupling step. Unreacted antigen or antigenic determinant may be optionally removed in a fourth step, for example by dialysis. Several hetero-bifunctional cross-linkers are known to the art. These include the cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage. Another class of cross-linkers suitable is characterized by the introduction of a disulfide linkage between the antigen or antigenic determinant and the VLP upon coupling. In one embodiment, cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i.e. the amount of antigens or antigenic determinants per subunits of the VLP can be adjusted by varying the experimental conditions described above to match the requirements of the vaccine.

In some embodiments, a method of binding of antigens or antigenic determinants to the VLP comprises linking of a lysine residue on the surface of the VLP with a cysteine residue on the antigen or antigenic determinant. In some embodiments, fusion of an amino acid linker containing a cysteine residue, as a second attachment site or as a part thereof, to the antigen or antigenic determinant for coupling to the VLP may be required.

In some embodiments, flexible amino acid linkers are used. Examples of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) (G)kC(G)n with n=0-12 and k=0-5; (g) N-terminal glycine-serine linkers; (h) (G)kC(G)m(S)l(GGGGS)n with n=0-3, k=0-5, m=0-10, l=0-2 (SEQ ID NO: 188); (i) GGC; (k) GGC-NH2; (l) C-terminal gamma 1-linker; (m) C-terminal gamma 3-linker; (n) C-terminal glycine linkers; (o) (G)nC(G)k with n=0-12 and k=0-5; (p) C-terminal glycine-serine linkers; (q) (G)m(S)l(GGGGS)n(G)oC(G)k with n=0-3, k=0-5, m=0-10, l=0-2, and o=0-8 (SEQ ID NO: 189).

Further examples of amino acid linkers are the hinge region of Immunoglobulins, glycine serine linkers (GGGGS)n (SEQ ID NO: 190), and glycine linkers (G)n all further containing a cysteine residue as second attachment site and optionally further glycine residues. Typical examples of said amino acid linkers are N-terminal gamma 1: CGDKTHTSPP (SEQ ID NO: 191); C-terminal gamma 1: DKTHTSPPCG (SEQ ID NO: 192); N-terminal gamma 3: CGGPKPSTPPGSSGGAP (SEQ ID NO: 193); C-terminal gamma 3: PKPSTPPGSSGGAPGGCG (SEQ ID NO: 194); N-terminal glycine linker: GCGGGG (SEQ ID NO: 195); C-terminal glycine linker: GGGGCG (SEQ ID NO: 196); C-terminal glycine-lysine linker: GGKKGC (SEQ ID NO: 197); N-terminal glycine-lysine linker: CGKKGG (SEQ ID NO: 198).

In some embodiments, other amino acid linkers when a hydrophobic antigen or antigenic determinant is bound to a VLP, are CGKKGG (SEQ ID NO: 199), or CGDEGG (SEQ ID NO: 200) for N-terminal linkers, or GGKKGC (SEQ ID NO: 201) and GGEDGC (SEQ ID NO: 202), for the C-terminal linkers. For the C-terminal linkers, the terminal cysteine is optionally C-terminally amidated.

In some embodiments, GGCG (SEQ ID NO: 203), GGC or GGC-NH2 ("NH2" stands for amidation) linkers at the C-terminus of the peptide or CGG at its N-terminus are used as amino acid linkers. In general, glycine residues will be inserted between bulky amino acids and the cysteine to be used as second attachment site, to avoid potential steric hindrance of the bulkier amino acid in the coupling reaction. In some embodiments, the amino acid linker GGC-NH2 is fused to the C-terminus of the antigen or antigenic determinant.

The cysteine residue present on the antigen or antigenic determinant has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or β-mercaptoethanol is required. Low concentrations of reducing agent are compatible with coupling as described in WO 02/05690, higher concentrations inhibit the coupling reaction, as a skilled artisan would know, in which case the reductand has to be removed or its concentration decreased prior to coupling, e.g. by dialysis, gel filtration or reverse phase BPLC.

Binding of the antigen or antigenic determinant to the VLP by using a hetero-bifunctional cross-linker according to the methods described above, allows coupling of the antigen or antigenic determinant to the VLP in an oriented fashion. Other methods of binding the antigen or antigenic determinant to the VLP include methods wherein the antigen or antigenic determinant is cross-linked to the VLP using the carbodiimide EDC, and NHS. In further methods, the antigen or antigenic determinant is attached to the VLP using a homo-bifunctional cross-linker such as glutaraldehyde, DSG, BM[PEO]4, BS3, (Pierce Chemical Company, Rockford, Ill., USA) or other known homo-bifunctional cross-linkers with functional groups reactive towards amine groups or carboxyl groups of the VLP.

Other methods of binding the VLP to an antigen or antigenic determinant include methods where the VLP is biotinylated, and the antigen or antigenic determinant expressed as a streptavidin-fusion protein, or methods wherein both the antigen or antigenic determinant and the VLP are biotinylated, for example as described in WO 00/23955. In this case, the antigen or antigenic determinant may be first bound to streptavidin or avidin by adjusting the ratio of antigen or antigenic determinant to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the antigen or antigenic determinant, may be used as binding agents for binding antigen or antigenic determinant to the VLP. Alternatively, either the ligand or the receptor may be fused to the antigen or antigenic determinant, and so mediate binding to the VLP chemically bound or fused either to the receptor, or the ligand respectively. Fusion may also be effected by insertion or substitution.

Pharmaceutical Compositions and Formulations

In certain embodiments, the invention provides for a pharmaceutical composition comprising an RLR agonist with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and/or rate of in vivo clearance of the RLR agonist.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an RLR agonist can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an RLR agonist can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising an RLR agonist, in a pharmaceutically acceptable vehicle. In certain embodiments, a vehicle for parenteral injection is sterile distilled water in which an RLR agonist is formulated as a sterile, isotonic solution, and properly preserved. In certain embodiments, the preparation can involve the formulation of the desired molecule with a delivery vehicle or agent, such as injectable microspheres, bio-erodible particles, polymeric compounds (such as polylactic acid, polyglycolic acid or polyethylenimine (e.g. JetPEI®)), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an RLR agonist can be formulated as a dry powder for inhalation. In certain embodiments, an inhalation solution comprising an RLR agonist can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, an RLR agonist that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an RLR agonist. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an RLR agonist or RIG-VLP in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an RLR agonist or RIG-VLP in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an RLR agonist or RIG-VLP to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an RLR agonist or RIG-VLP is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of an RLR agonist or RIG-VLP in the formulation used. In certain embodiments, a clinician will administer the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an RLR agonist in an ex vivo manner. In such instances, cells, tissues and/or organs that have been removed from the patient are exposed to a pharmaceutical composition comprising an RLR agonist or RIG-VLP after which the cells, tissues and/or organs are subsequently implanted back into the patient.

In certain embodiments, an RLR agonist or RIG-VLP can be delivered by implanting certain cells that have been genetically engineered, using methods such as those described herein, to express and secrete the agonist. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

In some aspects, the disclosure provides a pharmaceutical composition comprising an RLR agonist or RIG-VLP according to the disclosure for stimulating an immune response, treating or delaying progression of a cancer, or reducing or inhibiting tumor growth in a subject in need thereof, and a pharmaceutically acceptable carrier. In some embodiments, the RLR agonist is formulated in a polyethylenimine (PEI) carrier. In some embodiments, the PEI carrier is JetPEI®.

Applications

The compositions described herein can be used in diagnostic and therapeutic applications. For example, detectably-labeled RLR agonists or RIG-VLPs can be used in assays to detect the presence or amount of the target protein in a sample (e.g., a biological sample). The compositions can be used in in vitro assays for studying inhibition of target function (e.g. RLR-mediated cellular signaling or response). In some embodiments, e.g., in which the compositions bind to and activate a target (e.g. a protein or polypeptide), the compositions can be used as positive controls in assays designed to identify additional novel compounds that also induce activity of the target protein or polypeptide and/or are otherwise are useful for treating a disorder associated with the target protein or polypeptide. For example, a RLR-activating composition can be used as a positive control in an assay to identify additional compounds (e.g., small molecules, aptamers, or antibodies) that induce, increase, or stimulate RLR function. The compositions can also be used in therapeutic methods as elaborated on below.

Kits

A kit can include an RLR agonist or RIG-VLP as disclosed herein, and instructions for use. The kits may comprise, in a suitable container, an RLR agonist, one or more controls, and various buffers, reagents, enzymes and other standard ingredients well known in the art.

The container can include at least one vial, well, test tube, flask, bottle, syringe, or other container means, into which an RLR agonist or RIG-VLP may be placed, and in some instances, suitably aliquoted. Where an additional component is provided, the kit can contain additional containers into which this component may be placed. The kits can also include a means for containing an RLR agonist or RIG-VLP and any other reagent containers in close confinement for commercial sale. Such containers may include injection or blow-molded plastic containers into which the desired vials are retained. Containers and/or kits can include labeling with instructions for use and/or warnings.

In some aspects, the disclosure provides a kit comprising an RLR agonist or RIG-VLP provided by the disclosure, or comprising a pharmaceutical composition provided by the disclosure and instructions for use in stimulating an immune response in a subject, or treating or delaying progression of a cancer, or inhibiting tumor growth in a subject, optionally with instructions for use in combination with one or more additional therapeutic agents.

In some embodiments, the agonist or pharmaceutical composition is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator of a costimulatory molecule, an inhibitor of an inhibitory molecule, a vaccine, a cellular immunotherapy, or a combination thereof.

In some embodiments, the RLR agonist or pharmaceutical composition is administered preceding or subsequent to administration of the one or more additional therapeutic agents or wherein the one or more additional therapeutic agents is administered concurrently with, preceding or subsequent to the administration of the RLR agonist or pharmaceutical composition.

In some embodiments, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a toll-like receptor 3 (TLR3) agonist, a toll-like receptor 7 (TLR7) agonist, a toll-like receptor 9 (TLR9) agonist.

In some embodiments, the one or more additional therapeutic agents is an agonist comprising an polypeptide (e.g, antibody, or antigen binding portion thereof) that specifically binds to CD137 (4-1BB).

In some embodiments, the one or more additional therapeutic agents is an agonist comprising an polypeptide (e.g., antibody, or antigen binding portion thereof) that specifically binds to CD134 (OX40).

Methods of Use

The compositions of the present invention have numerous in vitro and in vivo utilities involving the detection and/or quantification of RLRs and/or the agonism of RLR function.

The above-described compositions are useful in, inter alia, methods for treating or preventing a variety of cancers or infectious diseases in a subject. The compositions can be administered to a subject, e.g., a human subject, using a variety of methods that depend, in part, on the route of administration. The route can be, e.g., intravenous injection or infusion (IV), subcutaneous injection (SC), intradermal injection (ID), intraperitoneal (IP) injection, intramuscular injection (IM), intratumoral injection (IT) or intrathecal injection. The injection can be in a bolus or a continuous infusion.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, an RLR agonist is therapeutically delivered to a subject by way of local administration. In some embodiments, an RLR agonist is packaged into a VLP. In one embodiment, the RLR agonist is therapeutically delivered with an antigen. In other embodiments, the VLP may be coupled to an antigen. In other embodiments, the RLR agonist is packaged into a VLP and administered in combination with a separate VLP coupled to an antigen.

A suitable dose of an RLR agonist or RIG-VLP described herein, which dose is capable of treating or preventing cancer in a subject, can depend on a variety of factors including, e.g., the age, sex, and weight of a subject to be treated and the particular inhibitor compound used. Other factors affecting the dose administered to the subject include, e.g., the type or severity of the cancer or infectious disease. For example, a subject having metastatic melanoma may require administration of a different dosage of an RLR agonist or RIG-VLP than a subject with glioblastoma. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse). Suitable dosages are described herein.

A pharmaceutical composition can include a therapeutically effective amount of an RLR agonist or RIG-VLP thereof described herein. Such effective amounts can be readily determined by one of ordinary skill in the art based, in part, on the effect of the administered RLR agonist or RIG-VLP, or the combinatorial effect of the RLR agonist or RIG-VLP and one or more additional active agents, if more than one agent is used. A therapeutically effective amount of an RLR agonist or RIG-VLP described herein can also vary according to factors such as the disease state, age, sex, and weight of the individual, and the ability of the agonist (and one or more additional active agents) to elicit a desired response in the individual, e.g., reduction in tumor growth. For example, a therapeutically effective amount of an RLR agonist or RIG-VLP can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the RLR agonists or RIG-VLP described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

In some embodiments, the composition contains any of the RLR agonists or RIG-VLPs described herein and one or more (e.g., two, three, four, five, six, seven, eight, nine, 10, or 11 or more) additional therapeutic agents such that the composition as a whole is therapeutically effective. For example, a composition can contain an RLR agonist or RIG-VLP described herein and an alkylating agent, wherein the agonist and agent are each at a concentration that when combined are therapeutically effective for treating or preventing a cancer (e.g., melanoma) in a subject.

Toxicity and therapeutic efficacy of such compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An RLR agonist or RIG-VLP that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. For an RLR agonist or RIG-VLP described herein, the therapeutically effective dose can be estimated initially from cell culture assays. A dose can be formulated in animal models to achieve a circulating plasma concentration range that includes the $EC_{50}$ (i.e., the concentration of the agonist which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for cancer or infectious disease. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

As described above, the compositions described herein (e.g., RLR agonist or RIG-VLP compositions) can be used to treat a variety of cancers such as but not limited to: Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma, marginal zone B cell lymphoma, polycythemia vera, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, rectal cancer; cancer of the respiratory system, sarcoma, skin cancer, stomach cancer, testicular cancer, thyroid cancer, uterine cancer, and cancer of the urinary system.

In some embodiments, the disclosure provides a vaccine comprising an RLR agonist packaged into a VLP, and an antigen or antigenic determinant bound to the VLP. In some embodiments, the vaccine induces an immune response against the antigen or antigenic determinant bound to the VLP. In some embodiments, the vaccine is prophylactic. In some embodiments, the vaccine is therapeutic. In some embodiments, the antigen or antigenic determinant bound to the VLP is a cancer or tumor antigen, and thus the vaccine induces an anti-tumor immune response. In some embodiments, the vaccine induces protective immunity.

In some aspects, the disclosure provides a method to increase RLR-mediated production of one or more cytokines in a cell, the method comprising contacting the cell with an RLR agonist or RIG-VLP provided by the disclosure, wherein the agonist increases RLR-mediated cytokine production in a cell.

In some aspects, the disclosure provides a method to increase RLR-mediated expression of one or more interferon-stimulated genes in a cell, the method comprising contacting the cell with an RLR agonist or RIG-VLP provided by the disclosure, wherein the agonist increases RLR-mediated expression of one or more interferon-stimulated genes in a cell.

In some aspects, the disclosure provides a method to increase RLR-dependent intracellular signaling in a cell, the method comprising contacting the cell with an RLR agonist or RIG-VLP provided by the disclosure, wherein the agonist increases RLR-dependent intracellular signaling.

In some aspects, the disclosure provides a method of stimulating an immune response in a subject, the method comprising administering to the subject an effective amount of an RLR agonist or RIG-VLP provided by the disclosure, or a pharmaceutical composition provided by the disclosure.

In some aspects, the disclosure provides a method of treating or delaying progression of a cancer in a subject, the method comprising administering to the subject an effective amount of an RLR agonist or RIG-VLP provided by the disclosure, or a pharmaceutical composition provided by the disclosure.

In some aspects, the disclosure provides a method of reducing or inhibiting tumor growth in a subject in need thereof, the method comprising administering to the subject an effective amount of an RLR agonist or RIG-VLP provided by the disclosure, or a pharmaceutical composition provided by the disclosure.

In some aspects, the disclosure provides a method for stimulating an immune response, treating or delaying progression of a cancer, or inhibiting tumor growth in a subject in need thereof, the method comprising administering to the subject an effective amount of an RLR agonist or RIG-VLP provided by the disclosure, or a pharmaceutical composition provided by the disclosure, wherein the agonist, or the pharmaceutical composition increases RLR-mediated production of one or more cytokines in a cell, increases RLR-mediated expression of one or more interferon-stimulated genes in a cell, and or increases RLR-dependent intracellular signaling in a cell, thereby stimulating the immune response, treating or delaying progression of the cancer, or inhibiting growth of the tumor.

Combinations of RLR Agonists with Additional Therapeutic Agents

In some embodiments, an RLR agonist or RIG-VLP described herein can be administered to a subject as a monotherapy. Alternatively, the RLR agonist or RIG-VLP can be administered to a subject as a combination therapy with another treatment, e.g., another treatment for a cancer. For example, the combination therapy can include administering to the subject (e.g., a human patient) one or more additional agents that provide a therapeutic benefit to a subject who has, or is at risk of developing, cancer.

In some embodiments of the methods provided by the disclosure, the RLR agonist or RIG-VLP or pharmaceutical composition is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator or agonist of a costimulatory molecule, an inhibitor of an inhibitory molecule, a vaccine, a cellular immunotherapy, or a combination thereof.

In some embodiments, combinations can be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In some embodiments, the RLR agonist, RIG-VLP, or pharmaceutical composition is administered preceding or subsequent to administration of the one or more additional therapeutic agents or wherein the one or more additional therapeutic agents is administered concurrently with, preceding or subsequent to the administration of the agonist or pharmaceutical composition.

In some embodiments, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a toll-like receptor 3 (TLR3) agonist, a toll-like receptor 7 (TLR7) agonist, a toll-like receptor 9 (TLR9) agonist.

Combination with Chemotherapeutic Agents

Chemotherapeutic agents suitable for combination and/or co-administration with compositions of the present invention include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g. mechlorethamine, thioTEPA, chlorambucil, melphalan, carmustine (BSNU), lomustine (CCNU), cyclophosphamide, busulfan, dibromomannitol, streptozotocin, mitomycin C, cis-dichlordiamine platinum (II)(DDP), procarbazine, altretamine, cisplatin, carboplatin, oxaliplatin, nedaplatin, satraplatin, or triplatin tetranitrate), anthracycline (e.g. daunorubicin (formerly daunomycin) and doxorubicin), antibiotics (e.g. dactinomcin (formerly actinomycin), bleomycin, mithramycin, and anthramycin (AMC)), and anti-mitotic agents (e.g. vincristine and vinblastine) and temozolomide.

Combination with PD-1/PD-L1 Antagonists

In some embodiments, a RLR agonist, RIG-VLP, or pharmaceutical compositions thereof, provided by the disclosure is combined (e.g., administered in combination) with one or more PD-1/PD-L1 antagonist that specifically binds to human PD-1 or PD-L1 and inhibits PD-1/PD-L1 biological activity and/or downstream pathway(s) and/or cellular processed mediated by human PD-1/PD-L1 signaling or other human PD-1/PD-L1-mediated functions.

Accordingly, provided herein are PD-1/PD-L1 antagonists that directly or allosterically block, antagonize, suppress, inhibit or reduce PD-1/PD-L1 biological activity, including downstream pathways and/or cellular processes mediated by PD-1/PD-L1 signaling, such as receptor binding and/or elicitation of a cellular response to PD-1/PD-L1. Also provided herein are PD-1/PD-L1 antagonists that reduce the quantity or amount of human PD-1 or PD-L1 produced by a cell or subject.

In some embodiments, the disclosure provides a PD-1/PD-L1 antagonist that binds human PD-1 and prevents, inhibits or reduces PD-L1 binding to PD-1. In some aspects, the PD-1/PD-L1 antagonist binds to the mRNA encoding PD-1 or PD-L1 and prevents translation. In some embodiments, the PD-1/PD-L1 antagonist binds to the mRNA encoding PD-1 or PD-L1 and causes degradation and/or turnover.

In some embodiments, the PD-1/PD-L1 antagonist inhibits PD-1 signaling or function. In some embodiments, the PD-1/PD-L1 antagonist blocks binding of PD-1 to PD-L1, PD-L2, or to both PD-L1 and PD-L2. In some embodiments, the PD-1/PD-L1 antagonist blocks binding of PD-1 to PD-L1. In some embodiments, the PD-1/PD-L1 antagonist blocks binding of PD-1 to PD-L2. In some embodiments, the PD-1/PD-L1 antagonist blocks the binding of PD-1 to PD-L1 and PD-L2. In some embodiments, the PD-1/PD-L1 antagonist specifically binds PD-1. In some embodiments, the PD-1/PD-L1 antagonist specifically binds PD-L1. In some embodiments, the PD-1/PD-L1 antagonist specifically binds PD-L2.

In some embodiments, the PD-1/PD-L1 antagonist inhibits the binding of PD-1 to its cognate ligand. In some embodiments, the PD-1/PD-L1 antagonist inhibits the binding of PD-1 to PD-L1, PD-1 to PD-L2, or PD-1 to both PD-L1 and PD-L2. In some embodiments, the PD-1/PD-L1 antagonist does not inhibit the binding of PD-1 to its cognate ligand.

In some embodiments, the PD-1/PD-L1 antagonist is an isolated monoclonal antibody (mAb), or antigen binding fragment thereof, which specifically binds to PD-1 or PD-L1. In some embodiments, the PD-1/PD-L1 antagonist is an antibody or antigen binding fragment thereof that specifically binds to human PD-1. In some embodiments, the PD-1/PD-L1 antagonist is an antibody or antigen binding fragment thereof that specifically binds to human PD-L1. In some embodiments, the PD-1/PD-L1 antagonist is an antibody or antigen binding fragment that binds to human PD-L1 and inhibits the binding of PD-L1 to PD-1. In some embodiments, the PD-1/PD-L1 antagonist is an antibody or antigen binding fragment that binds to human PD-1 and inhibits the binding of PD-L1 to PD-1.

Several immune checkpoint antagonists that inhibit or disrupt the interaction between PD-1 and either one or both of its ligands PD-L1 and PD-L2 are in clinical development or are currently available to clinicians for treating cancer.

Examples of anti-human PD-1 monoclonal antibodies, or antigen binding fragments thereof, that may comprise the PD-1/PD-L1 antagonist in any of the compositions, methods, and uses provided by the disclosure include, but are not limited to: KEYTRUDA® (pembrolizumab, MK-3475, h409A11; see U.S. Pat. Nos. 8,952,136, 8,354,509, 8,900,587, and EP2170959, all of which are included herein by reference in their entirety; Merck), OPDIVO® (nivolumab, BMS-936558, MDX-1106, ONO-4538; see U.S. Pat. Nos. 7,595,048, 8,728,474, 9,073,994, 9,067,999, EP1537878, U.S. Pat. Nos. 8,008,449, 8,779,105, and EP2161336, all of which are included herein by reference in their entirety; Bristol Myers Squibb), MEDI0680 (AMP-514), BGB-A317 and BGB-108 (BeiGene), 244C8 and 388D4 (see WO2016106159, which is incorporated herein by reference in its entirety; Enumeral Biomedical), PDR001 (Novartis), and REGN2810 (Regeneron). Accordingly, in some embodiments the PD-1/PD-L1 antagonist is pembrolizumab. In some embodiments, the PD-1/PD-L1 antagonist is nivolumab.

Examples of anti-human PD-L1 monoclonal antibodies, or antigen binding fragments thereof, that may comprise the PD-1/PD-L1 antagonist in any of the compositions, methods, and uses provided by the disclosure include, but are not limited to: BAVENCIO® (avelumab, MSB0010718C, see WO2013/79174, which is incorporated herein by reference in its entirety; Merck/Pfizer), IMFINZI® (durvalumab, MEDI4736), TECENTRIQ® (atezolizumab, MPDL3280A, RG7446; see WO2010/077634, which is incorporated herein by reference in its entirety; Roche), MDX-1105 (BMS-936559, 12A4; see U.S. Pat. No. 7,943,743 and WO2013/173223, both of which are incorporated herein by reference in their entirety; Medarex/BMS), and FAZ053 (Novartis). Accordingly, in some embodiments the PD-1/PD-L1 antagonist is avelumab. In some embodiments, the PD-1/PD-L1 antagonist is durvalumab. In some embodiments, the PD-1/PD-L1 antagonist is atezolizumab.

In some embodiments, the PD-1/PD-L1 antagonist is an immunoadhesin that specifically bind to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342, both of which are incorporated herein by reference in their entirety. In some embodiments, the PD-1/PD-L1 antagonist is AMP-224 (also known as B7-DCIg), which is a PD-L2-FC fusion protein that specifically binds to human PD-1.

It will be understood by one of ordinary skill that any PD-1/PD-L1 antagonist which binds to PD-1 or PD-L1 and disrupts the PD-1/PD-L1 signaling pathway, is suitable for compositions, methods, and uses disclosed herein.

In some embodiments, the PD-1/PD-L1 antagonist is a small molecule, a nucleic acid, a peptide, a peptide mimetic, a protein, a carbohydrate, a carbohydrate derivative, or a glycopolymer. Exemplary small molecule PD-1 inhibitors are described in Zhan et al., (2016) Drug Discov Today 21(6):1027-1036.

In some embodiments of the methods provided by the disclosure, the RLR agonist is combined with a PD-1/PD-L1 antagonist, wherein the PD-1/PD-L1 antagonist is selected from the group consisting of: PDR001, KEYTRUDA® (pembrolizumab), OPDIVO® (nivolumab), pidilizumab, MEDI0680, REGN2810, TSR-042, PF-06801591, and AMP-224. In some embodiments, the PD-1/PD-L1 antagonist is selected from the group consisting of: FAZ053, TENCENTRIQ® (atezolizumab), BAVENCIO® (avelumab), IMFINZI® (durvalumab), and BMS-936559.

Combinations with TIM-3 Antagonist

In some embodiments, an RLR agonist, RIG-VLP, or pharmaceutical compositions thereof, provided by the disclosure is combined (e.g., administered in combination) with a TIM-3 antagonist. The TIM-3 antagonist may be an antibody, an antigen binding fragment thereof, an immunoadhesin, a fusion protein, or an oligopeptide. In some embodiments, the TIM-3 antagonist is chosen from MGB453 (Novartis), TSR-022 (Tesaro), or LY3321367 (Eli Lilly).

Combinations with LAG-3 Antagonist

In some embodiments, an RLR agonist, RIG-VLP, or pharmaceutical compositions thereof, provided by the disclosure is combined (e.g., administered in combination) with a LAG-3 antagonist. The LAG-3 antagonist may be an antibody, an antigen binding fragment thereof, an immunoadhesin, a fusion protein, or oligopeptide. In some embodiments, the LAG-3 inhibitor is chosen from LAG525 (Novartis), BMS-986016 (Bristol-Myers Squibb), TSR-033 (Tesaro), MK-4280 (Merck & Co), or REGN3767 (Regeneron).

Combinations with Toll-Like Receptor (TLR) Agonists

In some embodiments, an RLR agonist, RIG-VLP, or pharmaceutical composition thereof, provided by the disclosure is combined (e.g. administered in combination) with a TLR agonist.

Toll-like receptors (TLRs) are a family of germline-encoded transmembrane proteins that facilitate pathogen recognition and activation of the innate immune system. (Hoffmann et al., (1999) Science 284:1313-1318; Rock et al., (1998) Proc Natl Acad Sci USA 95:588-593). TLRs are pattern recognition receptors (PRRs), and are expressed by cells of the innate immune system. Examples of known ligands for TLRs include gram positive bacteria (TLR-2), bacterial endotoxin (TLR-4), flagellin protein (TLR-5), bacterial DNA (TLR-9), double-stranded RNA and poly I:C (TLR-3), and yeast (TLR-2). In vivo activation of TLRs initiates an innate immune response involving specific cytokines, chemokines and growth factors. While all TLRs can activate certain intracellular signaling molecules such as nuclear factor kappa beta (NF-κB) and mitogen activated protein kinases (MAP kinases), the specific set of cytokines and chemokines released appears to be unique for each TLR. TLR7, 8, and 9 comprise a subfamily of TLRs which are located in endosomal or lysosomal compartments of immune cells such as dendritic cells and monocytes. In contrast to TLR7 and 9 which are highly expressed on plasmacytoid dendritic cells (pDC), TLR8 is mainly expressed on myeloid DC (mDC) and monocytes. This subfamily mediates recognition of microbial nucleic acids, such as single stranded RNA.

Small, low-molecular weight (less than 400 Daltons) synthetic imidazoquinoline compounds which resemble the purine nucleotides adenosine and guanosine were the first TLR7 and TLR8 agonists to be identified. A number of these compounds have demonstrated anti-viral and anti-cancer properties. For example, the TLR7 agonist imiquimod (ALDARA™) was approved by the U.S. Food and Drug Administration as a topical agent for the treatment of skin lesions caused by certain strains of the human papillomavirus. Imiquimod may also be useful for the treatment of primary skin cancers and cutaneous tumors such as basal cell carcinomas, keratoacanthomas, actinic keratoses, and Bowen's disease. The TLR7/8 agonist resiquimod (R-848) is being evaluated as a topical agent for the treatment of human genital herpes.

TLR agonists according to the disclosure can be any TLR agonist. For example, a TLR agonist can encompass a natural or synthetic TLR ligand, a mutein or derivative of a TLR ligand, a peptide mimetic of a TLR ligand, a small molecule that mimics the biological function of a TLR ligand, or an antibody that stimulates a TLR receptor. A TLR ligand is any molecule that binds to a TLR.

In some embodiments, an RLR agonist, RIG-VLP, or pharmaceutical composition thereof, provided by the disclosure, is combined with a TLR agonist, wherein the TLR agonist is selected from the group consisting of: a TLR1 agonist, a TLR2 agonist, a TLR3 agonist, a TLR4 agonist, a TLR5 agonist, a TLR6 agonist, a TLR7 agonist, a TLR8 agonist, a TLR9 agonist, a TLR10 agonist, and a TLR11 agonist.

In some embodiments, an RLR agonist or RIG-VLP provided by the disclosure is combined with a TLR3 agonist. A TLR3 agonist is an agonist that causes a signaling response through TLR3. Exemplary TLR3 agonists include, but are not limited to, polyinosinic:polycytidylic acid (poly I:C), HILTONOL® (poly ICLC), polyadenylic-polyuridylic acid (poly A:U), RIBOXXIM® (RGIC®100), RIBOXXON® (RGIC®50 bioconjugate), and RIBOXXOL® (RGIC®50).

In some embodiments, an RLR agonist or RIG-VLP provided by the disclosure is combined with polyinosinic: polycytidylic acid (poly I:C). In some embodiments, the RLR agonist or RIG-VLP is combined with HILTONOL® (poly ICLC). In some embodiments, the RLR agonist is combined with polyadenylic-polyuridylic acid (poly A:U). In some embodiments, the RLR agonist or RIG-VLP is combined with RIBOXXIM® (RGIC®100). In some embodiments, the RLR agonist or RIG-VLP is combined with RIBOXXON® (RGIC®50 bioconjugate). In some embodiments, the RLR agonist is combined with RIBOXXOL® (RGIC®50).

In some embodiments, an RLR agonist or RIG-VLP provided by the disclosure is combined with a TLR7 agonist. A TLR7 agonist is an agonist that causes a signaling response through TLR7. Non-limiting examples of TLR7 agonists include single stranded RNA (ssRNA), loxoribine (a guanosine analogue derivatized at positions N7 and C8), imidazoquinoline compounds (e.g., imiquimod and resiquimod), or derivatives thereof. Further exemplary TLR7 agonists include, but are not limited to, GS-9620 (Vesatolimod), imiquimod (ALDARA™), and resiquimod (R-848).

In some embodiments, an RLR agonist or RIG-VLP provided by the disclosure is combined with GS-9620 (Vesatolimod). In some embodiments, the RLR agonist is combined with imiquimod (ALDARA™). In some embodiments, the RLR agonist or RIG-VLP is combined with resiquimod (R-848).

In some embodiments, an RLR agonist or RIG-VLP provided by the disclosure is combined with a TLR9 agonist. A TLR9 agonist is an agonist that causes a signaling response through TLR9. Exemplary TLR9 agonists include, but are not limited to, CpG oligodeoxynucleotides (GpG ODNs). In some embodiments, the CpG ODN is a Class A CpG ODN (CpG-A ODN), a Class B CpG ODN (CpG-B ODN), or a Class C CpG ODN (CpG-B ODN).

In some embodiments, an RLR agonist or RIG-VLP provided by the disclosure is combined with a CpG oligodeoxynucleotide (CpG ODN). In some embodiments, the CpG ODN is a Class A CpG ODN (CpG-A ODN). In some embodiments, the CpG ODN is a Class B CpG ODN (CpG-B ODN). In some embodiments, the CpG ODN is a Class C CpG ODN (CpG-C ODN).

Other Combinations

In some embodiments, an RLR agonist, RIG-VLP or pharmaceutical compositions thereof, provided by the disclosure is combined (e.g., administered in combination) with a VISTA antagonist, an adenosine A2AR antagonist, a B7-H3 antagonist, a B7-H4 antagonist, a BTLA antagonist, a CTLA-4 antagonist, an IDO antagonist, or a KIR antagonist In some embodiments, an RLR agonist, RIG-VLP or pharmaceutical compositions thereof, provided by the disclosure is combined (e.g., administered in combination) with an agonist comprising an polypeptide (e.g, antibody, or antigen binding portion thereof) that specifically binds to CD137 (4-1BB).

In some embodiments, an RLR agonist, RIG-VLP, or pharmaceutical compositions thereof, provided by the disclosure is combined (e.g., administered in combination) with an agonist comprising an polypeptide (e.g., antibody, or antigen binding portion thereof) that specifically binds to CD134 (OX40).

An RLR agonist or RIG-VLP described herein can replace or augment a previously or currently administered therapy. For example, upon treating with an RLR agonist or RIG-VLP, administration of the one or more additional active agents can cease or diminish, e.g., be administered at lower levels or dosages. In some embodiments, administration of the previous therapy can be maintained. In some embodiments, a previous therapy will be maintained until the level of the RLR agonist or RIG-VLP reaches a level sufficient to provide a therapeutic effect. The two therapies can be administered in combination.

Monitoring a subject (e.g., a human patient) for an improvement in a cancer, as defined herein, means evaluating the subject for a change in a disease parameter, e.g., a reduction in tumor growth. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer described herein.

In some embodiments, an RLR agonist or RIG-VLP described herein is administered to modulate a T-cell response in a patient, for example, by increasing T-cell activation and/or proliferation. Enhancement of T cell proliferation, IFN production and secretion, and/or the cytolytic activity of T cells may be beneficial to patients in need thereof to treat a disease or condition. Accordingly, in some embodiments, an RLR agonist or RIG-VLP of the present disclosure is administered to a patent in need thereof to induce or increase T-cell activation, enhance T cell proliferation, induce the production and/or secretion of IFN, and/or induce a cytolytic T cell response.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Definitions

Terms used in the claims and specification are defined as set forth below unless otherwise specified. In the case of direct conflict with a term used in a parent provisional patent application, the term used in the instant application shall control.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

About: As used herein, the term "about" (alternatively "approximately") will be understood by persons of ordinary skill and will vary to some extent depending on the context in which it is used. If there are uses of the term which are not clear to persons of ordinary skill given the context in which it is used, "about" will mean up to plus or minus 10% of the particular value.

Agonist: As used herein, the term "agonist" is used in its broadest sense and encompasses any molecule or compound that partially or fully promotes, induces, increases, and/or activates a biological activity of a native polypeptide disclosed herein. Agonist molecules according to the disclosure may include nucleic acids (e.g., oligonucleotides, polynucleotides), antibodies or antigen-binding fragments, fragments or amino acid sequence variants of native polypeptides, peptides, oligonucleotides, lipids, carbohydrates, and small organic molecules. In some embodiments, activation in the presence of the agonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Also disclosed herein, are methods of identifying agonists suitable for use in the methods of the disclosure. For example, these methods include, but are not limited to, binding assays such as enzyme-linked immuno-absorbent assay (ELISA), Forte Bio© systems, fluorescence polarization (FP) assay, and radioimmunoassay (RIA). These assays determine the ability of an agonist to bind the polypeptide of interest (e.g., a receptor or ligand) and therefore indicate the ability of the agonist to promote, increase or activate the activity of the polypeptide. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response.

Ameliorating: As used herein, the term "ameliorating" refers to any therapeutically beneficial result in the treatment of a disease state, e.g., cancer, including prophylaxis, lessening in the severity or progression, remission, or cure thereof.

Amino acid: As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

Amino acid substitution: As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a T helper cell epitope (Th cell epitope) and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent, and again more preferably the association is through at least one, preferably one, non-peptide bond. As used herein, the term "association" as it applies to the first and second attachment sites, not only encompass the direct binding or association of the first and second attachment site forming the compositions of the invention but also, alternatively and preferably, the indirect association or binding of the first and second attachment site leading to the compositions of the invention, and hereby typically and preferably by using a heterobifunctional cross-linker.

First attachment site: As used herein, the phrase "first attachment site" refers to an element of non-natural or natural origin, typically and preferably being comprised by the virus-like particle, to which the second attachment site typically and preferably being comprised by the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the virus-like particle. Multiple first attachment sites are present on the surface of virus-like particle typically in a repetitive configuration. Preferably, the first attachment site is an amino acid or a chemically reactive group thereof.

Second attachment site: As used herein, the phrase "second attachment site" refers to an element associated with, typically and preferably being comprised by, the antigen or antigenic determinant to which the first attachment site located on the surface of the virus-like particle may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Base Composition: As used herein, the term "base composition" refers to the proportion of the total nucleotides of a nucleic acid (e.g., an RNA) consisting of guanine (or hypoxanthine)+cytosine and/or uracil (or thymine)+adenine nucleobases.

Base Pair: As used herein, the term "base pair" refers to two nucleobases on opposite complementary polynucleotide strands, or regions of the same strand, that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds.

Base pairing interactions that do not follow these rules can occur in natural, non-natural, and synthetic nucleic acids and are referred to herein as "non-Watson-Crick base pairing" or alternatively "non-canonical base pairing". A "wobble base pair" is a pairing between two nucleobases in RNA molecules that does not follow Watson-Crick base pair rules. For example, inosine is a nucleoside that is structurally similar to guanosine, but is missing the 2-amino group. Inosine is able to form two hydrogen bonds with each of the four natural nucleobases (Oda et al., (1991) Nucleic Acids Res 19:5263-5267) and it is often used by researchers as a "universal" base, meaning that it can base pair with all the naturally-occurring or canonical bases. The four main wobble base pairs are the guanine-uracil (G-U) base pair, the hypoxanthine-uracil (I-U) base pair, the hypoxanthine-adenine (I-A) base pair, and the hypoxanthine-cytosine (I-C) base pair. In order to maintain consistency of nucleic acid nomenclature, "I" is used for hypoxanthine because hypoxanthine is the nucleobase of inosine; nomenclature otherwise follows the names of nucleobases and their corresponding nucleosides (e.g., "G" for both guanine and guanosine—as well as for deoxyguanosine). The thermodynamic stability of a wobble base pair is comparable to that of a Watson-Crick base pair. Wobble base pairs play a role in the formation of secondary structure in RNA molecules.

In one aspect, the disclosure provides synthetic RNA molecules that agonize or activate one or more RIG-I-like receptors (RLRs), wherein inosine can only be inserted at positions where it will base pair with cytidine (I-C base pair); that is, inosine can be substituted for guanosine but cannot be substituted for the other nucleosides.

Biologically active: As used herein, the phrase "biologically active" refers to a characteristic of any substance that has activity in a biological system and/or organism. For instance, a substance that, when administered to an organism, has a biological effect on that organism, is considered to be biologically active and thus have "biological activity". In particular embodiments, where a nucleic acid is biologically active, a portion of that nucleic acid that shares at least one biological activity of the whole nucleic acid is typically referred to as a "biologically active" portion.

Bound: As used herein, the term "bound" refers to binding that may be covalent, e.g., by chemically coupling, or non-covalent, e.g., ionic interactions, hydrophobic interactions, hydrogen bonds, etc. Covalent bonds can be, for example, ester, ether, phosphodiester, amide, peptide, imide, carbon-sulfur bonds, carbon-phosphorus bonds, and the like. The term "bound" is broader than and includes terms such as "coupled", "fused", "associated" and "attached". Moreover, with respect to the RLR agonist being bound to the virus-like particle the term "bound" also includes the enclosement, or partial enclosement, of the RLR agonist. Therefore, with respect to the RLR agonist being bound to the virus-like particle the term "bound" is broader than and includes terms such as "coupled," "fused," "enclosed", "packaged" and "attached." For example, the RLR agonist can be enclosed by the VLP without the existence of an actual binding, neither covalently nor non-covalently.

Coat Protein: As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of bacteriophage Qβ is composed mainly of the Qβ CP, with a minor content of the A1 protein. Likewise, the VLP Qβ coat protein contains mainly Qβ CP, with a minor content of A1 protein.

Covalently linked: As used herein, the term "covalently linked" (alternatively "conjugated", "linked," "attached," "fused", or "tethered"), when used with respect to two or more moieties, means that the moieties are physically associated or connected with one another, by whatever means including chemical conjugation, recombinant techniques or enzymatic activity, either directly or via one or more additional moieties that serves as a linking agent, to form a structure that is sufficiently stable so that the moieties remain physically associated under the conditions in which the structure is used, e.g., physiological conditions.

Complementary: As used herein, the term "complementary" or "complementarity" refers to a relationship between the sequence of nucleotides comprising two polynucleotide strands, or regions of the same polynucleotide strand, and the formation of a duplex comprising the strands or regions, wherein the extent of consecutive base pairing between the two strands or regions is sufficient for the generation of a duplex structure. It is known that adenine (A) forms specific hydrogen bonds, or "base pairs", with thymine (T) or uracil (U). Similarly, it is known that a cytosine (C) base pairs with guanine (G). It is also known that non-canonical nucleobases (e.g., inosine) can hydrogen bond with natural bases. A sequence of nucleotides comprising a first strand of a polynucleotide, or a region, portion or fragment thereof, is said to be "sufficiently complementary" to a sequence of nucleotides comprising a second strand of the same or a different nucleic acid, or a region, portion, or fragment thereof, if, when the first and second strands are arranged in an antiparallel fashion, the extent of base pairing between the two strands maintains the duplex structure under the conditions in which the duplex structure is used (e.g., physiological conditions in a cell). It should be understood that complementary strands or regions of polynucleotides can include some base pairs that are non-complementary. Complementarity may be "partial," in which only some of the nucleobases comprising the polynucleotide are matched according to base pairing rules. Or, there may be "complete" or "total" complementarity between the nucleic acids. Although the degree of complementarity between polynucleotide strands or regions has significant effects on the efficiency and strength of hybridization between the strands or regions, it is not required for two complementary polynucleotides to base pair at every nucleotide position. In some embodiments, a first polynucleotide is 100% or "fully" complementary to a second polynucleotide and thus forms a base pair at every nucleotide position. In some embodiments, a first polynucleotide is not 100% complementary (e.g., is 90%, or 80% or 70% complementary) and contains mismatched nucleotides at one or more nucleotide positions. While perfect complementarity is often desired, some embodiments can include one or more but preferably 6, 5, 4, 3, 2, or 1 mismatches.

Contacting: As used herein, the term “contacting” means establishing a physical connection between two or more entities. For example, contacting a cell with an agent (e.g. an RNA, a lipid nanoparticle composition, or other pharmaceutical composition of the disclosure) means that the cell and the agent are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated RNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated RNA) and a cell may be contacted, for example, by adding the composition to the culture medium of the cell and may involve or result in transfection. Moreover, more than one cell may be contacted by an agent.

Coupled: As used herein, the term “coupled” refers to attachment by covalent bonds or by strong non-covalent interactions. With respect to the coupling of the antigen to the virus-like particle the term “coupled” preferably refers to attachment by covalent bonds. Moreover, with respect to the coupling of the antigen to the virus-like particle the term “coupled” preferably refers to association and attachment, respectively, by at least one non-peptide bond. Any method normally used by those skilled in the art for the coupling of biologically active materials can be used in the present invention.

Denaturation: As used herein, the term “denaturation” refers to the process by which the hydrogen bonding between base paired nucleotides in a nucleic acid is disrupted, resulting in the loss of secondary and/or tertiary nucleic acid structure (e.g. the separation of previously annealed strands). Denaturation can occur by the application of an external substance, energy, or biochemical process to a nucleic acid.

Antigen presenting cell: The term “antigen presenting cell” or “APC” is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

Apoptosis: As used herein, the term “apoptosis” refers to the process of programmed cell death that occurs in multicellular organisms (e.g. humans). The highly-regulated biochemical and molecular events that result in apoptosis can lead to observable and characteristic morphological changes to a cell, including membrane blebbing, cell volume shrinkage, chromosomal DNA condensation and fragmentation, and mRNA decay. A common method to identify cells, including T cells, undergoing apoptosis is to expose cells to a fluorophore-conjugated protein (Annexin V). Annexin V is commonly used to detect apoptotic cells by its ability to bind to phosphatidylserine on the outer leaflet of the plasma membrane, which is an early indicator that the cell is undergoing the process of apoptosis.

Blunt-end: As used herein, the term “blunt-end” “blunt-ended” refers to the structure of an end of a duplexed or double-stranded nucleic acid, wherein both complementary strands comprising the duplex terminate, at least at one end, in a base pair. Hence, neither strand comprising the duplex extends further from the end than the other.

Cancer antigen: As used herein, “cancer antigen” refers to (i) tumor-specific antigens, such as neoantigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

Carcinoma: As used herein, the term “carcinoma” is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The RIG-I-like receptor (RLR) agonists described herein can be used to treat patients who have, who are suspected of having, or who may be at high risk for developing any type of cancer, including renal carcinoma or melanoma. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An “adenocarcinoma” refers to a carcinoma derived from glandular tissue or in which the tumor cells form recognizable glandular structures.

Cytotoxic T lymphocyte (CTL) response: As used herein, the term “cytotoxic T lymphocyte (CTL) response” refers to an immune response induced by cytotoxic T cells. CTL responses are mediated primarily by CD8+ T cells.

Duplex: As used herein, the term “duplex” refers to a structure formed by complementary strands of a double-stranded polynucleotide, or complementary regions of a single-stranded polynucleotide that folds back on itself. The duplex structure of a nucleic acid arises as a consequence of complementary nucleotide sequences being bound together, or hybridizing, by base pairing interactions.

$EC_{50}$: As used herein, the term “$EC_{50}$” refers to the concentration of an agonist which induces a response, either in an in vitro or an in vivo assay, which is 50% of the maximal response, i.e., halfway between the maximal response and the baseline.

Effective dose: As used herein, the term “effective dose” or “effective dosage” is defined as an amount sufficient to achieve or at least partially achieve the desired effect.

Fusion: As used herein, the term “fusion” refers to the combination of amino acid sequences of different origin in one polypeptide chain by in-frame combination of their coding nucleotide sequences. The term “fusion” explicitly encompasses internal fusions, i.e., insertion of sequences of different origin within a polypeptide chain, in addition to fusion to one of its termini.

Hairpin RNA: As used herein, the term “hairpin RNA” or “RNA hairpin” refers to a self-complementary RNA comprising a double-stranded RNA (dsRNA) stem comprised of complementary nucleotide strands that base pair to form a duplex that terminates at one end in a nucleotide linker comprising a loop of unpaired nucleotides (e.g., a tetraloop) comprising unpaired nucleotides or in a non-nucleotide linker comprising a flexible chemical moiety (e.g., ethylene glycol), either of which connects the complementary nucleotide strands. RNA hairpins may differ in the length of the stem, the size and/or composition of the loop and/or linker, the number of base pair mismatches within the stem, and in the actual nucleotide sequence. RNA hairpins may provide one or more functions, including, but not limited to, guiding the overall folding of an RNA molecule comprising the hairpin, determining interactions in a ribozyme, protecting messenger RNA (e.g., mRNA) from degradation, serving as a recognition motif or structure for RNA binding proteins and acting as a substrate for enzymatic reactions. Further description of RNA hairpin structures and functions can be found in Svoboda and Di Cara (2006) Cell Mol Life Sci 63(7-8):901-908, and references contained therein. In some embodiments, the stem regions of the hairpin RNAs comprising the RLR agonists provided by the disclosure terminate in a blunt end with a 5' triphosphate or diphosphate.

Improved biological activity: As used herein, a composition which “improves” a biological activity refers to a substance in which an biological activity is observed that is greater or intensified or deviated in any way with the addition of the composition when compared to the same biological activity measured without the addition of the composition. For example, the amount of cytokines secreted can be measured, e.g. using an ELISA assay, from samples treated with and without the composition. The amount of the composition at which the cytokine secretion is enhanced as compared to cytokine secretion without the composition is said to be an amount sufficient to improve the biological activity. In one embodiment, the biological activity is improved by a factor of at least about 2, more preferably by a factor of about 3 or more. The lytic activity of cytotoxic T cells may also be altered.

In need: As used herein, a subject “in need of prevention,” “in need of treatment,” or “in need thereof,” refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising a RIG-I-like receptor agonist).

Linker: As used herein, the term “linker” (alternatively “tether” or “spacer”) refers to a moiety that covalently connects, attaches or couples two polynucleotide strands or regions together. As used herein, a linker comprising nucleotides is referred to as a “nucleotide linker” (e.g. a tetraloop). As used herein, the term “non-nucleotide linker” refers to a linker comprising a chemical moiety and that does not comprise a nucleotide. Non-limiting examples of non-nucleotide linkers include linkers comprising ethylene glycol (e.g. hexaethylene glycol), alkyl chains (e.g. C9 alkyl linker), and stilbene diether. Further description of linkers can be found in Paredes et al., (2011) Methods 54:251-259, which is incorporated herein by reference in its entirety.

LGP2: As used herein, the term “LGP2” refers to the Laboratory of Genetics and Physiology 2 polypeptide, a specific member of the RIG-I-like receptor family and is encoded by the DHX58 gene in humans. Alternative names and acronyms for LGP2 in the art include DHX58, D11LGP2, D11Igp2e, and RLR-3. An exemplary amino acid sequence of full-length human LGP2 is set forth in Table 4 (SEQ ID NO: 100) and here:

```
MELRSYQWEVIMPALEGKNIIIWLPTGAGKTRAAAYVAKRHLETVDGAKV
VVLVNRVHLVTQHGEEFRRMLDGRWTVTTLSGDMGPRAGFGHLARCHDLL
ICTAELLQMALTSPEEEEHVELTVFSLIVVDECHHTHKDTVYNVIMSQYL
ELKLQRAQPLPQVLGLTASPGTGGASKLDGAINHVLQLCANLDTWCIMSP
QNCCPQLQEHSQQPCKQYNLCHRRSQDPFGDLLKKLMDQIHDHLEMPELS
RKFGTQMYEQQVVKLSEAAALAGLQEQRVYALHLRRYNDALLIHDTVRAV
DALAALQDFYHREHVTKTQILCAERRLLALFDDRKNELAHLATHGPENPK
LEMLEKILQRQFSSSNSPRGIIFTRTRQSAHSLLLWLQQQQGLQTVDIRA
QLLIGAGNSSQSTHMTQRDQQEVIQKFQDGTLNLLVATSVAEEGLDIPHC
NVVVRYGLLTNEISMVQARGRARADQSVYAFVATEGSRELKRELINEALE
TLMEQAVAAVQKMDQAEYQAKIRDLQQAALTKRAAQAAQRENQRQQFPVE
HVQLLCINCMVAVGHGSDLRKVEGTHHVNVNPNFSNYYNVSRDPVVINKV
FKDWKPGGVISCRNCGEVWGLQMIYKSVKLPVLKVRSMLLETPQGRIQAK
KWSRVPFSVPDFDFLQHCAENLSDLSLD
(NCBP Accession Number: NP_077024.2)
```

Local administration: As used herein, “local administration” or “local delivery,” refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

MDA5: As used herein, the term “MDA5” refers to the Melanoma Differentiation-Associated Protein 5 polypeptide, a specific member of the RIG-I-like receptor family and is encoded by the IFIH1 gene in humans. Alternative names and acronyms for MDA5 in the art include AGS7, Hlcd, IDDM19, MDA-5, RLR-2, SGMRT1, and interferon induced with helicase C domain 1. An exemplary amino acid sequence of full-length human MDA5 is set forth in Table 4 (SEQ ID NO: 99) and here:

```
MSNGYSTDENFRYLISCFRARVKMYIQVEPVLDYLTFLPAEVKEQIQRTV
ATSGNMQAVELLLSTLEKGVWHLGWTREFVEALRRTGSPLAARYMNPELT
DLPSPSFENAHDEYLQLLNLLQPTLVDKLLVRDVLDKCMEEELLTIEDRN
RIAAAENNGNESGVRELLKRIVQKENWFSAFLNVLRQTGNNELVQELTGS
DCSESNAEIENLSQVDGPQVEEQLLSTTVQPNLEKEVWGMENNSSESSFA
DSSVVSESDTSLAEGSVSCLDESLGHNSNMGSDSGTMGSDSDEENVAARA
SPEPELQLRPYQMEVAQPALEGKNIIICLPTGSGKTRVAVYIAKDHLDKK
KKASEPGKVIVLVNKVLLVEQLFRKEFQPFLKKWYRVIGLSGDTQLKISF
PEVVKSCDIIISTAQILENSLLNLENGEDAGVQLSDFSLIIIDECHHTNK
EAVYNNIMRHYLMQKLKNNRLKKENKPVIPLPQILGLTASPGVGGATKQA
KAEEHILKLCANLDAFTIKTVKENLDQLKNQIQEPCKKFAIADATREDPF
KEKLLEIMTRIQTYCQMSPMSDFGTQPYEQWAIQMEKKAAKEGNRKERVC
AEHLRKYNEALQINDTIRMIDAYTHLETFYNEEKDKKFAVIEDDSDEGGD
```

-continued

```
DEYCDGDEDEDDLKKPLKLDETDRFLMTLFFENNKMLKRLAENPEYENEK

LTKLRNTIMEQYTRTEESARGIIFTKTRQSAYALSQWITENEKFAEVGVK

AHHLIGAGHSSEFKPMTQNEQKEVISKFRTGKINLLIATTVAEEGLDIKE

CNIVIRYGLVTNEIAMVQARGRARADESTYVLVAHSGSGVIEHETVNDFR

EKMMYKAIHCVQNMKPEEYAHKILELQMQSIMEKKMKTKRNIAKHYKNNP

SLITFLCKNCSVLACSGEDIHVIEKMHHVNMTPEFKELYIVRENKALQKK

CADYQINGEIICKCGQAWGTMMVHKGLDLPCLKIRNFVVVFKNNSTKKQY

KKWVELPITFPNLDYSECCLFSDED

(NCBI Accession Number: NP_071451.2)
```

Modified: As used herein "modified" or "modification" refers to a changed state or change in structure resulting from a modification of a polynucleotide, e.g., RNA. Polynucleotides may be modified in various ways including chemically, structurally, and/or functionally. For example, the RNA molecules of the present disclosure may be modified by the incorporation of a non-natural base or a sequence motif, comprising a functional sequence or secondary structure, that provides a biological activity. In one embodiment, the RNA is modified by the introduction of non-natural or chemically-modified bases, nucleosides and/or nucleotides, e.g., as it relates to the natural ribonucleotides A, U, G, and C.

Naturally-occurring: As used herein, the term "naturally-occurring" as applied to an object refers to the fact that an object can be found in nature. For example, a polypeptide or polynucleotide sequence, or components thereof such as amino acids or nucleotides, that is present in an organism (including viruses) that can be isolated from a source in nature and which has not been intentionally modified by man in the laboratory is naturally-occurring.

Nucleic acid: As used herein, the term "nucleic acid" refers to deoxyribonucleotides or ribonucleotides and polymers or oligomers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Polymers of nucleotides are referred to as "polynucleotides". Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases. "Modified nucleosides" include, for example, as inosine and thymine, when the latter is found in or comprises RNA. A variety of modifications can be made to DNA and RNA; thus, "polynucleotide" embraces chemically, enzymatically, or metabolically modified forms.

Nucleic Acid Structure: As used herein, the term "nucleic acid structure" refers to the arrangement or organization of atoms, chemical constituents, elements, motifs, and/or sequence of nucleobases that comprise a nucleic acid (e.g. an RNA) and/or can refer to the two-dimensional or three-dimensional state of a nucleic acid. Accordingly, the term "RNA structure" refers to the arrangement or organization of atoms, chemical constituents, elements, motifs, and/or sequence of nucleobases comprising an RNA molecule (e.g. an mRNA) and/or can refer to the two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g. binding affinity, nuclease resistance, chemical stability) to a nucleic acid or a portion or segment thereof. Adenine, cytosine, guanine, thymine, and uracil are the primary or canonical nucleobases predominately found in natural nucleic acids. Other natural, non-natural, non-canonical and/or synthetic nucleobases, can be incorporated into nucleic acids, such as those disclosed herein.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"). As used herein, the term "nucleotide" refers to a nucleoside covalently linked to a phosphate group. As used herein, the term "ribonucleoside" refers to a nucleoside that comprise a ribose and a nucleobase (e.g., adenosine (A), cytidine (C), guanosine (G), 5-methyluridine ($m^5U$), uridine (U), or inosine (I)).

Operably linked: As used herein, a nucleic acid, or fragment or portion thereof, such as a polynucleotide or oligonucleotide is "operably linked" when it is placed into a functional relationship with another nucleic acid sequence, or fragment or portion thereof.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In some embodiments, the repeating pattern may be a geometric pattern. Typical examples of suitable ordered and repetitive antigen or antigenic determinant arrays are those which possess strictly repetitive paracrystalline orders of antigens or antigenic determinants, preferably with spacings of 0.5 to 30 nanometers, more preferably 3 to 15 nanometers, even more preferably 3 to 8 nanometers.

Packaged: As used herein, the term "packaged" refers to the state of an RLR agonist in relation to the VLP. The term "packaged" as used herein includes binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term also includes the enclosement, or partial enclosement, of a substance. The term "packaged" includes terms such as "coupled, "enclosed" and "attached." For example, the RLR agonist can be enclosed by the VLP without the existence of an actual binding, neither covalently nor non-covalently. In some embodiments, the term "packaged" indicates that the nucleic acid in a packaged state is not accessible to DNAse or RNAse hydrolysis. In some embodiments, the RLR agonist is packaged inside the VLP capsids, most preferably in a non-covalent manner.

Polynucleotide/oligonucleotide: As used herein, the terms "polynucleotide" and "oligonucleotide" are used interchangeably and refer to a single-stranded or double-stranded polymer or oligomer of nucleotides or nucleoside monomers consisting of naturally-occurring bases, sugars and intersugar (backbone) linkages. The terms "polynucleotide" and "oligonucleotide" also includes polymers and oligomers comprising non-naturally occurring bases, sugars and intersugar (backbone) linkages, or portions thereof, which function similarly. Polynucleotides are not limited to any particular length of nucleotide sequence, as the term "polynucleotides" encompasses polymeric forms of nucleotides of any length. Short polynucleotides are typically referred to in the art as "oligonucleotides". In the context of the present disclosure, such modified or substituted polynucleotides and oligonucleotides are often used over native forms because the modification increases one or more desirable or beneficial biological properties or activities including, but not limited to, increased cytokine production, enhanced cellular uptake and/or increased stability in the presence of nucleases. In some embodiments, the agonists of the disclosure comprise polynucleotides and oligonucleotides that contain at least one region of modified nucleotides that confers one or more beneficial properties or increases biological activity (e.g., increased nuclease resistance, increased uptake into cells, increased duplex stability, increased binding affinity to a target polypeptide).

Palindromic sequence: As used herein, the term "palindromic sequence" (alternatively "palindrome") refers to a sequence of nucleotides that is self-complementary; wherein the sequence of nucleotides in the 5' to 3' direction is the same as the sequence of nucleotides comprising the complementary strand, when read in the 5' to 3'. For example, the sequence 5'-ACCTAGGT-3' is a palindromic sequence because its complementary sequence, 3'-TGGATCCA-5', when read in the 5' to 3' direction, is the same as the original sequence. In contrast, the sequence 5'-AGTGGCTG-3' is not a palindromic sequence because its complementary sequence, 3'-TCACCGAC-5', when read in the 5' to 3' direction, is not the same as the original sequence.

In one embodiment, the agonist is comprised of a first oligonucleotide, wherein the sequence of the first oligonucleotide is a palindromic sequence. In another embodiment, the agonist is comprised of a first oligonucleotide, wherein the first oligonucleotide comprises a palindromic sequence.

In one embodiment, palindromic sequences in oligonucleotides of the invention include both the 5' end of the oligonucleotide and the 3' end of the oligonucleotide, thus forming a blunt end. In one embodiment of the invention the oligonucleotide comprises a single palindromic sequence and in another embodiment of the invention the oligonucleotide comprises two complementary palindromes interrupted by an intervening sequence, spacer, or linker that connects the 2 palindromes within 1 or 2 different oligonucleotides so as to form a hairpin duplex with a blunt end.

Parenteral administration: As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

Patient: As used herein, the term "patient" includes human and other mammalian subjects that receive either prophylactic or therapeutic treatment.

Percent identity: As used herein, the term "percent identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website. The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See http://www.ncbi.nlm.nih.gov.

Pharmaceutically acceptable: As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

Pharmaceutically acceptable carrier: As used herein, the term "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

Phosphate: The term "phosphate" as used herein means a salt or ester of phosphoric acid. Polyphosphates are salts or esters of polymeric oxyanions formed from tetrahedral PO4 (phosphate) structural units linked together by sharing oxygen atoms. As used herein, the term "diphosphate" refers to a polyphosphate comprising two phosphate structural units. As used herein, the term "triphosphate" refers to a polyphosphate comprising three phosphate structural units. In some embodiments, the disclosure provides a RIG-I-like receptor agonist comprising a diphosphate moiety, or a derivative or analog thereof, linked to the 5' terminus. In some embodiments, the disclosure provides a RIG-I-like receptor agonist comprising a triphosphate moiety, or a derivative or analog thereof, linked to the 5' terminus. In some embodiments, the derivative or analog thereof is a phosphate bioisostere.

Phosphate bioisostere: As used herein, the term "phosphate bioisostere" (alternatively "phosphate mimic") refers to chemical substituents or groups with similar physical or chemical properties to phosphate and which produce broadly similar biological properties to phosphate, including diphosphate and triphosphate moieties. In drug design, the purpose of exchanging one bioisostere for another is to enhance the desired biological or physical properties of a compound without making significant changes in chemical structure. The use of bioisosteres is widespread in drug development and is used, for example, to reduce toxicity, change bioavailability, or modify the activity or metabolism of the parental or lead compound (see e.g., Rye and Baell (2005) Curr Med Chem 12(26):3127-3141; Elliot et al., (2012) MedChemCom 3(7):735-751, which are incorporated herein by reference in their entirety).

Polypeptide: As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Preventing: As used herein, the term "preventing" when used in relation to a condition, refers to administration of a composition which reduces the frequency of, or delays the onset of, symptoms of a medical condition in a subject relative to a subject which does not receive the composition.

Purified: As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

Reference ligand: As used herein, the term "reference ligand" (used interchangeably with "reference agonist") or "reference molecule" refers to a RIG-I-like receptor ligand and is used to establish a relationship between itself and one or more distinct RIG-I-like receptor ligands, wherein the relationship is the relative agonistic effect of the reference ligand and the one or more distinct RIG-I-like receptor ligands. As used herein, the term connotes a RIG-I-like receptor ligand or agonist that is useful in a test or assay, such as those described herein, (e.g., an IFN induction assay), as a competitor, wherein the assay is useful for the discovery, identification or development, of one or more distinct agonists that bind to RIG-I-like receptors.

RIG-I: As used herein, the term "RIG-I" refers to the Retinoic Acid-Inducible Gene I polypeptide, a specific member of the RIG-I-like receptor family and is encoded by the DDX58 gene in humans. Alternative names and acronyms for RIG-I in the art include DEAD box polypeptide 58, RIGI, RLR-1, SGMRT2, and DEXD/H-box helicase 58. An exemplary amino acid sequence of full-length human RIG-I is set forth in Table 4 (SEQ ID NO: 98) and here:

```
MTTEQRRSLQAFQDYIRKTLDPTYILSYMAPWFREEEVQYIQAEKNNKG
PMEAATLFLKFLLELQEEGWFRGFLDALDHAGYSGLYEAIESWDFKKIE
KLEEYRLLLKRLQPEFKTRIIPTDIISDLSECLINQECEEILQICSTKG
MMAGAEKLVECLLRSDKENWPKTLKLALEKERNKFSELWIVEKGIKDVE
TEDLEDKMETSDIQIFYQEDPECQNLSENSCPPSEVSDTNLYSPFKPRN
YQLELALPAMKGKNTIICAPTGCGKTFVSLLICEHHLKKFPQGQKGKVV
FFANQIPVYEQQKSVFSKYFERHGYRVTGISGATAENVPVEQIVENNDI
IILTPQILVNNLKKGTIPSLSIFTLMIFDECHNTSKQHPYNMIMFNYLD
QKLGGSSGPLPQVIGLTASVGVGDAKNTDEALDYICKLCASLDASVIAT
VKHNLEELEQVVYKPQKFFRKVESRISDKFKYIIAQLMRDTESLAKRIC
KDLENLSQIQNREFGTQKYEQWIVTVQKACMVFQMPDKDEESRICKALF
LYTSHLRKYNDALIISEHARMKDALDYLKDFFSNVRAAGFDEIEQDLTQ
RFEEKLQELESVSRDPSNENPKLEDLCFILQEEYHLNPETITILFVKTR
ALVDALKNWIEGNPKLSFLKPGILTGRGKTNQNTGMTLPAQKCILDAFK
ASGDHNILIATSVADEGIDIAQCNLVILYEYVGNVIKMIQTRGRGRARG
SKCFLLTSNAGVIEKEQINMYKEKMMNDSILRLQTWDEAVFREKILHIQ
THEKFIRDSQEKPKPVPDKENKKLLCRKCKALACYTADVRVIEECHYTV
LGDAFKECFVSRPHPKPKQFSSFEKRAKIFCARQNCSHDWGIHVKYKTF
EIPVIKIESFVVEDIATGVQTLYSKWKDFHFEKIPFDPAEMSK (NCBI
Accession Number: NP_055129.2)
```

RIG-I-like receptor: As used herein, the term "RIG-I-like receptor" (abbreviate as "RLR") refers to any member of a family of DExD/H box RNA helicases that function as cytoplasmic pattern recognition sensors of pathogen-associated molecular patterns (PAMPs) typically found in viral RNA. Upon ligand binding, RLRs signal downstream transcription factor activation to drive type 1 interferon (IFN) production and antiviral gene expression that elicits an intracellular immune response to control virus infection. Three RLR members have been identified: RIG-I (retinoic acid-inducible gene I), MDA5 (melanoma differentiation associated factor 5), and LGP2 (laboratory of genetics and physiology 2 and a homolog of mouse D111gp2) (Loo and Gale (2011) Immunity 34(5):680-692).

RIG-I-like receptor agonist: As used herein, the term "RIG-I-like receptor agonist" (used interchangeably with the term "RLR agonist") refers to a nucleic acid (e.g., an RNA) that binds to RIG-I-like receptors (RLRs) and partially or fully promotes, induces, increases, and/or activates a biological activity, response, and/or downstream pathway(s) mediated by RLR signaling or other RLR-mediated function. Examples of RIG-I-receptor agonists are provided herein. In some embodiments, a RLR agonist is a single-stranded nucleic acid (e.g., RNA). In some embodiments, a RLR agonist is a double-stranded nucleic acid (e.g., RNA).

Stable RNA secondary structure: As used herein, the term "stable RNA secondary structure" refers to a structure, fold, or conformation adopted by an RNA molecule, or local segment or portion thereof, that is persistently maintained under physiological conditions and characterized by a low free energy state. Typical examples of stable RNA secondary structures include duplexes, hairpins, and stem-loops. Stable RNA secondary structures are known in the art to exhibit various biological activities. The term "stable" as used in reference to a polynucleotide duplex, means that the duplex remains hybridized, structured or annealed essentially exclusively in the form of a duplex under physiological conditions or under typical salt and temperature conditions used in nucleic acid diagnostic or therapeutic applications.

Subject: As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

T cell: The term "T cell" refers to a type of white blood cell that can be distinguished from other white blood cells by the presence of a T cell receptor on the cell surface. There are several subsets of T cells, including, but not limited to, T helper cells (a.k.a. TH cells or CD4+ T cells) and subtypes, including TH1, TH2, TH3, TH17, TH9, and TFH cells, cytotoxic T cells (a.k.a TC cells, CD8+ T cells, cytotoxic T lymphocytes, T-killer cells, killer T cells), memory T cells and subtypes, including central memory T cells (TCM cells), effector memory T cells (TEM and TEMRA cells), and resident memory T cells (TRM cells), regulatory T cells (a.k.a. Treg cells or suppressor T cells) and subtypes, including CD4+FOXP3+ Treg cells, CD4+FOXP3-Treg cells, Tr1 cells, Th3 cells, and Treg17 cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

T cell activation: As used herein, the term "T cell activation" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. T cell activation requires at least two signals to become fully activated. The first occurs after engagement of the T cell antigen-specific receptor (TCR) by the antigen-major histocompatibility complex (MHC), and the second by subsequent engagement of co-stimulatory molecules (e.g., CD28). These signals are transmitted to the nucleus and result in clonal expansion of T cells, upregulation of activation markers on the cell surface, differentiation into effector cells, induction of cytotoxicity or cytokine secretion, induction of apoptosis, or a combination thereof.

T cell-mediated response: As used herein, the term "T cell-mediated response" refers to any response mediated by T cells, including, but not limited to, effector T cells (e.g., CD8+ cells) and helper T cells (e.g., CD4+ cells). T cell mediated responses include, for example, T cell cytotoxicity and proliferation.

Tetraloop: As used herein, the term "tetraloop" refers to a type of four-base loop motif found in hairpin or stem-loop RNA secondary structures that cap duplexes at one end, linking the two strands comprising the duplex, and provide stability to the hairpin structure.

Therapeutic agent: As used herein, the term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the terms "therapeutically effective amount" or "therapeutically effective dose," or similar terms used herein are intended to mean an amount of an agent (e.g., a synthetic RIG-I-like receptor agonist) that will elicit the desired biological or medical response, such as, for example, curing or at least partially arresting the condition or disease and its complications in a patient already suffering from the disease (e.g., an improvement in one or more symptoms of a cancer). Amounts effective for this use will depend on the severity of the disorder being treated and the general state of the patient's own immune system.

Treat: The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

Tumor microenvironment: As used herein, the term "tumor microenvironment" (alternatively "cancer microenvironment"; abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

Virus-like particle (VLP): As used herein, the term "virus-like particle" or "VLP" refers to a structure resembling a virus particle but which has not been demonstrated to be pathogenic. Typically, a virus-like particle in accordance with the disclosure does not carry genetic information encoding for the proteins of the virus-like particle. In general, virus-like particles lack the viral genome and, therefore, are noninfectious. Also, virus-like particles can often be produced in large quantities by heterologous expression and can be easily purified. Some virus-like particles may contain nucleic acid distinct from their genome. As indicated, a virus-like particle in accordance with the disclosure is non replicative and noninfectious since it lacks all or part of the viral genome, in particular the replicative and infectious components of the viral genome. A virus-like particle in accordance with the disclosure may contain nucleic acid distinct from their genome. In some embodiments, a virus-like particle in accordance with the present disclosure is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (generated by expression of a Qβ CP gene containing, for example, a TAA stop codon precluding any expression of the longer A1 protein through suppression, see Kozlovska, T. M., et al., Intervirology 39: 9-15 (1996)), or additionally contain A1 protein subunits in the capsid assembly.

Viral particle: The term "virus particle" as used herein refers to the morphological form of a virus. In some virus types it comprises a genome surrounded by a protein capsid; others have additional structures (e.g., envelopes, tails, etc.). Non-enveloped viral particles are made up of a proteinaceous capsid that surrounds and protects the viral genome. Enveloped viruses also have a capsid structure surrounding the genetic material of the virus but, in addition, have a lipid bilayer envelope that surrounds the capsid. In some embodiments, the VLP's are free of a lipoprotein envelope or a lipoprotein-containing envelope. In a further embodiment, the VLP's are free of an envelope altogether.

Unless otherwise defined, all technical and scientific terms used herein have the same meaning as commonly understood by one of ordinary skill in the art to which this disclosure pertains. Methods and materials are described below, although methods and materials similar or equivalent to those described herein can also be used in the practice or testing of the presently disclosed methods and compositions. All publications, patent applications, patents, and other references mentioned herein are incorporated by reference in their entirety.

EQUIVALENTS AND SCOPE

Those skilled in the art will recognize, or be able to ascertain using no more than routine experimentation, many equivalents to the specific embodiments, described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein.

It is also noted that the term "comprising" is intended to be open and permits but does not require the inclusion of additional elements or steps. When the term "comprising" is used herein, the term "consisting of" is thus also encompassed and disclosed Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Transfection of HuPBMCs with RLR Agonists Induces Cytokine Production In Vitro To determine the effect of RLR agonists comprising various modifications on cytokine induction, the ability of RLR agonists to induce cytokine production was assessed in vitro. Human peripheral blood mononuclear cells (huPBMCs) were prepared from two healthy donors and seeded at a density of $2\times10^5$ cells/well in a standard 96-well tissue culture plate in 100 μL of RPMI 1640 cell culture medium supplemented with fetal calf serum (FCS), L-glutamine, and Pen/Strep. Independent transfections of huPBMCs with RLR agonists, as indicated in FIG. 1, were carried out using Lipofectamine2000 as the transfection reagent. Cells were incubated for 24 hours at 37° C. in a humidified incubator followed by harvesting of cell culture supernatant. Supernatants were immediately frozen and stored at −20° C. Samples were thawed once for analysis of cytokines IFN-α2a (FIG. 1), as well as IFN-β, IL-1β, IP-10, IL-12p70, IL-6, MCP-1 and MIP-1β (data not shown) using a U-Plex MSD platform according to the manufacturer's instructions. FIG. 1 shows the dose-dependent induction of cytokine secretion from human PBMCs treated with novel candidate RLR agonists comprising various modifications and/or sequence motifs. RLR agonists were added at either 10 nM, 2 nM, or 0.4 nM. The amount of cytokines released by the cells in response to RLR agonist transfection is given in pg/mL.

Tables 3 and 4 show the sequences of each RLR agonist. Table 3 also shows the sequence and number corresponding to each compound tested in FIG. 1. For example, compound X25224 in FIG. 1 corresponds to "RIG7" which comprises a first oligonucleotide comprising SEQ ID NO: 42 linked via a linker "UUCG" to a second oligonucleotide comprising SEQ ID NO: 73 and has a 5' diphosphate moiety. The sequence of RIG7 is also set forth as SEQ ID NO: 6 in Table 4. For RLR agonists in Table 3 having a first and second oligonucleotide connected via a nucleotide linker, the agonist is synthesized as a single oligonucleotide using an oligonucleotide synthesizer. As shown in Table 3, certain RLR agonists have a first oligonucleotide linked via a synthetic linker to a second oligonucleotide. For example, "RIG 43a" comprises a first oligonucleotide comprising SEQ ID NO: 63 linked via a C9 alkyl linker to a second oligonucleotide comprising SEQ ID NO: 91; "RIG 43b" comprises a first oligonucleotide comprising SEQ ID NO: 63 linked via a C9 alkyl linker to a second oligonucleotide comprising SEQ ID NO: 91 and a 5' diphosphate moiety; and "RIG 44" comprises a first oligonucleotide comprising SEQ ID NO: 63 linked via a hexaethylene glycol linker to a second oligonucleotide comprising SEQ ID NO: 91 and a 5' diphosphate moiety.

Figure 2:
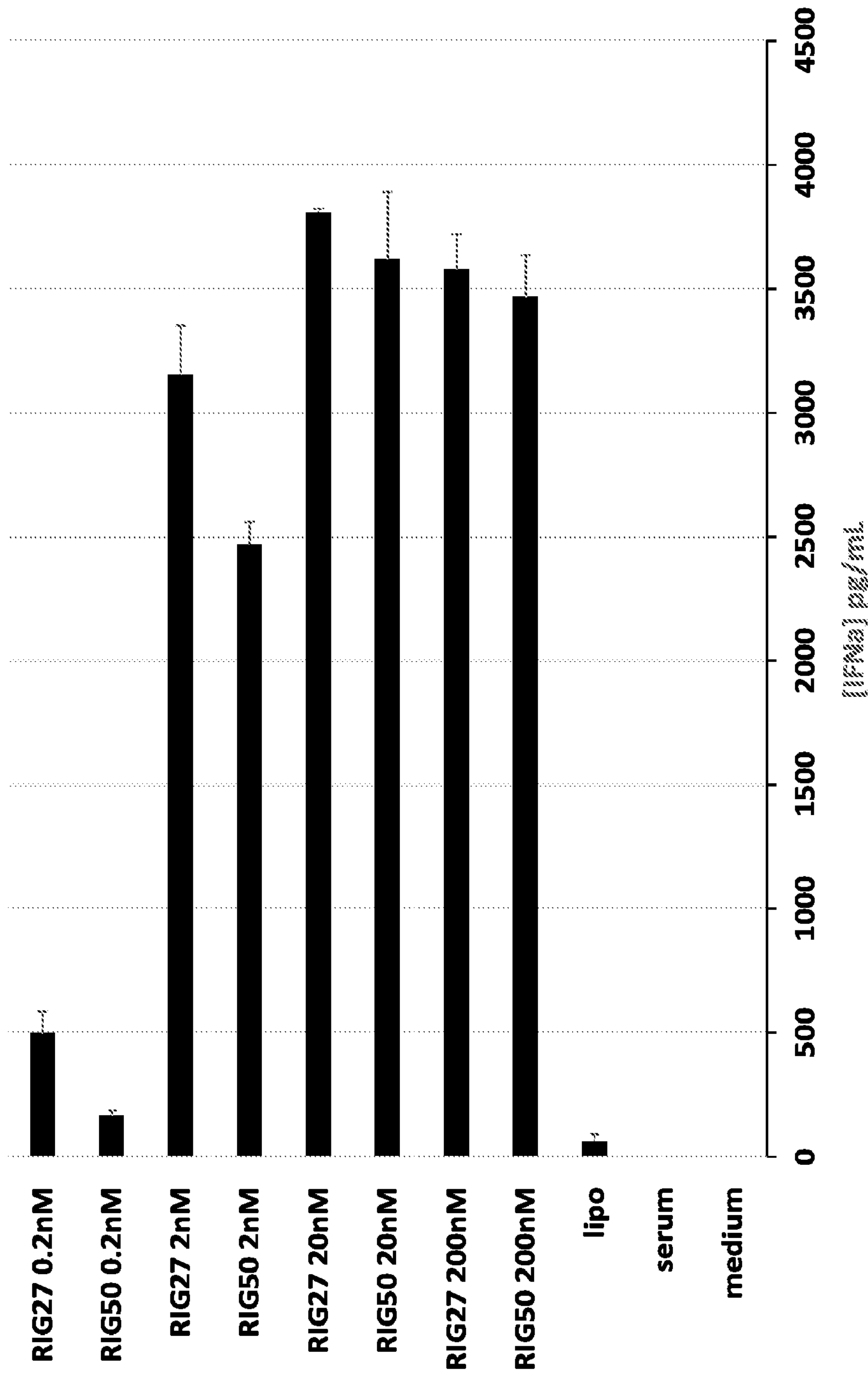
FIG. 2 provides a bar graph depicting the quantification of IFN-α secretion from human PBMCs treated with RIG 50c ($X_{24907}$) and the inosine-substituted RIG 27c ($X_{24935}$) at concentrations of 0.2 nM, 2 nM, 20 nM, and 200 nM.

In a separate experiment, the potency of two RLR agonists in inducing IFN-α expression at different concentration was further evaluated. RIG 50c (X24907) (Linehan et al., (2018) Sci. Adv. 4(2):e1701854) and the inosine-substituted RIG 27c (X24935) were tested in the in vitro assay as described above at concentrations of 0.2 nM, 2 nM, 20 nM, and 200 nM. FIG. 2 shows the dose-dependent induction of IFN-α expression by both compounds compared to cytokine levels induced by non-specific controls, i.e., PBMCs incubated with medium, lipofectamine, or immune serum. At the lower concentrations tested, incubating PBMCs with RIG 27c resulted in higher secretion of IFN-α compared to IFN-α levels elicited by incubation with RIG 50c. PBMCs transfected with 0.2 nM or 2 nM RIG 27c compared to PBMCs transfected with RIG 50c at the same concentrations elicited IFN-α levels of 498±87 pg/mL vs. 167.2±21 pg/mL and 3152±200 pg/mL vs. 2469±91 pg/mL, respectively. FIG. 2.

TABLE 3

OLIGONUCLEOTIDE COMBINATION TABLE

| RNA | First Oligo-nucleotide (FO) | Second Oligo-nucleotide (SO) | Linker | 5' Phosphate Moiety |
|---|---|---|---|---|
| RIG 2a (X32671) | 37 | 68 | UUCG | — |
| RIG 2b (X25217) | 37 | 68 | UUCG | pp |
| RIG 3a (X32666) | 38 | 69 | UUCG | — |
| RIG 3b (X25218) | 38 | 69 | UUCG | pp |
| RIG 4 (X25219) | 39 | 70 | UUCG | pp |
| RIG 5 (X25221) | 40 | 71 | UUCG | pp |
| RIG 6 (X25222) | 41 | 72 | UUCG | pp |
| RIG 7 (X25224) | 42 | 73 | UUCG | pp |
| RIG 8 (X25225) | 43 | 74 | UUCG | pp |
| RIG 9 (X25226) | 44 | 75 | UUCG | pp |
| RIG 10 (X25227) | 45 | 76 | UUCG | pp |
| RIG 11 (X25228) | 46 | 77 | UUCG | pp |
| RIG 12 (X25229) | 47 | 78 | UUCG | pp |
| RIG 13a (X32667) | 48 | 79 | UUCG | — |
| RIG 13b (X25230) | 48 | 79 | UUCG | pp |
| RIG 13c (X24921) | 48 | 79 | UUCG | ppp |
| RIG 14 (X25231) | 49 | 80 | UUCG | pp |
| RIG 15a (X32665) | 50 | 81 | UUCG | — |
| RIG 15b (X25232) | 50 | 81 | UUCG | pp |
| RIG 15c (X24923) | 50 | 81 | UUCG | ppp |
| RIG 16 (X25233) | 51 | 82 | UUCG | pp |
| RIG 18 (X25234) | 52 | 83 | UUCG | pp |
| RIG 20a (X32750) | 53 | 84 | UUCG | — |
| RIG 20b (X25235) | 53 | 84 | UUCG | pp |
| RIG 21 (X25237) | 54 | 85 | UUCG | pp |
| RIG 22a (X32672) | 55 | 86 | UUCG | — |
| RIG 22b (X25239) | 55 | 86 | UUCG | pp |
| RIG 24a (X25241) | 56 | 87 | UUCG | pp |
| RIG 24b (X25240) | 56 | 87 | UUCG | ppp |
| RIG 25 (X25242) | 57 | 88 | UUCG | pp |
| RIG 26 (X25243) | 58 | 89 | UUCG | pp |
| RIG 27a (X32669) | 59 | 89 | UUCG | — |
| RIG 27b (X25244) | 59 | 89 | UUCG | pp |
| RIG 27c (X24935) | 59 | 89 | UUCG | ppp |
| RIG 28a (X25245) | 60 | 90 | UUCG | pp |
| RIG 28b (X24936) | 60 | 90 | UUCG | ppp |
| RIG 35a (X32670) | 61 | 91 | UUCG | — |
| RIG 35b (X25247) | 61 | 91 | UUCG | pp |
| RIG 36 (X24945) | 62 | 92 | UUCG | pp |
| RIG 37a (X25249) | 63 | 91 | UUUGAU | pp |
| RIG 37b (X25248) | 63 | 91 | UUUGAU | ppp |
| RIG 38a (X32668) | 63 | 91 | UGUUU | — |
| RIG 38b (X25251) | 63 | 91 | UGUUU | pp |
| RIG 39 (X25253) | 63 | 91 | GAUC | pp |
| RIG 40 (X25255) | 64 | 93 | GAUC | pp |
| RIG 41 (X25257) | 65 | 94 | GAUC | pp |
| RIG 42 (X25259) | 64 | 93 | UUCG | pp |
| RIG 43a (X32673) | 63 | 91 | (C9) | — |
| RIG 43b (X25261) | 63 | 91 | (C9) | pp |
| RIG 44 (X25263) | 63 | 91 | (HEG) | pp |
| RIG 47 (X25265) | 66 | 95 | UUCG | pp |
| RIG 48 (X25267) | 67 | 96 | UUCG | pp |
| RIG 49a (X25269) | 63 | 97 | UUCG | pp |

TABLE 3-continued

OLIGONUCLEOTIDE COMBINATION TABLE

| RNA | First Oligo-nucleotide (FO) | Second Oligo-nucleotide (SO) | Linker | 5' Phosphate Moiety |
|---|---|---|---|---|
| RIG 49b (X25268) | 63 | 97 | UUCG | ppp |
| RIG 50a (14L) (X32664) | 63 | 91 | UUCG | — |
| RIG 50b (14L) (X24943) | 63 | 91 | UUCG | pp |
| RIG 50c (14L) (X24907) | 63 | 91 | UUCG | ppp |

(—) indicates no 5' phosphate;
(pp) indicates 5' diphosphate;
(ppp) indicates 5' triphosphate;
HEG = hexaethylene glycol linker

Example 2: Qβ VLP Synthesis

Synthesis of Qβ VLP is described in U.S. Pat. No. 9,518,095, incorporated herein by reference and described briefly below.

Cloning Strategy for the Expression Plasmid pTac-nSD-Qb-Mut (SEQ ID NO:101)

The coat protein-encoding gene (C) of *E. coli* RNA bacteriophage Qβ was amplified from plasmid pSDQb-rout (SEQ ID NO:109). The plasmid contains the sequence of gene C coding for the 133-aa Qβ coat protein (CP) and the 329-aa read through protein (A1). To prevent read-through, nucleotides 445-450 according to NCBI GenBank Acc. No. M99030 TGAACA (SEQ ID NO:102) are replaced by the sequence TAATGA (SEQ ID NO:103).

The coat protein-encoding gene C from plasmid pSDQb-mut was amplified by PCR. Oligonucleotide Qb-FOR3/2 (SEQ ID NO:104) with an internal EcoRI site and a synthetic Shine-Dalgarno (SD, SEQ ID NO:105) sequence anneals to the 5' end of the Qb CP gene. Oligonucleotide Qblang-REV2/2 (SEQ ID NO:106) contains an internal HindIII site and primes to the 3' end of the noncoding region of gene C. The 1054 bp amplified PCR fragment includes nucleotides 46-1062 of NCBI GenBank Acc. No. M99039 (except the nucleotide changes described above) and the synthetic SD sequence. The PCR fragment was digested with the restriction enzymes HindIII/EcoRI and the resulting 1036 bp fragment was inserted into the HindIII/EcoRI restriction sites of a modified pKK223-3 vector (Pharmacia, NCBI GenBank Acc. No.: M77749, SEQ ID NO:107). In this modified pKK223-3 vector the ampicillin resistance gene was replaced with the kanamycin resistance gene of vector pUC4K (Pharmacia, NCBI GenBank Acc. No.: X06404, SEQ ID NO:108).

Vector pTac-nSDQb-mut (SEQ ID NO:109) differs from vector pTacQb-mut in the Shine-Dalgarno sequence. This Shine-Dalgarno sequence (nSD, SEQ ID NO:110) was introduced by amplifying the Qβ coat protein-encoding gene C via PCR from plasmid pTacQb-mut. Oligonucleotide nSDQb-mutEcoRIfor (SEQ ID NO:111) with an internal EcoRI site and the corresponding synthetic Shine-Dalgarno (nSD) sequence anneals to the 5' end of the Qb CP gene.

Expression of Qβ CP Under Control of the Tac Promoter and nSD

The *E. coli* strain RB791 was transformed with plasmids pTac-nSD-Qb-mut (SEQ ID NO:101). The clone was grown in shake flasks. Each flask contained 100 ml of R40 medium (main culture medium, Hypep 7455, glycerol) with kanamycin (25 μg/ml) and was inoculated with overnight cultures at a start 0D600 of 0.3. The shake flasks were incubated for 4 hours (0D600 between 4 and 5) at 30° C. and an agitation of 220 rpm. The induction was carried out with 0.5% of lactose for 4 hours. Protein production was determined by SDS-PAGE. The gel showed a strong protein band which was identified as Qβ CP.

A scale-up process for manufacturing and purification of Qβ-VLP is disclosed in U.S. Pat. No. 9,657,065, incorporated herein by reference. Briefly, *E. coli* cell pellets were suspended in a 0.1% (v/v) Triton-X-100 solution and disrupted by three passages at 700±50 bar through an APV LAB 100 high pressure liquid homogenizer (HPLH). The homogenate was next processed by tangential flow filtration (TFF) and sterile filtration, and/or clarified by centrifugation.

The cell homogenate was further purified using Anion Exchange (AIX chromatography) on a FRACTOGEL.RT-M.EMD TMAE column, followed by 0.22 μM pore sterilizing filtration, and then loaded on a MACRO-PREP.RTM ceramic hydroxyapatite Type II column.

Example 3: Packaging RLR Agonists into VLP

RLR agonists may be packaged into VLPs as described in U.S. Pat. No. 9,950,055, incorporated herein by reference. Briefly, purified Qβ dimer protein is isolated as described in Example 2 above. The purified Qβ dimers capsid proteins are reassembled into VLP around the RLR agonists during the packaging step described below.

RLR agonist annealing is performed by dissolving an RLR agonist stock solution (3.3 mg/mL) in NaCP1 buffer (250 mM NaCl, 20 nM NaPi pH 7.2) to a concentration of 2.2 mg/mL. The mixture is heated to 70° C. for 5 minutes, and cooled at room temperature for 15 minutes before placing on ice until Qβ reduction is completed. The Qβ dimer (4.165 mg/mL) is reduced in 5 mM DTT and NaCP1 buffer. The Qβ dimer and RLR agonist are mixed by shaking at room temperature for 1 hour. $H_2O_2$ is then added to 10 mM, and the Qβ RLR agonist solution is shaken for another hour at room temperature. The Qβ RLR agonist reassembly mixture is then dialyzed with a 100 kDa MWCO membrane.

Alternatively, RLR agonists were dissolved in water and added to Qβ VLPs at 1, 10 and 100 nmol/ml in 0.2×HBS and incubated for 3 hours at 37° C. in a thermomixer. Excess nucleic acids were removed by enzymatic hydrolysis or dialysis.

Figure 3:
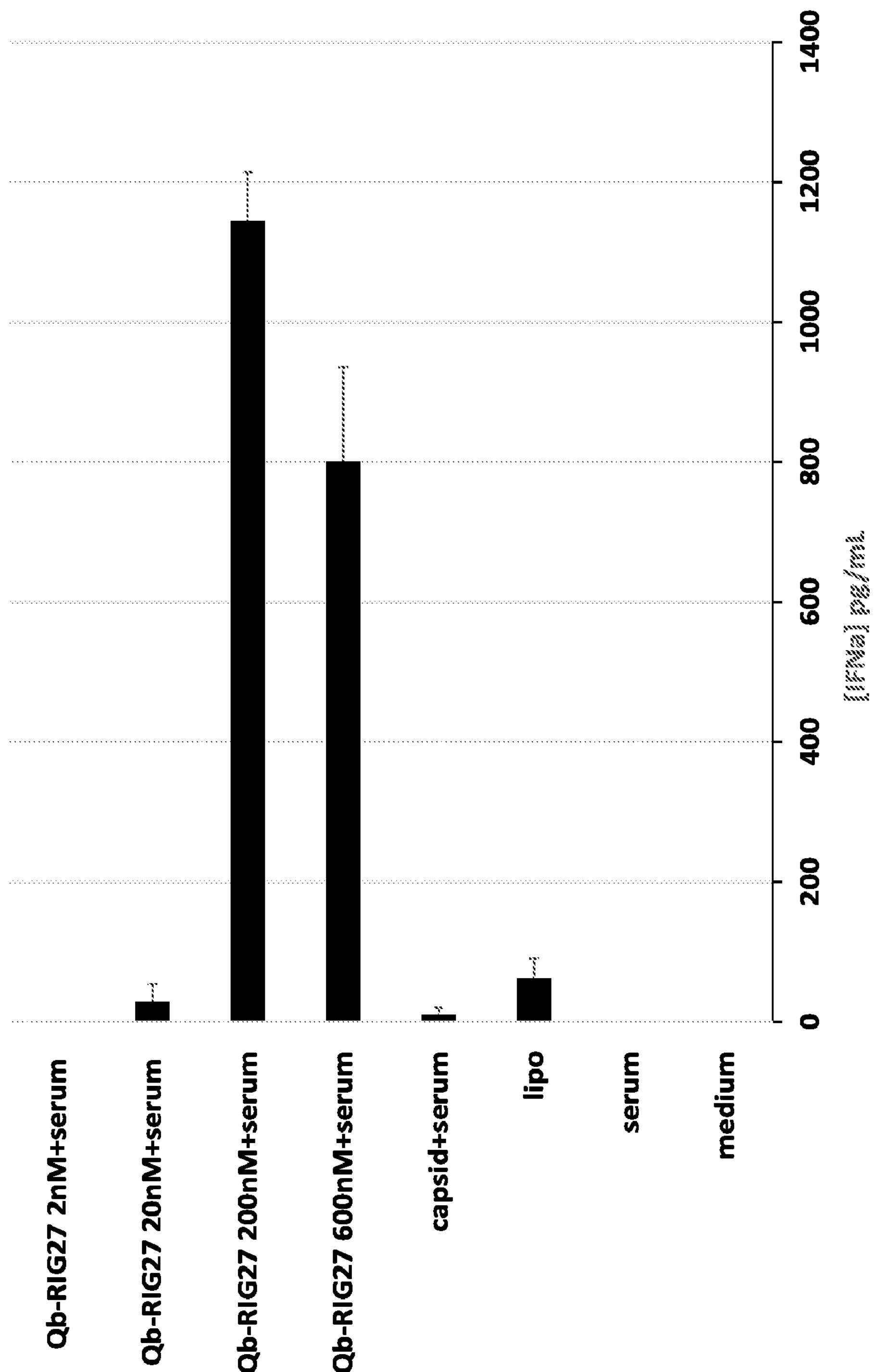
FIG. 3 provides a bar graph depicting the quantification of IFN-α secretion from human PBMCs treated with Qβ-RIG27 (RIG 27c packaged into a VLP with RNA-phage Qβ coat protein) at concentrations of 2 nM, 20 nM, 200 nM, and 600 nM.

Example 4: Transfection of HuPBMCs with Qβ RIG Induces Cytokine Production In Vitro The ability of a Qβ-RIG made according to Example 3 above, Qβ-RIG27c (a RLR agonist with nucleotide sequence of SEQ ID NO:23 packaged into a VLP with RNA-phage Qβ coat protein having the amino acid sequence of SEQ ID NO: 112), to induce IFN-α expression at different concentration was further evaluated. Specifically, Qβ-RIG27c was tested in the in vitro assay as described above at concentrations of 2 nM, 20 nM, 200 nM, and 600 nM (concentration based on the RLR agonist). FIG. 3 shows the dose-dependent induction of IFN-α expression by Qβ-RIG27c compared to cytokine expression levels elicited by non-specific controls, i.e., PBMCs incubated with medium, lipofectamine, or immune serum.

This result shows that the Qβ VLP delivery vehicle can be used to package RLR agonists and the resultant RIG-VLPs, e.g., Qβ-RIG27c, induce IFN-α expression from PBMCs in the presence of immune serum. While PBMCs transfected with an empty capsid, “capsid+serum” does not induce an IFN-α response.

Example 5: In Vivo Efficacy of Qβ-RIG

The in vivo efficacy of Qβ-RIGs may be evaluated in pre-clinical animal studies as described in U.S. Pat. No. 9,950,055, incorporated herein by reference. Mice are subcutaneously administered with Qβ-RIGs. The immunostimulatory effect of Qβ-RIGs is measured by intracellular cytokine staining of immune cells at various time-points post-administration.

In a prophylactic study, mice are subcutaneously primed with Qβ-RIGs and VLPs comprising a viral antigen (antigen-VLPs). At various time points post-prime, the frequency of antigen-specific are measured by tetramer staining. Mice are then challenged with live virus expressing the viral antigen, and the frequency of antigen-specific T cells are measured post-challenged in e.g., a tetramer assay. The immunostimulatory effect of Qβ-RIGS may be determined by comparing the frequency of antigen-specific T cells in mice that were primed with Qβ-RIGS and antigen-VLPs compared to mice primed with antigen-VLPs alone.

In a therapeutic study, mice are infected with live virus expressing a viral antigen. Tetramer staining is performed to measure the frequency of antigen-specific T cells post-infection. The mice are then subcutaneously administered Qβ-RIGS and antigen-VLPs, and the frequency of antigen-specific T cells are measured at various time-points post-administration. The immunostimulatory effect of Qβ-RIGS may be determined by comparing the frequency of antigen-specific T cells in mice that were administered Qβ-RIGS and antigen-VLPs compared to mice administered antigen-VLPs alone.

To evaluate the potency of Qβ-RIGs as anti-cancer therapy, mice are given bilateral subcutaneous administration of either A20 B cell lymphoma or B16F10 melanoma. Qβ-RIGs, or saline control, are delivered intratumorally (i.t.) on one flank starting 3-7 days after tumor challenge for a total of three doses to assess the local (treated tumor) and systemic (untreated tumor) effect of Qβ-RIG therapy. Body weights, tumor volumes (treated and untreated), and overall survival are measured.

The combination of Qβ-RIGs with an anti-cancer therapy, e.g., anti-PD1, is studied using the same tumor models. Mice are subcutaneously administered either A20 or B 16F10 tumor cells and treated with Qβ-RIGs alone as described above, or in combination with anti-PD-1 or saline control delivered intraperitoneally twice weekly starting 3-7 days after tumor challenge. The study also includes an additional treatment arm with anti-PD-1 alone. Enhancement of anti-cancer efficacy is measured by comparing body weights, tumor volumes (treated and untreated), and overall survival of mice treated with anti-PD1 or Qβ-RIGs alone, or in combination.

TABLE 4

| SEQUENCE LISTING | | |
|---|---|---|
| SEQ ID NO | Description | Sequence |
| 1 | RIG2 Nucleic acid sequence | GGATCGATCGATCGUUCGCGATCGATCGATCC |
| 2 | RIG3 Nucleic acid sequence | GGAUCGAUCGAUAUUUCGAUAUCGAUCGAUCC |
| 3 | RIG4 Nucleic acid sequence | GCGCGCGCGCGCUUCGGCGCGCGCGCGC |
| 4 | RIG5 Nucleic acid sequence | GGCGGCGCGCCGCCUUCGGGCGGCGCGCCGCC |
| 5 | RIG6 Nucleic acid sequence | GGCGGCGGCGGCGGUUCGCCGCCGCCGCCGCC |
| 6 | RIG7 Nucleic acid sequence | GGCGGCCGCCCGCGUUCGCGCGGGCGGCCGCC |
| 7 | RIG8 Nucleic acid sequence | CGACGUCGACGUCGUUCGCGACGUCGACGUCG |
| 8 | RIG9 Nucleic acid sequence | GCACGUCGACGUGCUUCGGCACGUCGACGUGC |
| 9 | RIG10 Nucleic acid sequence | GGACGUCGACGUCCUUCGGGACGUCGACGUCC |
| 10 | RIG11 Nucleic acid sequence | GGUCGCGACCAUAUUUCGAUAUGGUCGCGACC |
| 11 | RIG12 Nucleic acid sequence | GGAUACGUCGACGUUUCGACGUCGACGUAUCC |
| 12 | RIG13 Nucleic acid sequence | GAGAGAGAGAGAGAUUCGUCUCUCUCUCUCUC |
| 13 | RIG14 Nucleic acid sequence | GAGUCUAGACUCCGUUCGCGGAGUCUAGACUC |
| 14 | RIG15 Nucleic acid sequence (RIG 45) | CGAUCGAUCGAUCGUUCGCGAUCGAUCGAUCG |
| 15 | RIG16 Nucleic acid sequence | CCAUCGAUCGAUCGUUCGCGAUCGAUCGAUGG |
| 16 | RIG18 Nucleic acid sequence | GAAUCGAUCGAUCGUUCGCGAUCGAUCGAUUC |
| 17 | RIG20 Nucleic acid sequence | GGGAUCGAUCGUUCGCGAUCGAUCCC |
| 18 | RIG21 Nucleic acid sequence | CCCCCGAUCGAUCGUUCGCGAUCGAUCGGGGG |

TABLE 4-continued

| SEQUENCE LISTING | | |
|---|---|---|
| SEQ ID NO | Description | Sequence |
| 19 | RIG22 Nucleic acid sequence | GTGTGTGTGTGTGTUUCGACACACACACACAC |
| 20 | RIG24 Nucleic acid sequence | GTGTGTGGAUCGAUUUCGAUCGAUCCACACAC |
| 21 | RIG25 Nucleic acid sequence | GGAICGAICGAICGUUCGCGAICGAICGAICC |
| 22 | RIG26 Nucleic acid sequence | 1IAUCIAUCIAUCIUUCGCIAUCIAUCIAUCC |
| 23 | RIG27 Nucleic acid sequence | GGAUCIAUCIAUCIUUCGCIAUCIAUCIAUCC |
| 24 | RIG28 Nucleic acid sequence | GGIUCGIUCGIUCGUUCGCGIUCGIUCGIUCC |
| 25 | RIG35 Nucleic acid sequence | IGAUCGAUCGAUCGUUCGCGAUCGAUCGAUCC |
| 26 | RIG36 Nucleic acid sequence | AUCGAUCGAUCGUUCGCGAUCGAUCGAU |
| 27 | RIG37 Nucleic acid sequence | GGAUCGAUCGAUCGUUUGAUCGAUCGAUCGAUCC |
| 28 | RIG38 Nucleic acid sequence | GGAUCGAUCGAUCGUGUUUCGAUCGAUCGAUCC |
| 29 | RIG39 Nucleic acid sequence | GGAUCGAUCGAUCGGAUCCGAUCGAUCGAUCC |
| 30 | RIG40 Nucleic acid sequence | GGCAUGCGACCUCUGUUUGAUCAAACAGAGGUCGCAUGCC |
| 31 | RIG41 Nucleic acid sequence | GGCAUGCGACCUCUGAUCAGAGGUCGCAUGCC |
| 32 | RIG42 Nucleic acid sequence | GGCAUGCGACCUCUGUUUUUCGAAACAGAGGUCGCAUGCC |
| 33 | RIG47 Nucleic acid sequence | TGCUCGAUCGAUCGUUCGCGAUCGAUCGAGCA |
| 34 | RIG48 Nucleic acid sequence | TCGUCGAUCGAUCGUUCGCGAUCGAUCGACGA |
| 35 | RIG49 Nucleic acid sequence | GGAUCGAUCGAUCGUUCGTGAUCGAUCGAUGG |
| 36 | RIG 0 Nucleic acid sequence (14L) | GGAUCGAUCGAUCGUUCGCGAUCGAUCGAUCC |

TABLE 4-continued

SEQUENCE LISTING

| SEQ ID NO | Description | Sequence |
|---|---|---|
| 37 | FO1 Nucleic acid sequence | GGATCGATCGATCG |
| 38 | FO2 Nucleic acid sequence | GGAUCGAUCGAUAU |
| 39 | FO3 Nucleic acid sequence | GCGCGCGCGCGCGC |
| 40 | FO4 Nucleic acid sequence | GGCGGCGCGCCGCC |
| 41 | FO5 Nucleic acid sequence | GGCGGCGGCGGCGG |
| 42 | FO6 Nucleic acid sequence | GGCGGCCGCCCGCG |
| 43 | FO7 Nucleic acid sequence | CGACGUCGACGUCG |
| 44 | FO8 Nucleic acid sequence | GCACGUCGACGUGC |
| 45 | FO9 Nucleic acid sequence | GGACGUCGACGUCC |
| 46 | FO10 Nucleic acid sequence | GGUCGCGACCAUAU |
| 47 | FO11 Nucleic acid sequence | GGAUACGUCGACGU |
| 48 | FO12 Nucleic acid sequence | GAGAGAGAGAGAGA |
| 49 | FO13 Nucleic acid sequence | GAGUCUAGACUCCG |
| 50 | FO14 Nucleic acid sequence | CGAUCGAUCGAUCG |
| 51 | FO15 Nucleic acid sequence | CGAUCGAUCGAUCG |
| 52 | FO16 Nucleic acid sequence | GAAUCGAUCGAUCG |
| 53 | FO17 Nucleic acid sequence | GGGAUCGAUCG |
| 54 | FO18 Nucleic acid sequence | CCCCCGAUCGAUCG |
| 55 | FO19 Nucleic acid sequence | GTGTGTGTGTGTGT |

TABLE 4-continued

SEQUENCE LISTING

| SEQ ID NO | Description | Sequence |
|---|---|---|
| 56 | FO20 Nucleic acid sequence | GTGTGTGGAUCGAU |
| 57 | FO21 Nucleic acid sequence | GGAICGAICGAICG |
| 58 | FO22 Nucleic acid sequence | IIAUCIAUCIAUCI |
| 59 | FO23 Nucleic acid sequence | GGAUCIAUCIAUCI |
| 60 | FO24 Nucleic acid sequence | GGIUCGIUCGIUCG |
| 61 | FO25 Nucleic acid sequence | IGAUCGAUCGAUCG |
| 62 | FO26 Nucleic acid sequence | AUCGAUCGAUCG |
| 63 | FO27 Nucleic acid sequence | GGAUCGAUCGAUCG |
| 64 | FO28 Nucleic acid sequence | GGCAUGCGACCUCUGUUU |
| 65 | FO29 Nucleic acid sequence | GGCAUGCGACCUCU |
| 66 | FO30 Nucleic acid sequence | TGCUCGAUCGAUCG |
| 67 | FO31 Nucleic acid sequence | TCGUCGAUCGAUCG |
| 68 | SO1 Nucleic acid sequence | CGATCGATCGATCC |
| 69 | SO2 Nucleic acid sequence | AUAUCGAUCGAUCC |
| 70 | SO3 Nucleic acid sequence | GCGCGCGCGCGCGC |
| 71 | SO4 Nucleic acid sequence | GGCGGCGCGCCGCC |
| 72 | SO5 Nucleic acid sequence | CCGCCGCCGCCGCC |
| 73 | SO6 Nucleic acid sequence | CGCGGGCGGCCGCC |

TABLE 4-continued

| SEQUENCE LISTING | | |
|---|---|---|
| SEQ ID NO | Description | Sequence |
| 74 | SO7 Nucleic acid sequence | CGACGUCGACGUCG |
| 75 | SO8 Nucleic acid sequence | GCACGUCGACGUGC |
| 76 | SO9 Nucleic acid sequence | GGACGUCGACGUCC |
| 77 | SO10 Nucleic acid sequence | AUAUGGUCGCGACC |
| 78 | SO11 Nucleic acid sequence | ACGUCGACGUAUCC |
| 79 | SO12 Nucleic acid sequence | UCUCUCUCUCUCUC |
| 80 | SO13 Nucleic acid sequence | CGGAGUCUAGACUC |
| 81 | SO14 Nucleic acid sequence | CGAUCGAUCGAUCG |
| 82 | SO15 Nucleic acid sequence | CGAUCGAUCGAUGG |
| 83 | SO16 Nucleic acid sequence | CGAUCGAUCGAUUC |
| 84 | SO17 Nucleic acid sequence | CGAUCGAUCCC |
| 85 | SO18 Nucleic acid sequence | CGAUCGAUCGGGGG |
| 86 | SO19 Nucleic acid sequence | ACACACACACACAC |
| 87 | SO20 Nucleic acid sequence | AUCGAUCCACACAC |
| 88 | SO21 Nucleic acid sequence | CGAICGAICGAICC |
| 89 | SO22 Nucleic acid sequence | CIAUCIAUCIAUCC |
| 90 | SO23 Nucleic acid sequence | CGIUCGIUCGIUCC |
| 91 | SO24 Nucleic acid sequence | CGAUCGAUCGAUCC |
| 92 | SO25 Nucleic acid sequence | CGAUCGAUCGAU |

TABLE 4-continued

| SEQUENCE LISTING | | |
|---|---|---|
| SEQ ID NO | Description | Sequence |
| 93 | SO26 Nucleic acid sequence | AAACAGAGGUCGCAUGCC |
| 94 | SO27 Nucleic acid sequence | AGAGGUCGCAUGCC |
| 95 | SO28 Nucleic acid sequence | CGAUCGAUCGAGCA |
| 96 | SO29 Nucleic acid sequence | CGAUCGAUCGACGA |
| 97 | SO30 Nucleic acid sequence | TGAUCGAUCGAUGG |
| 98 | Human RIG-I Amino acid sequence | MTTEQRRSLQAFQDYIRKTLDPTYILSYMAPWFREEEVQYIQAEKNN<br>KGPMEAATLFLKFLLELQEEGWFRGFLDALDHAGYSGLYEAIESWDF<br>KKIEKLEEYRLLLKRLQPEFKTRIIPTDIISDLSECLINQECEEILQ<br>ICSTKGMMAGAEKLVECLLRSDKENWPKTLKLALEKERNKFSELWIV<br>EKGIKDVETEDLEDKMETSDIQIFYQEDPECQNLSENSCPPSEVSDT<br>NLYSPFKPRNYQLELALPAMKGKNTIICAPTGCGKTFVSLLICEHHL<br>KKFPQGQKGKVVFFANQIPVYEQQKSVFSKYFERHGYRVTGISGATA<br>ENVPVEQIVENNDIIILTPQILVNNLKKGTIPSLSIFTLMIFDECHN<br>TSKQHPYNMIMFNYLDQKLGGSSGPLPQVIGLTASVGVGDAKNTDEA<br>LDYICKLCASLDASVIATVKHNLEELEQVVYKPQKFFRKVESRISDK<br>FKYIIAQLMRDTESLAKRICKDLENLSQIQNREFGTQKYEQWIVTVQ<br>KACMVFQMPDKDEESRICKALFLYTSHLRKYNDALIISEHARMKDAL<br>DYLKDFFSNVRAAGFDEIEQDLTQRFEEKLQELESVSRDPSNENPKL<br>EDLCFILQEEYHLNPETITILFVKTRALVDALKNWIEGNPKLSFLKP<br>GILTGRGKTNQNTGMTLPAQKCILDAFKASGDHNILIATSVADEGID<br>IAQCNLVILYEYVGNVIKMIQTRGRGRARGSKCFLLTSNAGVIEKEQ<br>INMYKEKMMNDSILRLQTWDEAVFREKILHIQTHEKFIRDSQEKPKP<br>VPDKENKKLLCRKCKALACYTADVRVIEECHYTVLGDAFKECFVSRP<br>HPKPKQFSSFEKRAKIFCARQNCSHDWGIHVKYKTFEIPVIKIESFV<br>VEDIATGVQTLYSKWKDFHFEKIPFDPAEMSK |
| 99 | Human MDA5 Amino acid sequence | MSNGYSTDENFRYLISCFRARVKMYIQVEPVLDYLTFLPAEVKEQIQ<br>RTVATSGNMQAVELLLSTLEKGVWHLGWTREFVEALRRTGSPLAARY<br>MNPELTDLPSPSFENAHDEYLQLLNLLQPTLVDKLLVRDVLDKCMEE<br>ELLTIEDRNRIAAAENNGNESGVRELLKRIVQKENWFSAFLNVLRQT<br>GNNELVQELTGSDCSESNAEIENLSQVDGPQVEEQLLSTTVQPNLEK<br>EVWGMENNSSESSEADSSVVSESDTSLAEGSVSCLDESLGHNSNMGS<br>DSGTMGSDSDEENVAARASPEPELQLRPYQMEVAQPALEGKNIIICL<br>PTGSGKTRVAVYIAKDHLDKKKKASEPGKVIVLVNKVLLVEQLFRKE<br>FQPFLKKWYRVIGLSGDTQLKISFPEVVKSCDIIISTAQILENSLLN<br>LENGEDAGVQLSDFSLIIIDECHHTNKEAVYNNIMRHYLMQKLKNNR<br>LKKENKPVIPLPQILGLTASPGVGGATKQAKAEEHILKLCANLDAFT<br>IKTVKENLDQLKNQIQEPCKKFAIADATREDPFKEKLLEIMTRIQTY<br>CQMSPMSDFGTQPYEQWAIQMEKKAAKEGNRKERVCAEHLRKYNEAL<br>QINDTIRMIDAYTHLETFYNEEKDKKFAVIEDDSDEGGDDEYCDGDE<br>DEDDLKKPLKLDETDRELMTLFFENNKMLKRLAENPEYENEKLTKLR<br>NTIMEQYTRTEESARGIIFTKTRQSAYALSQWITENEKFAEVGVKAH<br>HLIGAGHSSEFKPMTQNEQKEVISKFRTGKINLLIATTVAEEGLDIK<br>ECNIVIRYGLVTNEIAMVQARGRARADESTYVLVAHSGSGVIEHETV<br>NDFREKMMYKAIHCVQNMKPEEYAHKILELQMQSIMEKKMKTKRNIA<br>KHYKNNPSLITFLCKNCSVLACSGEDIHVIEKMHHVNMTPEFKELYI<br>VRENKALQKKCADYQINGEIICKCGQAWGTMMVHKGLDLPCLKIRNF<br>VVVFKNNSTKKQYKKWVELPITFPNLDYSECCLFSDED |
| 100 | Human LGP2 Amino acid sequence | MELRSYQWEVIMPALEGKNIIIWLPTGAGKTRAAAYVAKRHLETVDG<br>AKVVVLVNRVHLVTQHGEEFRRMLDGRWTVTTLSGDMGPRAGFGHLA<br>RCHDLLICTAELLQMALTSPEEEEHVELTVFSLIVVDECHHTHKDTV<br>YNVIMSQYLELKLQRAQPLPQVLGLTASPGTGGASKLDGAINHVLQL<br>CANLDTWCIMSPQNCCPQLQEHSQQPCKQYNLCHRRSQDPFGDLLKK<br>LMDQIHDHLEMPELSRKFGTQMYEQQVVKLSEAAALAGLQEQRVYAL<br>HLRRYNDALLIHDTVRAVDALAALQDFYHREHVTKTQILCAERRLLA<br>LFDDRKNELAHLATHGPENPKLEMLEKILQRQFSSSNSPRGIIFTRT<br>RQSAHSLLLWLQQQQGLQTVDIRAQLLIGAGNSSQSTHMTQRDQQEV<br>IQKFQDGTLNLLVATSVAEEGLDIPHCNVVVRYGLLTNEISMVQARG |

TABLE 4-continued

| SEQUENCE LISTING | | |
|---|---|---|
| SEQ ID NO | Description | Sequence |
| | | RARADQSVYAFVATEGSRELKRELINEALETLMEQAVAAVQKMDQAE YQAKIRDLQQAALTKRAAQAAQRENQRQQFPVEHVQLLCINCMVAVG HGSDLRKVEGTHHVNVNPNFSNYYNVSRDPVVINKVFKDWKPGGVIS CRNCGEVWGLQMIYKSVKLPVLKVRSMLLETPQGRIQAKKWSRVPFS VPDFDFLQHCAENLSDLSLD |
| 101 | pTac-nSD-Qb-Mut plasmid | GGCTGTGCAGGTCGTAAATCACTGCATAATTCGTGTCGCTCAAGGCG CACTCCCGTTCTGGATAATGTTTTTTGCGCCGACATCATAACGGTTC TGGCAAATATTCTGAAATGAGCTGTTGACAATTAATCATCGGCTCGT ATAATGTGTGGAATTGTGAGCGGATAACAATTTCACACAGGAAACAG AATTCTAAGGAGGAAAAAAAAAATGGCAAAATTAGAGACTGTTACTTT AGGTAACATCGGGAAAGATGGAAAACAAACTCTGGTCCTCAATCCGC GTGGGGTAAATCCCACTAACGGCGTTGCCTCGCTTTCACAAGCGGGT GCAGTTCCTGCGCTGGAGAAGCGTGTTACCGTTTCGGTATCTCAGCC TTCTCGCAATCGTAAGAACTACAAGGTCCAGGTTAAGATCCAGAACC CGACCGCTTGCACTGCAAACGGTTCTTGTGACCCATCCGTTACTCGC CAGGCATATGCTGACGTGACCTTTTCGTTCACGCAGTATAGTACCGA TGAGGAACGAGCTTTTGTTCGTACAGAGCTTGCTGCTCTGCTCGCTA GTCCTCTGCTGATCGATGCTATTGATCAGCTGAACCCAGCGTATTAA TGACTGCTCATTGCCGGTGGTGGCTCAGGGTCAAAACCCGATCCGGT TATTCCGGATCCACCGATTGATCCGCCGCCAGGGACAGGTAAGTATA CCTGTCCCTTCGCAATTTGGTCCCTAGAGGAGGTTTACGAGCCTCCT ACTAAGAACCGACCGTGGCCTATCTATAATGCTGTTGAACTCCAGCC TCGCGAATTTGATGTTGCCCTCAAAGATCTTTTGGGCAATACAAAGT GGCGTGATTGGGATTCTCGGCTTAGTTATACCACGTTCCGCGGTTGC CGTGGCAATGGTTATATTGACCTTGATGCGACTTATCTTGCTACTGA TCAGGCTATGCGTGATCAGAAGTATGATATTCGCGAGGGCAAGAAAC CTGGTGCTTTCGGTAACATTGAGCGATTCATTTATCTTAAGTCGATA AATGCTTATTGCTCTCTTAGCGATATTGCGGCCTATCACGCCGATGG CGTGATAGTTGGCTTTTGGCGCGATCCATCCAGTGGTGGTGCCATAC CGTTTGACTTCACTAAGTTTGATAAGACTAAATGTCCTATTCAAGCC GTGATAGTCGTTCCTCGTGCTTAGTAACTAAGGATGAAATGCATGTC TAAGCTTGGCTGTTTTGGCGGATGAGAGAAGATTTTCAGCCTGATAC AGATTAAATCAGAACGCAGAAGCGGTCTGATAAAACAGAATTTGCCT GGCGGCAGTAGCGCGGTGGTCCCACCTGACCCCATGCCGAACTCAGA AGTGAAACGCCGTAGCGCCGATGGTAGTGTGGGGTCTCCCCATGCGA GAGTAGGGAACTGCCAGGCATCAAATAAAACGAAAGGCTCAGTCGAA AGACTGGGCCTTTCGTTTTATCTGTTGTTTGTCGGTGAACGCTCTCC TGAGTAGGACAAATCCGCCGGGAGCGGATTTGAACGTTGCGAAGCAA CGGCCCGGAGGGTGGCGGGCAGGACGCCCGCCATAAACTGCCAGGCA TCAAATTAAGCAGAAGGCCATCCTGACGGATGGCCTTTTTGCGTTTC TACAAACTCTTTTGTTTATTTTTCTAGAGCCACGTTGTGTCTCAAAA TCTCTGATGTTACATTGCACAAGATAAAAATATATCATCATGAACAA TAAAACTGTCTGCTTACATAAACAGTAATACAAGGAGTGTTATGAGC CATATTCAACGGGAAACGTCTTGCTCGAGGCCGCGATTAAATTCCAA CATGGATGCTGATTTATATGGGTATAAATGGGCTCGCGATAATGTCG GGCAATCAGGTGCGACAATCTATCGATTGTATGGGAAGCCCGATGCG CCAGAGTTGTTTCTGAAACATGGCAAAGGTAGCGTTGCCAATGATGT TACAGATGAGATGGTCAGACTAAACTGGCTGACGGAATTTATGCCTC TTCCGACCATCAAGCATTTTATCCGTACTCCTGATGATGCATGGTTA CTCACCACTGCGATCCCCGGGAAAACAGCATTCCAGGTATTAGAAGA ATATCCTGATTCAGGTGAAAATATTGTTGATGCGCTGGCAGTGTTCC TGCGCCGGTTGCATTCGATTCCTGTTTGTAATTGTCCTTTTAACAGC GATCGCGTATTTCGTCTCGCTCAGGCGCAATCACGAATGAATAACGG TTTGGTTGATGCGAGTGATTTTGATGACGAGCGTAATGGCTGGCCTG TTGAACAAGTCTGGAAAGAAATGCATAAGCTTTTGCCATTCTCACCG GATTCAGTCGTCACTCATGGTGATTTCTCACTTGATAACCTTATTTT TGACGAGGGGAAATTAATAGGTTGTATTGATGTTGGACGAGTCGGAA TCGCAGACCGATACCAGGATCTTGCCATCCTATGGAACTGCCTCGGT GAGTTTTCTCCTTCATTACAGAAACGGCTTTTTCAAAAATATGGTAT TGATAATCCTGATATGAATAAATTGCAGTTTCATTTGATGCTCGATG AGTTTTTCTAAACGCGTGACCAAGTTTACTCATATGTACTTTAGATT GATTTAAAACTTCATTTTTAATTTAAAAGGATCTAGGTGAAGATCCT TTTTGATAATCTCATGACCAAAATCCCTTAACGTGAGTTTTCGTTCC ACTGAGCGTCAGACCCCGTAGAAAAGATCAAAGGATCTTCTTGAGAT CCTTTTTTTCTGCGCGTAATCTGCTGCTTGCAAACAAAAAAACCACC GCTACCAGCGGTGGTTTGTTTGCCGGATCAAGAGCTACCAACTCTTT TTCCGAAGGTAACTGGCTTCAGCAGAGCGCAGATACCAAATACTGTC CTTCTAGTGTAGCCGTAGTTAGGCCACCACTTCAAGAACTCTGTAGC ACCGCCTACATACCTCGCTCTGCTAATCCTGTTACCAGTGGCTGCTG CCAGTGGCGATAAGTCGTGTCTTACCGGGTTGGACTCAAGACGATAG TTACCGGATAAGGCGCAGCGGTCGGGCTGAACGGGGGGTTCGTGCAC ACAGCCCAGCTTGGAGCGAACGACCTACACCGAACTGAGATACCTAC AGCGTGAGCTATGAGAAAGCGCCACGCTTCCCGAAGGGAGAAAGGCG GACAGGTATCCGGTAAGCGGCAGGGTCGGAACAGGAGAGCGCACGAG |

TABLE 4-continued

| SEQ ID NO | Description | Sequence |
|---|---|---|
| | | GGAGCTCCCAGGGGGAAACGCCTGGTATCTTTATAGTCCTGTCGGGT TTCGCCACCTCTGACTTGAGCGTCGATTTTTGTGATGCTCGTCAGGG GGGCGGAGCCTATGGAAAAACGCCAGCAACGCGGCCTTTTTACGGTT CCTGGCCTTTTGCTGGCCTTTTGCTCACATGTTCTTTCCTGCGTTAT CCCCTGATTCTGTGGATAACCGTATTACCGCCTTTGAGTGAGCTGAT ACCGCTCGCCGCAGCCGAACGACCGAGCGCAGCGAGTCAGTGAGCGA GGAAGCGGAAGAGCGCCTGATGCGGTATTTTCTCCTTACGCATCTGT GCGGTATTTCACACCGCATATGGTGCACTCTCAGTACAATCTGCTCT GATGCCGCATAGTTAAGCCAGTATACACTCCGCTATCGCTACGTGAC TGGGTCATGGCTGCGCCCCGACACCCGCCAACACCCGCTGACGCGCC CTGACGGGCTTGTCTGCTCCCGGCATCCGCTTACAGACAAGCTGTGA CCGTCTCCGGGAGCTGCATGTGTCAGAGGTTTTCACCGTCATCACCG AAACGCGCGAGGCAGCTGCGGTAAAGCTCATCAGCGTGGTCGTGAAG CGATTCACAGATGTCTGCCTGTTCATCCGCGTCCAGCTCGTTGAGTT TCTCCAGAAGCGTTAATGTCTGGCTTCTGATAAAGCGGGCCATGTTA AGGGCGGTTTTTTCCTGTTTGGTCACTGATGCCTCCGTGTAAGGGGG ATTTCTGTTCATGGGGGTAATGATACCGATGAAACGAGAGAGGATGC TCACGATACGGGTTACTGATGATGAACATGCCCGGTTACTGGAACGT TGTGAGGGTAAACAACTGGCGGTATGGATGCGGCGGGACCAGAGAAA AATCACTCAGGGTCAATGCCAGCGCTTCGTTAATACAGATGTAGGTG TTCCACAGGGTAGCCAGCAGCATCCTGCGATGCAGATCCGGAACATA ATGGTGCAGGGCGCTGACTTCCGCGTTTCCAGACTTTACGAAACACG GAAACCGAAGACCATTCATGTTGTTGCTCAGGTCGCAGACGTTTTGC AGCAGCAGTCGCTTCACGTTCGCTCGCGTATCGGTGATTCATTCTGC TAACCAGTAAGGCAACCCCGCCAGCCTAGCCGGGTCCTCAACGACAG GAGCACGATCATGCGCACCCGTGGCCAGGACCCAACGCTGCCCGAGA TGCGCCGCGTGCGGCTGCTGGAGATGGCGGACGCGATGGATATGTTC TGCCAAGGGTTGGTTTGCGCATTCACAGTTCTCCGCAAGAATTGATT GGCTCCAATTCTTGGAGTGGTGAATCCGTTAGCGAGGTGCCGCCGGC TTCCATTCAGGTCGAGGTGGCCCGGCTCCATGCACCGCGACGCAACG CGGGGAGGCAGACAAGGTATAGGGCGGCGCCTACAATCCATGCCAAC CCGTTCCATGTGCTCGCCGAGGCGGCATAAATCGCCGTGACGATCAG CGGTCCAATGATCGAAGTTAGGCTGGTAAGAGCCGCGAGCGATCCTT GAAGCTGTCCCTGATGGTCGTCATCTACCTGCCTGGACAGCATGGCC TGCAACGCGGGCATCCCGATGCCGCCGGAAGCGAGAAGAATCATAAT GGGGAAGGCCATCCAGCCTCGCGTCGCGAACGCCAGCAAGACGTAGC CCAGCGCGTCGGCCGCCATGCCGGCGATAATGGCCTGCTTCTCGCCG AAACGTTTGGTGGCGGGACCAGTGACGAAGGCTTGAGCGAGGGCGTG CAAGATTCCGAATACCGCAAGCGACAGGCCGATCATCGTCGCGCTCC AGCGAAAGCGGTCCTCGCCGAAAATGACCCAGAGCGCTGCCGGCACC TGTCCTACGAGTTGCATGATAAAGAAGACAGTCATAAGTGCGGCGAC GATAGTCATGCCCCGCGCCCACCGGAAGGAGCTGACTGGGTTGAAGG CTCTCAAGGGCATCGGTCGACGCTCTCCCTTATGCGACTCCTGCATT AGGAAGCAGCCCAGTAGTAGGTTGAGGCCGTTGAGCACCGCCGCCGC AAGGAATGGTGCATGCAAGGAGATGGCGCCCAACAGTCCCCCGGCCA CGGGGCCTGCCACCATACCCACGCCGAAACAAGCGCTCATGAGCCCG AAGTGGCGAGCCCGATCTTCCCCATCGGTGATGTCGGCGATATAGGC GCCAGCAACCGCACCTGTGGCGCCGGTGATGCCGGCCACGATGCGTC CGGCGTAGAGGATCCGGGCTTATCGACTGCACGGTGCACCAATGCTT CTGGCGTCAGGCAGCCATCGGAAGCTGTGGTAT |
| 102 | Stop codon | TGAACA |
| 103 | Stop codon | TAATGA |
| 104 | Qb-FOR3/2 sequence | GCGCGCGAATTCAGGAGGTAAAAAACGATGGCAAAATTAGAGACTGT TACTTTAGG |
| 105 | Shine-Dalgano sequence | AGGAGGTAAAAAACGATG |
| 106 | Qblang-REV2/2 sequence | GCATGCAAGCTTAGACATGCATTTCATCCTTAG |
| 107 | modified pKK223-3 cloning vector | TTCTGTTTCCTGTGTGAAATTGTTATCCGCTCACAATTCCACACATT ATACGAGCCGATGATTAATTGTCAACAGCTCATTTCAGAATATTTGC CAGAACCGTTATGATGTCGGCGCAAAAAACATTATCCAGAACGGGAG TGCGCCTTGAGCGACACGAATTATGCAGTGATTTACGACCTGCACAG CCATACCACAGCTTCCGATGGCTGCCTGACGCCAGAAGCATTGGTGC ACCGTGCAGTCGATAAGCTCCGGATCCTCTACGCCGGACGCATCGTG GCCGGCATCACCGGCGCCACAGGTGCGGTTGCTGGCGCCTATATCGC CGACATCACCGATGGGGAAGATCGGGCTCGCCACTTCGGGCTCATGA GCGCTTGTTTCGGCGTGGGTATGGTGGCAGGCCCCGTGGCCGGGGGA |

TABLE 4-continued

| SEQUENCE LISTING | | |
|---|---|---|
| SEQ ID NO | Description | Sequence |
| | | CTGTTGGGCGCCATCTCCTTGCATGCACCATTCCTTGCGGCGGCGGT<br>GCTCAACGGCCTCAACCTACTACTGGGCTGCTTCCTAATGCAGGAGT<br>CGCATAAGGGAGAGCGTCGACCGATGCCCTTGAGAGCCTTCAACCCA<br>GTCAGCTCCTTCCGGTGGGCGCGGGGCATGACTATCGTCGCCGCACT<br>TATGACTGTCTTCTTTATCATGCAACTCGTAGGACAGGTGCCGGCAG<br>CGCTCTGGGTCATTTTCGGCGAGGACCGCTTTCGCTGGAGCGCGACG<br>ATGATCGGCCTGTCGCTTGCGGTATTCGGAATCTTGCACGCCCTCGC<br>TCAAGCCTTCGTCACTGGTCCCGCCACCAAACGTTTCGGCGAGAAGC<br>AGGCCATTATCGCCGGCATGGCGGCCGACGCGCTGGGCTACGTCTTG<br>CTGGCGTTCGCGACGCGAGGCTGGATGGCCTTCCCCATTATGATTCT<br>TCTCGCTTCCGGCGGCATCGGGATGCCCGCGTTGCAGGCCATGCTGT<br>CCAGGCAGGTAGATGACGACCATCAGGGACAGCTTCAAGGATCGCTC<br>GCGGCTCTTACCAGCCTAACTTCGATCACTGGACCGCTGATCGTCAC<br>GGCGATTTATGCCGCCTCGGCGAGCACATGGAACGGGTTGGCATGGA<br>TTGTAGGCGCCGCCCTATACCTTGTCTGCCTCCCCGCGTTGCGTCGC<br>GGTGCATGGAGCCGGGCCACCTCGACCTGAATGGAAGCCGGCGGCAC<br>CTCGCTAACGGATTCACCACTCCAAGAATTGGAGCCAATCAATTCTT<br>GCGGAGAACTGTGAATGCGCAAACCAACCCTTGGCAGAACATATCCA<br>TCGCGTCCGCCATCTCCAGCAGCCGCACGCGGCGCATCTCGGGCAGC<br>GTTGGGTCCTGGCCACGGGTGCGCATGATCGTGCTCCTGTCGTTGAG<br>GACCCGGCTAGGCTGGCGGGGTTGCCTTACTGGTTAGCAGAATGAAT<br>CACCGATACGCGAGCGAACGTGAAGCGACTGCTGCTGCAAAACGTCT<br>GCGACCTGAGCAACAACATGAATGGTCTTCGGTTTCCGTGTTTCGTA<br>AAGTCTGGAAACGCGGAAGTCAGCGCCCTGCACCATTATGTTCCGGA<br>TCTGCATCGCAGGATGCTGCTGGCTACCCTGTGGAACACCTACATCT<br>GTATTAACGAAGCGCTGGCATTGACCCTGAGTGATTTTTCTCTGGTC<br>CCGCCGCATCCATACCGCCAGTTGTTTACCCTCACAACGTTCCAGTA<br>ACCGGGCATGTTCATCATCAGTAACCCGTATCGTGAGCATCCTCTCT<br>CGTTTCATCGGTATCATTACCCCCATGAACAGAAATTCCCCCTTACA<br>CGGAGGCATCAAGTGACCAAACAGGAAAAAACCGCCCTTAACATGGC<br>CCGCTTTATCAGAAGCCAGACATTAACGCTTCTGGAGAAACTCAACG<br>AGCTGGACGCGGATGAACAGGCAGACATCTGTGAATCGCTTCACGAC<br>CACGCTGATGAGCTTTACCGCAGCTGCCTCGCGCGTTTCGGTGATGA<br>CGGTGAAAACCTCTGACACATGCAGCTCCCGGAGACGGTCACAGCTT<br>GTCTGTAAGCGGATGCCGGGAGCAGACAAGCCCGTCAGGGCGCGTCA<br>GCGGGTGTTGGCGGGTGTCGGGGCGCAGCCATGACCCAGTCACGTAG<br>CGATAGCGGAGTGTATACTGGCTTAACTATGCGGCATCAGAGCAGAT<br>TGTACTGAGAGTGCACCATATGCGGTGTGAAATACCGCACAGATGCG<br>TAAGGAGAAAATACCGCATCAGGCGCTCTTCCGCTTCCTCGCTCACT<br>GACTCGCTGCGCTCGGTCGTTCGGCTGCGGCGAGCGGTATCAGCTCA<br>CTCAAAGGCGGTAATACGGTTATCCACAGAATCAGGGGATAACGCAG<br>GAAAGAACATGTGAGCAAAAGGCCAGCAAAAGGCCAGGAACCGTAAA<br>AAGGCCGCGTTGCTGGCGTTTTTCCATAGGCTCCGCCCCCCTGACGA<br>GCATCACAAAAATCGACGCTCAAGTCAGAGGTGGCGAAACCCGACAG<br>GACTATAAAGATACCAGGCGTTTCCCCCTGGAAGCTCCCTCGTGCGC<br>TCTCCTGTTCCGACCCTGCCGCTTACCGGATACCTGTCCGCCTTTCT<br>CCCTTCGGGAAGCGTGGCGCTTTCTCATAGCTCACGCTGTAGGTATC<br>TCAGTTCGGTGTAGGTCGTTCGCTCCAAGCTGGGCTGTGTGCACGAA<br>CCCCCCGTTCAGCCCGACCGCTGCGCCTTATCCGGTAACTATCGTCT<br>TGAGTCCAACCCGGTAAGACACGACTTATCGCCACTGGCAGCAGCCA<br>CTGGTAACAGGATTAGCAGAGCGAGGTATGTAGGCGGTGCTACAGAG<br>TTCTTGAAGTGGTGGCCTAACTACGGCTACACTAGAAGGACAGTATT<br>TGGTATCTGCGCTCTGCTGAAGCCAGTTACCTTCGGAAAAAGAGTTG<br>GTAGCTCTTGATCCGGCAAACAAACCACCGCTGGTAGCGGTGGTTTT<br>TTTGTTTGCAAGCAGCAGATTACGCGCAGAAAAAAAGGATCTCAAGA<br>AGATCCTTTGATCTTTTCTACGGGGTCTGACGCTCAGTGGAACGAAA<br>ACTCACGTTAAGGGATTTTGGTCATGAGATTATCAAAAAGGATCTTC<br>ACCTAGATCCTTTTAAATTAAAAATGAAGTTTTAAATCAATCTAAAG<br>TATATATGAGTAAACTTGGTCTGACAGTTACCAATGCTTAATCAGTG<br>AGGCACCTATCTCAGCGATCTGTCTATTTCGTTCATCCATAGTTGCC<br>TGACTCCCCGTCGTGTAGATAACTACGATACGGGAGGGCTTACCATC<br>TGGCCCCAGTGCTGCAATGATACCGCGAGACCCACGCTCACCGGCTC<br>CAGATTTATCAGCAATAAACCAGCCAGCCGGAAGGGCCGAGCGCAGA<br>AGTGGTCCTGCAACTTTATCCGCCTCCATCCAGTCTATTAATTGTTG<br>CCGGGAAGCTAGAGTAAGTAGTTCGCCAGTTAATAGTTTGCGCAACG<br>TTGTTGCCATTGCTACAGGCATCGTGGTGTCACGCTCGTCGTTTGGT<br>ATGGCTTCATTCAGCTCCGGTTCCCAACGATCAAGGCGAGTTACATG<br>ATCCCCCATGTTGTGCAAAAAAGCGGTTAGCTCCTTCGGTCCTCCGA<br>TCGTTGTCAGAAGTAAGTTGGCCGCAGTGTTATCACTCATGGTTATG<br>GCAGCACTGCATAATTCTCTTACTGTCATGCCATCCGTAAGATGCTT<br>TTCTGTGACTGGTGAGTACTCAACCAAGTCATTCTGAGAATAGTGTA<br>TGCGGCGACCGAGTTGCTCTTGCCCGGCGTCAACACGGGATAATACC<br>GCGCCACATAGCAGAACTTTAAAAGTGCTCATCATTGGAAAACGTTC<br>TTCGGGGCGAAAACTCTCAAGGATCTTACCGCTGTTGAGATCCAGTT<br>CGATGTAACCCACTCGTGCACCCAACTGATCTTCAGCATCTTTTACT |

TABLE 4-continued

| SEQ ID NO | Description | Sequence |
|---|---|---|
| | | TTCACCAGCGTTTCTGGGTGAGCAAAAACAGGAAGGCAAAATGCCGC AAAAAAGGGAATAAGGGCGACACGGAAATGTTGAATACTCATACTCT TCCTTTTTCAATATTATTGAAGCATTTATCAGGGTTATTGTCTCATG AGCGGATACATATTTGAATGTATTTAGAAAAATAAACAAAAGAGTTT GTAGAAACGCAAAAAGGCCATCCGTCAGGATGGCCTTCTGCTTAATT TGATGCCTGGCAGTTTATGGCGGGCGTCCTGCCCGCCACCCTCCGGG CCGTTGCTTCGCAACGTTCAAATCCGCTCCCGGCGGATTTGTCCTAC TCAGGAGAGCGTTCACCGACAAACAACAGATAAAACGAAAGGCCCAG TCTTTCGACTGAGCCTTTCGTTTTATTTGATGCCTGGCAGTTCCCTA CTCTCGCATGGGGAGACCCCACACTACCATCGGCGCTACGGCGTTTC ACTTCTGAGTTCGGCATGGGGTCAGGTGGGACCACCGCGCTACTGCC GCCAGGCAAATTCTGTTTTATCAGACCGCTTCTGCGTTCTGATTTAA TCTGTATCAGGCTGAAAATCTTCTCTCATCCGCCAAAACAGAAGCTT GGCTGCAGGTCGACGGATCCCCGGGAA |
| 108 | modified pKK223-3 cloning vector | TCGCGCGTTTCGGTGATGACGGTGAAAACCTCTGACACATGCAGCTC CCGGAGACGGTCACAGCTTGTCTGTAAGCGGATGCCGGGAGCAGACA AGCCCGTCAGGGCGCGTCAGCGGGTGTTGGCGGGTGTCGGGGCTGGC TTAACTATGCGGCATCAGAGCAGATTGTACTGAGAGTGCACCATATG CGGTGTGAAATACCGCACAGATGCGTAAGGAGAAAATACCGCATCAG GCGCCATTCGCCATTCAGGCTGCGCAACTGTTGGGAAGGGCGATCGG TGCGGGCCTCTTCGCTATTACGCCAGCTGGCGAAAGGGGGATGTGCT GCAAGGCGATTAAGTTGGGTAACGCCAGGGTTTTCCCAGTCACGACG TTGTAAAACGACGGCCAGTGAATTCCCCGGATCCGTCGACCTGCAGG GGGGGGGGGGCGCTGAGGTCTGCCTCGTGAAGAAGGTGTTGCTGACT CATACCAGGCCTGAATCGCCCCATCATCCAGCCAGAAAGTGAGGGAG CCACGGTTGATGAGAGCTTTGTTGTAGGTGGACCAGTTGGTGATTTT GAACTTTTGCTTTGCCACGGAACGGTCTGCGTTGTCGGGAAGATGCG TGATCTGATCCTTCAACTCAGCAAAAGTTCGATTTATTCAACAAAGC CGCCGTCCCGTCAAGTCAGCGTAATGCTCTGCCAGTGTTACAACCAA TTAACCAATTCTGATTAGAAAAACTCATCGAGCATCAAATGAAACTG CAATTTATTCATATCAGGATTATCAATACCATATTTTTGAAAAAGCC GTTTCTGTAATGAAGGAGAAAACTCACCGAGGCAGTTCCATAGGATG GCAAGATCCTGGTATCGGTCTGCGATTCCGACTCGTCCAACATCAAT ACAACCTATTAATTTCCCCTCGTCAAAAATAAGGTTATCAAGTGAGA AATCACCATGAGTGACGACTGAATCCGGTGAGAATGGCAAAAGCTTA TGCATTTCTTTCCAGACTTGTTCAACAGGCCAGCCATTACGCTCGTC ATCAAAATCACTCGCATCAACCAAACCGTTATTCATTCGTGATTGCG CCTGAGCGAGACGAAATACGCGATCGCTGTTAAAAGGACAATTACAA ACAGGAATCGAATGCAACCGGCGCAGGAACACTGCCAGCGCATCAAC AATATTTTCACCTGAATCAGGATATTCTTCTAATACCTGGAATGCTG TTTTCCCGGGGATCGCAGTGGTGAGTAACCATGCATCATCAGGAGTA CGGATAAAATGCTTGATGGTCGGAAGAGGCATAAATTCCGTCAGCCA GTTTAGTCTGACCATCTCATCTGTAACATCATTGGCAACGCTACCTT TGCCATGTTTCAGAAACAACTCTGGCGCATCGGGCTTCCCATACAAT CGATAGATTGTCGCACCTGATTGCCCGACATTATCGCGAGCCCATTT ATACCCATATAAATCAGCATCCATGTTGGAATTTAATCGCGGCCTCG AGCAAGACGTTTCCCGTTGAATATGGCTCATAACACCCCTTGTATTA CTGTTTATGTAAGCAGACAGTTTTATTGTTCATGATGATATATTTTT ATCTTGTGCAATGTAACATCAGAGATTTTGAGACACAACGTGGCTTT CCCCCCCCCCCCTGCAGGTCGACGGATCCGGGGAATTCGTAATCATG GTCATAGCTGTTTCCTGTGTGAAATTGTTATCCGCTCACAATTCCAC ACAACATACGAGCCGGAAGCATAAAGTGTAAAGCCTGGGGTGCCTAA TGAGTGAGCTAACTCACATTAATTGCGTTGCGCTCACTGCCCGCTTT CCAGTCGGGAAACCTGTCGTGCCAGCTGCATTAATGAATCGGCCAAC GCGCGGGGAGAGGCGGTTTGCGTATTGGGCGCTCTTCCGCTTCCTCG CTCACTGACTCGCTGCGCTCGGTCGTTCGGCTGCGGCGAGCGGTATC AGCTCACTCAAAGGCGGTAATACGGTTATCCACAGAATCAGGGGATA ACGCAGGAAAGAACATGTGAGCAAAAGGCCAGCAAAAGGCCAGGAAC CGTAAAAAGGCCGCGTTGCTGGCGTTTTTCCATAGGCTCCGCCCCCC TGACGAGCATCACAAAAATCGACGCTCAAGTCAGAGGTGGCGAAACC CGACAGGACTATAAAGATACCAGGCGTTTCCCCCTGGAAGCTCCCTC GTGCGCTCTCCTGTTCCGACCCTGCCGCTTACCGGATACCTGTCCGC CTTTCTCCCTTCGGGAAGCGTGGCGCTTTCTCAATGCTCACGCTGTA GGTATCTCAGTTCGGTGTAGGTCGTTCGCTCCAAGCTGGGCTGTGTG CACGAACCCCCCGTTCAGCCCGACCGCTGCGCCTTATCCGGTAACTA TCGTCTTGAGTCCAACCCGGTAAGACACGACTTATCGCCACTGGCAG CAGCCACTGGTAACAGGATTAGCAGAGCGAGGTATGTAGGCGGTGCT ACAGAGTTCTTGAAGTGGTGGCCTAACTACGGCTACACTAGAAGGAC AGTATTTGGTATCTGCGCTCTGCTGAAGCCAGTTACCTTCGGAAAAA GAGTTGGTAGCTCTTGATCCGGCAAACAAACCACCGCTGGTAGCGGT GGTTTTTTTGTTTGCAAGCAGCAGATTACGCGCAGAAAAAAAGGATC TCAAGAAGATCCTTTGATCTTTTCTACGGGGTCTGACGCTCAGTGGA ACGAAAACTCACGTTAAGGGATTTTGGTCATGAGATTATCAAAAAGG ATCTTCACCTAGATCCTTTTAAATTAAAAATGAAGTTTTAAATCAAT |

TABLE 4-continued

SEQUENCE LISTING

| SEQ ID NO | Description | Sequence |
|---|---|---|
| | | CTAAAGTATATATGAGTAAACTTGGTCTGACAGTTACCAATGCTTAA<br>TCAGTGAGGCACCTATCTCAGCGATCTGTCTATTTCGTTCATCCATA<br>GTTGCCTGACTCCCCGTCGTGTAGATAACTACGATACGGGAGGGCTT<br>ACCATCTGGCCCCAGTGCTGCAATGATACCGCGAGACCCACGCTCAC<br>CGGCTCCAGATTTATCAGCAATAAACCAGCCAGCCGGAAGGGCCGAG<br>CGCAGAAGTGGTCCTGCAACTTTATCCGCCTCCATCCAGTCTATTAA<br>TTGTTGCCGGGAAGCTAGAGTAAGTAGTTCGCCAGTTAATAGTTTGC<br>GCAACGTTGTTGCCATTGCTACAGGCATCGTGGTGTCACGCTCGTCG<br>TTTGGTATGGCTTCATTCAGCTCCGGTTCCCAACGATCAAGGCGAGT<br>TACATGATCCCCCATGTTGTGCAAAAAAGCGGTTAGCTCCTTCGGTC<br>CTCCGATCGTTGTCAGAAGTAAGTTGGCCGCAGTGTTATCACTCATG<br>GTTATGGCAGCACTGCATAATTCTCTTACTGTCATGCCATCCGTAAG<br>ATGCTTTTCTGTGACTGGTGAGTACTCAACCAAGTCATTCTGAGAAT<br>AGTGTATGCGGCGACCGAGTTGCTCTTGCCCGGCGTCAATACGGGAT<br>AATACCGCGCCACATAGCAGAACTTTAAAAGTGCTCATCATTGGAAA<br>ACGTTCTTCGGGGCGAAAACTCTCAAGGATCTTACCGCTGTTGAGAT<br>CCAGTTCGATGTAACCCACTCGTGCACCCAACTGATCTTCAGCATCT<br>TTTACTTTCACCAGCGTTTCTGGGTGAGCAAAAACAGGAAGGCAAAA<br>TGCCGCAAAAAAGGGAATAAGGGCGACACGGAAATGTTGAATACTCA<br>TACTCTTCCTTTTTCAATATTATTGAAGCATTTATCAGGGTTATTGT<br>CTCATGAGCGGATACATATTTGAATGTATTTAGAAAAATAAACAAAT<br>AGGGGTTCCGCGCACATTTCCCCGAAAAGTGCCACCTGACGTCTAAG<br>AAACCATTATTATCATGACATTAACCTATAAAAATAGGCGTATCACG<br>AGGCCCTTTCGTC |
| 109 | pSDQb-rout plasmid | TCGCGCGTTTCGGTGATGACGGTGAAAACCTCTGACACATGCAGCTC<br>CCGGAGACGGTCACAGCTTGTCTGTAAGCGGATGCCGGGAGCAGACA<br>AGCCCGTCAGGGCGCGTCAGCGGGTGTTGGCGGGTGTCGGGGCTGGC<br>TTAACTATGCGGCATCAGAGCAGATTGTACTGAGAGTGCACCATATG<br>CGGTGTGAAATACCGCACAGATGCGTAAGGAGAAAATACCGCATCAG<br>GCGCCATTCGCCATTCAGGCTGCGCAACTGTTGGGAAGGGCGATCGG<br>TGCGGGCCTCTTCGCTATTACGCCAGCTGGCGAAAGGGGGATGTGCT<br>GCAAGGCGATTAAGTTGGGTAACGCCAGGGTTTTCCCAGTCACGACG<br>TTGTAAAACGACGGCCAGTGAATTCAGACATGCATTTCATCCTTAGT<br>TACTAAGCACGAGGAACGACTATCACGGCTTGAATAGGACATTTAGT<br>CTTATCAAACTTAGTGAAGTCAAACGGTATGGCACCACCACTGGATG<br>GATCGCGCCAAAAGCCAACTATCACGCCATCGGCGTGATAGGCCGCA<br>ATATCGCTAAGAGAGCAATAAGCATTTATCGACTTAAGATAAATGAA<br>TCGCTCAATGTTACCGAAAGCACCAGGTTTCTTGCCCTCGCGAATAT<br>CATACTTCTGATCACGCATAGCCTGATCAGTAGCAAGATAAGTCGCA<br>TCAAGGTCAATATAACCATTGCCACGGCAACCGCGGAACGTGGTATA<br>ACTAAGCCGAGAATCCCAATCACGCCACTTTGTATTGCCCAAAAGAT<br>CTTTGAGGGCAACATCAAATTCGCGAGGCTGGAGTTCAACAGCATTA<br>TAGATAGGCCACGGTCGGTTCTTAGTAGGAGGCTCGTAAACCTCCTC<br>TAGGGACCAAATTGCGAAGGGACAGGTATACTTACCTGTCCCTGGCG<br>GCGGATCAATCGGTGGATCCGGAATAACCGGATCGGGTTTTGACCCT<br>GAGCCACCACCGGCAATGAGCAGTCATTAATACGCTGGGTTCAGCTG<br>ATCAATAGCATCGATCAGCAGAGGACTAGCGAGCAGAGCAGCAAGCT<br>CTGTACGAACAAAAGCTCGTTCCTCATCGGTACTATACTGCGTGAAC<br>GAAAAGGTCACGTCAGCATATGCCTGGCGAGTAACGGATGGGTCACA<br>AGAACCGTTTGCAGTGCAAGCGGTCGGGTTCTGGATCTTAACCTGGA<br>CCTTGTAGTTCTTACGATTGCGAGAAGGCTGAGATACCGAAACGGTA<br>ACACGCTTCTCCAGCGCAGGAACTGCACCCGCTTGTGAAAGCGAGGC<br>AACGCCGTTAGTGGGATTTACCCCACGCGGATTGAGGACCAGAGTTT<br>GTTTTCCATCTTTCCCGATGTTACCTAAAGTAACAGTCTCTAATTTT<br>GCCATCGTTTTTTACCTCCTTCTAGAGTCATTATGGTTTTGCCATAC<br>ATCAGTATGGTGTAGCAGCACTTATTATAATCTTTATTGCCTCTTAA<br>AACTTAATCCACATCAAAACTCAAATACTTTTAACCCCAGCGTCCTG<br>TAAGCTCTGCATTAATGAATCGGCCAACGCGCGGGGAGAGGCGGTTT<br>GCGTATTGGGCGCTCTTCCGCTTCCTCGCTCACTGACTCGCTGCGCT<br>CGGTCGTTCGGCTGCGGCGAGCGGTATCAGCTCACTCAAAGGCGGTA<br>ATACGGTTATCCACAGAATCAGGGGATAACGCAGGAAAGAACATGTG<br>AGCAAAAGGCCAGCAAAAGGCCAGGAACCGTAAAAAGGCCGCGTTGC<br>TGGCGTTTTTCCATAGGCTCCGCCCCCCTGACGAGCATCACAAAAAT<br>CGACGCTCAAGTCAGAGGTGGCGAAACCCGACAGGACTATAAAGATA<br>CCAGGCGTTTCCCCCTGGAAGCTCCCTCGTGCGCTCTCCTGTTCCGA<br>CCCTGCCGCTTACCGGATACCTGTCCGCCTTTCTCCCTTCGGGAAGC<br>GTGGCGCTTTCTCATAGCTCACGCTGTAGGTATCTCAGTTCGGTGTA<br>GGTCGTTCGCTCCAAGCTGGGCTGTGTGCACGAACCCCCCGTTCAGC<br>CCGACCGCTGCGCCTTATCCGGTAACTATCGTCTTGAGTCCAACCCG<br>GTAAGACACGACTTATCGCCACTGGCAGCAGCCACTGGTAACAGGAT<br>TAGCAGAGCGAGGTATGTAGGCGGTGCTACAGAGTTCTTGAAGTGGT<br>GGCCTAACTACGGCTACACTAGAAGAACAGTATTTGGTATCTGCGCT<br>CTGCTGAAGCCAGTTACCTTCGGAAAAAGAGTTGGTAGCTCTTGATC<br>CGGCAAACAAACCACCGCTGGTAGCGGTGGTTTTTTTGTTTGCAAGC |

TABLE 4-continued

| SEQUENCE LISTING | | |
|---|---|---|
| SEQ ID NO | Description | Sequence |
| | | AGCAGATTACGCGCAGAAAAAAAGGATCTCAAGAAGATCCTTTGATC<br>TTTTCTACGGGGTCTGACGCTCAGTGGAACGAAAACTCACGTTAAGG<br>GATTTTGGTCATGAGATTATCAAAAAGGATCTTCACCTAGATCCTTT<br>TAAATTAAAAATGAAGTTTTAAATCAATCTAAAGTATATATGAGTAA<br>ACTTGGTCTGACAGTTACCAATGCTTAATCAGTGAGGCACCTATCTC<br>AGCGATCTGTCTATTTCGTTCATCCATAGTTGCCTGACTCCCCGTCG<br>TGTAGATAACTACGATACGGGAGGGCTTACCATCTGGCCCCAGTGCT<br>GCAATGATACCGCGAGACCCACGCTCACCGGCTCCAGATTTATCAGC<br>AATAAACCAGCCAGCCGGAAGGGCCGAGCGCAGAAGTGGTCCTGCAA<br>CTTTATCCGCCTCCATCCAGTCTATTAATTGTTGCCGGGAAGCTAGA<br>GTAAGTAGTTCGCCAGTTAATAGTTTGCGCAACGTTGTTGCCATTGC<br>TACAGGCATCGTGGTGTCACGCTCGTCGTTTGGTATGGCTTCATTCA<br>GCTCCGGTTCCCAACGATCAAGGCGAGTTACATGATCCCCCATGTTG<br>TGCAAAAAAGCGGTTAGCTCCTTCGGTCCTCCGATCGTTGTCAGAAG<br>TAAGTTGGCCGCAGTGTTATCACTCATGGTTATGGCAGCACTGCATA<br>ATTCTCTTACTGTCATGCCATCCGTAAGATGCTTTTCTGTGACTGGT<br>GAGTGGGGGGGGGGGGCGCTGAGGTCTGCCTCGTGAAGAAGGTGTTG<br>CTGACTCATACCAGGCCTGAATCGCCCCATCATCCAGCCAGAAAGTG<br>AGGGAGCCACGGTTGATGAGAGCTTTGTTGTAGGTGGACCAGTTGGT<br>GATTTTGAACTTTTGCTTTGCCACGGAACGGTCTGCGTTGTCGGGAA<br>GATGCGTGATCTGATCCTTCAACTCAGCAAAAGTTCGATTTATTCAA<br>CAAAGCCGCCGTCCCGTCAAGTCAGCGTAATGCTCTGCCAGTGTTAC<br>AACCAATTAACCAATTCTGATTAGAAAAACTCATCGAGCATCAAATG<br>AAACTGCAATTTATTCATATCAGGATTATCAATACCATATTTTTGAA<br>AAAGCCGTTTCTGTAATGAAGGAGAAAACTCACCGAGGCAGTTCCAT<br>AGGATGGCAAGATCCTGGTATCGGTCTGCGATTCCGACTCGTCCAAC<br>ATCAATACAACCTATTAATTTCCCCTCGTCAAAAATAAGGTTATCAA<br>GTGAGAAATCACCATGAGTGACGACTGAATCCGGTGAGAATGGCAAA<br>AGCTTATGCATTTCTTTCCAGACTTGTTCAACAGGCCAGCCATTACG<br>CTCGTCATCAAAATCACTCGCATCAACCAAACCGTTATTCATTCGTG<br>ATTGCGCCTGAGCGAGACGAAATACGCGATCGCTGTTAAAAGGACAA<br>TTACAAACAGGAATCGAATGCAACCGGCGCAGGAACACTGCCAGCGC<br>ATCAACAATATTTTCACCTGAATCAGGATATTCTTCTAATACCTGGA<br>ATGCTGTTTTCCCGGGGATCGCAGTGGTGAGTAACCATGCATCATCA<br>GGAGTACGGATAAAATGCTTGATGGTCGGAAGAGGCATAAATTCCGT<br>CAGCCAGTTTAGTCTGACCATCTCATCTGTAACATCATTGGCAACGC<br>TACCTTTGCCATGTTTCAGAAACAACTCTGGCGCATCGGGCTTCCCA<br>TACAATCGATAGATTGTCGCACCTGATTGCCCGACATTATCGCGAGC<br>CCATTTATACCCATATAAATCAGCATCCATGTTGGAATTTAATCGCG<br>GCCTCGAGCAAGACGTTTCCCGTTGAATATGGCTCATAACACCCCTT<br>GTATTACTGTTTATGTAAGCAGACAGTTTTATTGTTCATGATGATAT<br>ATTTTTATCTTGTGCAATGTAACATCAGAGATTTTGAGACACAACGT<br>GGCTTTCCCCCCCCCCCCATTATTGAAGCATTTATCAGGGTTATTGT<br>CTCATGAGCGGATACATATTTGAATGTATTTAGAAAAATAAACAAAT<br>AGGGGTTCCGCGCACATTTCCCCGAAAAGTGCCACCTGACGTCTAAG<br>AAACCATTATTATCATGACATTAACCTATAAAAATAGGCGTATCACG<br>AGGCCCTTTCGTC |
| 110 | Shine-Dalgano sequence | TAAGGAGGAAAAAAAAATG |
| 111 | nSDQb-mutEcoRIfor sequence | GCGCGCGAATTCTAAGGAGGAAAAAAAAATGGCAAAATTAGAGACTG<br>TTACTTTAGG |
| 112 | RNA-phage Qβ CP | MAKLETVTLGNIGKDGKQTLVLNPRGVNPTNGVASLSQAGAVPALEK<br>RVTVSVSQPSRNRKNYKVQVKIQNPTACTANGSCDPSVTRQAYADVT<br>FSFTQYSTDEERAFVRTELAALLASPLLIDAIDQLNPAY |
| 113 | RNA-phage Qβ A1 protein | MAKLETVTLGNIGKDGKQTLVLNPRGVNPTNGVASLSQAGAVPALEK<br>RVTVSVSQPSRNRKNYKVQVKIQNPTACTANGSCDPSVTRQAYADVT<br>FSFTQYSTDEERAFVRTELAALLASPLLIDAIDQLNPAYWTLLIAGG<br>GSGSKPDPVIPDPPIDPPPGTGKYTCPFAIWSLEEVYEPPTKNRPWP<br>IYNAVELQPREFDVALKDLLGNTKWRDWDSRLSYTTFRGCRGNGYID<br>LDATYLATDQAMRDQKYDIREGKKPGAFGNIERFIYLKSINAYCSLS<br>DIAAYHADGVIVGFWRDPSSGGAIPFDFTKFDKTKCPIQAVIVVPRA |
| 114 | bacteriophage R17 | ASNFTQFVLVNDGGTGNVTVAPSNFANGVAEWISSNSRSQAYKVTCS<br>VRQSSAQNRKYTIKVEVPKVATQTVGGVELPVAAWRSYLNMELTIPI<br>FATNSDCELIVKAMQGLLKDGNPIPSAIAANSGIY |
| 115 | bacteriophage fr | MASNFEEFVLVDNGGTGDVKVAPSNFANGVAEWISSNSRSQAYKVTC<br>SVRQSSANNRKYTVKVEVPKVATQVQGGVELPVAAWRSYMNMELTIP<br>VFATNDDCALIVKALQGTFKTGNPIATAIAANSGIY |

TABLE 4-continued

SEQUENCE LISTING

| SEQ ID NO | Description | Sequence |
|---|---|---|
| 116 | bacteriophage GA | MATLRSFVLVDNGGTGNVTVVPVSNANGVAEWLSNNSRSQAYRVTAS<br>YRASGADKRKYAIKLEVPKIVTQVVNGVELPGSAWKAYASIDLTIPI<br>FAATDDVTVISKSLAGLFKVGNPIAEAISSQSGFYA |
| 117 | bacteriophage SP CP | MAKLNQVTLSKIGKNGDQTLTLTPRGVNPTNGVASLSEAGAVPALEK<br>RVTVSVAQPSRNRKNFKVQIKLQNPTACTRDACDPSVTRSAFADVTL<br>SFTSYSTDEERALIRTELAALLADPLIVDAIDNLNPAY |
| 118 | bacteriophage SP A1 protein | AKLNQVTLSKIGKNGDQTLTLTPRGVNPTNGVASLSEAGAVPALEKR<br>VTVSVAQPSRNRKNFKVQIKLQNPTACTRDACDPSVTRSAFADVTLS<br>FTSYSTDEERALIRTELAALLADPLIVDAIDNLNPAYWAALLVASSG<br>GGDNPSDPDVPVVPDVKPPDGTGRYKCPFACYRLGSIYEVGKEGSPD<br>IYERGDEVSVTFDYALEDFLGNTNWRNWDQRLSDYDIANRRRCRGNG<br>YIDLDATAMQSDDFVLSGRYGVRKVKFPGAFGSIKYLLNIQGDAWLD<br>LSEVTAYRSYGMVIGFWTDSKSPQLPTDFTQFNSANCPVQTVIIIPS |
| 119 | bacteriophage MS2 | MASNFTQFVLVDNGGTGDVTVAPSNFANGVAEWISSNSRSQAYKVTC<br>SVRQSSAQNRKYTIKVEVPKVATQTVGGVELPVAAWRSYLNMELTIP<br>IFATNSDCELIVKAMQGLLKDGNPIPSAIAANSGIY |
| 120 | bacteriophage M11 | MAKLQAITLSGIGKKGDVTLDLNPRGVNPTNGVAALSEAGAVPALEK<br>RVTISVSQPSRNRKNYKVQVKIQNPTSCTASGTCDPSVTRSAYSDVT<br>FSFTQYSTVEERALVRTELQALLADPMLVNAIDNLNPAY |
| 121 | bacteriophage MX1 | MAKLQAITLSGIGKNGDVTLNLNPRGVNPTNGVAALSEAGAVPALEK<br>RVTISVSQPSRNRKNYKVQVKIQNPTSCTASGTCDPSVTRSAYADVT<br>FSFTQYSTDEERALVRTELKALLADPMLIDAIDNLNPAY |
| 122 | bacteriophage NL95 | MAKLNKVTLTGIGKAGNQTLTLTPRGVNPTNGVASLSEAGAVPALEK<br>RVTVSVAQPSRNRKNYKVQIKLQNPTACTKDACDPSVTRSGSRDVTL<br>SFTSYSTERERALIRTELAALLKDDLIVDAIDNLNPAYWAALLAASP<br>GGGNNPYPGVPDSPNVKPPGGTGTYRCPFACYRRGELITEAKDGACA<br>LYACGSEALVEFEYALEDFLGNEFWRNWDGRLSKYDIETHRRCRGNG<br>YVDLDASVMQSDEYVLSGAYDVVKMQPPGTFDSPRYYLHLMDGIYVD<br>LAEVTAYRSYGMVIGFWTDSKSPQLPTDFTRFNRHNCPVQTVIVIPS<br>L |
| 123 | bacteriophage f2 | ASNFTQFVLVNDGGTGNVTVAPSNFANGVAEWISSNSRSQAYKVTCS<br>VRQSSAQNRKYTIKVEVPKVATQTVGGVELPVAAWRSYLNLELTIPI<br>FATNSDCELIVKAMQGLLKDGNPIPSAIAANSGIY |
| 124 | bacteriophage PP7 | MSKTIVLSVGEATRTLTEIQSTADRQIFEEKVGPLVGRLRLTASLRQ<br>NGAKTAYRVNLKLDQADVVDCSTSVCGELPKVRYTQVWSHDVTIVAN<br>STEASRKSLYDLTKSLVATSQVEDLVVNLVPLGR |
| 125 | Qβ-240 (K13R) | AKLETVTLGNIG**R**DGKQTLVLNPRGVNPTNGVASLSQAGAVPALEKR<br>VTVSVSQPSRNRKNYKVQVKIQNPTACTANGSCDPSVTRQKYADVTF<br>SFTQYSTDEERAFVRTELAALLASPLLIDAIDQLNPAY |
| 126 | Qβ-243 (N10K) | AKLETVTLG**K**IGKDGKQTLVLNPRGVNPTNGVASLSQAGAVPALEKR<br>VTVSVSQPSRNRKNYKVQVKIQNPTACTANGSCDPSVTRQKYADVTF<br>SFTQYSTDEERAFVRTELAALLASPLLIDAIDQLNPAY |
| 127 | Qβ-250 (K2R, K13R) | A**R**LETVTLGNIG**R**DGKQTLVLNPRGVNPTNGVASLSQAGAVPALEKR<br>VTVSVSQPSRNRKNYKVQVKIQNPTACTANGSCDPSVTRQKYADVTF<br>SFTQYSTDEERAFVRTELAALLASPLLIDAIDQLNPAY |
| 128 | Qβ-251 | AKLETVTLGNIGKDGRQTLVLNPRGVNPTNGVASLSQAGAVPALEKR<br>VTVSVSQPSRNRKNYKVQVKIQNPTACTANGSCDPSVTRQKYADVTF<br>SFTQYSTDEERAFVRTELAALLASPLLIDAIDQLNPAY |
| 129 | Qβ-259 (K2R, K16R) | A**R**LETVTLGNIGKDG**R**QTLVLNPRGVNPTNGVASLSQAGAVPALEKR<br>VTVSVSQPSRNRKNYKVQVKIQNPTACTANGSCDPSVTRQKYADVTF<br>SFTQYSTDEERAFVRTELAALLASPLLIDAIDQLNPAY |
| 130 | Plasmid pAP283-58 | CGAGCTCGCCCCTGGCTTATCGAAATTAATACGACTCACTATAGGGA<br>GACCGGAATTCGAGCTCGCCCGGGGATCCTCTAGAATTTTCTGCGCA<br>CCCATCCCGGGTGGCGCCCAAAGTGAGGAAAATCACATGGCAAATAA<br>GCCAATGCAACCGATCACATCTACAGCAAATAAAATTGTGTGGTCGG<br>ATCCAACTCGTTTATCAACTACATTTTCAGCAAGTCTGTTACGCCAA<br>CGTGTTAAAGTTGGTATAGCCGAACTGAATAATGTTTCAGGTCAATA<br>TGTATCTGTTTATAAGCGTCCTGCACCTAAACCGGAAGGTTGTGCAG<br>ATGCCTGTGTCATTATGCCGAATGAAAACCAATCCATTCGCACAGTG<br>ATTTCAGGGTCAGCCGAAAACTTGGCTACCTTAAAAGCAGAATGGGA |

TABLE 4-continued

| SEQ ID NO | Description | Sequence |
|---|---|---|
| | | AACTCACAAACGTAACGTTGACACACTCTTCGCGAGCGGCAACGCCG GTTTGGGTTTCCTTGACCCTACTGCGGCTATCGTATCGTCTGATACT ACTGCTTAAGCTTGTATTCTATAGTGTCACCTAAATCGTATGTGTAT GATACATAAGGTTATGTATTAATTGTAGCCGCGTTCTAACGACAATA TGTACAAGCCTAATTGTGTAGCATCTGGCTTACTGAAGCAGACCCTA TCATCTCTCTCGTAAACTGCCGTCAGAGTCGGTTTGGTTGGACGAAC CTTCTGAGTTTCTGGTAACGCCGTTCCGCACCCCGGAAATGGTCACC GAACCAATCAGCAGGGTCATCGCTAGCCAGATCCTCTACGCCGGACG CATCGTGGCCGGCATCACCGGCGCACACAGTGCGGTTGCTGGCGCCT ATATCGCCGACATCACCGATGGGGAAGATCGGGCTCGCCACTTCGGG CTCATGAGCGCTTGTTTCGGCGTGGGTATGGTGGCAGGCCCCGTGGC CGGGGGACTGTTGGGCGCCATCTCCTTGCATGCACCATTCCTTGCGG CGGCGGTGCTTCAACGGCCTCAACCTACTACTGGGCTGCTTCCTAAT GCAGGAGTCGCATAAGGGAGAGCGTCGATATGGTGCACTCTCAGTAC AATCTGCTCTGATGCCGCATAGTTAAGCCAACTCCGCTATCGCTACG TGACTGGGTCATGGCTGCGCCCCGACACCCGCCAACACCCGCTGACG CGCCCTGACGGGCTTGTCTGCTCCCGGCATCCGCTTACAGACAAGCT GTGACCGTCTCCGGGAGCTGCATGTGTCAGAGGTTTTCACCGTCATC ACCGAAACGCGCGAGGCAGCTTGAAGACGAAAGGGCCTCGTGATACG CCTATTTTTATAGGTTAATGTCATGATAATAATGGTTTCTTAGACGT CAGGTGGCACTTTTCGGGGAAATGTGCGCGGAACCCCTATTTGTTTA TTTTTCTAAATACATTCAAATATGTATCCGCTCATGAGACAATAACC CTGATAAATGCTTCAATAATATTGAAAAAGGAAGAGTATGAGTATTC AACATTTCCGTGTCGCCCTTATTCCCTTTTTTGCGGCATTTTGCCTT CCTGTTTTTGCTCACCCAGAAACGCTGGTGAAAGTAAAAGATGCTGA AGATCAGTTGGGTGCACGAGTGGGTTACATCGAACTGGATCTCAACA GCGGTAAGATCCTTGAGAGTTTTCGCCCCGAAGAACGTTTTCCAATG ATGAGCACTTTTAAAGTTCTGCTATGTGGCGCGGTATTATCCCGTAT TGACGCCGGGCAAGAGCAACTCGGTCGCCGCATACACTATTCTCAGA ATGACTTGGTTGAGTACTCACCAGTCACAGAAAAGCATCTTACGGAT GGCATGACAGTAAGAGAATTATGCAGTGCTGCCATAACCATGAGTGA TAACACTGCGGCCAACTTACTTCTGACAACGATCGGAGGACCGAAGG AGCTAACCGCTTTTTTGCACAACATGGGGGATCATGTAACTCGCCTT GATCGTTGGGAACCGGAGCTGAATGAAGCCATACCAAACGACGAGCG TGACACCACGATGCCTGTAGCAATGGCAACAACGTTGCGCAAACTAT TAACTGGCGAACTACTTACTCTAGCTTCCCGGCAACAATTAATAGAC TGGATGGAGGCGGATAAAGTTGCAGGACCACTTCTGCGCTCGGCCCT TCCGGCTGGCTGGTTTATTGCTGATAAATCTGGAGCCGGTGAGCGTG GGTCTCGCGGTATCATTGCAGCACTGGGGCCAGATGGTAAGCCCTCC CGTATCGTAGTTATCTACACGACGGGGAGTCAGGCAACTATGGATGA ACGAAATAGACAGATCGCTGAGATAGGTGCCTCACTGATTAAGCATT GGTAACTGTCAGACCAAGTTTACTCATATATACTTTAGATTGATTTA AAACTTCATTTTTAATTTAAAAGGATCTAGGTGAAGATCCTTTTTGA TAATCTCATGACCAAAATCCCTTAACGTGAGTTTTCGTTCCACTGAG CGTCAGACCCCGTAGAAAAGATCAAAGGATCTTCTTGAGATCCTTTT TTTCTGCGCGTAATCTGCTGCTTGCAAACAAAAAAACCACCGCTACC AGCGGTGGTTTGTTTGCCGGATCAAGAGCTACCAACTCTTTTTCCGA AGGTAACTGGCTTCAGCAGAGCGCAGATACCAAATACTGTCCTTCTA GTGTAGCCGTAGTTAGGCCACCACTTCAAGAACTCTGTAGCACCGCC TACATACCTCGCTCTGCTAATCCTGTTACCAGTGGCTGCTGCCAGTG GCGATAAGTCGTGTCTTACCGGGTTGGACTCAAGACGATAGTTACCG GATAAGGCGCAGCGGTCGGGCTGAACGGGGGGTTCGTGCACACAGCC CAGCTTGGAGCGAACGACCTACACCGAACTGAGATACCTACAGCGCG AGCATTGAGAAAGCGCCACGCTTCCCGAAGGGAGAAAGGCGGACAGG TATCCGGTAAGCGGCAGGGTCGGAACAGGAGAGCGCACGAGGGAGCT TCCAGGGGGAAACGCCTGGTATCTTTATAGTCCTGTCGGGTTTCGCC ACCTCTGACTTGAGCGTCGATTTTTGTGATGCTCGTCAGGGGGGCGG AGCCTATGGAAAAACGCCAGCAACGCGGCCTTTTTACGGTTCCTGGC CTTTTGCTGGCCTTTTGCTCACATGTTCTTTCCTGCGTTATCCCCTG ATTCTGTGGATAACCGTATTACCGCCTTTGAGTGAGCTGATACCGCT CGCCGCAGCCGAACGACGAGCGCAGCGAGTCAGTGAGCGAGGAAGCG GAAGAGCGCCCAATACGCAAACCGCCTCTCCCCGCGCGTTGGCCGAT TCATTAATGCAGCTGTGGTGTCATGGTCGGTGATCGCCAGGGTGCCG ACGCGCATCTCGACTGCATGGTGCACCAATGCTTCTGGCGTCAGGCA GCCATCGGAAGCTGTGGTATGGCCGTGCAGGTCGTAAATCACTGCAT AATTCGTGTCGCTCAAGGCGCACTCCCGTTCTGGATAATGTTTTTTG CGCCGACATCATAACGGTTCTGGCAAATATTCTGAAATGAGCTGTTG ACAATTAATCATCGAACTAGTTAACTAGTACGCAAGTTCACGTAAAA AGGGTATCGCGGAATT |
| 131 | AP205 | tctagaATTTTCTGCGCACCCATCCCGGGTGGCGCCCAAAGTGAGGA AAATCACatg |

TABLE 4-continued

SEQUENCE LISTING

| SEQ ID NO | Description | Sequence |
|---|---|---|
| 132 | Shine delgarno sequence | tctagaTTAACCCAACGCGTAGGAGTCAGGCCatg |
| 133 | AP205 coat protein | MANKPMQPITSTANKIVWSDPTRLSTTFSASLLRQRVKVGIAELNNV<br>SGQYVSVYKRPAPKPEGCADACVIMPNENQSIRTVISGSAENLATLK<br>AEWETHKRNVDTLFASGNAGLGFLDPTAAIVSSDTTA |
| 134 | AP205 coat protein (P5T) | MANK**T**MQPITSTANKIVWSDPTRLSTTFSASLLRQRVKVGIAELNNV<br>SGQYVSVYKRPAPKPEGCADACVIMPNENQSIRTVISGSAENLATLK<br>AEWETHKRNVDTLFASGNAGLGFLDPTAAIVSSDTTA |
| 135 | Plasmid pAP281-32 | CGAGCTCGCCCCTGGCTTATCGAAATTAATACGACTCACTATAGGGA<br>GACCGGAATTCGAGCTCGCCCGGGGATCCTCTAGATTAACCCAACGC<br>GTAGGAGTCAGGCCATGGCAAATAAGACAATGCAACCGATCACATCT<br>ACAGCAAATAAAATTGTGTGGTCGGATCCAACTCGTTTATCAACTAC<br>ATTTTCAGCAAGTCTGTTACGCCAACGTGTTAAAGTTGGTATAGCCG<br>AACTGAATAATGTTTCAGGTCAATATGTATCTGTTTATAAGCGTCCT<br>GCACCTAAACCGAAGGTCAGATGCCTGTGTCATTATGCCGAATGAAA<br>ACCAATCCATTCGCACAGTGATTTCAGGGTCAGCCGAAAACTTGGCT<br>ACCTTAAAAGCAGAATGGGAAACTCACAAACGTAACGTTGACACACT<br>CTTCGCGAGCGGCAACGCCGGTTTGGGTTTCCTTGACCCTACTGCGG<br>CTATCGTATCGTCTGATACTACTGCTTAAGCTTGTATTCTATAGTGT<br>CACCTAAATCGTATGTGTATGATACATAAGGTTATGTATTAATGGTA<br>GCCGCGTTCTAACGACAATATGTACAAGCCTAATTGTGTAGCATCTG<br>GCTTACTGAAGCAGACCCTATCATCTCTCTCGTAAACTGCCGTCAGA<br>GTCGGTTGGGTTGGACAGACCTCTGAGTTTCTGGTAACGCCGTTCCG<br>CACCCCGGAAATGGTCACCGAACCATTCAGCAGGGTCATCGCTAGCC<br>AGATCCTCTACGCCGGACGCATCGTGGCCCGCATCACCGGCGCCACA<br>GGTGCGGTGCTGGCGCCTATATCGCCGACATCACCGATGGGGAAGAT<br>CGGGCTCGCCACTTCGGGCTCATGATCGCTGGTTTCCGCCTGGGTAT<br>GGTGGCAGGCCCCGTGGCCCGGGGGACTGTTGGGCGCCATCTCCTTG<br>CATGCACCATTCCTTGCGGCGGCGGTGCTCAACGGCCTCAACCTACT<br>ACTGGGCTGCTTCCTAATGCAGGAGTCGCATAAGGGAGAGCGTCGAT<br>ATGGTGCACTCTCAGTACAATCTGCTCTGATGCCGCATAGTTAAGCC<br>AACTCCGCTATCGCTACGTGACTGGGTCATGGCTGCGCCCCGACACC<br>CGCCAACACCCGCTGACGCGCCCTGACGGGCTTGTCTGCTTCCGGCA<br>TCCGCTTACAGACAAGCTGTGACCGTCTCCGGGAGCTGCATGTGTCA<br>GAGGTTTTCACCGTCATCACCGAAACGCGCGAGGCAGCTTGAAGACG<br>AAAGGGCCTCGTGATACGCCTATTTTTATAGGTTAATGTCATGATAA<br>TAATGGTTTCTTAGACGTCAGGTGGCACTTTTCGGGGAAATGTGCGC<br>GGACCCCCTATTGGTTTATTTTTCTAAATACATTCAAATATGTATCC<br>GCTCATGAGACAATAACCCTGATAAATGCTTCAATAATATTGAAAAA<br>GGAAGAGTATGAGTATTCAACATTTCCGTGTCGCCCTTATTCCCTTT<br>TTTGCGGCATTTTGCCTTCCTGTTTTTGCTCACCCAGAAACGCTGGT<br>GAAAGTAAAAGATGCTGAAGATCAGTTGGGTGCACGAGTGGGTTACA<br>TCGAACTGGATCTCAACAGCGGTAAGATCCTTGAGAGTTTTCGCCCC<br>GAAGAACGTTTTCAATGATGAGCACTTTTAAAGTTCTGCTATGTGT<br>CGCGGTATTATCCCGTATTGACGCCGGGCAAGAGCAACTCGGTCGCC<br>GCATACACTATTCTCAGAATGACTTGGTGGTACCTACCAGTCACAGA<br>AAAGCATCTTACGGATGGCATGACAGTAAGAGAATTATGCAGTGCTG<br>CCATAACCATGAGTGATAACACTGCGGCCAACTTACTTCTGACAACG<br>ATCGGAGGACCGAAGGAGCTAACCGCTTTTTTGCACAACATGGGGGA<br>TCATGTAACTCGCCTTGATCGTTGGGAACCGGAGCTGAATGAAGCCA<br>TACCAAACGACGAGCGTGACACCACGATGCCTGTACGAACGGCAACA<br>ACGTTGCGCAAACTATTAACTGGCGAACTACTTACTCTAGCTTCCCG<br>GCAACAATTAATAGACTGGATGGAGGCGGATAAAGTTGCAGGACCAC<br>TTCTGCGCTCGGCCCTTCCGGCTGGCTGGTTTATTGCTGATAAATCT<br>GGAGCCGGTGAGCGTGGGTCTCGCGGTATCATTGCAGCACTGGGGCC<br>AGATGGTAAGCCCTCCCGTATCGTAGTTATCTACACGACGGGGAGTC<br>AGGCAACTATGGATGAACGAAATAGACAGATCGCTGAGATAGGTGCC<br>TCACTGATTAAGCATTGGTAACTGTCAGACCAAGTTTACTCATATAT<br>ACTTTAGATTGATTTAAAACTTCATTTTTAATTTAAAAGGATCTAGG<br>TGAAGATCCTTTTTGATAATCTCATGACCAAAATCCCTTAACGTGAG<br>TTTTCGTTCCACTGAGCGGTCAGACCCCGTAGAAAGATCAAAGGATC<br>TTCTTGAGATCCTTTTTTTCTGCGCGTAATCTGCTGCTTGCAAACAA<br>AAAAACCACCGCTACCAGCGGTGGTTTGTTTGCCGGATCAAGAGCTA<br>CCAACTCTTTTTCCGAAGGTAACTGGCTTCAGCAGAGCGCAGATACC<br>AAATACTGTCCTTCTAGTGTAGCCGTAGTTAGGCCACCACTTCAAGA<br>ACTCTGTAGCACCGCCTACATACCTCGCTCTGCTAATCCTGTTACCA<br>GTGGCTGCTGCCAGTGGCGATAAGTCGTGTCTTACCGGGTTGGACTC<br>AAGACGATAGGTACCGGATAAGGCGCAGCGGTCGGGCTGAACGGGGG<br>GTTCGTGCACACAGCCCAGCTTGGAGCGAACGACCTACACCGAACTG<br>AGATACCTACAGCGCGAGCATTGAGAAAGCGCCACGCTTCCCGAAGG<br>GAGAAAGGCGGACAGGTATCCGGTAAGCGGCAGGGTCGGAACAAGAG |

TABLE 4-continued

| SEQ ID NO | Description | Sequence |
|---|---|---|
| | | AGCGCACGAGGGAGCTTCCAGGGGGAAACGCCTGGTATCTTTATAGT CCTGTCGGGTTTCGCCACCTCTGACTTGAGCGTCGATTTTTGTGATG CTCGTCAGGGGGGCGGAGCCTATGGAAAAACGCCAGCAACGCGGCCT TTTTACGGTTCCTGGCCTTTTGCTGGCCTTTTGCTCACATGTTCTTT CCTGCGTTATCCCCTGATTCTGTGGATAACCGTATTACCGCCTTTGA GTGAGCTGATACCGCTCGCCGCAGCCGAACGACCGACGGCGCAGCGA GTCAGTGAGCGAGGAAGCGGAAGAGCGCCCAATACGCAAACCGCCTC TCCCCGCGCGTTGGCCGATTCATTAATGCAGCTGTGGTGTCATGGTC GGTGATCGCCAGGGTGCCGACGCGCATCTCGACTGCATGGTGCACCA ATGCTTCTGGCGTCAGGCAGCCATCGGAAGCTGTGGTATGGCCGTGC AGGTCGTAAATCACTGCATAATTCGTGTCGCTCAAGGCGCACTCCCG TTCTGGATAATGTTTTTTGCGGCGACATCATAACGGTTCTGGCAAAT ATTCTGAAATGAGCTGGTGACAATTAATCATCGAACTAGTTAACTAG TACGCAAGTTCACGTAAAAAGGGTATCGCGGAATT |
| 136 | HBcAG protein | MDIDPYKEFGATVELLSFLPSDFFPSVRDLLDTASALYREALESPEH CSPHHTALRQAILCWGELMTLATWVGNNLEDPASRDLVVNYVNTNMG LKIRQLLWFHISCLTFGRETVLEYLVSFGVWIRTPPAYRPPNAPILS TLPETTVVRRRDRGRSPRRRTPSPRRRRSQSPRRRRSQSRESQCL |
| 137 | HBcAG protein variant | MDIDPYEFGATVELLSFLPSDFFPSVRDLLDTASALYREALESPEHC SPHHTALRQAILCWGELMTLATWVGNNLEDPASRDLVVNYVNTNMGL KIRQLLWFHISCLTFGRETVLEYLVSFGVWIRTPPAYRPPNAPILST LPETTVVRRRDRGRSPRRRTPSPRRRRSQSPRRRRSQSRESQC |
| 138 | HBcAG protein variant | MDIDPYKEFGATVELLSFLPSDFFPSVRDLLDTASALYREALESPEH CSPHHTALRQAILCWGELMTLATWVGGNLEDPISRDLVVSYVNTNMG LKFRQLLWFHISCLTFGRETVIEYLVSFGVWIRTPPAYRPPNAPILS TLPETTVVRRRGRSPRRRTPSPRRRRSQSPRRRRSQSRGSQC |
| 139 | HBcAG protein variant | MDIDPYKEFGATVELLSFLPSDFFPSVRDLLDTASALYREALESPEH CSPHHTALRQAILCWGELMTLATWVGGNLEDPTSRDLVVSYVNTNMG LKFRQLLWFHISCLTFGRETVIEYLVSFGVWIRTPPAYRPTNAPILS TLPETCVIRRRGRSPRRRTPSPRRRRSQSPRRRRSQSRGSQC |
| 140 | HBcAG protein variant | MQLFHLCLIISCSCPTVQASKLCLGWLWGMDIDPYKEFGATVELLSF LPSDFFPSVRDLLDTASALYREALESPEHCSPHHTALRQAILCWGEL MTLATWVGGNLEDPISRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 141 | HBcAG protein variant | MQLFHLCLIISCSCPTVQASKLCLGWLWGMDIDPYKEFGATVELLSF LPSDFFPSVRDLLDNASALYREALESPEHCSPHHTALRQAILCWGEL MTLATWVGGNLEDPISRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 142 | HBcAG protein variant | MDIDPYKEFGATVELLSFLPTDFFPSVRDLLDTASALYREALESPEH CSPHHTALRQAILCWGELMTLATWVGVNLEDPASRDLVVSYVNTNMG LKFRQLLWFHISCLTFGRETVIEYLVSFGVWIRTPPAYRPPNAPILS TLPETCVVRRRGRSPRRRTPSPRRRRSQSPRRRRSQSRESQC |
| 143 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGDL MTLATWVGGNLEDPVSRDLVVSYVNTNVGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 144 | HBcAG protein Variant | MQLFHLCLIISCSCPTVQASKLCLGWLWDMDIDPYKEFGATVELLSF LPSDFFPSVRDLLDTASALYREALESPEHCSPHHTALRQAILCWGDL MTLATWVGGNLEDPVSRDLVVSYVNTNVGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 145 | HBcAG protein Variant | MQLFHLCLIISCSCPTVQASKLCLGWLWGMDIDPYKEFGATVELLSF LPSDFFPSVRDLLDTASALYREALESPEHCSPQHTALRQAILCWGEL MTLATWVGGNLEDPISRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 146 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGEL MTLATWVGVNLEDPASRDLVVSYVNTNMGLKFRQLLWFHISCLTFGR ETVIEYLVSFGVWIRTPPAYKPPNAPILSTLPETTVVRRRGRSPRRR TPSPRRRRSQSPRRRRSQSRGSQC |

TABLE 4-continued

| SEQ ID NO | Description | Sequence |
|---|---|---|
| SEQUENCE LISTING | | |
| 147 | HBcAG protein Variant | MDIDPYKEFGATVELLSFLPSDFFPSVRDLLDTASALFRDALESPEH CSPHHTALRQAILCWGELMTLATWVGGNLEDPASRDLVVSYVNTNMG LKFRQLLWFHISCLTFGRDTVIEYLVSFGVWIRTPPAYRPSNAPILS TLPETCVVRRRGRSPRRRTPSPRRRRSQSPRRRRSQSRESQC |
| 148 | HBcAG protein Variant | MDIDPYKEFGATVELLSFLPSDFFPSVRDLLDTASALYREALESPEH CSPHHTALRQAILCWGELMTLATWVGVNLEDPASRDLVVSYVNTNMG LKFRQLLWFHISCLTFGRETVIEYLVSFGVWIRTPPAYRPPNAPILS TLPETTVVRRRGRSPRRRTPSPRRRRSQSPRRRRSQSRESQC |
| 149 | HBcAG protein Variant | MQLFHLCLIISCSCPTVQASKLCLGWLWGMDIDPYKEFGATVELLSF LPSDFFPSVRDLLDTASALYREALESPEHCSPHHTALRHAILCWGDL RTLATWVGGNLEDPISRDLVVSYVNTNMGLKFRQLLYFHISCLTFGR ETVIEYLVSFGVWIRTPPAYRPPNAPILSTLPETTVVRRRGRSPRRR TPSPRRRRSQSPRRRRSQSRESQC |
| 150 | HBcAG protein variant | MQLFHLCLIISCSCPTVQASKLCLGWLWDMDIDPYKEFGATVELLSF LPSDFFPSVRDLLDTASALFRDALESPEHCSPHHTALRQAILCWGEL MTLATWVGANLEDPASRDLVVSYVNTNMGLKFRQLLWFHISCLTFGR ETVIEYLVSFGVWIRTPQAYRPPNAPILSTLPETCVVRRRGRSPRRR TPSPRRRRSQSPRRRRSQSRESQC |
| 151 | HBcAG protein Variant | MDIDPYKEFGATVELLSFLPSDFFPSVRDLLDTASALYREALESPEH CSPHHTALRQAILCWGELMTLATWVGVNLEDPASRDLVVSYVNTNMG LKFRQLLWFHISCLTFGRETVLEYLVSFGVWIRTPPAYRPPNAPILS TLPETTVVRRRGRSPRRRTPSPRRRRSQSPRRRRSQSRESQC |
| 152 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGDL MSLATWVGVNLEDPISRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 153 | HBcAG protein Variant | MDIDPYKEFGATVELLSFLPSDFFPSVRDLLDTASALYRDALESPEH CSPHHTALRQAILCWGELMTLATWVGVNLEDPASRDLVVSYVNTNMG LKFRQLLWFHISCLTFGRETVIEYLVSFGVWIRTPPAYRPPNAPILS TLPETTVVRRRGRSPRRRTPSPRRRRSQSPRRRRSQSRESQC |
| 154 | HBcAG protein Variant | MDIDPYKEFGATVELLSFLPSDFFPSVRDLLDTASALYREALESPEH CSPHHTALRQAILCWGDLMTLATWVGVNLEDPASRDLVVSYVNTNMG LKFRQLLWFHISCLTFGRETVIEYLVSFGVWIRTPPAYRPPNAPILS TLPETTVVRRRGRSPRRRTPSPRRRRSQSPRRRRSQSRESQC |
| 155 | HBcAG protein Variant | MDIDPYKEFGATVELLSFLPSDFFPSVRDLLDTASALYRDALESPEH CSPHHTALRQAILCWGELMTLATWVGANLEDPASRDLVVSYVNTNMG LKFRQLLWFHISCLTFGRETVIEYLVSFGVWIRTPPAYRPPNAPILS TLPETTVVRRRGRTPRRRTPSPRRRRSQSPRRRRSQSRESQC |
| 156 | HBcAG protein Variant | MQLFHLCLIISCSCPTVQASKLCLGWLWGMDIDPYKEFGATVELLSF LPSDFFPSVRDLLDTASALYRDALESPEHCSPHHTALRQAILCWGEL MTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 157 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGDL MTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 158 | HBcAG protein Variant | MQLFHLCLIISCTCPTVQASKLCLGWLWGMDIDPYKQFGATVELLSF LPSDFFPSVRDLLDTASALYREALESPEHCSPHHTALRQAILCWGEL MTLATWVGVNLEDPASRDLVVSYVNTNMGLKFRQLLWFHISCLTFGR ETVIEYLVAFGVWIRTPPAYRPPNAPILSTLPETTVVRRRGRSPRRR TPSPRRRRSQSPRRRRSQSRESQC |
| 159 | HBcAG protein variant | MQLFHLCLIISCSCPTVQASKLCLGWLWGMDIDPYKEFGATVELLSF LPSDFFPSVRDLLDTASALYREAFECSEHCSPHHTALRQAILCWGEL MTLATWVGGNLEDPISRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |

TABLE 4-continued

SEQUENCE LISTING

| SEQ ID NO | Description | Sequence |
|---|---|---|
| 160 | HBcAG protein Variant | MQLFHLCLIISCSCPTVQASKLCLGWLXAADMDIDPYKEFGATVELL SFLPSDFFPSVRDLLDTASALYREALESPEHCSPHHTALRQAILCWG DLITLSTWVGGNLEDPTSRDLVVSYVNTNMGLKFRQLLWFHISCLTF GRETVIEYLVSFGVWIRTPPAYRPPNAPILSTLPETTVVRRRGRSPR RRTPSPRRRRSQSPRRRRTQSRESQC |
| 161 | HBcAG protein Variant | MQLFHLCLIISCSCPTVQASKLCLGWLWGMDIDPYKEFGATVELLSF LPSDFFPSVRDLLDNASALYREALESPEHCSPHHTALRQAILCWGEL MTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 162 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGEL MTLATWVGVNLEDPASRDLVVSYVNTNMGLKFRQLLWFHICCLTFGR ETVIEYLVSFGVWIRTPPAYRPPNAPILSTLPETTVVRRRGRSPRRR TPSPRRRRSQSPRRRRSQSRESQC |
| 163 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGEL MTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSREPQC |
| 164 | HBcAG protein Variant | MQLFHLCLIISCSCPTVQASKLCLGWLWGMDIDPYKEFGATVELLSF LPSDFFPSVRDLLSTASALYREALESPEHCSPHHTALRQAILCWGEL MTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 165 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGEL MTLATWVGVNLEDPASRDLVVSYVNTNMGLKFRQLLWFHISCLTFGR ETVIEYLVSFGVWIRTPPAYRPPNAPILLTLPETTVVRRRGRSPRRR TPSPRRRRSQSPRRRRSQSRESQC |
| 166 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGDL MTLATWVGVNLEDPASRDLVVSYVNTNMGLKFKQLLWFHISCLTFGR ETVIEYLVSFGVWIRTPPAYRPPNAPILSTLPETTVVRRRGRSPRRR TPSPRRRRSQSPRRRRSQSRESQC |
| 167 | HBcAG protein Variant | MQLFHLCLIISCSCPTVQASKLCLGWLWGMDIDPYKEFGATVELLSF LPSDFFPSVRDLLDTAAALYRDALESPEHCSPHHTALRQAILCWGEL MTLATWVGTNLEDPASRDLVVSYVNTNMGLKFRQLLWFHISCLTFGR ETVLEYLVSFGVWIRTPPAYRPPNAPILSTLPETTVVRRRGRSPRRR TPSPRRRRSQSPRRRRSQSRESQC |
| 168 | HBcAG protein variant | MDIDPYKEFGASMELLSFLPSDFYPSVRDLLDTASALYREALESPEH CTPHHTALRQAILCWGELMTLATWVGGNLQDPTSRDLVVSYVNTNMG LKFRQLLWFHVSCLTFGRETVVEYLVSFGVWIRTPQAYRPPNAPILS TLPETCVVRRRGRSPRRRTPSPRRRRSQSPRRRRSQSRESQC |
| 169 | HBcAG protein Variant | MDIDPYKEFGATVELLSFLPSDFFPSVRDLLDTASALYREALESPEH CSPHHTALRHVFLCWGDLMTLATWVGGNLEDPTSRDLVVSYVNTNMG LKFRQLLWFHISCLTFGRETVIEYLVSFGVWIRTPPAYRPPNAPILS TLPETTVVRRRGRSPRRRTPSPRRRRSQSPRRRRSQSRESQC |
| 170 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGDL TTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 171 | HBcAG protein Variant | MQLFHLCLIISCSCPTVQASKLCLGWLWGMDIDPYKEFGATVELLSF LPSDFFPSVRDLLDTASALYRDALESPEHCSPHHTALRQAILCWGEL MTLATWVGVNLEDPASRDLVVSYVNTNMGLKFRQLLWFHISCLIFGR ETVIEYLVSFGVWIRTPPAYRPPNAPILSTLPETTVVRRRGRSPRRR TPSPRRRRSQSPRRRRSQSRESQC |
| 172 | HBcAG protein variant | MDIDPYKEFGATVELLSFLPSDFFPSVRDLLDTASALYREALESPEH CSPHHTALRQAILCWGDLMTLATWVGVNLEDPVSRDLVVSYVNTNVG LKFRQLLWFHISCLTFGRETVIEYLVSFGVWIRTPPAYRPPNAPILS TLPETTVVRRRGRSPRRRTPSPARRRSQSPRRRRSQSRESQC |

TABLE 4-continued

SEQUENCE LISTING

| SEQ ID NO | Description | Sequence |
|---|---|---|
| 173 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGDL MNLATWVGGNLEDPVSRDLVVGYVNTTVGLKFRQLLWFHISCLTFGR ETVIEYLVSFGVWIRTPPAYRPPNAPILSTLPETTVVRRRGRSPRRR TPSPPRRRRSQSPRRRRSQSRESQC |
| 174 | HBcAG protein Variant | MDIDPYKEFGATVELLSFLPSDFFPSVRDLLDTASALYRDALESPEH CSPHHTALRQAILCWGDLMTLATWVGVNLEDPASRDLVVSYVNTNMG LKFRQLLWFHISCLTFGRETVIEYLVSFGVWIRTPPAYRPPNAPILS TLPETTVVRRRGRTPRRRTPSPRRRRSQSPRRRRSQSRESQC |
| 175 | HBcAG protein Variant | MQLFHLCLIISCSCPTVQASKLCLGWLWGMDIDPYKEFGATVELLSF LPSDFFPSVRALLDTASALYREALESPEHCSPHHTALRQAILCWGEL MTLATWVGVNLEDPASRDLVVSYVNTNMGLKFRQILWFHISCLTFGR ETVIEYLVSFGVWIRTPPAYRPPNAPILSTLPETTVVRRRGRSPRRR TPSPRRRRSQSPRRRRSQSRESQC |
| 176 | HBcAG protein Variant | MQLFHLCLIISCSCPTVQASKLCLGWLWGMDIDPYKEFGATVELLSF LPSDFFPSVRDLLDTASALYREALESPEHCSPHHTALRQAILCWGDL MTLATWVGVNLEDPATRDLVVSYVNTNVGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 177 | HBcAG protein variant | MQLFHLCLIISCSCPTVQASKLCLGWLWGMDIDPYKEFGATVELLSF LPSDFFPSVRDLLDTASALYREALESPEHCSPHHTALRQRILCWGEL MTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRTRSQSRESQC |
| 178 | HBcAG protein Variant | MQLFHLCLVISCSCPTVQASKLCLGWLWGMDIDPYKEFGATVELLSF LPSDFFPSVRDLLDTAAALYREALESPEHCSPHHTALRQAILCWGEL MTLATWVGNNLEDPASRDLVVNYVNTNMGLKIRQLLWFHISCLTFGR ETVLEYLVSFGVWIRTPPAYRPPNAPILSTLPETTVVRRRGRSPRRR TPSPRRRRSQSPRRRRSQSRESQC |
| 179 | HBcAG protein Variant | MQLFHLCLIISCSCPTVQASKLCLGWLWGMDIDPYKEFGATVELLSF LPSAFFPSVRDLLDTASALYREALESPEHCSPHHTALRQAILCWGDL MTLATWVGVNLEDPASRDLVVSYVNTNMGLKFRQLLWFHISCLTFGR ETVIEYLVSFGVWIRTPPAYRPPNAPILSTLPETTVVRRRGRSPRRR TPSPRRRRSQSPRRRRSQSRESQC |
| 180 | HBcAG protein Variant | MDIDPYKEFGATVELLSFLPSDFFPSVRDLLDTAAALYREALESPEH CSPHHTALRQAILCWGELMTLATWVGNNLEDPASRDLVVNYVNTNMG LKIRQLLWFHISCLTFGRETVLEYLVSFGVWIRTPPAYRPPNAPILS TLPETTVVRRRGRSPRRRTPSPRRRRSQSPRRRRSQSRESQC |
| 181 | HBcAG protein Variant | MDIDPYKEFGATVELLSFLPSDFFPSVRDLLDTASALYREALESPEH CSPHHTALRQAILCWGELMTLATWVGGNLEDPISRDLVVSYVNTNMG LKFRQLLWFHISCLTFGRETVIEYLVSFGVWIRTPPAYRPPNAPILS TLPETCVVRRRGRSPRRRTPSPRRRRSQSPRRRRSQSRGSQC |
| 182 | HBcAG protein Variant | MDIDPYKEFGSSYQLLNFLPLDFFPDLNALVDTATALYEEELTGREH CSPHHTAIRQALVCWDELTKLIAWMSSNITSEQVRTIIVNHVNDTWG LKVRQSLWFHLSCLTFGQHTVQEFLVSFGVWIRTPAPYRPPNAPILS TLPEHTVIRRRGGARASRSPRRRTPSPRRRRSQSPRRRRSQSPSTNC |
| 183 | HBcAG protein Variant | MYLFHLCLVFACVPCPTVQASKLCLGWLWDMDIDPYKEFGSSYQLLN FLPLDFFPDLNALVDTAAALYEEELTGREHCSPHHTAIRQALVCWEE LTRLITWMSENTTEEVRRIIVDHVNNTWGLKVRQTLWFHLSCLTFGQ HTVQEFLVSFGVWIRTPAPYRPPNAPILSTLPEHTVIRRRGGSRAAR SPRRRTPSPRRRRSQSPRRRRSQSPASNC |
| 184 | HBcAG protein Variant | MDVNASRALANVYDLPDDFFPKIEDLVRDAKDALEPYWKSDSIKKHV LIATHFVDLIEDFWQTTQGMHEIAEAIRAVIPPTTAPVPSGYLIQHD EAEEIPLGDLFKEQEERIVSFQPDYPITARIHAHLKAYAKINEESLD RARRLLWWHYNCLLWGEATVTNYISRLRTWLSTPEKYRGRDAPTIEA ITRPIQVAQGGRKTSTATRKPRGLEPRRRKVKTTVVYGRRRSKSRER RASSPQRAGSPLPRSSSSHHRSPSPRK |

TABLE 4-continued

| SEQUENCE LISTING | | |
|---|---|---|
| SEQ ID NO | Description | Sequence |
| 185 | HBcAG protein variant | MWDLRLHPSPFGAACQGIFTSSLLLFLVTVPLVCTIVYDSCLCMDIN ASRALANVYDLPDDFFPKIDDLVRDAKDALEPYWRNDSIKKHVLIAT HFVDLIEDFWQTTQGMHEIAEALRAIIPATTAPVPQGFLVQHEEAEE IPLGELFRYQEERLTNFQPDYPVTARIHAHLKAYAKINEESLDRARR LLWWHYNCLLWGEPNVTNYISRLRTWLSTPEKYRGKDAPTIEAITRP IQVAQGGRNKTQGVRKSRGLEPRRRRVKTTIVYGRRRSKSRERRAPT PQRAGSPLPRTSRDHHRSPSPRE |
| 186 | HBcAG protein variant | MDIDPYKEFGATVELLSFLPSDFFPSVRDLLDTASALYREALESPEH CSPHHTALRQAILCWGELMTLATWVGNNLEDPASRDLVVNYVNTNMG LKIRQLLWFHISCLTFGRETVLEYLVSFGVWIRTPPAYRPPNAPILS TLPETTVVRRRDRGRSPRRRTPSPRRRRSQSPRRRRSQSRESQC |
| 187 | Amino acid sequence | GGKGG |
| 188 | Amino acid linker | (G)kC(G)m(S)l(GGGGS)n with n = 0-3, k = 0-5, m = 0-10, l = 0-2 |
| 189 | Amino acid linker | (G)m(S)l(GGGGS)n(G)oC(G)k with n = 0-3, k = 0-5, m = 0-10, l = 0-2, and o = 0-8 |
| 190 | Amino acid linker | (GGGGS)n |
| 191 | Amino acid linker | CGDKTHTSPP |
| 192 | Amino acid linker | DKTHTSPPCG |
| 193 | Amino acid linker | CGGPKPSTPPGSSGGAP |
| 194 | Amino acid linker | PKPSTPPGSSGGAPGGCG |
| 195 | Amino acid linker | GCGGGG |
| 196 | Amino acid linker | GGGGCG |
| 197 | Amino acid linker | GGKKGC |
| 198 | Amino acid linker | CGKKGG |
| 199 | Amino acid linker | CGKKGG |
| 200 | Amino acid linker | CGDEGG |
| 201 | Amino acid linker | GGKKGC |
| 202 | Amino acid linker | GGEDGC |
| 203 | Amino acid linker | GGCG |

The invention claimed is:

1. A composition comprising:

(a) a virus-like particle; and (b) at least one synthetic RIG-I like receptor (RLR) agonist that specifically binds to a RLR, wherein the RLR agonist comprises a blunt-ended, hairpin RNA comprising a first polynucleotide connected to a second polynucleotide by a linker;

wherein the first polynucleotide is sufficiently complementary to the second polynucleotide to form a duplex, wherein the duplex comprises less than 19 base pairs, wherein the 5' most nucleotide of the first polynucleotide comprises a 5' diphosphate or triphosphate moiety, or derivative or analog thereof, wherein the RLR agonist comprises a [AUCG]n repeat motif, wherein n=3, and wherein:

(a) the 5' most AUCG repeat motif is preceded by CG;

(b) the 5' most AUCG repeat motif is preceded by IG; or (c) the 5' most AUCG repeat is preceded by GG and wherein each G in the AUCG motif is substituted by inosine; and wherein the at least one RLR agonist is packaged in the virus-like particle.

2. The composition of claim 1, wherein the linker is a nucleotide linker or a non-nucleotide linker.

3. The composition of claim 2, wherein the nucleotide linker comprises a tetraloop comprising the sequence UUCG.

4. The composition of claim 2, wherein the non-nucleotide linker is a hexaethylene glycol linker or a C9 alkyl linker.

5. The composition of claim 1, wherein the virus-like particle comprises recombinant proteins of an RNA-phage, wherein said RNA-phage is selected from the group consisting of: (a) bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; (j) bacteriophage f2; (k) bacteriophage PP7; and (1) bacteriophage AP205.

6. The composition of claim 5, wherein the virus-like particle comprises recombinant proteins, or fragments thereof, of RNA-phage Qβ.

7. The composition of claim 1, wherein the virus-like particle comprises RNA-phage QB coat proteins each having an amino acid sequence at least 80%, 85%, 90%, 95%, 96%, 97%, 98%, 99% or 100% identical to SEQ ID NO: 112.

8. The composition of claim 1 wherein the RLR agonist is non-covalently bound to the virus-like particle.

9. The composition of claim 1, further comprising at least one antigen or antigenic determinant bound to the virus-like particle.

10. A pharmaceutical composition, comprising the composition of claim 1 and a pharmaceutically acceptable carrier.

11. A kit comprising the composition of claim 1 and instructions for use.

12. A method of stimulating an immune response, treating or delaying progression of a cancer, or inhibiting tumor growth in a subject in need thereof, comprising administering to the subject the composition of claim 1.

13. The method of claim 12, wherein the composition is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent, a cytotoxic agent, an immune-based therapy, a cytokine, an activator of a costimulatory molecule, an inhibitor of an inhibitory molecule, a vaccine, a cellular immunotherapy, and a combination thereof.

14. The method of claim 13, wherein the opsonizing agent is an opsonizing antibody.

15. The method of claim 13, wherein the composition is administered preceding or subsequent to administration of the one or more additional therapeutic agents, or wherein the one or more additional therapeutic agents is administered concurrently with, preceding, or subsequent to the administration of the composition.

16. The method of claim 13, wherein the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a Toll-like receptor 3 (TLR3) agonist, a Toll-like receptor 7 (TLR7) agonist, a Toll-like receptor 9 (TLR9) agonist, or an agonist comprising a polypeptide (e.g, antibody, or antigen binding portion thereof) that specifically binds to CD137 (4-1BB) or CD134 (OX40).

17. A method of producing the composition of claim 1, comprising:

(a) disassembling the virus-like particle, optionally removing nucleic acids of the disassembled virus-like particle;

(b) adding the RLR agonist; and (c) reassembling the virus-like particle.

18. The method of claim 17, further comprising purifying the composition after reassembly.

19. The method of claim 17, further comprising (d) binding an antigen or antigenic determinant to the virus-like particle.

20. The composition of claim 1, wherein the first polynucleotide comprises SEQ ID NO: 50 and the second polynucleotide comprises SEQ ID NO: 81.

21. The composition of claim 1, wherein the first polynucleotide comprises SEQ ID NO: 61 and the second polynucleotide comprises SEQ ID NO: 91.

22. The composition of claim 1, wherein the first polynucleotide comprises SEQ ID NO: 59 and the second polynucleotide comprises SEQ ID NO: 89.

* * * * *

SEQUENCE LISTING

<160> NUMBER OF SEQ ID NOS: 203

<210> SEQ ID NO 1
<211> LENGTH: 32
<212> TYPE: DNA
<213> ORGANISM: Artificial Sequence
<220> FEATURE:
<223> OTHER INFORMATION: Synthetic: RIG2 Nucleic acid sequence

<400> SEQUENCE: 1
ggatcgatcg atcguucgcg atcgatcgat cc 32

<210> SEQ ID NO 2
<211> LENGTH: 32
<212> TYPE: RNA
<213> ORGANISM: Artificial Sequence
<220> FEATURE:
<223> OTHER INFORMATION: Synthetic: RIG3 Nucleic acid sequence

<400> SEQUENCE: 2
ggaucgaucg auauuucgau aucgaucgau cc 32

<210> SEQ ID NO 3
<211> LENGTH: 32
<212> TYPE: RNA
<213> ORGANISM: Artificial Sequence
<220> FEATURE:
<223> OTHER INFORMATION: Synthetic: RIG4 Nucleic acid sequence

<400> SEQUENCE: 3
gcgcgcgcgc gcgcuucggc gcgcgcgcgc gc 32

<210> SEQ ID NO 4
<211> LENGTH: 32
<212> TYPE: RNA
<213> ORGANISM: Artificial Sequence
<220> FEATURE:
<223> OTHER INFORMATION: Synthetic: RIG5 Nucleic acid sequence

<400> SEQUENCE: 4
ggcggcgcgc cgccuucggg cggcgcgccg cc 32

<210> SEQ ID NO 5
<211> LENGTH: 32
<212> TYPE: RNA
<213> ORGANISM: Artificial Sequence
<220> FEATURE:
<223> OTHER INFORMATION: Synthetic: RIG6 Nucleic acid sequence

<400> SEQUENCE: 5
ggcggcggcg gcgguucgcc gccgccgccg cc 32

<210> SEQ ID NO 6
<211> LENGTH: 32
<212> TYPE: RNA
<213> ORGANISM: Artificial Sequence
<220> FEATURE:
<223> OTHER INFORMATION: Synthetic: RIG7 Nucleic acid sequence

<400> SEQUENCE: 6
ggcggccgcc cgcguucgcg cgggcggccg cc 32

<210> SEQ ID NO 7
<211> LENGTH: 32
<212> TYPE: RNA
<213> ORGANISM: Artificial Sequence
<220> FEATURE:
<223> OTHER INFORMATION: Synthetic: RIG8 Nucleic acid sequence

<400> SEQUENCE: 7
cgacgucgac gucguucgcg acgucgacgu cg 32

<210> SEQ ID NO 8
<211> LENGTH: 32
<212> TYPE: RNA
<213> ORGANISM: Artificial Sequence
<220> FEATURE:
<223> OTHER INFORMATION: Synthetic: RIG9 Nucleic acid sequence

<400> SEQUENCE: 8
gcacgucgac gugcuucggc acgucgacgu gc 32

<210> SEQ ID NO 9
<211> LENGTH: 32
<212> TYPE: RNA
<213> ORGANISM: Artificial Sequence
<220> FEATURE:
<223> OTHER INFORMATION: Synthetic: RIG10 Nucleic acid sequence

<400> SEQUENCE: 9
ggacgucgac guccuucggg acgucgacgu cc 32

<210> SEQ ID NO 10
<211> LENGTH: 32
<212> TYPE: RNA
<213> ORGANISM: Artificial Sequence
<220> FEATURE:
<223> OTHER INFORMATION: Synthetic: RIG11 Nucleic acid sequence

<400> SEQUENCE: 10
ggucgcgacc auauuucgau auggucgcga cc 32

<210> SEQ ID NO 11
<211> LENGTH: 32
<212> TYPE: RNA
<213> ORGANISM: Artificial Sequence
<220> FEATURE:
<223> OTHER INFORMATION: Synthetic: RIG12 Nucleic acid sequence

<400> SEQUENCE: 11
ggauacgucg acguuucgac gucgacguau cc 32

<210> SEQ ID NO 12
<211> LENGTH: 32
<212> TYPE: RNA
<213> ORGANISM: Artificial Sequence
<220> FEATURE:
<223> OTHER INFORMATION: Synthetic: RIG13 Nucleic acid sequence

<400> SEQUENCE: 12
gagagagaga gagauucguc ucucucucuc uc 32

<210> SEQ ID NO 13
<211> LENGTH: 32
<212> TYPE: RNA
<213> ORGANISM: Artificial Sequence
<220> FEATURE:
<223> OTHER INFORMATION: Synthetic: RIG14 Nucleic acid sequence

<400> SEQUENCE: 13
gagucuagac uccguucgcg gagucuagac uc 32

<210> SEQ ID NO 14
<211> LENGTH: 32
<212> TYPE: RNA
<213> ORGANISM: Artificial Sequence
<220> FEATURE:
<223> OTHER INFORMATION: Synthetic: RIG15 Nucleic acid sequence (RIG 45)

<400> SEQUENCE: 14
cgaucgaucg aucguucgcg aucgaucgau cg 32

<210> SEQ ID NO 15
<211> LENGTH: 32
<212> TYPE: RNA
<213> ORGANISM: Artificial Sequence
<220> FEATURE:
<223> OTHER INFORMATION: Synthetic: RIG16 Nucleic acid sequence

<400> SEQUENCE: 15
ccaucgaucg aucguucgcg aucgaucgau gg 32

<210> SEQ ID NO 16
<211> LENGTH: 32
<212> TYPE: RNA
<213> ORGANISM: Artificial Sequence
<220> FEATURE:
<223> OTHER INFORMATION: Synthetic: RIG18 Nucleic acid sequence

<400> SEQUENCE: 16
gaaucgaucg aucguucgcg aucgaucgau uc 32

<210> SEQ ID NO 17
<211> LENGTH: 26
<212> TYPE: RNA
<213> ORGANISM: Artificial Sequence
<220> FEATURE:
<223> OTHER INFORMATION: Synthetic: RIG20 Nucleic acid sequence

<400> SEQUENCE: 17
gggaucgauc guucgcgauc gauccc 26

<210> SEQ ID NO 18
<211> LENGTH: 32
<212> TYPE: RNA
<213> ORGANISM: Artificial Sequence
<220> FEATURE:
<223> OTHER INFORMATION: Synthetic: RIG21 Nucleic acid sequence

<400> SEQUENCE: 18
cccccgaucg aucguucgcg aucgaucggg gg 32

<210> SEQ ID NO 19
<211> LENGTH: 32
<212> TYPE: DNA
<213> ORGANISM: Artificial Sequence
<220> FEATURE:
<223> OTHER INFORMATION: Synthetic: RIG22 Nucleic acid sequence

<400> SEQUENCE: 19
gtgtgtgtgt gtgtuucgac acacacacac ac 32

<210> SEQ ID NO 20
<211> LENGTH: 32
<212> TYPE: DNA
<213> ORGANISM: Artificial Sequence
<220> FEATURE:
<223> OTHER INFORMATION: Synthetic: RIG24 Nucleic acid sequence

<400> SEQUENCE: 20
gtgtgtggau cgauuucgau cgauccacac ac 32

<210> SEQ ID NO 21
<211> LENGTH: 32
<212> TYPE: RNA
<213> ORGANISM: Artificial Sequence
<220> FEATURE:
<223> OTHER INFORMATION: Synthetic: RIG25 Nucleic acid sequence
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (26)..(26)
<223> OTHER INFORMATION: n is inosine
<220> FEATURE:
<221> NAME/KEY: misc_feature
<222> LOCATION: (30)..(30)
<223> OTHER INFORMATION: n is inosine

<400> SEQUENCE: 21
ggancgancg ancguucgcg ancgancgan cc 32

<210> SEQ ID NO 22
<211> LENGTH: 32
<212> TYPE: RNA
<213> ORGANISM: Artificial Sequence
<220> FEATURE:
<223> OTHER INFORMATION: Synthetic: RIG26 Nucleic acid sequence
<220> FEATURE:
<221> NAME/KEY: misc_feature
<222> LOCATION: (1)..(2)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine
<220> FEATURE:
<221> NAME/KEY: misc_feature
<222> LOCATION: (20)..(20)
<223> OTHER INFORMATION: n is inosine
<220> FEATURE:
<221> NAME/KEY: misc_feature
<222> LOCATION: (24)..(24)
<223> OTHER INFORMATION: n is inosine
<220> FEATURE:
<221> NAME/KEY: misc_feature
<222> LOCATION: (28)..(28)
<223> OTHER INFORMATION: n is inosine

<400> SEQUENCE: 22
nnaucnaucn aucnuucgcn aucnaucnau cc 32

<210> SEQ ID NO 23
<211> LENGTH: 32
<212> TYPE: RNA
<213> ORGANISM: Artificial Sequence
<220> FEATURE:
<223> OTHER INFORMATION: Synthetic: RIG27 Nucleic acid sequence
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine
<220> FEATURE:
<221> NAME/KEY: misc_feature
<222> LOCATION: (20)..(20)
<223> OTHER INFORMATION: n is inosine
<220> FEATURE:
<221> NAME/KEY: misc_feature
<222> LOCATION: (24)..(24)
<223> OTHER INFORMATION: n is inosine
<220> FEATURE:
<221> NAME/KEY: misc_feature
<222> LOCATION: (28)..(28)
<223> OTHER INFORMATION: n is inosine

<400> SEQUENCE: 23
ggaucnaucn aucnuucgcn aucnaucnau cc 32

<210> SEQ ID NO 24
<211> LENGTH: 32
<212> TYPE: RNA
<213> ORGANISM: Artificial Sequence
<220> FEATURE:
<223> OTHER INFORMATION: Synthetic: RIG28 Nucleic acid sequence
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (11)..(11)
<223> OTHER INFORMATION: n is inosine
<220> FEATURE:
<221> NAME/KEY: misc_feature
<222> LOCATION: (21)..(21)
<223> OTHER INFORMATION: n is inosine
<220> FEATURE:
<221> NAME/KEY: misc_feature
<222> LOCATION: (25)..(25)
<223> OTHER INFORMATION: n is inosine
<220> FEATURE:
<221> NAME/KEY: misc_feature
<222> LOCATION: (29)..(29)
<223> OTHER INFORMATION: n is inosine

<400> SEQUENCE: 24
ggnucgnucg nucguucgcg nucgnucgnu cc 32

<210> SEQ ID NO 25
<211> LENGTH: 32
<212> TYPE: RNA
<213> ORGANISM: Artificial Sequence
<220> FEATURE:
<223> OTHER INFORMATION: Synthetic: RIG35 Nucleic acid sequence
<220> FEATURE:
<221> NAME/KEY: misc_feature
<222> LOCATION: (1)..(1)
<223> OTHER INFORMATION: n is inosine

<400> SEQUENCE: 25
ngaucgaucg aucguucgcg aucgaucgau cc 32

<210> SEQ ID NO 26
<211> LENGTH: 28
<212> TYPE: RNA
<213> ORGANISM: Artificial Sequence
<220> FEATURE:
<223> OTHER INFORMATION: Synthetic: RIG36 Nucleic acid sequence

<400> SEQUENCE: 26
aucgaucgau cguucgcgau cgaucgau 28

<210> SEQ ID NO 27
<211> LENGTH: 34
<212> TYPE: RNA
<213> ORGANISM: Artificial Sequence
<220> FEATURE:
<223> OTHER INFORMATION: Synthetic: RIG37 Nucleic acid sequence

<400> SEQUENCE: 27
ggaucgaucg aucguuugau cgaucgaucg aucc 34

<210> SEQ ID NO 28
<211> LENGTH: 33
<212> TYPE: RNA
<213> ORGANISM: Artificial Sequence
<220> FEATURE:
<223> OTHER INFORMATION: Synthetic: RIG38 Nucleic acid sequence

<400> SEQUENCE: 28
ggaucgaucg aucguguuuc gaucgaucga ucc 33

<210> SEQ ID NO 29
<211> LENGTH: 32
<212> TYPE: RNA
<213> ORGANISM: Artificial Sequence
<220> FEATURE:
<223> OTHER INFORMATION: Synthetic: RIG39 Nucleic acid sequence

<400> SEQUENCE: 29
ggaucgaucg aucggauccg aucgaucgau cc 32

<210> SEQ ID NO 30
<211> LENGTH: 40
<212> TYPE: RNA
<213> ORGANISM: Artificial Sequence
<220> FEATURE:
<223> OTHER INFORMATION: Synthetic: RIG40 Nucleic acid sequence

<400> SEQUENCE: 30
ggcaugcgac cucuguuuga ucaaacagag gucgcaugcc 40

<210> SEQ ID NO 31
<211> LENGTH: 32
<212> TYPE: RNA
<213> ORGANISM: Artificial Sequence
<220> FEATURE:
<223> OTHER INFORMATION: Synthetic: RIG41 Nucleic acid sequence

<400> SEQUENCE: 31
ggcaugcgac cucugaucag aggucgcaug cc 32

<210> SEQ ID NO 32
<211> LENGTH: 40
<212> TYPE: RNA
<213> ORGANISM: Artificial Sequence
<220> FEATURE:
<223> OTHER INFORMATION: Synthetic: RIG42 Nucleic acid sequence

<400> SEQUENCE: 32
ggcaugcgac cucuguuuuu cgaaacagag gucgcaugcc 40

<210> SEQ ID NO 33
<211> LENGTH: 32
<212> TYPE: DNA
<213> ORGANISM: Artificial Sequence
<220> FEATURE:
<223> OTHER INFORMATION: Synthetic: RIG47 Nucleic acid sequence

<400> SEQUENCE: 33
tgcucgaucg aucguucgcg aucgaucgag ca 32

<210> SEQ ID NO 34
<211> LENGTH: 32
<212> TYPE: DNA
<213> ORGANISM: Artificial Sequence
<220> FEATURE:
<223> OTHER INFORMATION: Synthetic: RIG48 Nucleic acid sequence

<400> SEQUENCE: 34
tcgucgaucg aucguucgcg aucgaucgac ga 32

<210> SEQ ID NO 35
<211> LENGTH: 32
<212> TYPE: DNA
<213> ORGANISM: Artificial Sequence
<220> FEATURE:
<223> OTHER INFORMATION: Synthetic: RIG49 Nucleic acid sequence

<400> SEQUENCE: 35
ggaucgaucg aucguucgtg aucgaucgau gg 32

<210> SEQ ID NO 36
<211> LENGTH: 32
<212> TYPE: RNA
<213> ORGANISM: Artificial Sequence
<220> FEATURE:
<223> OTHER INFORMATION: Synthetic: RIG 0 Nucleic acid sequence (14L)

<400> SEQUENCE: 36
ggaucgaucg aucguucgcg aucgaucgau cc 32

<210> SEQ ID NO 37
<211> LENGTH: 14
<212> TYPE: DNA
<213> ORGANISM: Artificial Sequence
<220> FEATURE:
<223> OTHER INFORMATION: Synthetic: FO1 Nucleic acid sequence

<400> SEQUENCE: 37
ggatcgatcg atcg 14

<210> SEQ ID NO 38
<211> LENGTH: 14

<212> TYPE: RNA
<213> ORGANISM: Artificial Sequence
<220> FEATURE:
<223> OTHER INFORMATION: Synthetic: F02 Nucleic acid sequence

<400> SEQUENCE: 38
ggaucgaucg auau 14

<210> SEQ ID NO 39
<211> LENGTH: 14
<212> TYPE: DNA
<213> ORGANISM: Artificial Sequence
<220> FEATURE:
<223> OTHER INFORMATION: Synthetic: F03 Nucleic acid sequence

<400> SEQUENCE: 39
gcgcgcgcgc gcgc 14

<210> SEQ ID NO 40
<211> LENGTH: 14
<212> TYPE: DNA
<213> ORGANISM: Artificial Sequence
<220> FEATURE:
<223> OTHER INFORMATION: Synthetic: F04 Nucleic acid sequence

<400> SEQUENCE: 40
ggcggcgcgc cgcc 14

<210> SEQ ID NO 41
<211> LENGTH: 14
<212> TYPE: DNA
<213> ORGANISM: Artificial Sequence
<220> FEATURE:
<223> OTHER INFORMATION: Synthetic: F05 Nucleic acid sequence

<400> SEQUENCE: 41
ggcggcggcg gcgg 14

<210> SEQ ID NO 42
<211> LENGTH: 14
<212> TYPE: DNA
<213> ORGANISM: Artificial Sequence
<220> FEATURE:
<223> OTHER INFORMATION: Synthetic: F06 Nucleic acid sequence

<400> SEQUENCE: 42
ggcggccgcc cgcg 14

<210> SEQ ID NO 43
<211> LENGTH: 14
<212> TYPE: RNA
<213> ORGANISM: Artificial Sequence
<220> FEATURE:
<223> OTHER INFORMATION: Synthetic: F07 Nucleic acid sequence

<400> SEQUENCE: 43
cgacgucgac gucg 14

<210> SEQ ID NO 44
<211> LENGTH: 14
<212> TYPE: RNA
<213> ORGANISM: Artificial Sequence
<220> FEATURE:
<223> OTHER INFORMATION: Synthetic: F08 Nucleic acid sequence

<400> SEQUENCE: 44
gcacgucgac gugc 14

<210> SEQ ID NO 45
<211> LENGTH: 14
<212> TYPE: RNA
<213> ORGANISM: Artificial Sequence
<220> FEATURE:
<223> OTHER INFORMATION: Synthetic: FO9 Nucleic acid sequence

<400> SEQUENCE: 45
ggacgucgac gucc 14

<210> SEQ ID NO 46
<211> LENGTH: 14
<212> TYPE: RNA
<213> ORGANISM: Artificial Sequence
<220> FEATURE:
<223> OTHER INFORMATION: Synthetic: FO10 Nucleic acid sequence

<400> SEQUENCE: 46
ggucgcgacc auau 14

<210> SEQ ID NO 47
<211> LENGTH: 14
<212> TYPE: RNA
<213> ORGANISM: Artificial Sequence
<220> FEATURE:
<223> OTHER INFORMATION: Synthetic: FO11 Nucleic acid sequence

<400> SEQUENCE: 47
ggauacgucg acgu 14

<210> SEQ ID NO 48
<211> LENGTH: 14
<212> TYPE: DNA
<213> ORGANISM: Artificial Sequence
<220> FEATURE:
<223> OTHER INFORMATION: Synthetic: FO12 Nucleic acid sequence

<400> SEQUENCE: 48
gagagagaga gaga 14

<210> SEQ ID NO 49
<211> LENGTH: 14
<212> TYPE: RNA
<213> ORGANISM: Artificial Sequence
<220> FEATURE:
<223> OTHER INFORMATION: Synthetic: FO13 Nucleic acid sequence

<400> SEQUENCE: 49
gagucuagac uccg 14

<210> SEQ ID NO 50
<211> LENGTH: 14
<212> TYPE: RNA
<213> ORGANISM: Artificial Sequence
<220> FEATURE:
<223> OTHER INFORMATION: Synthetic: FO14 Nucleic acid sequence

<400> SEQUENCE: 50
cgaucgaucg aucg 14

<210> SEQ ID NO 51
<211> LENGTH: 14
<212> TYPE: RNA
<213> ORGANISM: Artificial Sequence

```
<220> FEATURE:
<223> OTHER INFORMATION: Synthetic: FO15 Nucleic acid sequence

<400> SEQUENCE: 51

ccaucgaucg aucg                                                      14


<210> SEQ ID NO 52
<211> LENGTH: 14
<212> TYPE: RNA
<213> ORGANISM: Artificial Sequence
<220> FEATURE:
<223> OTHER INFORMATION: Synthetic: FO16 Nucleic acid sequence

<400> SEQUENCE: 52

gaaucgaucg aucg                                                      14


<210> SEQ ID NO 53
<211> LENGTH: 11
<212> TYPE: RNA
<213> ORGANISM: Artificial Sequence
<220> FEATURE:
<223> OTHER INFORMATION: Synthetic: FO17 Nucleic acid sequence

<400> SEQUENCE: 53

gggaucgauc g                                                         11


<210> SEQ ID NO 54
<211> LENGTH: 14
<212> TYPE: RNA
<213> ORGANISM: Artificial Sequence
<220> FEATURE:
<223> OTHER INFORMATION: Synthetic: FO18 Nucleic acid sequence

<400> SEQUENCE: 54

cccccgaucg aucg                                                      14


<210> SEQ ID NO 55
<211> LENGTH: 14
<212> TYPE: DNA
<213> ORGANISM: Artificial Sequence
<220> FEATURE:
<223> OTHER INFORMATION: Synthetic: FO19 Nucleic acid sequence

<400> SEQUENCE: 55

gtgtgtgtgt gtgt                                                      14


<210> SEQ ID NO 56
<211> LENGTH: 14
<212> TYPE: DNA
<213> ORGANISM: Artificial Sequence
<220> FEATURE:
<223> OTHER INFORMATION: Synthetic: FO20 Nucleic acid sequence

<400> SEQUENCE: 56

gtgtgtggau cgau                                                      14


<210> SEQ ID NO 57
<211> LENGTH: 14
<212> TYPE: DNA
<213> ORGANISM: Artificial Sequence
<220> FEATURE:
<223> OTHER INFORMATION: Synthetic: FO21 Nucleic acid sequence
<220> FEATURE:
<221> NAME/KEY: misc_feature
<222> LOCATION: (4)..(4)
<223> OTHER INFORMATION: n is inosine
<220> FEATURE:
```

<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (12)..(12)
<223> OTHER INFORMATION: n is inosine

<400> SEQUENCE: 57
ggancgancg ancg 14

<210> SEQ ID NO 58
<211> LENGTH: 14
<212> TYPE: RNA
<213> ORGANISM: Artificial Sequence
<220> FEATURE:
<223> OTHER INFORMATION: Synthetic: FO22 Nucleic acid sequence
<220> FEATURE:
<221> NAME/KEY: misc_feature
<222> LOCATION: (1)..(2)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine

<400> SEQUENCE: 58
nnaucnaucn aucn 14

<210> SEQ ID NO 59
<211> LENGTH: 14
<212> TYPE: RNA
<213> ORGANISM: Artificial Sequence
<220> FEATURE:
<223> OTHER INFORMATION: Synthetic: FO23 Nucleic acid sequence
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine

<400> SEQUENCE: 59
ggaucnaucn aucn 14

<210> SEQ ID NO 60
<211> LENGTH: 14
<212> TYPE: RNA
<213> ORGANISM: Artificial Sequence
<220> FEATURE:
<223> OTHER INFORMATION: Synthetic: FO24 Nucleic acid sequence
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (11)..(11)
<223> OTHER INFORMATION: n is inosine

<400> SEQUENCE: 60
ggnucgnucg nucg 14

<210> SEQ ID NO 61
<211> LENGTH: 14
<212> TYPE: RNA
<213> ORGANISM: Artificial Sequence
<220> FEATURE:
<223> OTHER INFORMATION: Synthetic: FO25 Nucleic acid sequence
<220> FEATURE:
<221> NAME/KEY: misc_feature
<222> LOCATION: (1)..(1)
<223> OTHER INFORMATION: n is inosine

<400> SEQUENCE: 61
ngaucgaucg aucg 14

<210> SEQ ID NO 62
<211> LENGTH: 12
<212> TYPE: RNA
<213> ORGANISM: Artificial Sequence
<220> FEATURE:
<223> OTHER INFORMATION: Synthetic: FO26 Nucleic acid sequence

<400> SEQUENCE: 62
aucgaucgau cg 12

<210> SEQ ID NO 63
<211> LENGTH: 14
<212> TYPE: RNA
<213> ORGANISM: Artificial Sequence
<220> FEATURE:
<223> OTHER INFORMATION: Synthetic: FO27 Nucleic acid sequence

<400> SEQUENCE: 63
ggaucgaucg aucg 14

<210> SEQ ID NO 64
<211> LENGTH: 18
<212> TYPE: RNA
<213> ORGANISM: Artificial Sequence
<220> FEATURE:
<223> OTHER INFORMATION: Synthetic: FO28 Nucleic acid sequence

<400> SEQUENCE: 64
ggcaugcgac cucuguuu 18

<210> SEQ ID NO 65
<211> LENGTH: 14
<212> TYPE: RNA
<213> ORGANISM: Artificial Sequence
<220> FEATURE:
<223> OTHER INFORMATION: Synthetic: FO29 Nucleic acid sequence

<400> SEQUENCE: 65
ggcaugcgac cucu 14

<210> SEQ ID NO 66
<211> LENGTH: 14
<212> TYPE: DNA
<213> ORGANISM: Artificial Sequence
<220> FEATURE:

<223> OTHER INFORMATION: Synthetic: FO30 Nucleic acid sequence

<400> SEQUENCE: 66
tgcucgaucg aucg 14

<210> SEQ ID NO 67
<211> LENGTH: 14
<212> TYPE: DNA
<213> ORGANISM: Artificial Sequence
<220> FEATURE:
<223> OTHER INFORMATION: Synthetic: FO31 Nucleic acid sequence

<400> SEQUENCE: 67
tcgucgaucg aucg 14

<210> SEQ ID NO 68
<211> LENGTH: 14
<212> TYPE: DNA
<213> ORGANISM: Artificial Sequence
<220> FEATURE:
<223> OTHER INFORMATION: Synthetic: SO1 Nucleic acid sequence

<400> SEQUENCE: 68
cgatcgatcg atcc 14

<210> SEQ ID NO 69
<211> LENGTH: 14
<212> TYPE: RNA
<213> ORGANISM: Artificial Sequence
<220> FEATURE:
<223> OTHER INFORMATION: Synthetic: SO2 Nucleic acid sequence

<400> SEQUENCE: 69
auaucgaucg aucc 14

<210> SEQ ID NO 70
<211> LENGTH: 14
<212> TYPE: DNA
<213> ORGANISM: Artificial Sequence
<220> FEATURE:
<223> OTHER INFORMATION: Synthetic: SO3 Nucleic acid sequence

<400> SEQUENCE: 70
gcgcgcgcgc gcgc 14

<210> SEQ ID NO 71
<211> LENGTH: 14
<212> TYPE: DNA
<213> ORGANISM: Artificial Sequence
<220> FEATURE:
<223> OTHER INFORMATION: Synthetic: SO4 Nucleic acid sequence

<400> SEQUENCE: 71
ggcggcgcgc cgcc 14

<210> SEQ ID NO 72
<211> LENGTH: 14
<212> TYPE: DNA
<213> ORGANISM: Artificial Sequence
<220> FEATURE:
<223> OTHER INFORMATION: Synthetic: SO5 Nucleic acid sequence

<400> SEQUENCE: 72
ccgccgccgc cgcc 14

<210> SEQ ID NO 73
<211> LENGTH: 14
<212> TYPE: DNA
<213> ORGANISM: Artificial Sequence
<220> FEATURE:
<223> OTHER INFORMATION: Synthetic: SO6 Nucleic acid sequence

<400> SEQUENCE: 73
cgcgggcggc cgcc 14

<210> SEQ ID NO 74
<211> LENGTH: 14
<212> TYPE: RNA
<213> ORGANISM: Artificial Sequence
<220> FEATURE:
<223> OTHER INFORMATION: Synthetic: SO7 Nucleic acid sequence

<400> SEQUENCE: 74
cgacgucgac gucg 14

<210> SEQ ID NO 75
<211> LENGTH: 14
<212> TYPE: RNA
<213> ORGANISM: Artificial Sequence
<220> FEATURE:
<223> OTHER INFORMATION: Synthetic: SO8 Nucleic acid sequence

<400> SEQUENCE: 75
gcacgucgac gugc 14

<210> SEQ ID NO 76
<211> LENGTH: 14
<212> TYPE: RNA
<213> ORGANISM: Artificial Sequence
<220> FEATURE:
<223> OTHER INFORMATION: Synthetic: SO9 Nucleic acid sequence

<400> SEQUENCE: 76
ggacgucgac gucc 14

<210> SEQ ID NO 77
<211> LENGTH: 14
<212> TYPE: RNA
<213> ORGANISM: Artificial Sequence
<220> FEATURE:
<223> OTHER INFORMATION: Synthetic: SO10 Nucleic acid sequence

<400> SEQUENCE: 77
auauggucgc gacc 14

<210> SEQ ID NO 78
<211> LENGTH: 14
<212> TYPE: RNA
<213> ORGANISM: Artificial Sequence
<220> FEATURE:
<223> OTHER INFORMATION: Synthetic: SO11 Nucleic acid sequence

<400> SEQUENCE: 78
acgucgacgu aucc 14

<210> SEQ ID NO 79
<211> LENGTH: 14
<212> TYPE: RNA
<213> ORGANISM: Artificial Sequence
<220> FEATURE:
<223> OTHER INFORMATION: Synthetic: SO12 Nucleic acid sequence

<400> SEQUENCE: 79
ucucucucuc ucuc 14

<210> SEQ ID NO 80
<211> LENGTH: 14
<212> TYPE: RNA
<213> ORGANISM: Artificial Sequence
<220> FEATURE:
<223> OTHER INFORMATION: Synthetic: SO13 Nucleic acid sequence

<400> SEQUENCE: 80
cggagucuag acuc 14

<210> SEQ ID NO 81
<211> LENGTH: 14
<212> TYPE: RNA
<213> ORGANISM: Artificial Sequence
<220> FEATURE:
<223> OTHER INFORMATION: Synthetic: SO14 Nucleic acid sequence

<400> SEQUENCE: 81
cgaucgaucg aucg 14

<210> SEQ ID NO 82
<211> LENGTH: 14
<212> TYPE: RNA
<213> ORGANISM: Artificial Sequence
<220> FEATURE:
<223> OTHER INFORMATION: Synthetic: SO15 Nucleic acid sequence

<400> SEQUENCE: 82
cgaucgaucg augg 14

<210> SEQ ID NO 83
<211> LENGTH: 14
<212> TYPE: RNA
<213> ORGANISM: Artificial Sequence
<220> FEATURE:
<223> OTHER INFORMATION: Synthetic: SO16 Nucleic acid sequence

<400> SEQUENCE: 83
cgaucgaucg auuc 14

<210> SEQ ID NO 84
<211> LENGTH: 11
<212> TYPE: RNA
<213> ORGANISM: Artificial Sequence
<220> FEATURE:
<223> OTHER INFORMATION: Synthetic: SO17 Nucleic acid sequence

<400> SEQUENCE: 84
cgaucgaucc c 11

<210> SEQ ID NO 85
<211> LENGTH: 14
<212> TYPE: RNA
<213> ORGANISM: Artificial Sequence
<220> FEATURE:
<223> OTHER INFORMATION: Synthetic: SO18 Nucleic acid sequence

<400> SEQUENCE: 85
cgaucgaucg gggg 14

<210> SEQ ID NO 86
<211> LENGTH: 14

<212> TYPE: DNA
<213> ORGANISM: Artificial Sequence
<220> FEATURE:
<223> OTHER INFORMATION: Synthetic: SO19 Nucleic acid sequence

<400> SEQUENCE: 86
acacacacac acac 14

<210> SEQ ID NO 87
<211> LENGTH: 14
<212> TYPE: RNA
<213> ORGANISM: Artificial Sequence
<220> FEATURE:
<223> OTHER INFORMATION: Synthetic: SO20 Nucleic acid sequence

<400> SEQUENCE: 87
aucgauccac acac 14

<210> SEQ ID NO 88
<211> LENGTH: 14
<212> TYPE: DNA
<213> ORGANISM: Artificial Sequence
<220> FEATURE:
<223> OTHER INFORMATION: Synthetic: SO21 Nucleic acid sequence
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (12)..(12)
<223> OTHER INFORMATION: n is inosine

<400> SEQUENCE: 88
cgancgancg ancc 14

<210> SEQ ID NO 89
<211> LENGTH: 14
<212> TYPE: RNA
<213> ORGANISM: Artificial Sequence
<220> FEATURE:
<223> OTHER INFORMATION: Synthetic: SO22 Nucleic acid sequence
<220> FEATURE:
<221> NAME/KEY: misc_feature
<222> LOCATION: (2)..(2)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine

<400> SEQUENCE: 89
cnaucnaucn aucc 14

<210> SEQ ID NO 90
<211> LENGTH: 14
<212> TYPE: RNA
<213> ORGANISM: Artificial Sequence
<220> FEATURE:
<223> OTHER INFORMATION: Synthetic: SO23 Nucleic acid sequence
<220> FEATURE:
<221> NAME/KEY: misc_feature
<222> LOCATION: (3)..(3)

<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (11)..(11)
<223> OTHER INFORMATION: n is inosine

<400> SEQUENCE: 90
cgnucgnucg nucc 14

<210> SEQ ID NO 91
<211> LENGTH: 14
<212> TYPE: RNA
<213> ORGANISM: Artificial Sequence
<220> FEATURE:
<223> OTHER INFORMATION: Synthetic: SO24 Nucleic acid sequence

<400> SEQUENCE: 91
cgaucgaucg aucc 14

<210> SEQ ID NO 92
<211> LENGTH: 12
<212> TYPE: RNA
<213> ORGANISM: Artificial Sequence
<220> FEATURE:
<223> OTHER INFORMATION: Synthetic: SO25 Nucleic acid sequence

<400> SEQUENCE: 92
cgaucgaucg au 12

<210> SEQ ID NO 93
<211> LENGTH: 18
<212> TYPE: RNA
<213> ORGANISM: Artificial Sequence
<220> FEATURE:
<223> OTHER INFORMATION: Synthetic: SO26 Nucleic acid sequence

<400> SEQUENCE: 93
aaacagaggu cgcaugcc 18

<210> SEQ ID NO 94
<211> LENGTH: 14
<212> TYPE: RNA
<213> ORGANISM: Artificial Sequence
<220> FEATURE:
<223> OTHER INFORMATION: Synthetic: SO27 Nucleic acid sequence

<400> SEQUENCE: 94
agaggucgca ugcc 14

<210> SEQ ID NO 95
<211> LENGTH: 14
<212> TYPE: RNA
<213> ORGANISM: Artificial Sequence
<220> FEATURE:
<223> OTHER INFORMATION: Synthetic: SO28 Nucleic acid sequence

<400> SEQUENCE: 95
cgaucgaucg agca 14

<210> SEQ ID NO 96
<211> LENGTH: 14
<212> TYPE: RNA
<213> ORGANISM: Artificial Sequence
<220> FEATURE:
<223> OTHER INFORMATION: Synthetic: SO29 Nucleic acid sequence

<400> SEQUENCE: 96
cgaucgaucg acga 14

<210> SEQ ID NO 97
<211> LENGTH: 14
<212> TYPE: DNA
<213> ORGANISM: Artificial Sequence
<220> FEATURE:
<223> OTHER INFORMATION: Synthetic: SO30 Nucleic acid sequence

<400> SEQUENCE: 97
tgaucgaucg augg 14

<210> SEQ ID NO 98
<211> LENGTH: 925
<212> TYPE: PRT
<213> ORGANISM: Homo sapiens
<220> FEATURE:
<221> NAME/KEY: misc_feature
<223> OTHER INFORMATION: Human RIG-I Amino acid sequence

<400> SEQUENCE: 98

```
Met Thr Thr Glu Gln Arg Arg Ser Leu Gln Ala Phe Gln Asp Tyr Ile
1               5                   10                  15

Arg Lys Thr Leu Asp Pro Thr Tyr Ile Leu Ser Tyr Met Ala Pro Trp
            20                  25                  30

Phe Arg Glu Glu Glu Val Gln Tyr Ile Gln Ala Glu Lys Asn Asn Lys
        35                  40                  45

Gly Pro Met Glu Ala Ala Thr Leu Phe Leu Lys Phe Leu Leu Glu Leu
    50                  55                  60

Gln Glu Glu Gly Trp Phe Arg Gly Phe Leu Asp Ala Leu Asp His Ala
65                  70                  75                  80

Gly Tyr Ser Gly Leu Tyr Glu Ala Ile Glu Ser Trp Asp Phe Lys Lys
                85                  90                  95

Ile Glu Lys Leu Glu Glu Tyr Arg Leu Leu Leu Lys Arg Leu Gln Pro
            100                 105                 110

Glu Phe Lys Thr Arg Ile Ile Pro Thr Asp Ile Ile Ser Asp Leu Ser
        115                 120                 125

Glu Cys Leu Ile Asn Gln Glu Cys Glu Glu Ile Leu Gln Ile Cys Ser
    130                 135                 140

Thr Lys Gly Met Met Ala Gly Ala Glu Lys Leu Val Glu Cys Leu Leu
145                 150                 155                 160

Arg Ser Asp Lys Glu Asn Trp Pro Lys Thr Leu Lys Leu Ala Leu Glu
                165                 170                 175

Lys Glu Arg Asn Lys Phe Ser Glu Leu Trp Ile Val Glu Lys Gly Ile
            180                 185                 190

Lys Asp Val Glu Thr Glu Asp Leu Glu Asp Lys Met Glu Thr Ser Asp
        195                 200                 205

Ile Gln Ile Phe Tyr Gln Glu Asp Pro Glu Cys Gln Asn Leu Ser Glu
    210                 215                 220

Asn Ser Cys Pro Pro Ser Glu Val Ser Asp Thr Asn Leu Tyr Ser Pro
225                 230                 235                 240

Phe Lys Pro Arg Asn Tyr Gln Leu Glu Leu Ala Leu Pro Ala Met Lys
                245                 250                 255

Gly Lys Asn Thr Ile Ile Cys Ala Pro Thr Gly Cys Gly Lys Thr Phe
```

```
            260                 265                 270

Val Ser Leu Leu Ile Cys Glu His His Leu Lys Lys Phe Pro Gln Gly
        275                 280                 285

Gln Lys Gly Lys Val Val Phe Phe Ala Asn Gln Ile Pro Val Tyr Glu
    290                 295                 300

Gln Gln Lys Ser Val Phe Ser Lys Tyr Phe Glu Arg His Gly Tyr Arg
305                 310                 315                 320

Val Thr Gly Ile Ser Gly Ala Thr Ala Glu Asn Val Pro Val Glu Gln
                325                 330                 335

Ile Val Glu Asn Asn Asp Ile Ile Ile Leu Thr Pro Gln Ile Leu Val
            340                 345                 350

Asn Asn Leu Lys Lys Gly Thr Ile Pro Ser Leu Ser Ile Phe Thr Leu
        355                 360                 365

Met Ile Phe Asp Glu Cys His Asn Thr Ser Lys Gln His Pro Tyr Asn
    370                 375                 380

Met Ile Met Phe Asn Tyr Leu Asp Gln Lys Leu Gly Gly Ser Ser Gly
385                 390                 395                 400

Pro Leu Pro Gln Val Ile Gly Leu Thr Ala Ser Val Gly Val Gly Asp
                405                 410                 415

Ala Lys Asn Thr Asp Glu Ala Leu Asp Tyr Ile Cys Lys Leu Cys Ala
            420                 425                 430

Ser Leu Asp Ala Ser Val Ile Ala Thr Val Lys His Asn Leu Glu Glu
        435                 440                 445

Leu Glu Gln Val Val Tyr Lys Pro Gln Lys Phe Phe Arg Lys Val Glu
    450                 455                 460

Ser Arg Ile Ser Asp Lys Phe Lys Tyr Ile Ile Ala Gln Leu Met Arg
465                 470                 475                 480

Asp Thr Glu Ser Leu Ala Lys Arg Ile Cys Lys Asp Leu Glu Asn Leu
                485                 490                 495

Ser Gln Ile Gln Asn Arg Glu Phe Gly Thr Gln Lys Tyr Glu Gln Trp
            500                 505                 510

Ile Val Thr Val Gln Lys Ala Cys Met Val Phe Gln Met Pro Asp Lys
        515                 520                 525

Asp Glu Glu Ser Arg Ile Cys Lys Ala Leu Phe Leu Tyr Thr Ser His
    530                 535                 540

Leu Arg Lys Tyr Asn Asp Ala Leu Ile Ile Ser Glu His Ala Arg Met
545                 550                 555                 560

Lys Asp Ala Leu Asp Tyr Leu Lys Asp Phe Phe Ser Asn Val Arg Ala
                565                 570                 575

Ala Gly Phe Asp Glu Ile Glu Gln Asp Leu Thr Gln Arg Phe Glu Glu
            580                 585                 590

Lys Leu Gln Glu Leu Glu Ser Val Ser Arg Asp Pro Ser Asn Glu Asn
        595                 600                 605

Pro Lys Leu Glu Asp Leu Cys Phe Ile Leu Gln Glu Glu Tyr His Leu
    610                 615                 620

Asn Pro Glu Thr Ile Thr Ile Leu Phe Val Lys Thr Arg Ala Leu Val
625                 630                 635                 640

Asp Ala Leu Lys Asn Trp Ile Glu Gly Asn Pro Lys Leu Ser Phe Leu
                645                 650                 655

Lys Pro Gly Ile Leu Thr Gly Arg Gly Lys Thr Asn Gln Asn Thr Gly
            660                 665                 670

Met Thr Leu Pro Ala Gln Lys Cys Ile Leu Asp Ala Phe Lys Ala Ser
        675                 680                 685
```

```
Gly Asp His Asn Ile Leu Ile Ala Thr Ser Val Ala Asp Glu Gly Ile
    690                 695                 700

Asp Ile Ala Gln Cys Asn Leu Val Ile Leu Tyr Glu Tyr Val Gly Asn
705                 710                 715                 720

Val Ile Lys Met Ile Gln Thr Arg Gly Arg Gly Arg Ala Arg Gly Ser
                725                 730                 735

Lys Cys Phe Leu Leu Thr Ser Asn Ala Gly Val Ile Glu Lys Glu Gln
            740                 745                 750

Ile Asn Met Tyr Lys Glu Lys Met Met Asn Asp Ser Ile Leu Arg Leu
        755                 760                 765

Gln Thr Trp Asp Glu Ala Val Phe Arg Glu Lys Ile Leu His Ile Gln
    770                 775                 780

Thr His Glu Lys Phe Ile Arg Asp Ser Gln Glu Lys Pro Lys Pro Val
785                 790                 795                 800

Pro Asp Lys Glu Asn Lys Lys Leu Leu Cys Arg Lys Cys Lys Ala Leu
                805                 810                 815

Ala Cys Tyr Thr Ala Asp Val Arg Val Ile Glu Glu Cys His Tyr Thr
            820                 825                 830

Val Leu Gly Asp Ala Phe Lys Glu Cys Phe Val Ser Arg Pro His Pro
        835                 840                 845

Lys Pro Lys Gln Phe Ser Ser Phe Glu Lys Arg Ala Lys Ile Phe Cys
    850                 855                 860

Ala Arg Gln Asn Cys Ser His Asp Trp Gly Ile His Val Lys Tyr Lys
865                 870                 875                 880

Thr Phe Glu Ile Pro Val Ile Lys Ile Glu Ser Phe Val Val Glu Asp
                885                 890                 895

Ile Ala Thr Gly Val Gln Thr Leu Tyr Ser Lys Trp Lys Asp Phe His
            900                 905                 910

Phe Glu Lys Ile Pro Phe Asp Pro Ala Glu Met Ser Lys
        915                 920                 925


<210> SEQ ID NO 99
<211> LENGTH: 1025
<212> TYPE: PRT
<213> ORGANISM: Homo sapiens
<220> FEATURE:
<221> NAME/KEY: misc_feature
<223> OTHER INFORMATION: Human MDA5 Amino acid sequence

<400> SEQUENCE: 99

Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
```

```
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Ala Glu Asn Asn Gly Asn
145                 150                 155                 160

Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn Leu Ser Gln Val Asp Gly Pro Gln Val Glu Glu Gln Leu
    210                 215                 220

Leu Ser Thr Thr Val Gln Pro Asn Leu Glu Lys Glu Val Trp Gly Met
225                 230                 235                 240

Glu Asn Asn Ser Ser Glu Ser Ser Phe Ala Asp Ser Ser Val Val Ser
                245                 250                 255

Glu Ser Asp Thr Ser Leu Ala Glu Gly Ser Val Ser Cys Leu Asp Glu
            260                 265                 270

Ser Leu Gly His Asn Ser Asn Met Gly Ser Asp Ser Gly Thr Met Gly
        275                 280                 285

Ser Asp Ser Asp Glu Glu Asn Val Ala Ala Arg Ala Ser Pro Glu Pro
    290                 295                 300

Glu Leu Gln Leu Arg Pro Tyr Gln Met Glu Val Ala Gln Pro Ala Leu
305                 310                 315                 320

Glu Gly Lys Asn Ile Ile Ile Cys Leu Pro Thr Gly Ser Gly Lys Thr
                325                 330                 335

Arg Val Ala Val Tyr Ile Ala Lys Asp His Leu Asp Lys Lys Lys Lys
            340                 345                 350

Ala Ser Glu Pro Gly Lys Val Ile Val Leu Val Asn Lys Val Leu Leu
        355                 360                 365

Val Glu Gln Leu Phe Arg Lys Glu Phe Gln Pro Phe Leu Lys Lys Trp
    370                 375                 380

Tyr Arg Val Ile Gly Leu Ser Gly Asp Thr Gln Leu Lys Ile Ser Phe
385                 390                 395                 400

Pro Glu Val Val Lys Ser Cys Asp Ile Ile Ile Ser Thr Ala Gln Ile
                405                 410                 415

Leu Glu Asn Ser Leu Leu Asn Leu Glu Asn Gly Glu Asp Ala Gly Val
            420                 425                 430

Gln Leu Ser Asp Phe Ser Leu Ile Ile Ile Asp Glu Cys His His Thr
        435                 440                 445

Asn Lys Glu Ala Val Tyr Asn Asn Ile Met Arg His Tyr Leu Met Gln
    450                 455                 460

Lys Leu Lys Asn Asn Arg Leu Lys Lys Glu Asn Lys Pro Val Ile Pro
465                 470                 475                 480

Leu Pro Gln Ile Leu Gly Leu Thr Ala Ser Pro Gly Val Gly Gly Ala
                485                 490                 495

Thr Lys Gln Ala Lys Ala Glu Glu His Ile Leu Lys Leu Cys Ala Asn
            500                 505                 510

Leu Asp Ala Phe Thr Ile Lys Thr Val Lys Glu Asn Leu Asp Gln Leu
        515                 520                 525

Lys Asn Gln Ile Gln Glu Pro Cys Lys Lys Phe Ala Ile Ala Asp Ala
    530                 535                 540
```

```
Thr Arg Glu Asp Pro Phe Lys Glu Lys Leu Leu Glu Ile Met Thr Arg
545                 550                 555                 560

Ile Gln Thr Tyr Cys Gln Met Ser Pro Met Ser Asp Phe Gly Thr Gln
                565                 570                 575

Pro Tyr Glu Gln Trp Ala Ile Gln Met Glu Lys Lys Ala Ala Lys Glu
            580                 585                 590

Gly Asn Arg Lys Glu Arg Val Cys Ala Glu His Leu Arg Lys Tyr Asn
        595                 600                 605

Glu Ala Leu Gln Ile Asn Asp Thr Ile Arg Met Ile Asp Ala Tyr Thr
    610                 615                 620

His Leu Glu Thr Phe Tyr Asn Glu Glu Lys Asp Lys Lys Phe Ala Val
625                 630                 635                 640

Ile Glu Asp Asp Ser Asp Glu Gly Gly Asp Asp Glu Tyr Cys Asp Gly
                645                 650                 655

Asp Glu Asp Glu Asp Asp Leu Lys Lys Pro Leu Lys Leu Asp Glu Thr
            660                 665                 670

Asp Arg Phe Leu Met Thr Leu Phe Phe Glu Asn Asn Lys Met Leu Lys
        675                 680                 685

Arg Leu Ala Glu Asn Pro Glu Tyr Glu Asn Glu Lys Leu Thr Lys Leu
    690                 695                 700

Arg Asn Thr Ile Met Glu Gln Tyr Thr Arg Thr Glu Glu Ser Ala Arg
705                 710                 715                 720

Gly Ile Ile Phe Thr Lys Thr Arg Gln Ser Ala Tyr Ala Leu Ser Gln
                725                 730                 735

Trp Ile Thr Glu Asn Glu Lys Phe Ala Glu Val Gly Val Lys Ala His
            740                 745                 750

His Leu Ile Gly Ala Gly His Ser Ser Glu Phe Lys Pro Met Thr Gln
        755                 760                 765

Asn Glu Gln Lys Glu Val Ile Ser Lys Phe Arg Thr Gly Lys Ile Asn
    770                 775                 780

Leu Leu Ile Ala Thr Thr Val Ala Glu Glu Gly Leu Asp Ile Lys Glu
785                 790                 795                 800

Cys Asn Ile Val Ile Arg Tyr Gly Leu Val Thr Asn Glu Ile Ala Met
                805                 810                 815

Val Gln Ala Arg Gly Arg Ala Arg Ala Asp Glu Ser Thr Tyr Val Leu
            820                 825                 830

Val Ala His Ser Gly Ser Gly Val Ile Glu His Glu Thr Val Asn Asp
        835                 840                 845

Phe Arg Glu Lys Met Met Tyr Lys Ala Ile His Cys Val Gln Asn Met
    850                 855                 860

Lys Pro Glu Glu Tyr Ala His Lys Ile Leu Glu Leu Gln Met Gln Ser
865                 870                 875                 880

Ile Met Glu Lys Lys Met Lys Thr Lys Arg Asn Ile Ala Lys His Tyr
                885                 890                 895

Lys Asn Asn Pro Ser Leu Ile Thr Phe Leu Cys Lys Asn Cys Ser Val
            900                 905                 910

Leu Ala Cys Ser Gly Glu Asp Ile His Val Ile Glu Lys Met His His
        915                 920                 925

Val Asn Met Thr Pro Glu Phe Lys Glu Leu Tyr Ile Val Arg Glu Asn
    930                 935                 940

Lys Ala Leu Gln Lys Lys Cys Ala Asp Tyr Gln Ile Asn Gly Glu Ile
945                 950                 955                 960
```

```
Ile Cys Lys Cys Gly Gln Ala Trp Gly Thr Met Met Val His Lys Gly
                965                 970                 975

Leu Asp Leu Pro Cys Leu Lys Ile Arg Asn Phe Val Val Val Phe Lys
            980                 985                 990

Asn Asn Ser Thr Lys Lys Gln Tyr  Lys Lys Trp Val Glu  Leu Pro Ile
        995                 1000                 1005

Thr Phe  Pro Asn Leu Asp Tyr  Ser Glu Cys Cys Leu  Phe Ser Asp
    1010                 1015                 1020

Glu Asp
    1025


<210> SEQ ID NO 100
<211> LENGTH: 678
<212> TYPE: PRT
<213> ORGANISM: Homo sapiens
<220> FEATURE:
<221> NAME/KEY: misc_feature
<223> OTHER INFORMATION: Human LGP2 Amino acid sequence

<400> SEQUENCE: 100

Met Glu Leu Arg Ser Tyr Gln Trp Glu Val Ile Met Pro Ala Leu Glu
1               5                   10                  15

Gly Lys Asn Ile Ile Ile Trp Leu Pro Thr Gly Ala Gly Lys Thr Arg
            20                  25                  30

Ala Ala Ala Tyr Val Ala Lys Arg His Leu Glu Thr Val Asp Gly Ala
        35                  40                  45

Lys Val Val Val Leu Val Asn Arg Val His Leu Val Thr Gln His Gly
    50                  55                  60

Glu Glu Phe Arg Arg Met Leu Asp Gly Arg Trp Thr Val Thr Thr Leu
65                  70                  75                  80

Ser Gly Asp Met Gly Pro Arg Ala Gly Phe Gly His Leu Ala Arg Cys
                85                  90                  95

His Asp Leu Leu Ile Cys Thr Ala Glu Leu Leu Gln Met Ala Leu Thr
            100                 105                 110

Ser Pro Glu Glu Glu Glu His Val Glu Leu Thr Val Phe Ser Leu Ile
        115                 120                 125

Val Val Asp Glu Cys His His Thr His Lys Asp Thr Val Tyr Asn Val
    130                 135                 140

Ile Met Ser Gln Tyr Leu Glu Leu Lys Leu Gln Arg Ala Gln Pro Leu
145                 150                 155                 160

Pro Gln Val Leu Gly Leu Thr Ala Ser Pro Gly Thr Gly Gly Ala Ser
                165                 170                 175

Lys Leu Asp Gly Ala Ile Asn His Val Leu Gln Leu Cys Ala Asn Leu
            180                 185                 190

Asp Thr Trp Cys Ile Met Ser Pro Gln Asn Cys Cys Pro Gln Leu Gln
        195                 200                 205

Glu His Ser Gln Gln Pro Cys Lys Gln Tyr Asn Leu Cys His Arg Arg
    210                 215                 220

Ser Gln Asp Pro Phe Gly Asp Leu Leu Lys Lys Leu Met Asp Gln Ile
225                 230                 235                 240

His Asp His Leu Glu Met Pro Glu Leu Ser Arg Lys Phe Gly Thr Gln
                245                 250                 255

Met Tyr Glu Gln Gln Val Val Lys Leu Ser Glu Ala Ala Ala Leu Ala
            260                 265                 270

Gly Leu Gln Glu Gln Arg Val Tyr Ala Leu His Leu Arg Arg Tyr Asn
        275                 280                 285
```

```
Asp Ala Leu Leu Ile His Asp Thr Val Arg Ala Val Asp Ala Leu Ala
    290                 295                 300

Ala Leu Gln Asp Phe Tyr His Arg Glu His Val Thr Lys Thr Gln Ile
305                 310                 315                 320

Leu Cys Ala Glu Arg Arg Leu Leu Ala Leu Phe Asp Asp Arg Lys Asn
                325                 330                 335

Glu Leu Ala His Leu Ala Thr His Gly Pro Glu Asn Pro Lys Leu Glu
            340                 345                 350

Met Leu Glu Lys Ile Leu Gln Arg Gln Phe Ser Ser Ser Asn Ser Pro
        355                 360                 365

Arg Gly Ile Ile Phe Thr Arg Thr Arg Gln Ser Ala His Ser Leu Leu
    370                 375                 380

Leu Trp Leu Gln Gln Gln Gln Gly Leu Gln Thr Val Asp Ile Arg Ala
385                 390                 395                 400

Gln Leu Leu Ile Gly Ala Gly Asn Ser Ser Gln Ser Thr His Met Thr
                405                 410                 415

Gln Arg Asp Gln Gln Glu Val Ile Gln Lys Phe Gln Asp Gly Thr Leu
            420                 425                 430

Asn Leu Leu Val Ala Thr Ser Val Ala Glu Glu Gly Leu Asp Ile Pro
        435                 440                 445

His Cys Asn Val Val Val Arg Tyr Gly Leu Leu Thr Asn Glu Ile Ser
    450                 455                 460

Met Val Gln Ala Arg Gly Arg Ala Arg Ala Asp Gln Ser Val Tyr Ala
465                 470                 475                 480

Phe Val Ala Thr Glu Gly Ser Arg Glu Leu Lys Arg Glu Leu Ile Asn
                485                 490                 495

Glu Ala Leu Glu Thr Leu Met Glu Gln Ala Val Ala Ala Val Gln Lys
            500                 505                 510

Met Asp Gln Ala Glu Tyr Gln Ala Lys Ile Arg Asp Leu Gln Gln Ala
        515                 520                 525

Ala Leu Thr Lys Arg Ala Ala Gln Ala Ala Gln Arg Glu Asn Gln Arg
    530                 535                 540

Gln Gln Phe Pro Val Glu His Val Gln Leu Leu Cys Ile Asn Cys Met
545                 550                 555                 560

Val Ala Val Gly His Gly Ser Asp Leu Arg Lys Val Glu Gly Thr His
                565                 570                 575

His Val Asn Val Asn Pro Asn Phe Ser Asn Tyr Tyr Asn Val Ser Arg
            580                 585                 590

Asp Pro Val Val Ile Asn Lys Val Phe Lys Asp Trp Lys Pro Gly Gly
        595                 600                 605

Val Ile Ser Cys Arg Asn Cys Gly Glu Val Trp Gly Leu Gln Met Ile
    610                 615                 620

Tyr Lys Ser Val Lys Leu Pro Val Leu Lys Val Arg Ser Met Leu Leu
625                 630                 635                 640

Glu Thr Pro Gln Gly Arg Ile Gln Ala Lys Lys Trp Ser Arg Val Pro
                645                 650                 655

Phe Ser Val Pro Asp Phe Asp Phe Leu Gln His Cys Ala Glu Asn Leu
            660                 665                 670

Ser Asp Leu Ser Leu Asp
        675
```

<210> SEQ ID NO 101
<211> LENGTH: 5579

<212> TYPE: DNA
<213> ORGANISM: Artificial Sequence
<220> FEATURE:
<223> OTHER INFORMATION: Synthetic: pTac-nSD-Qb-Mut plasmid

<400> SEQUENCE: 101
ggctgtgcag gtcgtaaatc actgcataat tcgtgtcgct caaggcgcac tcccgttctg 60
gataatgttt tttgcgccga catcataacg gttctggcaa atattctgaa atgagctgtt 120
gacaattaat catcggctcg tataatgtgt ggaattgtga gcggataaca atttcacaca 180
ggaaacagaa ttctaaggag gaaaaaaaaa tggcaaaatt agagactgtt actttaggta 240
acatcgggaa agatggaaaa caaactctgg tcctcaatcc gcgtggggta aatcccacta 300
acggcgttgc ctcgctttca caagcgggtg cagttcctgc gctggagaag cgtgttaccg 360
tttcggtatc tcagccttct cgcaatcgta agaactacaa ggtccaggtt aagatccaga 420
acccgaccgc ttgcactgca aacggttctt gtgacccatc cgttactcgc caggcatatg 480
ctgacgtgac cttttcgttc acgcagtata gtaccgatga ggaacgagct tttgttcgta 540
cagagcttgc tgctctgctc gctagtcctc tgctgatcga tgctattgat cagctgaacc 600
cagcgtatta atgactgctc attgccggtg gtggctcagg gtcaaaaccc gatccggtta 660
ttccggatcc accgattgat ccgccgccag ggacaggtaa gtatacctgt cccttcgcaa 720
tttggtccct agaggaggtt tacgagcctc ctactaagaa ccgaccgtgg cctatctata 780
atgctgttga actccagcct cgcgaatttg atgttgccct caaagatctt ttgggcaata 840
caaagtggcg tgattgggat tctcggctta gttataccac gttccgcggt tgccgtggca 900
atggttatat tgaccttgat gcgacttatc ttgctactga tcaggctatg cgtgatcaga 960
agtatgatat tcgcgagggc aagaaacctg gtgctttcgg taacattgag cgattcattt 1020
atcttaagtc gataaatgct tattgctctc ttagcgatat tgcggcctat cacgccgatg 1080
gcgtgatagt tggcttttgg cgcgatccat ccagtggtgg tgccataccg tttgacttca 1140
ctaagtttga taagactaaa tgtcctattc aagccgtgat agtcgttcct cgtgcttagt 1200
aactaaggat gaaatgcatg tctaagcttg gctgttttgg cggatgagag aagattttca 1260
gcctgataca gattaaatca gaacgcagaa gcggtctgat aaaacagaat ttgcctggcg 1320
gcagtagcgc ggtggtccca cctgacccca tgccgaactc agaagtgaaa cgccgtagcg 1380
ccgatggtag tgtggggtct ccccatgcga gagtagggaa ctgccaggca tcaaataaaa 1440
cgaaaggctc agtcgaaaga ctgggccttt cgttttatct gttgtttgtc ggtgaacgct 1500
ctcctgagta ggacaaatcc gccgggagcg gatttgaacg ttgcgaagca acggcccgga 1560
gggtggcggg caggacgccc gccataaact gccaggcatc aaattaagca gaaggccatc 1620
ctgacggatg gcctttttgc gtttctacaa actcttttgt ttatttttct agagccacgt 1680
tgtgtctcaa aatctctgat gttacattgc acaagataaa aatatatcat catgaacaat 1740
aaaactgtct gcttacataa acagtaatac aaggagtgtt atgagccata ttcaacggga 1800
aacgtcttgc tcgaggccgc gattaaattc caacatggat gctgatttat atgggtataa 1860
atgggctcgc gataatgtcg ggcaatcagg tgcgacaatc tatcgattgt atgggaagcc 1920
cgatgcgcca gagttgtttc tgaaacatgg caaaggtagc gttgccaatg atgttacaga 1980
tgagatggtc agactaaact ggctgacgga atttatgcct cttccgacca tcaagcattt 2040
tatccgtact cctgatgatg catggttact caccactgcg atccccggga aaacagcatt 2100
ccaggtatta gaagaatatc ctgattcagg tgaaaatatt gttgatgcgc tggcagtgtt 2160

```
cctgcgccgg ttgcattcga ttcctgtttg taattgtcct tttaacagcg atcgcgtatt   2220
tcgtctcgct caggcgcaat cacgaatgaa taacggtttg gttgatgcga gtgattttga   2280
tgacgagcgt aatggctggc ctgttgaaca agtctggaaa gaaatgcata agcttttgcc   2340
attctcaccg gattcagtcg tcactcatgg tgatttctca cttgataacc ttatttttga   2400
cgaggggaaa ttaataggtt gtattgatgt tggacgagtc ggaatcgcag accgatacca   2460
ggatcttgcc atcctatgga actgcctcgg tgagttttct ccttcattac agaaacggct   2520
ttttcaaaaa tatggtattg ataatcctga tatgaataaa ttgcagtttc atttgatgct   2580
cgatgagttt ttctaaacgc gtgaccaagt ttactcatat gtactttaga ttgatttaaa   2640
acttcatttt taatttaaaa ggatctaggt gaagatcctt tttgataatc tcatgaccaa   2700
aatcccttaa cgtgagtttt cgttccactg agcgtcagac cccgtagaaa agatcaaagg   2760
atcttcttga gatccttttt ttctgcgcgt aatctgctgc ttgcaaacaa aaaaaccacc   2820
gctaccagcg gtggtttgtt tgccggatca agagctacca actctttttc cgaaggtaac   2880
tggcttcagc agagcgcaga taccaaatac tgtccttcta gtgtagccgt agttaggcca   2940
ccacttcaag aactctgtag caccgcctac atacctcgct ctgctaatcc tgttaccagt   3000
ggctgctgcc agtggcgata agtcgtgtct taccgggttg gactcaagac gatagttacc   3060
ggataaggcg cagcggtcgg gctgaacggg gggttcgtgc acacagccca gcttggagcg   3120
aacgacctac accgaactga gatacctaca gcgtgagcta tgagaaagcg ccacgcttcc   3180
cgaagggaga aaggcggaca ggtatccggt aagcggcagg gtcggaacag gagagcgcac   3240
gagggagctc ccagggggaa acgcctggta tctttatagt cctgtcgggt ttcgccacct   3300
ctgacttgag cgtcgatttt tgtgatgctc gtcagggggg cggagcctat ggaaaaacgc   3360
cagcaacgcg gcctttttac ggttcctggc cttttgctgg ccttttgctc acatgttctt   3420
tcctgcgtta tcccctgatt ctgtggataa ccgtattacc gcctttgagt gagctgatac   3480
cgctcgccgc agccgaacga ccgagcgcag cgagtcagtg agcgaggaag cggaagagcg   3540
cctgatgcgg tattttctcc ttacgcatct gtgcggtatt tcacaccgca tatggtgcac   3600
tctcagtaca atctgctctg atgccgcata gttaagccag tatacactcc gctatcgcta   3660
cgtgactggg tcatggctgc gccccgacac ccgccaacac ccgctgacgc gccctgacgg   3720
gcttgtctgc tcccggcatc cgcttacaga caagctgtga ccgtctccgg gagctgcatg   3780
tgtcagaggt tttcaccgtc atcaccgaaa cgcgcgaggc agctgcggta aagctcatca   3840
gcgtggtcgt gaagcgattc acagatgtct gcctgttcat ccgcgtccag ctcgttgagt   3900
ttctccagaa gcgttaatgt ctggcttctg ataaagcggg ccatgttaag ggcggttttt   3960
tcctgtttgg tcactgatgc ctccgtgtaa gggggatttc tgttcatggg ggtaatgata   4020
ccgatgaaac gagagaggat gctcacgata cgggttactg atgatgaaca tgcccggtta   4080
ctggaacgtt gtgagggtaa acaactggcg gtatggatgc ggcgggacca gagaaaaatc   4140
actcagggtc aatgccagcg cttcgttaat acagatgtag gtgttccaca gggtagccag   4200
cagcatcctg cgatgcagat ccggaacata atggtgcagg gcgctgactt ccgcgtttcc   4260
agactttacg aaacacggaa accgaagacc attcatgttg ttgctcaggt cgcagacgtt   4320
ttgcagcagc agtcgcttca cgttcgctcg cgtatcggtg attcattctg ctaaccagta   4380
aggcaacccc gccagcctag ccgggtcctc aacgacagga gcacgatcat gcgcacccgt   4440
ggccaggacc caacgctgcc cgagatgcgc cgcgtgcggc tgctggagat ggcggacgcg   4500
atggatatgt tctgccaagg gttggtttgc gcattcacag ttctccgcaa gaattgattg   4560
```

```
gctccaattc ttggagtggt gaatccgtta gcgaggtgcc gccggcttcc attcaggtcg   4620

aggtggcccg gctccatgca ccgcgacgca acgcggggag gcagacaagg tatagggcgg   4680

cgcctacaat ccatgccaac ccgttccatg tgctcgccga ggcggcataa atcgccgtga   4740

cgatcagcgg tccaatgatc gaagttaggc tggtaagagc cgcgagcgat ccttgaagct   4800

gtccctgatg gtcgtcatct acctgcctgg acagcatggc ctgcaacgcg ggcatcccga   4860

tgccgccgga agcgagaaga atcataatgg ggaaggccat ccagcctcgc gtcgcgaacg   4920

ccagcaagac gtagcccagc gcgtcggccg ccatgccggc gataatggcc tgcttctcgc   4980

cgaaacgttt ggtggcggga ccagtgacga aggcttgagc gagggcgtgc aagattccga   5040

ataccgcaag cgacaggccg atcatcgtcg cgctccagcg aaagcggtcc tcgccgaaaa   5100

tgacccagag cgctgccggc acctgtccta cgagttgcat gataaagaag acagtcataa   5160

gtgcggcgac gatagtcatg ccccgcgccc accggaagga gctgactggg ttgaaggctc   5220

tcaagggcat cggtcgacgc tctcccttat gcgactcctg cattaggaag cagcccagta   5280

gtaggttgag gccgttgagc accgccgccg caaggaatgg tgcatgcaag gagatggcgc   5340

ccaacagtcc cccggccacg gggcctgcca ccatacccac gccgaaacaa gcgctcatga   5400

gcccgaagtg gcgagcccga tcttccccat cggtgatgtc ggcgatatag gcgccagcaa   5460

ccgcacctgt ggcgccggtg atgccggcca cgatgcgtcc ggcgtagagg atccgggctt   5520

atcgactgca cggtgcacca atgcttctgg cgtcaggcag ccatcggaag ctgtggtat    5579
```

```
<210> SEQ ID NO 102
<211> LENGTH: 6
<212> TYPE: DNA
<213> ORGANISM: Artificial Sequence
<220> FEATURE:
<223> OTHER INFORMATION: Synthetic: Stop codon

<400> SEQUENCE: 102

tgaaca                                                                6


<210> SEQ ID NO 103
<211> LENGTH: 6
<212> TYPE: DNA
<213> ORGANISM: Artificial Sequence
<220> FEATURE:
<223> OTHER INFORMATION: Synthetic: Stop codon

<400> SEQUENCE: 103

taatga                                                                6


<210> SEQ ID NO 104
<211> LENGTH: 56
<212> TYPE: DNA
<213> ORGANISM: Artificial Sequence
<220> FEATURE:
<223> OTHER INFORMATION: Synthetic: Qb-FOR3/2 sequence

<400> SEQUENCE: 104

gcgcgcgaat tcaggaggta aaaaacgatg gcaaaattag agactgttac tttagg        56


<210> SEQ ID NO 105
<211> LENGTH: 18
<212> TYPE: DNA
<213> ORGANISM: Artificial Sequence
<220> FEATURE:
<223> OTHER INFORMATION: Synthetic: Shine-Dalgano sequence
```

<400> SEQUENCE: 105
aggaggtaaa aaacgatg 18

<210> SEQ ID NO 106
<211> LENGTH: 33
<212> TYPE: DNA
<213> ORGANISM: Artificial Sequence
<220> FEATURE:
<223> OTHER INFORMATION: Synthetic: Qblang-REV2/2 sequence

<400> SEQUENCE: 106
gcatgcaagc ttagacatgc atttcatcct tag 33

<210> SEQ ID NO 107
<211> LENGTH: 4586
<212> TYPE: DNA
<213> ORGANISM: Artificial Sequence
<220> FEATURE:
<223> OTHER INFORMATION: Synthetic: modified pKK223-3 cloning vector

<400> SEQUENCE: 107
ttctgtttcc tgtgtgaaat tgttatccgc tcacaattcc acacattata cgagccgatg 60
attaattgtc aacagctcat ttcagaatat ttgccagaac cgttatgatg tcggcgcaaa 120
aaacattatc cagaacggga gtgcgccttg agcgacacga attatgcagt gatttacgac 180
ctgcacagcc ataccacagc ttccgatggc tgcctgacgc cagaagcatt ggtgcaccgt 240
gcagtcgata agctccggat cctctacgcc ggacgcatcg tggccggcat caccggcgcc 300
acaggtgcgg ttgctggcgc ctatatcgcc gacatcaccg atggggaaga tcgggctcgc 360
cacttcgggc tcatgagcgc ttgtttcggc gtgggtatgg tggcaggccc cgtggccggg 420
ggactgttgg gcgccatctc cttgcatgca ccattccttg cggcggcggt gctcaacggc 480
ctcaacctac tactgggctg cttcctaatg caggagtcgc ataagggaga gcgtcgaccg 540
atgcccttga gagccttcaa cccagtcagc tccttccggt gggcgcgggg catgactatc 600
gtcgccgcac ttatgactgt cttctttatc atgcaactcg taggacaggt gccggcagcg 660
ctctgggtca ttttcggcga ggaccgcttt cgctggagcg cgacgatgat cggcctgtcg 720
cttgcggtat tcggaatctt gcacgccctc gctcaagcct tcgtcactgg tcccgccacc 780
aaacgtttcg gcgagaagca ggccattatc gccggcatgg cggccgacgc gctgggctac 840
gtcttgctgg cgttcgcgac gcgaggctgg atggccttcc ccattatgat tcttctcgct 900
tccggcggca tcgggatgcc cgcgttgcag gccatgctgt ccaggcaggt agatgacgac 960
catcagggac agcttcaagg atcgctcgcg gctcttacca gcctaacttc gatcactgga 1020
ccgctgatcg tcacggcgat ttatgccgcc tcggcgagca catggaacgg gttggcatgg 1080
attgtaggcg ccgccctata ccttgtctgc ctccccgcgt tgcgtcgcgg tgcatggagc 1140
cgggccacct cgacctgaat ggaagccggc ggcacctcgc taacggattc accactccaa 1200
gaattggagc caatcaattc ttgcggagaa ctgtgaatgc gcaaaccaac ccttggcaga 1260
acatatccat cgcgtccgcc atctccagca gccgcacgcg gcgcatctcg ggcagcgttg 1320
ggtcctggcc acgggtgcgc atgatcgtgc tcctgtcgtt gaggacccgg ctaggctggc 1380
ggggttgcct tactggttag cagaatgaat caccgatacg cgagcgaacg tgaagcgact 1440
gctgctgcaa aacgtctgcg acctgagcaa caacatgaat ggtcttcggt ttccgtgttt 1500
cgtaaagtct ggaaacgcgg aagtcagcgc cctgcaccat tatgttccgg atctgcatcg 1560
caggatgctg ctggctaccc tgtggaacac ctacatctgt attaacgaag cgctggcatt 1620

```
gaccctgagt gatttttctc tggtcccgcc gcatccatac cgccagttgt ttaccctcac   1680
aacgttccag taaccgggca tgttcatcat cagtaacccg tatcgtgagc atcctctctc   1740
gtttcatcgg tatcattacc cccatgaaca gaaattcccc cttacacgga ggcatcaagt   1800
gaccaaacag gaaaaaaccg cccttaacat ggcccgcttt atcagaagcc agacattaac   1860
gcttctggag aaactcaacg agctggacgc ggatgaacag gcagacatct gtgaatcgct   1920
tcacgaccac gctgatgagc tttaccgcag ctgcctcgcg cgtttcggtg atgacggtga   1980
aaacctctga cacatgcagc tcccggagac ggtcacagct tgtctgtaag cggatgccgg   2040
gagcagacaa gcccgtcagg gcgcgtcagc gggtgttggc gggtgtcggg gcgcagccat   2100
gacccagtca cgtagcgata gcggagtgta tactggctta actatgcggc atcagagcag   2160
attgtactga gagtgcacca tatgcggtgt gaaataccgc acagatgcgt aaggagaaaa   2220
taccgcatca ggcgctcttc cgcttcctcg ctcactgact cgctgcgctc ggtcgttcgg   2280
ctgcggcgag cggtatcagc tcactcaaag gcggtaatac ggttatccac agaatcaggg   2340
gataacgcag gaaagaacat gtgagcaaaa ggccagcaaa aggccaggaa ccgtaaaaag   2400
gccgcgttgc tggcgttttt ccataggctc cgcccccctg acgagcatca caaaaatcga   2460
cgctcaagtc agaggtggcg aaacccgaca ggactataaa gataccaggc gtttccccct   2520
ggaagctccc tcgtgcgctc tcctgttccg accctgccgc ttaccggata cctgtccgcc   2580
tttctccctt cgggaagcgt ggcgctttct catagctcac gctgtaggta tctcagttcg   2640
gtgtaggtcg ttcgctccaa gctgggctgt gtgcacgaac cccccgttca gcccgaccgc   2700
tgcgccttat ccggtaacta tcgtcttgag tccaacccgg taagacacga cttatcgcca   2760
ctggcagcag ccactggtaa caggattagc agagcgaggt atgtaggcgg tgctacagag   2820
ttcttgaagt ggtggcctaa ctacggctac actagaagga cagtatttgg tatctgcgct   2880
ctgctgaagc cagttacctt cggaaaaaga gttggtagct cttgatccgg caaacaaacc   2940
accgctggta gcggtggttt ttttgtttgc aagcagcaga ttacgcgcag aaaaaaagga   3000
tctcaagaag atcctttgat cttttctacg gggtctgacg ctcagtggaa cgaaaactca   3060
cgttaaggga ttttggtcat gagattatca aaaaggatct tcacctagat ccttttaaat   3120
taaaaatgaa gttttaaatc aatctaaagt atatatgagt aaacttggtc tgacagttac   3180
caatgcttaa tcagtgaggc acctatctca gcgatctgtc tatttcgttc atccatagtt   3240
gcctgactcc ccgtcgtgta gataactacg atacgggagg gcttaccatc tggccccagt   3300
gctgcaatga taccgcgaga cccacgctca ccggctccag atttatcagc aataaaccag   3360
ccagccggaa gggccgagcg cagaagtggt cctgcaactt tatccgcctc catccagtct   3420
attaattgtt gccgggaagc tagagtaagt agttcgccag ttaatagttt gcgcaacgtt   3480
gttgccattg ctacaggcat cgtggtgtca cgctcgtcgt ttggtatggc ttcattcagc   3540
tccggttccc aacgatcaag gcgagttaca tgatccccca tgttgtgcaa aaaagcggtt   3600
agctccttcg gtcctccgat cgttgtcaga agtaagttgg ccgcagtgtt atcactcatg   3660
gttatggcag cactgcataa ttctcttact gtcatgccat ccgtaagatg cttttctgtg   3720
actggtgagt actcaaccaa gtcattctga gaatagtgta tgcggcgacc gagttgctct   3780
tgcccggcgt caacacggga taataccgcg ccacatagca gaactttaaa agtgctcatc   3840
attggaaaac gttcttcggg gcgaaaactc tcaaggatct taccgctgtt gagatccagt   3900
tcgatgtaac ccactcgtgc acccaactga tcttcagcat cttttacttt caccagcgtt   3960
```

```
tctgggtgag caaaaacagg aaggcaaaat gccgcaaaaa agggaataag ggcgacacgg   4020

aaatgttgaa tactcatact cttccttttt caatattatt gaagcattta tcagggttat   4080

tgtctcatga gcggatacat atttgaatgt atttagaaaa ataaacaaaa gagtttgtag   4140

aaacgcaaaa aggccatccg tcaggatggc cttctgctta atttgatgcc tggcagttta   4200

tggcgggcgt cctgcccgcc accctccggg ccgttgcttc gcaacgttca aatccgctcc   4260

cggcggattt gtcctactca ggagagcgtt caccgacaaa caacagataa aacgaaaggc   4320

ccagtctttc gactgagcct ttcgttttat ttgatgcctg gcagttccct actctcgcat   4380

ggggagaccc cacactacca tcggcgctac ggcgtttcac ttctgagttc ggcatggggt   4440

caggtgggac caccgcgcta ctgccgccag gcaaattctg ttttatcaga ccgcttctgc   4500

gttctgattt aatctgtatc aggctgaaaa tcttctctca tccgccaaaa cagaagcttg   4560

gctgcaggtc gacggatccc cgggaa                                        4586
```

<210> SEQ ID NO 108
<211> LENGTH: 3914
<212> TYPE: DNA
<213> ORGANISM: Artificial Sequence
<220> FEATURE:
<223> OTHER INFORMATION: Synthetic: modified pKK223-3 cloning vector

<400> SEQUENCE: 108

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ccccggatcc gtcgacctgc    420

aggggggggg gggcgctgag gtctgcctcg tgaagaaggt gttgctgact cataccaggc    480

ctgaatcgcc ccatcatcca gccagaaagt gagggagcca cggttgatga gagctttgtt    540

gtaggtggac cagttggtga ttttgaactt ttgctttgcc acggaacggt ctgcgttgtc    600

gggaagatgc gtgatctgat ccttcaactc agcaaaagtt cgatttattc aacaaagccg    660

ccgtcccgtc aagtcagcgt aatgctctgc cagtgttaca accaattaac caattctgat    720

tagaaaaact catcgagcat caaatgaaac tgcaatttat tcatatcagg attatcaata    780

ccatattttt gaaaaagccg tttctgtaat gaaggagaaa actcaccgag gcagttccat    840

aggatggcaa gatcctggta tcggtctgcg attccgactc gtccaacatc aatacaacct    900

attaatttcc cctcgtcaaa aataaggtta tcaagtgaga aatcaccatg agtgacgact    960

gaatccggtg agaatggcaa aagcttatgc atttctttcc agacttgttc aacaggccag   1020

ccattacgct cgtcatcaaa atcactcgca tcaaccaaac cgttattcat tcgtgattgc   1080

gcctgagcga gacgaaatac gcgatcgctg ttaaaaggac aattacaaac aggaatcgaa   1140

tgcaaccggc gcaggaacac tgccagcgca tcaacaatat tttcacctga atcaggatat   1200

tcttctaata cctggaatgc tgttttcccg gggatcgcag tggtgagtaa ccatgcatca   1260

tcaggagtac ggataaaatg cttgatggtc ggaagaggca taaattccgt cagccagttt   1320

agtctgacca tctcatctgt aacatcattg gcaacgctac ctttgccatg tttcagaaac   1380

aactctggcg catcgggctt cccatacaat cgatagattg tcgcacctga ttgcccgaca   1440
```

```
ttatcgcgag cccatttata cccatataaa tcagcatcca tgttggaatt taatcgcggc   1500
ctcgagcaag acgtttcccg ttgaatatgg ctcataacac cccttgtatt actgtttatg   1560
taagcagaca gttttattgt tcatgatgat atatttttat cttgtgcaat gtaacatcag   1620
agattttgag acacaacgtg gctttccccc cccccctgc aggtcgacgg atccggggaa   1680
ttcgtaatca tggtcatagc tgtttcctgt gtgaaattgt tatccgctca caattccaca   1740
caacatacga gccggaagca taaagtgtaa agcctggggt gcctaatgag tgagctaact   1800
cacattaatt gcgttgcgct cactgcccgc tttccagtcg ggaaacctgt cgtgccagct   1860
gcattaatga atcggccaac gcgcggggag aggcggtttg cgtattgggc gctcttccgc   1920
ttcctcgctc actgactcgc tgcgctcggt cgttcggctg cggcgagcgg tatcagctca   1980
ctcaaaggcg gtaatacggt tatccacaga atcaggggat aacgcaggaa agaacatgtg   2040
agcaaaaggc cagcaaaagg ccaggaaccg taaaaaggcc gcgttgctgg cgtttttcca   2100
taggctccgc ccccctgacg agcatcacaa aaatcgacgc tcaagtcaga ggtggcgaaa   2160
cccgacagga ctataaagat accaggcgtt tccccctgga agctccctcg tgcgctctcc   2220
tgttccgacc ctgccgctta ccggatacct gtccgccttt ctcccttcgg gaagcgtggc   2280
gctttctcaa tgctcacgct gtaggtatct cagttcggtg taggtcgttc gctccaagct   2340
gggctgtgtg cacgaacccc ccgttcagcc cgaccgctgc gccttatccg gtaactatcg   2400
tcttgagtcc aacccggtaa gacacgactt atcgccactg gcagcagcca ctggtaacag   2460
gattagcaga gcgaggtatg taggcggtgc tacagagttc ttgaagtggt ggcctaacta   2520
cggctacact agaaggacag tatttggtat ctgcgctctg ctgaagccag ttaccttcgg   2580
aaaaagagtt ggtagctctt gatccggcaa acaaaccacc gctggtagcg gtggtttttt   2640
tgtttgcaag cagcagatta cgcgcagaaa aaaaggatct caagaagatc ctttgatctt   2700
ttctacgggg tctgacgctc agtggaacga aaactcacgt taagggattt tggtcatgag   2760
attatcaaaa aggatcttca cctagatcct tttaaattaa aaatgaagtt ttaaatcaat   2820
ctaaagtata tatgagtaaa cttggtctga cagttaccaa tgcttaatca gtgaggcacc   2880
tatctcagcg atctgtctat ttcgttcatc catagttgcc tgactccccg tcgtgtagat   2940
aactacgata cgggagggct taccatctgg ccccagtgct gcaatgatac cgcgagaccc   3000
acgctcaccg gctccagatt tatcagcaat aaaccagcca gccggaaggg ccgagcgcag   3060
aagtggtcct gcaactttat ccgcctccat ccagtctatt aattgttgcc gggaagctag   3120
agtaagtagt tcgccagtta atagtttgcg caacgttgtt gccattgcta caggcatcgt   3180
ggtgtcacgc tcgtcgtttg gtatggcttc attcagctcc ggttcccaac gatcaaggcg   3240
agttacatga tcccccatgt tgtgcaaaaa agcggttagc tccttcggtc ctccgatcgt   3300
tgtcagaagt aagttggccg cagtgttatc actcatggtt atggcagcac tgcataattc   3360
tcttactgtc atgccatccg taagatgctt ttctgtgact ggtgagtact caaccaagtc   3420
attctgagaa tagtgtatgc ggcgaccgag ttgctcttgc ccggcgtcaa tacgggataa   3480
taccgcgcca catagcagaa ctttaaaagt gctcatcatt ggaaaacgtt cttcggggcg   3540
aaaactctca aggatcttac cgctgttgag atccagttcg atgtaaccca ctcgtgcacc   3600
caactgatct tcagcatctt ttactttcac cagcgtttct gggtgagcaa aaacaggaag   3660
gcaaaatgcc gcaaaaaagg gaataagggc gacacggaaa tgttgaatac tcatactctt   3720
cctttttcaa tattattgaa gcatttatca gggttattgt ctcatgagcg gatacatatt   3780
```

```
tgaatgtatt tagaaaaata aacaaatagg ggttccgcgc acatttcccc gaaaagtgcc   3840

acctgacgtc taagaaacca ttattatcat gacattaacc tataaaaata ggcgtatcac   3900

gaggcccttt cgtc                                                     3914


<210> SEQ ID NO 109
<211> LENGTH: 4525
<212> TYPE: DNA
<213> ORGANISM: Artificial Sequence
<220> FEATURE:
<223> OTHER INFORMATION: Synthetic: pSDQb-rout plasmid

<400> SEQUENCE: 109

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cagacatgca tttcatcctt    420

agttactaag cacgaggaac gactatcacg gcttgaatag gacatttagt cttatcaaac    480

ttagtgaagt caaacggtat ggcaccacca ctggatggat cgcgccaaaa gccaactatc    540

acgccatcgg cgtgataggc cgcaatatcg ctaagagagc aataagcatt tatcgactta    600

agataaatga atcgctcaat gttaccgaaa gcaccaggtt tcttgccctc gcgaatatca    660

tacttctgat cacgcatagc ctgatcagta gcaagataag tcgcatcaag gtcaatataa    720

ccattgccac ggcaaccgcg gaacgtggta taactaagcc gagaatccca atcacgccac    780

tttgtattgc ccaaaagatc tttgagggca acatcaaatt cgcgaggctg gagttcaaca    840

gcattataga taggccacgg tcggttctta gtaggaggct cgtaaacctc ctctagggac    900

caaattgcga agggacaggt atacttacct gtccctggcg gcggatcaat cggtggatcc    960

ggaataaccg gatcgggttt tgaccctgag ccaccaccgg caatgagcag tcattaatac   1020

gctgggttca gctgatcaat agcatcgatc agcagaggac tagcgagcag agcagcaagc   1080

tctgtacgaa caaaagctcg ttcctcatcg gtactatact gcgtgaacga aaaggtcacg   1140

tcagcatatg cctggcgagt aacggatggg tcacaagaac cgtttgcagt gcaagcggtc   1200

gggttctgga tcttaacctg gaccttgtag ttcttacgat tgcgagaagg ctgagatacc   1260

gaaacggtaa cacgcttctc cagcgcagga actgcacccg cttgtgaaag cgaggcaacg   1320

ccgttagtgg gatttacccc acgcggattg aggaccagag tttgttttcc atctttcccg   1380

atgttaccta aagtaacagt ctctaatttt gccatcgttt tttacctcct tctagagtca   1440

ttatggtttt gccatacatc agtatggtgt agcagcactt attataatct ttattgcctc   1500

ttaaaactta atccacatca aaactcaaat acttttaacc ccagcgtcct gtaagctctg   1560

cattaatgaa tcggccaacg cgcggggaga ggcggtttgc gtattgggcg ctcttccgct   1620

tcctcgctca ctgactcgct gcgctcggtc gttcggctgc ggcgagcggt atcagctcac   1680

tcaaaggcgg taatacggtt atccacagaa tcaggggata acgcaggaaa gaacatgtga   1740

gcaaaaggcc agcaaaaggc caggaaccgt aaaaaggccg cgttgctggc gtttttccat   1800

aggctccgcc cccctgacga gcatcacaaa aatcgacgct caagtcagag gtggcgaaac   1860

ccgacaggac tataaagata ccaggcgttt ccccctggaa gctccctcgt gcgctctcct   1920
```

```
gttccgaccc tgccgcttac cggatacctg tccgcctttc tcccttcggg aagcgtggcg   1980
ctttctcata gctcacgctg taggtatctc agttcggtgt aggtcgttcg ctccaagctg   2040
ggctgtgtgc acgaaccccc cgttcagccc gaccgctgcg ccttatccgg taactatcgt   2100
cttgagtcca acccggtaag acacgactta tcgccactgg cagcagccac tggtaacagg   2160
attagcagag cgaggtatgt aggcggtgct acagagttct tgaagtggtg gcctaactac   2220
ggctacacta gaagaacagt atttggtatc tgcgctctgc tgaagccagt taccttcgga   2280
aaaagagttg gtagctcttg atccggcaaa caaaccaccg ctggtagcgg tggttttttt   2340
gtttgcaagc agcagattac gcgcagaaaa aaaggatctc aagaagatcc tttgatcttt   2400
tctacggggt ctgacgctca gtggaacgaa aactcacgtt aagggatttt ggtcatgaga   2460
ttatcaaaaa ggatcttcac ctagatcctt ttaaattaaa aatgaagttt taaatcaatc   2520
taaagtatat atgagtaaac ttggtctgac agttaccaat gcttaatcag tgaggcacct   2580
atctcagcga tctgtctatt tcgttcatcc atagttgcct gactccccgt cgtgtagata   2640
actacgatac gggagggctt accatctggc cccagtgctg caatgatacc gcgagaccca   2700
cgctcaccgg ctccagattt atcagcaata aaccagccag ccggaagggc cgagcgcaga   2760
agtggtcctg caactttatc cgcctccatc cagtctatta attgttgccg ggaagctaga   2820
gtaagtagtt cgccagttaa tagtttgcgc aacgttgttg ccattgctac aggcatcgtg   2880
gtgtcacgct cgtcgtttgg tatggcttca ttcagctccg gttcccaacg atcaaggcga   2940
gttacatgat cccccatgtt gtgcaaaaaa gcggttagct ccttcggtcc tccgatcgtt   3000
gtcagaagta agttggccgc agtgttatca ctcatggtta tggcagcact gcataattct   3060
cttactgtca tgccatccgt aagatgcttt tctgtgactg gtgagtgggg ggggggggcg   3120
ctgaggtctg cctcgtgaag aaggtgttgc tgactcatac caggcctgaa tcgccccatc   3180
atccagccag aaagtgaggg agccacggtt gatgagagct ttgttgtagg tggaccagtt   3240
ggtgattttg aacttttgct ttgccacgga acggtctgcg ttgtcgggaa gatgcgtgat   3300
ctgatccttc aactcagcaa aagttcgatt tattcaacaa agccgccgtc ccgtcaagtc   3360
agcgtaatgc tctgccagtg ttacaaccaa ttaaccaatt ctgattagaa aaactcatcg   3420
agcatcaaat gaaactgcaa tttattcata tcaggattat caataccata tttttgaaaa   3480
agccgtttct gtaatgaagg agaaaactca ccgaggcagt tccataggat ggcaagatcc   3540
tggtatcggt ctgcgattcc gactcgtcca acatcaatac aacctattaa tttcccctcg   3600
tcaaaaataa ggttatcaag tgagaaatca ccatgagtga cgactgaatc cggtgagaat   3660
ggcaaaagct tatgcatttc tttccagact tgttcaacag gccagccatt acgctcgtca   3720
tcaaaatcac tcgcatcaac caaaccgtta ttcattcgtg attgcgcctg agcgagacga   3780
aatacgcgat cgctgttaaa aggacaatta caaacaggaa tcgaatgcaa ccggcgcagg   3840
aacactgcca gcgcatcaac aatattttca cctgaatcag gatattcttc taatacctgg   3900
aatgctgttt tcccggggat cgcagtggtg agtaaccatg catcatcagg agtacggata   3960
aaatgcttga tggtcggaag aggcataaat tccgtcagcc agtttagtct gaccatctca   4020
tctgtaacat cattggcaac gctacctttg ccatgtttca gaaacaactc tggcgcatcg   4080
ggcttcccat acaatcgata gattgtcgca cctgattgcc cgacattatc gcgagcccat   4140
ttatacccat ataaatcagc atccatgttg gaatttaatc gcggcctcga gcaagacgtt   4200
tcccgttgaa tatggctcat aacacccctt gtattactgt ttatgtaagc agacagtttt   4260
```

```
attgttcatg atgatatatt tttatcttgt gcaatgtaac atcagagatt ttgagacaca   4320

acgtggcttt cccccccccc ccattattga agcatttatc agggttattg tctcatgagc   4380

ggatacatat ttgaatgtat ttagaaaaat aaacaaatag gggttccgcg cacatttccc   4440

cgaaaagtgc cacctgacgt ctaagaaacc attattatca tgacattaac ctataaaaat   4500

aggcgtatca cgaggccctt tcgtc                                         4525
```

```
<210> SEQ ID NO 110
<211> LENGTH: 19
<212> TYPE: DNA
<213> ORGANISM: Artificial Sequence
<220> FEATURE:
<223> OTHER INFORMATION: Synthetic: Shine-Dalgano sequence

<400> SEQUENCE: 110

taaggaggaa aaaaaaatg                                                  19


<210> SEQ ID NO 111
<211> LENGTH: 57
<212> TYPE: DNA
<213> ORGANISM: Artificial Sequence
<220> FEATURE:
<223> OTHER INFORMATION: Synthetic: nSDQb-mutEcoRIfor  sequence

<400> SEQUENCE: 111

gcgcgcgaat tctaaggagg aaaaaaaaat ggcaaaatta gagactgtta ctttagg        57


<210> SEQ ID NO 112
<211> LENGTH: 133
<212> TYPE: PRT
<213> ORGANISM: Artificial Sequence
<220> FEATURE:
<223> OTHER INFORMATION: Synthetic: RNA-phage Qb CP

<400> SEQUENCE: 112

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130


<210> SEQ ID NO 113
<211> LENGTH: 329
<212> TYPE: PRT
<213> ORGANISM: Artificial Sequence
<220> FEATURE:
<223> OTHER INFORMATION: Synthetic: RNA-phage Qb A1 protein
```

<400> SEQUENCE: 113

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
    130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 114
<211> LENGTH: 129
<212> TYPE: PRT
<213> ORGANISM: Artificial Sequence
<220> FEATURE:
<223> OTHER INFORMATION: Synthetic: bacteriophage R17

<400> SEQUENCE: 114

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp

```
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr


<210> SEQ ID NO 115
<211> LENGTH: 130
<212> TYPE: PRT
<213> ORGANISM: Artificial Sequence
<220> FEATURE:
<223> OTHER INFORMATION: Synthetic: bacteriophage fr

<400> SEQUENCE: 115

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130


<210> SEQ ID NO 116
<211> LENGTH: 130
<212> TYPE: PRT
<213> ORGANISM: Artificial Sequence
<220> FEATURE:
<223> OTHER INFORMATION: Synthetic: bacteriophage GA

<400> SEQUENCE: 116

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
```

```
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130


<210> SEQ ID NO 117
<211> LENGTH: 132
<212> TYPE: PRT
<213> ORGANISM: Artificial Sequence
<220> FEATURE:
<223> OTHER INFORMATION: Synthetic: bacteriophage SP CP

<400> SEQUENCE: 117

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130


<210> SEQ ID NO 118
<211> LENGTH: 329
<212> TYPE: PRT
<213> ORGANISM: Artificial Sequence
<220> FEATURE:
<223> OTHER INFORMATION: Synthetic: bacteriophage SP A1 protein

<400> SEQUENCE: 118

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
    50                  55                  60

Gln Ile Lys Leu Gln Asn Pro Thr Ala Cys Thr Arg Asp Ala Cys Asp
65                  70                  75                  80
```

```
Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Leu Val Ala Ser Ser Gly Gly Gly Asp
    130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Asp Tyr Asp
    210                 215                 220

Ile Ala Asn Arg Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Gln Phe Asn Ser Ala Asn Cys Pro
305                 310                 315                 320

Val Gln Thr Val Ile Ile Ile Pro Ser
                325
```

<210> SEQ ID NO 119
<211> LENGTH: 130
<212> TYPE: PRT
<213> ORGANISM: Artificial Sequence
<220> FEATURE:
<223> OTHER INFORMATION: Synthetic: bacteriophage MS2

<400> SEQUENCE: 119

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110
```

```
Leu Lys Asp Gly Asn Pro Ile Pro Ser Ala Ile Ala Ala Asn Ser Gly
        115                 120                 125

Ile Tyr
    130


<210> SEQ ID NO 120
<211> LENGTH: 133
<212> TYPE: PRT
<213> ORGANISM: Artificial Sequence
<220> FEATURE:
<223> OTHER INFORMATION: Synthetic: bacteriophage M11

<400> SEQUENCE: 120

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125

Leu Asn Pro Ala Tyr
    130


<210> SEQ ID NO 121
<211> LENGTH: 133
<212> TYPE: PRT
<213> ORGANISM: Artificial Sequence
<220> FEATURE:
<223> OTHER INFORMATION: Synthetic: bacteriophage MX1

<400> SEQUENCE: 121

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
    130
```

<210> SEQ ID NO 122
<211> LENGTH: 330
<212> TYPE: PRT
<213> ORGANISM: Artificial Sequence
<220> FEATURE:
<223> OTHER INFORMATION: Synthetic: bacteriophage NL95

<400> SEQUENCE: 122

```
Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330
```

<210> SEQ ID NO 123
<211> LENGTH: 129
<212> TYPE: PRT
<213> ORGANISM: Artificial Sequence

```
<220> FEATURE:
<223> OTHER INFORMATION: Synthetic: bacteriophage f2

<400> SEQUENCE: 123

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr


<210> SEQ ID NO 124
<211> LENGTH: 128
<212> TYPE: PRT
<213> ORGANISM: Artificial Sequence
<220> FEATURE:
<223> OTHER INFORMATION: Synthetic: bacteriophage PP7

<400> SEQUENCE: 124

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125


<210> SEQ ID NO 125
<211> LENGTH: 132
<212> TYPE: PRT
<213> ORGANISM: Artificial Sequence
<220> FEATURE:
<223> OTHER INFORMATION: Synthetic: Qb-240 (K13R)

<400> SEQUENCE: 125

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
```

```
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 126
<211> LENGTH: 132
<212> TYPE: PRT
<213> ORGANISM: Artificial Sequence
<220> FEATURE:
<223> OTHER INFORMATION: Synthetic: Qb-243 (N10K)

<400> SEQUENCE: 126

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 127
<211> LENGTH: 132
<212> TYPE: PRT
<213> ORGANISM: Artificial Sequence
<220> FEATURE:
<223> OTHER INFORMATION: Synthetic: Qb-250 (K2R, K13R)

<400> SEQUENCE: 127

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45
```

```
Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 128
<211> LENGTH: 132
<212> TYPE: PRT
<213> ORGANISM: Artificial Sequence
<220> FEATURE:
<223> OTHER INFORMATION: Synthetic: Qb -251

<400> SEQUENCE: 128

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 129
<211> LENGTH: 132
<212> TYPE: PRT
<213> ORGANISM: Artificial Sequence
<220> FEATURE:
<223> OTHER INFORMATION: Synthetic: Qb-259 (K2R, K16R)

<400> SEQUENCE: 129

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80
```

```
Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 130
<211> LENGTH: 3635
<212> TYPE: DNA
<213> ORGANISM: Artificial Sequence
<220> FEATURE:
<223> OTHER INFORMATION: Synthetic: Plasmid pAP283-58

<400> SEQUENCE: 130

```
cgagctcgcc cctggcttat cgaaattaat acgactcact atagggagac cggaattcga     60

gctcgcccgg ggatcctcta gaattttctg cgcacccatc ccgggtggcg cccaaagtga    120

ggaaaatcac atggcaaata agccaatgca accgatcaca tctacagcaa ataaaattgt    180

gtggtcggat ccaactcgtt tatcaactac attttcagca agtctgttac gccaacgtgt    240

taaagttggt atagccgaac tgaataatgt ttcaggtcaa tatgtatctg tttataagcg    300

tcctgcacct aaaccggaag gttgtgcaga tgcctgtgtc attatgccga atgaaaacca    360

atccattcgc acagtgattt cagggtcagc cgaaaacttg gctaccttaa aagcagaatg    420

ggaaactcac aaacgtaacg ttgacacact cttcgcgagc ggcaacgccg gtttgggttt    480

ccttgaccct actgcggcta tcgtatcgtc tgatactact gcttaagctt gtattctata    540

gtgtcaccta aatcgtatgt gtatgataca taaggttatg tattaattgt agccgcgttc    600

taacgacaat atgtacaagc ctaattgtgt agcatctggc ttactgaagc agaccctatc    660

atctctctcg taaactgccg tcagagtcgg tttggttgga cgaaccttct gagtttctgg    720

taacgccgtt ccgcaccccg gaaatggtca ccgaaccaat cagcagggtc atcgctagcc    780

agatcctcta cgccggacgc atcgtggccg gcatcaccgg cgcacacagt gcggttgctg    840

gcgcctatat cgccgacatc accgatgggg aagatcgggc tcgccacttc gggctcatga    900

gcgcttgttt cggcgtgggt atggtggcag gccccgtggc cgggggactg ttgggcgcca    960

tctccttgca tgcaccattc cttgcggcgg cggtgcttca acggcctcaa cctactactg   1020

ggctgcttcc taatgcagga gtcgcataag ggagagcgtc gatatggtgc actctcagta   1080

caatctgctc tgatgccgca tagttaagcc aactccgcta tcgctacgtg actgggtcat   1140

ggctgcgccc cgacacccgc caacacccgc tgacgcgccc tgacgggctt gtctgctccc   1200

ggcatccgct tacagacaag ctgtgaccgt ctccgggagc tgcatgtgtc agaggttttc   1260

accgtcatca ccgaaacgcg cgaggcagct tgaagacgaa agggcctcgt gatacgccta   1320

tttttatagg ttaatgtcat gataataatg gtttcttaga cgtcaggtgg cacttttcgg   1380

ggaaatgtgc gcggaacccc tatttgttta tttttctaaa tacattcaaa tatgtatccg   1440

ctcatgagac aataaccctg ataaatgctt caataatatt gaaaaaggaa gagtatgagt   1500

attcaacatt tccgtgtcgc ccttattccc ttttttgcgg cattttgcct tcctgttttt   1560

gctcacccag aaacgctggt gaaagtaaaa gatgctgaag atcagttggg tgcacgagtg   1620

ggttacatcg aactggatct caacagcggt aagatccttg agagttttcg ccccgaagaa   1680
```

cgttttccaa tgatgagcac ttttaaagtt ctgctatgtg gcgcggtatt atcccgtatt 1740
gacgccgggc aagagcaact cggtcgccgc atacactatt ctcagaatga cttggttgag 1800
tactcaccag tcacagaaaa gcatcttacg gatggcatga cagtaagaga attatgcagt 1860
gctgccataa ccatgagtga taacactgcg gccaacttac ttctgacaac gatcggagga 1920
ccgaaggagc taaccgcttt tttgcacaac atgggggatc atgtaactcg ccttgatcgt 1980
tgggaaccgg agctgaatga agccatacca aacgacgagc gtgacaccac gatgcctgta 2040
gcaatggcaa caacgttgcg caaactatta actggcgaac tacttactct agcttcccgg 2100
caacaattaa tagactggat ggaggcggat aaagttgcag gaccacttct gcgctcggcc 2160
cttccggctg gctggtttat tgctgataaa tctggagccg gtgagcgtgg gtctcgcggt 2220
atcattgcag cactggggcc agatggtaag ccctcccgta tcgtagttat ctacacgacg 2280
gggagtcagg caactatgga tgaacgaaat agacagatcg ctgagatagg tgcctcactg 2340
attaagcatt ggtaactgtc agaccaagtt tactcatata tactttagat tgatttaaaa 2400
cttcattttt aatttaaaag gatctaggtg aagatccttt ttgataatct catgaccaaa 2460
atcccttaac gtgagttttc gttccactga gcgtcagacc ccgtagaaaa gatcaaagga 2520
tcttcttgag atcctttttt tctgcgcgta atctgctgct tgcaaacaaa aaaaccaccg 2580
ctaccagcgg tggtttgttt gccggatcaa gagctaccaa ctctttttcc gaaggtaact 2640
ggcttcagca gagcgcagat accaaatact gtccttctag tgtagccgta gttaggccac 2700
cacttcaaga actctgtagc accgcctaca tacctcgctc tgctaatcct gttaccagtg 2760
gctgctgcca gtggcgataa gtcgtgtctt accgggttgg actcaagacg atagttaccg 2820
gataaggcgc agcggtcggg ctgaacgggg ggttcgtgca cacagcccag cttggagcga 2880
acgacctaca ccgaactgag atacctacag cgcgagcatt gagaaagcgc cacgcttccc 2940
gaagggagaa aggcggacag gtatccggta agcggcaggg tcggaacagg agagcgcacg 3000
agggagcttc cagggggaaa cgcctggtat ctttatagtc ctgtcgggtt tcgccacctc 3060
tgacttgagc gtcgattttt gtgatgctcg tcaggggggc ggagcctatg gaaaaacgcc 3120
agcaacgcgg cctttttacg gttcctggcc ttttgctggc cttttgctca catgttcttt 3180
cctgcgttat cccctgattc tgtggataac cgtattaccg cctttgagtg agctgatacc 3240
gctcgccgca gccgaacgac gagcgcagcg agtcagtgag cgaggaagcg gaagagcgcc 3300
caatacgcaa accgcctctc cccgcgcgtt ggccgattca ttaatgcagc tgtggtgtca 3360
tggtcggtga tcgccagggt gccgacgcgc atctcgactg catggtgcac caatgcttct 3420
ggcgtcaggc agccatcgga agctgtggta tggccgtgca ggtcgtaaat cactgcataa 3480
ttcgtgtcgc tcaaggcgca ctcccgttct ggataatgtt ttttgcgccg acatcataac 3540
ggttctggca aatattctga aatgagctgt tgacaattaa tcatcgaact agttaactag 3600
tacgcaagtt cacgtaaaaa gggtatcgcg gaatt 3635

<210> SEQ ID NO 131
<211> LENGTH: 57
<212> TYPE: DNA
<213> ORGANISM: Artificial Sequence
<220> FEATURE:
<223> OTHER INFORMATION: Synthetic: AP205

<400> SEQUENCE: 131
tctagaattt tctgcgcacc catcccgggt ggcgcccaaa gtgaggaaaa tcacatg 57

```
<210> SEQ ID NO 132
<211> LENGTH: 35
<212> TYPE: DNA
<213> ORGANISM: Artificial Sequence
<220> FEATURE:
<223> OTHER INFORMATION: Synthetic: Shine delgarno sequence

<400> SEQUENCE: 132

tctagattaa cccaacgcgt aggagtcagg ccatg                              35


<210> SEQ ID NO 133
<211> LENGTH: 131
<212> TYPE: PRT
<213> ORGANISM: Artificial Sequence
<220> FEATURE:
<223> OTHER INFORMATION: Synthetic: AP205 coat protein

<400> SEQUENCE: 133

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130


<210> SEQ ID NO 134
<211> LENGTH: 131
<212> TYPE: PRT
<213> ORGANISM: Artificial Sequence
<220> FEATURE:
<223> OTHER INFORMATION: Synthetic: AP205 coat protein (P5T)

<400> SEQUENCE: 134

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110
```

```
Ala Gly Leu Gly Phe Leu Asp Pro Thr Ala Ala Ile Val Ser Ser Asp
        115                 120                 125

Thr Thr Ala
    130


<210> SEQ ID NO 135
<211> LENGTH: 3607
<212> TYPE: DNA
<213> ORGANISM: Artificial Sequence
<220> FEATURE:
<223> OTHER INFORMATION: Synthetic: Plasmid pAP281-32

<400> SEQUENCE: 135

cgagctcgcc cctggcttat cgaaattaat acgactcact atagggagac cggaattcga     60

gctcgcccgg ggatcctcta gattaaccca acgcgtagga gtcaggccat ggcaaataag    120

acaatgcaac cgatcacatc tacagcaaat aaaattgtgt ggtcggatcc aactcgttta    180

tcaactacat tttcagcaag tctgttacgc caacgtgtta aagttggtat agccgaactg    240

aataatgttt caggtcaata tgtatctgtt tataagcgtc ctgcacctaa accgaaggtc    300

agatgcctgt gtcattatgc cgaatgaaaa ccaatccatt cgcacagtga tttcagggtc    360

agccgaaaac ttggctacct taaaagcaga atgggaaact cacaaacgta acgttgacac    420

actcttcgcg agcggcaacg ccggtttggg tttccttgac cctactgcgg ctatcgtatc    480

gtctgatact actgcttaag cttgtattct atagtgtcac ctaaatcgta tgtgtatgat    540

acataaggtt atgtattaat ggtagccgcg ttctaacgac aatatgtaca agcctaattg    600

tgtagcatct ggcttactga agcagaccct atcatctctc tcgtaaactg ccgtcagagt    660

cggttgggtt ggacagacct ctgagtttct ggtaacgccg ttccgcaccc cggaaatggt    720

caccgaacca ttcagcaggg tcatcgctag ccagatcctc tacgccggac gcatcgtggc    780

ccgcatcacc ggcgccacag gtgcggtgct ggcgcctata tcgccgacat caccgatggg    840

gaagatcggg ctcgccactt cgggctcatg atcgctggtt tccgcctggg tatggtggca    900

ggccccgtgg cccgggggac tgttgggcgc catctccttg catgcaccat tccttgcggc    960

ggcggtgctc aacggcctca acctactact gggctgcttc ctaatgcagg agtcgcataa   1020

gggagagcgt cgatatggtg cactctcagt acaatctgct ctgatgccgc atagttaagc   1080

caactccgct atcgctacgt gactgggtca tggctgcgcc ccgacacccg ccaacacccg   1140

ctgacgcgcc ctgacgggct tgtctgcttc cggcatccgc ttacagacaa gctgtgaccg   1200

tctccgggag ctgcatgtgt cagaggtttt caccgtcatc accgaaacgc gcgaggcagc   1260

ttgaagacga aagggcctcg tgatacgcct atttttatag gttaatgtca tgataataat   1320

ggtttcttag acgtcaggtg gcacttttcg gggaaatgtg cgcggacccc ctattggttt   1380

atttttctaa atacattcaa atatgtatcc gctcatgaga caataaccct gataaatgct   1440

tcaataatat tgaaaaagga agagtatgag tattcaacat ttccgtgtcg cccttattcc   1500

cttttttgcg gcattttgcc ttcctgtttt tgctcaccca gaaacgctgg tgaaagtaaa   1560

agatgctgaa gatcagttgg gtgcacgagt gggttacatc gaactggatc tcaacagcgg   1620

taagatcctt gagagttttc gccccgaaga acgttttcca atgatgagca cttttaaagt   1680

tctgctatgt gtcgcggtat tatcccgtat tgacgccggg caagagcaac tcggtcgccg   1740

catacactat tctcagaatg acttggtggt acctaccagt cacagaaaag catcttacgg   1800

atggcatgac agtaagagaa ttatgcagtg ctgccataac catgagtgat aacactgcgg   1860

ccaacttact tctgacaacg atcggaggac cgaaggagct aaccgctttt ttgcacaaca   1920
```

```
tgggggatca tgtaactcgc cttgatcgtt gggaaccgga gctgaatgaa gccataccaa   1980

acgacgagcg tgacaccacg atgcctgtac gaacggcaac aacgttgcgc aaactattaa   2040

ctggcgaact acttactcta gcttcccggc aacaattaat agactggatg gaggcggata   2100

aagttgcagg accacttctg cgctcggccc ttccggctgg ctggtttatt gctgataaat   2160

ctggagccgg tgagcgtggg tctcgcggta tcattgcagc actggggcca gatggtaagc   2220

cctcccgtat cgtagttatc tacacgacgg ggagtcaggc aactatggat gaacgaaata   2280

gacagatcgc tgagataggt gcctcactga ttaagcattg gtaactgtca gaccaagttt   2340

actcatatat actttagatt gatttaaaac ttcattttta atttaaaagg atctaggtga   2400

agatcctttt tgataatctc atgaccaaaa tcccttaacg tgagttttcg ttccactgag   2460

cggtcagacc ccgtagaaag atcaaaggat cttcttgaga tccttttttt ctgcgcgtaa   2520

tctgctgctt gcaaacaaaa aaaccaccgc taccagcggt ggtttgtttg ccggatcaag   2580

agctaccaac tctttttccg aaggtaactg gcttcagcag agcgcagata ccaaatactg   2640

tccttctagt gtagccgtag ttaggccacc acttcaagaa ctctgtagca ccgcctacat   2700

acctcgctct gctaatcctg ttaccagtgg ctgctgccag tggcgataag tcgtgtctta   2760

ccgggttgga ctcaagacga taggtaccgg ataaggcgca gcggtcgggc tgaacggggg   2820

gttcgtgcac acagcccagc ttggagcgaa cgacctacac cgaactgaga tacctacagc   2880

gcgagcattg agaaagcgcc acgcttcccg aagggagaaa ggcggacagg tatccggtaa   2940

gcggcagggt cggaacaaga gagcgcacga gggagcttcc agggggaaac gcctggtatc   3000

tttatagtcc tgtcgggttt cgccacctct gacttgagcg tcgatttttg tgatgctcgt   3060

caggggggcg gagcctatgg aaaaacgcca gcaacgcggc ctttttacgg ttcctggcct   3120

ttgctggcc ttttgctcac atgttctttc ctgcgttatc ccctgattct gtggataacc   3180

gtattaccgc ctttgagtga gctgataccg ctcgccgcag ccgaacgacc gacggcgcag   3240

cgagtcagtg agcgaggaag cggaagagcg cccaatacgc aaaccgcctc tccccgcgcg   3300

ttggccgatt cattaatgca gctgtggtgt catggtcggt gatcgccagg gtgccgacgc   3360

gcatctcgac tgcatggtgc accaatgctt ctggcgtcag gcagccatcg gaagctgtgg   3420

tatggccgtg caggtcgtaa atcactgcat aattcgtgtc gctcaaggcg cactcccgtt   3480

ctggataatg ttttttgcgg cgacatcata acggttctgg caaatattct gaaatgagct   3540

ggtgacaatt aatcatcgaa ctagttaact agtacgcaag ttcacgtaaa aagggtatcg   3600

cggaatt                                                             3607
```

<210> SEQ ID NO 136
<211> LENGTH: 186
<212> TYPE: PRT
<213> ORGANISM: Artificial Sequence
<220> FEATURE:
<223> OTHER INFORMATION: Synthetic: HBcAG protein

<400> SEQUENCE: 136

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
```

```
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys Leu
            180                 185


<210> SEQ ID NO 137
<211> LENGTH: 184
<212> TYPE: PRT
<213> ORGANISM: Artificial Sequence
<220> FEATURE:
<223> OTHER INFORMATION: Synthetic: HBcAG protein  variant

<400> SEQUENCE: 137

Met Asp Ile Asp Pro Tyr Glu Phe Gly Ala Thr Val Glu Leu Leu Ser
1               5                   10                  15

Phe Leu Pro Ser Asp Phe Phe Pro Ser Val Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Asn Asn Leu Glu Asp Pro Ala Ser
65                  70                  75                  80

Arg Asp Leu Val Val Asn Tyr Val Asn Thr Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
        115                 120                 125

Pro Ala Tyr Arg Pro Pro Asn Ala Pro Ile Leu Ser Thr Leu Pro Glu
    130                 135                 140

Thr Thr Val Val Arg Arg Arg Asp Arg Gly Arg Ser Pro Arg Arg Arg
145                 150                 155                 160

Thr Pro Ser Pro Arg Arg Arg Arg Ser Gln Ser Pro Arg Arg Arg Arg
                165                 170                 175

Ser Gln Ser Arg Glu Ser Gln Cys
            180


<210> SEQ ID NO 138
<211> LENGTH: 183
<212> TYPE: PRT
<213> ORGANISM: Artificial Sequence
<220> FEATURE:
<223> OTHER INFORMATION: Synthetic: HBcAG protein  variant
```

<400> SEQUENCE: 138

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180
```

<210> SEQ ID NO 139
<211> LENGTH: 183
<212> TYPE: PRT
<213> ORGANISM: Artificial Sequence
<220> FEATURE:
<223> OTHER INFORMATION: Synthetic: HBcAG protein variant

<400> SEQUENCE: 139

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Thr Asn Ala Pro Ile Leu Ser Thr Leu Pro
    130                 135                 140

Glu Thr Cys Val Ile Arg Arg Arg Gly Arg Ser Pro Arg Arg Arg Thr
145                 150                 155                 160
```

```
Pro Ser Pro Arg Arg Arg Arg Ser Gln Ser Pro Arg Arg Arg Arg Ser
                165                 170                 175

Gln Ser Arg Gly Ser Gln Cys
            180


<210> SEQ ID NO 140
<211> LENGTH: 212
<212> TYPE: PRT
<213> ORGANISM: Artificial Sequence
<220> FEATURE:
<223> OTHER INFORMATION: Synthetic: HBcAG protein  variant

<400> SEQUENCE: 140

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 141
<211> LENGTH: 212
<212> TYPE: PRT
<213> ORGANISM: Artificial Sequence
<220> FEATURE:
<223> OTHER INFORMATION: Synthetic: HBcAG protein  variant

<400> SEQUENCE: 141

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60
```

```
Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 142
<211> LENGTH: 183
<212> TYPE: PRT
<213> ORGANISM: Artificial Sequence
<220> FEATURE:
<223> OTHER INFORMATION: Synthetic: HBcAG protein  variant

<400> SEQUENCE: 142

Met Asp Ile Asp Pro Tyr Lys Glu Phe Gly Ala Thr Val Glu Leu Leu
1               5                   10                  15

Ser Phe Leu Pro Thr Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 143
```

```
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 143

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Gly Asn Leu Glu Asp Pro Val Ser Arg Asp
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 144
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 144

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Gly Asn Leu Glu Asp Pro Val Ser Arg Asp
```

```
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 145
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 145

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro Gln
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 146
<211> LENGTH: 212
<212> TYPE: PRT
```

<213> ORGANISM: Artificial Sequence
<220> FEATURE:
<223> OTHER INFORMATION: Synthetic: HBcAG protein Variant

<400> SEQUENCE: 146

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Lys Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Gly Ser Gln Cys
    210
```

<210> SEQ ID NO 147
<211> LENGTH: 183
<212> TYPE: PRT
<213> ORGANISM: Artificial Sequence
<220> FEATURE:
<223> OTHER INFORMATION: Synthetic: HBcAG protein Variant

<400> SEQUENCE: 147

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Phe Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110
```

```
Asp Thr Val Ile Glu Tyr Leu Val Ser Phe Gly Val Trp Ile Arg Thr
        115                 120                 125

Pro Pro Ala Tyr Arg Pro Ser Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 148
<211> LENGTH: 183
<212> TYPE: PRT
<213> ORGANISM: Artificial Sequence
<220> FEATURE:
<223> OTHER INFORMATION: Synthetic: HBcAG protein  Variant

<400> SEQUENCE: 148

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 149
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 149

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45
```

```
Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg His Ala Ile Leu Cys Trp Gly Asp Leu Arg Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Tyr Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 150
<211> LENGTH: 212
<212> TYPE: PRT
<213> ORGANISM: Artificial Sequence
<220> FEATURE:
<223> OTHER INFORMATION: Synthetic: HBcAG protein  variant

<400> SEQUENCE: 150

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Phe Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Ala Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Gln Ala
145                 150                 155                 160

Tyr Arg Pro Pro Asn Ala Pro Ile Leu Ser Thr Leu Pro Glu Thr Cys
                165                 170                 175

Val Val Arg Arg Arg Gly Arg Ser Pro Arg Arg Arg Thr Pro Ser Pro
            180                 185                 190
```

```
Arg Arg Arg Arg Ser Gln Ser Pro Arg Arg Arg Arg Ser Gln Ser Arg
        195                 200                 205

Glu Ser Gln Cys
    210
```

<210> SEQ ID NO 151
<211> LENGTH: 183
<212> TYPE: PRT
<213> ORGANISM: Artificial Sequence
<220> FEATURE:
<223> OTHER INFORMATION: Synthetic: HBcAG protein Variant

<400> SEQUENCE: 151

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 152
<211> LENGTH: 212
<212> TYPE: PRT
<213> ORGANISM: Artificial Sequence
<220> FEATURE:
<223> OTHER INFORMATION: Synthetic: HBcAG protein Variant

<400> SEQUENCE: 152

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Ser
```

```
                85                  90                  95

Leu Ala Thr Trp Val Gly Val Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 153
<211> LENGTH: 183
<212> TYPE: PRT
<213> ORGANISM: Artificial Sequence
<220> FEATURE:
<223> OTHER INFORMATION: Synthetic: HBcAG protein Variant

<400> SEQUENCE: 153

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 154
<211> LENGTH: 183
<212> TYPE: PRT
<213> ORGANISM: Artificial Sequence
<220> FEATURE:
<223> OTHER INFORMATION: Synthetic: HBcAG protein Variant

<400> SEQUENCE: 154

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ser Ala Leu Tyr Arg Glu Ala Leu Glu Ser Pro Glu His Cys
35 40 45

Ser Pro His His Thr Ala Leu Arg Gln Ala Ile Leu Cys Trp Gly Asp
50 55 60

Leu Met Thr Leu Ala Thr Trp Val Gly Val Asn Leu Glu Asp Pro Ala
65 70 75 80

Ser Arg Asp Leu Val Val Ser Tyr Val Asn Thr Asn Met Gly Leu Lys
85 90 95

Phe Arg Gln Leu Leu Trp Phe His Ile Ser Cys Leu Thr Phe Gly Arg
100 105 110

Glu Thr Val Ile Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Arg Arg Arg Gly Arg Ser Pro Arg Arg Arg Thr
145 150 155 160

Pro Ser Pro Arg Arg Arg Arg Ser Gln Ser Pro Arg Arg Arg Arg Ser
165 170 175

Gln Ser Arg Glu Ser Gln Cys
180

<210> SEQ ID NO 155
<211> LENGTH: 183
<212> TYPE: PRT
<213> ORGANISM: Artificial Sequence
<220> FEATURE:
<223> OTHER INFORMATION: Synthetic: HBcAG protein Variant

<400> SEQUENCE: 155

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ser Ala Leu Tyr Arg Asp Ala Leu Glu Ser Pro Glu His Cys
35 40 45

Ser Pro His His Thr Ala Leu Arg Gln Ala Ile Leu Cys Trp Gly Glu
50 55 60

Leu Met Thr Leu Ala Thr Trp Val Gly Ala Asn Leu Glu Asp Pro Ala
65 70 75 80

Ser Arg Asp Leu Val Val Ser Tyr Val Asn Thr Asn Met Gly Leu Lys
85 90 95

Phe Arg Gln Leu Leu Trp Phe His Ile Ser Cys Leu Thr Phe Gly Arg
100 105 110

Glu Thr Val Ile Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Arg Arg Arg Gly Arg Thr Pro Arg Arg Arg Thr
145 150 155 160

```
Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 156
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 156

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 157
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 157

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60
```

```
Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 158
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 158

Met Gln Leu Phe His Leu Cys Leu Ile Ile Ser Cys Thr Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Gln Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ala Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

```
Glu Ser Gln Cys
    210


<210> SEQ ID NO 159
<211> LENGTH: 212
<212> TYPE: PRT
<213> ORGANISM: Artificial Sequence
<220> FEATURE:
<223> OTHER INFORMATION: Synthetic: HBcAG protein  variant

<400> SEQUENCE: 159

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Phe Glu Cys Ser Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 160
<211> LENGTH: 214
<212> TYPE: PRT
<213> ORGANISM: Artificial Sequence
<220> FEATURE:
<223> OTHER INFORMATION: Synthetic: HBcAG protein  Variant
<220> FEATURE:
<221> NAME/KEY: misc_feature
<222> LOCATION: (28)..(28)
<223> OTHER INFORMATION: Xaa can be any naturally occurring amino acid

<400> SEQUENCE: 160

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Xaa Ala Ala Asp Met
            20                  25                  30

Asp Ile Asp Pro Tyr Lys Glu Phe Gly Ala Thr Val Glu Leu Leu Ser
        35                  40                  45
```

```
Phe Leu Pro Ser Asp Phe Phe Pro Ser Val Arg Asp Leu Leu Asp Thr
    50                  55                  60

Ala Ser Ala Leu Tyr Arg Glu Ala Leu Glu Ser Pro Glu His Cys Ser
65                  70                  75                  80

Pro His His Thr Ala Leu Arg Gln Ala Ile Leu Cys Trp Gly Asp Leu
                85                  90                  95

Ile Thr Leu Ser Thr Trp Val Gly Gly Asn Leu Glu Asp Pro Thr Ser
            100                 105                 110

Arg Asp Leu Val Val Ser Tyr Val Asn Thr Asn Met Gly Leu Lys Phe
        115                 120                 125

Arg Gln Leu Leu Trp Phe His Ile Ser Cys Leu Thr Phe Gly Arg Glu
    130                 135                 140

Thr Val Ile Glu Tyr Leu Val Ser Phe Gly Val Trp Ile Arg Thr Pro
145                 150                 155                 160

Pro Ala Tyr Arg Pro Pro Asn Ala Pro Ile Leu Ser Thr Leu Pro Glu
                165                 170                 175

Thr Thr Val Val Arg Arg Arg Gly Arg Ser Pro Arg Arg Arg Thr Pro
            180                 185                 190

Ser Pro Arg Arg Arg Arg Ser Gln Ser Pro Arg Arg Arg Arg Thr Gln
        195                 200                 205

Ser Arg Glu Ser Gln Cys
    210


<210> SEQ ID NO 161
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 161

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190
```

```
Arg Arg Arg Arg Ser Gln Ser Pro Arg Arg Arg Arg Ser Gln Ser Arg
        195                 200                 205

Glu Ser Gln Cys
    210


<210> SEQ ID NO 162
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 162

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Cys Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 163
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 163

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60
```

```
Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Pro Gln Cys
    210


<210> SEQ ID NO 164
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 164

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Ser Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

```
Glu Ser Gln Cys
    210


<210> SEQ ID NO 165
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 165

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Leu Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 166
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 166

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
```

```
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Lys Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 167
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 167

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Thr Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
```

210

<210> SEQ ID NO 168
<211> LENGTH: 183
<212> TYPE: PRT
<213> ORGANISM: Artificial Sequence
<220> FEATURE:
<223> OTHER INFORMATION: Synthetic: HBcAG protein variant

<400> SEQUENCE: 168

```
Met Asp Ile Asp Pro Tyr Lys Glu Phe Gly Ala Ser Met Glu Leu Leu
1               5                   10                  15

Ser Phe Leu Pro Ser Asp Phe Tyr Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Thr Pro His His Thr Ala Leu Arg Gln Ala Ile Leu Cys Trp Gly Glu
    50                  55                  60

Leu Met Thr Leu Ala Thr Trp Val Gly Gly Asn Leu Gln Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Val Ser Cys Leu Thr Phe Gly Arg
            100                 105                 110

Glu Thr Val Val Glu Tyr Leu Val Ser Phe Gly Val Trp Ile Arg Thr
        115                 120                 125

Pro Gln Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 169
<211> LENGTH: 183
<212> TYPE: PRT
<213> ORGANISM: Artificial Sequence
<220> FEATURE:
<223> OTHER INFORMATION: Synthetic: HBcAG protein Variant

<400> SEQUENCE: 169

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg His Val Phe Leu Cys Trp Gly Asp
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110
```

```
Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 170
<211> LENGTH: 212
<212> TYPE: PRT
<213> ORGANISM: Artificial Sequence
<220> FEATURE:
<223> OTHER INFORMATION: Synthetic: HBcAG protein Variant

<400> SEQUENCE: 170

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Thr Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 171
<211> LENGTH: 212
<212> TYPE: PRT
<213> ORGANISM: Artificial Sequence
<220> FEATURE:
<223> OTHER INFORMATION: Synthetic: HBcAG protein Variant

<400> SEQUENCE: 171

```
Met Gln Leu Phe His Leu Cys Leu Ile Ile Ser Cys Ser Cys Pro Thr
1               5                   10                  15
```

```
Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Ile Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

```
<210> SEQ ID NO 172
<211> LENGTH: 183
<212> TYPE: PRT
<213> ORGANISM: Artificial Sequence
<220> FEATURE:
<223> OTHER INFORMATION: Synthetic: HBcAG protein  variant

<400> SEQUENCE: 172

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Val
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160
```

```
Pro Ser Pro Ala Arg Arg Arg Ser Gln Ser Pro Arg Arg Arg Arg Ser
                165                 170                 175

Gln Ser Arg Glu Ser Gln Cys
            180


<210> SEQ ID NO 173
<211> LENGTH: 213
<212> TYPE: PRT
<213> ORGANISM: Artificial Sequence
<220> FEATURE:
<223> OTHER INFORMATION: Synthetic: HBcAG protein  Variant

<400> SEQUENCE: 173

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Asn
                85                  90                  95

Leu Ala Thr Trp Val Gly Gly Asn Leu Glu Asp Pro Val Ser Arg Asp
            100                 105                 110

Leu Val Val Gly Tyr Val Asn Thr Thr Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Pro Arg Arg Arg Arg Ser Gln Ser Pro Arg Arg Arg Arg Ser Gln Ser
        195                 200                 205

Arg Glu Ser Gln Cys
    210


<210> SEQ ID NO 174
<211> LENGTH: 183
<212> TYPE: PRT
<213> ORGANISM: Artificial Sequence
<220> FEATURE:
<223> OTHER INFORMATION: Synthetic: HBcAG protein  Variant

<400> SEQUENCE: 174

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
```

```
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Thr Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 175
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 175

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Ala Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Ile Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

```
<210> SEQ ID NO 176
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 176

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Thr Arg Asp
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 177
<211> LENGTH: 212
<212> TYPE: PRT
<213> ORGANISM: Artificial Sequence
<220> FEATURE:
<223> OTHER INFORMATION: Synthetic: HBcAG protein  variant

<400> SEQUENCE: 177

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Arg Ile Leu Cys Trp Gly Glu Leu Met Thr
                85                  90                  95
```

```
Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Thr Arg Ser Gln Ser Arg
        195                 200                 205

Glu Ser Gln Cys
    210


<210> SEQ ID NO 178
<211> LENGTH: 212
<212> TYPE: PRT
<213> ORGANISM: Artificial Sequence
<220> FEATURE:
<223> OTHER INFORMATION: Synthetic: HBcAG protein  Variant

<400> SEQUENCE: 178

Met Gln Leu Phe His Leu Cys Leu Val Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Asn Asn Leu Glu Asp Pro Ala Ser Arg Asp
            100                 105                 110

Leu Val Val Asn Tyr Val Asn Thr Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 179
<211> LENGTH: 212
```

```
<212> TYPE: PRT
<213> ORGANISM: Artificial Sequence
<220> FEATURE:
<223> OTHER INFORMATION: Synthetic: HBcAG protein  Variant

<400> SEQUENCE: 179

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Ala Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 180
<211> LENGTH: 183
<212> TYPE: PRT
<213> ORGANISM: Artificial Sequence
<220> FEATURE:
<223> OTHER INFORMATION: Synthetic: HBcAG protein  Variant

<400> SEQUENCE: 180

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110
```

```
Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 181
<211> LENGTH: 183
<212> TYPE: PRT
<213> ORGANISM: Artificial Sequence
<220> FEATURE:
<223> OTHER INFORMATION: Synthetic: HBcAG protein  Variant

<400> SEQUENCE: 181

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180


<210> SEQ ID NO 182
<211> LENGTH: 188
<212> TYPE: PRT
<213> ORGANISM: Artificial Sequence
<220> FEATURE:
<223> OTHER INFORMATION: Synthetic: HBcAG protein  Variant

<400> SEQUENCE: 182

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
```

```
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ser Thr Asn Cys
            180                 185


<210> SEQ ID NO 183
<211> LENGTH: 217
<212> TYPE: PRT
<213> ORGANISM: Artificial Sequence
<220> FEATURE:
<223> OTHER INFORMATION: Synthetic: HBcAG protein  Variant

<400> SEQUENCE: 183

Met Tyr Leu Phe His Leu Cys Leu Val Phe Ala Cys Val Pro Cys Pro
1               5                   10                  15

Thr Val Gln Ala Ser Lys Leu Cys Leu Gly Trp Leu Trp Asp Met Asp
            20                  25                  30

Ile Asp Pro Tyr Lys Glu Phe Gly Ser Ser Tyr Gln Leu Leu Asn Phe
        35                  40                  45

Leu Pro Leu Asp Phe Phe Pro Asp Leu Asn Ala Leu Val Asp Thr Ala
    50                  55                  60

Ala Ala Leu Tyr Glu Glu Glu Leu Thr Gly Arg Glu His Cys Ser Pro
65                  70                  75                  80

His His Thr Ala Ile Arg Gln Ala Leu Val Cys Trp Glu Glu Leu Thr
                85                  90                  95

Arg Leu Ile Thr Trp Met Ser Glu Asn Thr Thr Glu Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gln His Thr Val
    130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Arg Ser Gln Ser Pro Arg Arg Arg
        195                 200                 205

Arg Ser Gln Ser Pro Ala Ser Asn Cys
```

```
    210                 215


<210> SEQ ID NO 184
<211> LENGTH: 262
<212> TYPE: PRT
<213> ORGANISM: Artificial Sequence
<220> FEATURE:
<223> OTHER INFORMATION: Synthetic: HBcAG protein  Variant

<400> SEQUENCE: 184

Met Asp Val Asn Ala Ser Arg Ala Leu Ala Asn Val Tyr Asp Leu Pro
1               5                   10                  15

Asp Asp Phe Phe Pro Lys Ile Glu Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ala Ile Arg Ala Val Ile Pro Pro
65                  70                  75                  80

Thr Thr Ala Pro Val Pro Ser Gly Tyr Leu Ile Gln His Asp Glu Ala
                85                  90                  95

Glu Glu Ile Pro Leu Gly Asp Leu Phe Lys Glu Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val Ala Gln Gly Gly Arg Lys Thr Ser Thr Ala Thr Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Glu Arg Arg Ala Ser Ser Pro
225                 230                 235                 240

Gln Arg Ala Gly Ser Pro Leu Pro Arg Ser Ser Ser Ser His His Arg
                245                 250                 255

Ser Pro Ser Pro Arg Lys
            260


<210> SEQ ID NO 185
<211> LENGTH: 305
<212> TYPE: PRT
<213> ORGANISM: Artificial Sequence
<220> FEATURE:
<223> OTHER INFORMATION: Synthetic: HBcAG protein  variant

<400> SEQUENCE: 185

Met Trp Asp Leu Arg Leu His Pro Ser Pro Phe Gly Ala Ala Cys Gln
1               5                   10                  15

Gly Ile Phe Thr Ser Ser Leu Leu Leu Phe Leu Val Thr Val Pro Leu
            20                  25                  30
```

```
Val Cys Thr Ile Val Tyr Asp Ser Cys Leu Cys Met Asp Ile Asn Ala
        35                  40                  45

Ser Arg Ala Leu Ala Asn Val Tyr Asp Leu Pro Asp Asp Phe Phe Pro
    50                  55                  60

Lys Ile Asp Asp Leu Val Arg Asp Ala Lys Asp Ala Leu Glu Pro Tyr
65                  70                  75                  80

Trp Arg Asn Asp Ser Ile Lys Lys His Val Leu Ile Ala Thr His Phe
                85                  90                  95

Val Asp Leu Ile Glu Asp Phe Trp Gln Thr Thr Gln Gly Met His Glu
            100                 105                 110

Ile Ala Glu Ala Leu Arg Ala Ile Ile Pro Ala Thr Thr Ala Pro Val
        115                 120                 125

Pro Gln Gly Phe Leu Val Gln His Glu Glu Ala Glu Glu Ile Pro Leu
    130                 135                 140

Gly Glu Leu Phe Arg Tyr Gln Glu Glu Arg Leu Thr Asn Phe Gln Pro
145                 150                 155                 160

Asp Tyr Pro Val Thr Ala Arg Ile His Ala His Leu Lys Ala Tyr Ala
                165                 170                 175

Lys Ile Asn Glu Glu Ser Leu Asp Arg Ala Arg Arg Leu Leu Trp Trp
            180                 185                 190

His Tyr Asn Cys Leu Leu Trp Gly Glu Pro Asn Val Thr Asn Tyr Ile
        195                 200                 205

Ser Arg Leu Arg Thr Trp Leu Ser Thr Pro Glu Lys Tyr Arg Gly Lys
    210                 215                 220

Asp Ala Pro Thr Ile Glu Ala Ile Thr Arg Pro Ile Gln Val Ala Gln
225                 230                 235                 240

Gly Gly Arg Asn Lys Thr Gln Gly Val Arg Lys Ser Arg Gly Leu Glu
                245                 250                 255

Pro Arg Arg Arg Arg Val Lys Thr Thr Ile Val Tyr Gly Arg Arg Arg
            260                 265                 270

Ser Lys Ser Arg Glu Arg Arg Ala Pro Thr Pro Gln Arg Ala Gly Ser
        275                 280                 285

Pro Leu Pro Arg Thr Ser Arg Asp His His Arg Ser Pro Ser Pro Arg
    290                 295                 300

Glu
305


<210> SEQ ID NO 186
<211> LENGTH: 185
<212> TYPE: PRT
<213> ORGANISM: Artificial Sequence
<220> FEATURE:
<223> OTHER INFORMATION: Synthetic: HBcAG protein  variant

<400> SEQUENCE: 186

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80
```

```
Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185


<210> SEQ ID NO 187
<211> LENGTH: 5
<212> TYPE: PRT
<213> ORGANISM: Artificial Sequence
<220> FEATURE:
<223> OTHER INFORMATION: Synthetic: Amino acid sequence

<400> SEQUENCE: 187

Gly Gly Lys Gly Gly
1               5


<210> SEQ ID NO 188
<211> LENGTH: 33
<212> TYPE: PRT
<213> ORGANISM: Artificial Sequence
<220> FEATURE:
<223> OTHER INFORMATION: Synthetic: Amino acid linker
<220> FEATURE:
<221> NAME/KEY: misc_feature
<222> LOCATION: (1)..(5)
<223> OTHER INFORMATION: Gly may or may not be present
<220> FEATURE:
<221> NAME/KEY: misc_feature
<222> LOCATION: (7)..(16)
<223> OTHER INFORMATION: Gly may or may not be present
<220> FEATURE:
<221> NAME/KEY: misc_feature
<222> LOCATION: (17)..(18)
<223> OTHER INFORMATION: Ser may or may not be present
<220> FEATURE:
<221> NAME/KEY: misc_feature
<222> LOCATION: (19)..(33)
<223> OTHER INFORMATION: Gly Gly Gly Gly Ser may or may not be present

<400> SEQUENCE: 188

Gly Gly Gly Gly Gly Cys Gly Gly Gly Gly Gly Gly Gly Gly Gly Gly
1               5                   10                  15

Ser Ser Gly Gly Gly Gly Ser Gly Gly Gly Gly Ser Gly Gly Gly Gly
            20                  25                  30

Ser


<210> SEQ ID NO 189
<211> LENGTH: 41
<212> TYPE: PRT
<213> ORGANISM: Artificial Sequence
<220> FEATURE:
<223> OTHER INFORMATION: Synthetic: Amino acid linker
<220> FEATURE:
<221> NAME/KEY: misc_feature
<222> LOCATION: (1)..(10)
<223> OTHER INFORMATION: Gly may or may not be present
```

```
<220> FEATURE:
<221> NAME/KEY: misc_feature
<222> LOCATION: (11)..(12)
<223> OTHER INFORMATION: Ser may or may not be present
<220> FEATURE:
<221> NAME/KEY: misc_feature
<222> LOCATION: (13)..(27)
<223> OTHER INFORMATION: Gly Gly Gly Gly Ser may or may not be present
<220> FEATURE:
<221> NAME/KEY: misc_feature
<222> LOCATION: (28)..(35)
<223> OTHER INFORMATION: Gly may or may not be present
<220> FEATURE:
<221> NAME/KEY: misc_feature
<222> LOCATION: (37)..(41)
<223> OTHER INFORMATION: Gly may or may not be present

<400> SEQUENCE: 189

Gly Gly Gly Gly Gly Gly Gly Gly Gly Gly Ser Ser Gly Gly Gly Gly
1               5                   10                  15

Ser Gly Gly Gly Gly Ser Gly Gly Gly Gly Ser Gly Gly Gly Gly Gly
            20                  25                  30

Gly Gly Gly Cys Gly Gly Gly Gly Gly
        35                  40


<210> SEQ ID NO 190
<211> LENGTH: 5
<212> TYPE: PRT
<213> ORGANISM: Artificial Sequence
<220> FEATURE:
<223> OTHER INFORMATION: Synthetic: Amino acid linker
<220> FEATURE:
<221> NAME/KEY: misc_feature
<222> LOCATION: (1)..(5)
<223> OTHER INFORMATION: "Gly Gly Gly Gly Ser" repeats indefinitely

<400> SEQUENCE: 190

Gly Gly Gly Gly Ser
1               5


<210> SEQ ID NO 191
<211> LENGTH: 10
<212> TYPE: PRT
<213> ORGANISM: Artificial Sequence
<220> FEATURE:
<223> OTHER INFORMATION: Synthetic: Amino acid linker

<400> SEQUENCE: 191

Cys Gly Asp Lys Thr His Thr Ser Pro Pro
1               5                   10


<210> SEQ ID NO 192
<211> LENGTH: 10
<212> TYPE: PRT
<213> ORGANISM: Artificial Sequence
<220> FEATURE:
<223> OTHER INFORMATION: Synthetic: Amino acid linker

<400> SEQUENCE: 192

Asp Lys Thr His Thr Ser Pro Pro Cys Gly
1               5                   10


<210> SEQ ID NO 193
<211> LENGTH: 17
<212> TYPE: PRT
<213> ORGANISM: Artificial Sequence
<220> FEATURE:
<223> OTHER INFORMATION: Synthetic: Amino acid linker
```

<400> SEQUENCE: 193

Cys Gly Gly Pro Lys Pro Ser Thr Pro Pro Gly Ser Ser Gly Gly Ala
1 5 10 15

Pro

<210> SEQ ID NO 194
<211> LENGTH: 18
<212> TYPE: PRT
<213> ORGANISM: Artificial Sequence
<220> FEATURE:
<223> OTHER INFORMATION: Synthetic: Amino acid linker

<400> SEQUENCE: 194

Pro Lys Pro Ser Thr Pro Pro Gly Ser Ser Gly Gly Ala Pro Gly Gly
1 5 10 15

Cys Gly

<210> SEQ ID NO 195
<211> LENGTH: 6
<212> TYPE: PRT
<213> ORGANISM: Artificial Sequence
<220> FEATURE:
<223> OTHER INFORMATION: Synthetic: Amino acid linker

<400> SEQUENCE: 195

Gly Cys Gly Gly Gly Gly
1 5

<210> SEQ ID NO 196
<211> LENGTH: 6
<212> TYPE: PRT
<213> ORGANISM: Artificial Sequence
<220> FEATURE:
<223> OTHER INFORMATION: Synthetic: Amino acid linker

<400> SEQUENCE: 196

Gly Gly Gly Gly Cys Gly
1 5

<210> SEQ ID NO 197
<211> LENGTH: 6
<212> TYPE: PRT
<213> ORGANISM: Artificial Sequence
<220> FEATURE:
<223> OTHER INFORMATION: Synthetic: Amino acid linker

<400> SEQUENCE: 197

Gly Gly Lys Lys Gly Cys
1 5

<210> SEQ ID NO 198
<211> LENGTH: 6
<212> TYPE: PRT
<213> ORGANISM: Artificial Sequence
<220> FEATURE:
<223> OTHER INFORMATION: Synthetic: Amino acid linker

<400> SEQUENCE: 198

Cys Gly Lys Lys Gly Gly
1 5

<210> SEQ ID NO 199
<211> LENGTH: 6
<212> TYPE: PRT
<213> ORGANISM: Artificial Sequence

```
<220> FEATURE:
<223> OTHER INFORMATION: Synthetic: Amino acid linker

<400> SEQUENCE: 199

Cys Gly Lys Lys Gly Gly
1               5


<210> SEQ ID NO 200
<211> LENGTH: 6
<212> TYPE: PRT
<213> ORGANISM: Artificial Sequence
<220> FEATURE:
<223> OTHER INFORMATION: Synthetic: Amino acid linker

<400> SEQUENCE: 200

Cys Gly Asp Glu Gly Gly
1               5


<210> SEQ ID NO 201
<211> LENGTH: 6
<212> TYPE: PRT
<213> ORGANISM: Artificial Sequence
<220> FEATURE:
<223> OTHER INFORMATION: Synthetic: Amino acid linker

<400> SEQUENCE: 201

Gly Gly Lys Lys Gly Cys
1               5


<210> SEQ ID NO 202
<211> LENGTH: 6
<212> TYPE: PRT
<213> ORGANISM: Artificial Sequence
<220> FEATURE:
<223> OTHER INFORMATION: Synthetic: Amino acid linker

<400> SEQUENCE: 202

Gly Gly Glu Asp Gly Cys
1               5


<210> SEQ ID NO 203
<211> LENGTH: 4
<212> TYPE: PRT
<213> ORGANISM: Artificial Sequence
<220> FEATURE:
<223> OTHER INFORMATION: Synthetic: Amino acid linker

<400> SEQUENCE: 203

Gly Gly Cys Gly
1
```